US012454525B2

(12) United States Patent
Cash et al.

(10) Patent No.: US 12,454,525 B2
(45) Date of Patent: Oct. 28, 2025

(54) IL4I1 INHIBITORS AND METHODS OF USE

(71) Applicant: Merck Sharp & Dohme LLC, Rahway, NJ (US)

(72) Inventors: Brandon D. Cash, Natick, MA (US); Wenlang Fu, Madison, NJ (US); George Madalin Giambasu, Natick, MA (US); Andrew M. Haidle, Somerville, MA (US); Brett A. Hopkins, Brownsburg, IN (US); Matthew A. Larsen, Templeton, CA (US); Charles A. Lesburg, Waban, MA (US); Ping Liu, Westfield, NJ (US); Meredeth A. Mcgowan, Boston, MA (US); Qinglin Pu, Needham, MA (US); Sulagna Sanyal, Belmont, MA (US); Phieng Siliphaivanh, Newton, MA (US); Catherine M. White, Canton, MA (US); Xin Yan, Newton, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 527 days.

(21) Appl. No.: 17/920,850

(22) PCT Filed: May 4, 2021

(86) PCT No.: PCT/US2021/030541

§ 371 (c)(1),
(2) Date: Oct. 24, 2022

(87) PCT Pub. No.: WO2021/226003

PCT Pub. Date: Nov. 11, 2021

(65) Prior Publication Data

US 2023/0183214 A1 Jun. 15, 2023

Related U.S. Application Data

(60) Provisional application No. 63/020,614, filed on May 6, 2020.

(51) Int. Cl.

| | |
|---|---|
| ***C07D 403/10*** | (2006.01) |
| ***C07D 235/26*** | (2006.01) |
| ***C07D 401/06*** | (2006.01) |
| ***C07D 401/08*** | (2006.01) |
| ***C07D 401/12*** | (2006.01) |
| ***C07D 401/14*** | (2006.01) |
| ***C07D 403/06*** | (2006.01) |
| ***C07D 405/06*** | (2006.01) |
| ***C07D 409/06*** | (2006.01) |
| ***C07D 409/14*** | (2006.01) |
| ***C07D 413/10*** | (2006.01) |
| ***C07D 417/10*** | (2006.01) |
| ***C07D 419/10*** | (2006.01) |
| ***C07D 495/04*** | (2006.01) |

(52) U.S. Cl.

CPC ......... *C07D 403/10* (2013.01); *C07D 235/26* (2013.01); *C07D 401/06* (2013.01); *C07D 401/08* (2013.01); *C07D 401/12* (2013.01); *C07D 401/14* (2013.01); *C07D 403/06* (2013.01); *C07D 405/06* (2013.01); *C07D 409/06* (2013.01); *C07D 409/14* (2013.01); *C07D 413/10* (2013.01); *C07D 417/10* (2013.01); *C07D 419/10* (2013.01); *C07D 495/04* (2013.01)

(58) Field of Classification Search

CPC .. C07D 403/10; C07D 235/26; C07D 401/06; C07D 401/08; C07D 401/12; C07D 401/14; C07D 403/06; C07D 405/06; C07D 409/06; C07D 409/14; C07D 413/10; C07D 417/10; C07D 419/10; C07D 495/04; C07D 209/34; Y02A 50/30; A61P 35/00; A61K 31/4184; A61K 31/4188; A61K 31/4192; A61K 31/4196; A61K 31/4245; A61K 31/427; A61K 31/4439; A61K 31/454; A61K 31/4709; A61K 31/496

See application file for complete search history.

(56) References Cited

U.S. PATENT DOCUMENTS

| | | | |
|---|---|---|---|
| 5,162,318 | A | 11/1992 | Hara et al. |
| 6,420,410 | B1 | 7/2002 | Sperl et al. |
| 2003/0100545 | A1 | 5/2003 | Kelly et al. |
| 2015/0126553 | A1 | 5/2015 | Hommes et al. |
| 2016/0067240 | A1 | 3/2016 | Zajac-Kaye et al. |
| 2019/0177338 | A1 | 6/2019 | Kettle et al. |

(Continued)

FOREIGN PATENT DOCUMENTS

| | | | |
|---|---|---|---|
| CN | 1970544 | A | 5/2007 |
| JP | 11292720 | A | 10/1999 |
| WO | 9534555 | A1 | 12/1995 |

(Continued)

OTHER PUBLICATIONS

Ermann, Monika et al., Use of polymer supported thiophenol for the synthesis and purification of a benzimidazol-2-one library, Tetrahedron Letters, 2000, 2483-2485, 41(14).

(Continued)

*Primary Examiner* — Jessica Worsham

(74) *Attorney, Agent, or Firm* — Janet E. Fair; John C. Todaro

(57) ABSTRACT

Described herein are compounds of Formula I or a pharmaceutically acceptable salt thereof. The compounds of Formula I act as IL4I1 inhibitors and can be useful in preventing, treating or acting as a remedial agent for IL4I1-related diseases.

25 Claims, No Drawings

(56) References Cited

U.S. PATENT DOCUMENTS

| | | | |
|---|---|---|---|
| 2020/0166512 | A1 | 5/2020 | Molinier Frenkel et al. |
| 2021/0023034 | A1 | 1/2021 | Presset et al. |

FOREIGN PATENT DOCUMENTS

| | | | |
|---|---|---|---|
| WO | 1995034555 | A1 | 12/1995 |
| WO | 2003028720 | A1 | 4/2003 |
| WO | 2004058720 | A2 | 7/2004 |
| WO | 2006048727 | A1 | 5/2006 |
| WO | 2010066858 | A1 | 6/2010 |
| WO | 2012136492 | A1 | 10/2012 |
| WO | 2012178208 | A2 | 12/2012 |
| WO | 2019185907 | A1 | 10/2019 |
| WO | 2019198692 | A1 | 10/2019 |
| WO | 2021116357 | A1 | 6/2021 |

OTHER PUBLICATIONS

Fabis, Frédéric et al., Efficient synthesis of N1- or N3-substituted thieno [2, 3-d] imidazol-2-ones, Tetrahedron, 1999, 6167-6174, 55.

Meanwell, Nicholas A. et al., Regiospecific Functionalization of 1,3-Dihydro-2H-benzimidazol-2-one and Structurally Related Cyclic Urea Derivatives, The Journal of Organic Chemistry, 1995, 1565-1582, 60.

Oh, Sangmi et al., Synthesis and biological evaluation of 2,3-dihydroimidazo[1,2-a] benzimidazole derivatives against Leishmania donovani and Trypanosoma cruzi, European Journal of Medicinal Chemistry, 2014, 395-403, 84.

Online article STN CAS Registry No. 537702-31-1, Date Entered STN: Jun. 26, 2003, 1 page.

Presset, Marc et al., Identification of inhibitors of the immunosuppressive enzyme IL411, Bioorganic Chemistry, Jan. 9, 2020, 94:103463.

CAS Registry No. 1895984-76-5, 1894202-28-8, 1893168-18-7, 1893051-64-3, Database Registry, [online], 2016, [Mar. 27, 2023 retrieval], Retrieved from :STN, 4 pages.

Kumar, Surendra et al., QSAR modeling of the inhibition of reverse transcriptase enzyme with benzimidazolone analogs, Med Chem Res, 2011, 1530-1541, 20.

Rossi, A. et al., Benzimidazol-Derivate und verwandte Heterocyclen. IV Die Kondensation von o-Phenylendiamin mit α-Aryl- und γ-Aryl-acetessigester, Helvetica Chimica Acta, 1960, 1046-1056, 43(4).

STN CAS Registry No. 886593-36-8, Date Entered STN: Jan. 2, 2006, 1 page.

Molinier-Frenkel, Valérie et al., The IL4I1 Enzyme: A New Player in the Immunosuppressive Tumor Microenvironment, Cells, 2019, 757-765, 8(757).

Chemical Abstract, STNext compound RN 1893051-64-3 (Entered STN: Apr. 19, 2016), 1 page.

Chemical Abstract, STNext compound RN 1893168-18-7 (Entered STN: Apr. 19, 2016), 1 page.

Chemical Abstract, STNext compound RN 1894202-28-8 (Entered STN: Apr. 20, 2016), 1 page.

Presset, Marc et al., Identification of inhibitors of the immunosuppressive enzyme IL4I1, Bioorganic Chemistry, Jan. 9, 2020, 94:103463.

IL4I1 INHIBITORS AND METHODS OF USE

CROSS-REFERENCE TO RELATED APPLICATIONS

This application is a U.S. National Phase application under 35 U.S.C. § 371 of PCT Application No. PCT/US2021/030541, filed May 4, 2021, which published as WO 2021/226003 on Nov. 11, 2021, and claims priority under 35 U.S.C. § 365 (b) from U.S. Provisional Patent Application No. 63/020,614, filed May 6, 2020.

FIELD OF THE INVENTION

The present invention is directed to IL4I1 inhibitors. Specifically, the IL4I1 inhibitors described herein can be useful in preventing, treating or acting as a remedial agent for IL4I1-related diseases.

BACKGROUND OF THE INVENTION

IL4I1 is a glycosylated protein that belongs to the L-amino-acid oxidase (LAAO) family of flavin adenine dinucleotide (FAD)-bound enzymes. IL4I1 is secreted from certain cells and performs oxidative deamination of phenylalanine into phenylpyruvate, liberating $H_2O_2$ and $NH_3$.

The highest production of IL4I1 is found in cells of myeloid origin (monocyte/macrophages and dendritic cells) of the human immune system, particularly after stimulation with inflammatory and T helper type 1 (Th1) stimuli. Accordingly, IL4I1 is strongly produced by dendritic cell and macrophage populations from chronic Th1 granulomas of sarcoidosis and tuberculosis, but not Th2 granulomas (schistosomiasis). Moreover, tumor-infiltrating macrophages from various histological types of tumors strongly produce IL4I1. Molinier-Frenkel V., Prévost-Blondel A. and Castellano F., The IL4I1 Enzyme: A New Player in the Immunosuppressive Tumor Microenvironment, Cells, 2019, 8, 757-765.

The presence of IL4I1-producing cells in the tumor cell microenvironment restrains the anti-tumor immune response by directly limiting the proliferation and functionality of cytotoxic T cells and Th1 cells, or indirectly by facilitating the accumulation of Treg cells. Analyses of human tumor and normal tissue biopsies have identified increased expression of both IL4I1 mRNA and protein in tumor infiltrating myeloid cells. The Cancer Genome Atlas (TCGA) indicate that, among solid tumors, endometrial carcinoma contains the highest levels of IL4I1 mRNA expression, followed by serious ovarian and triple negative breast cancers. Phenylpyruvic acid, the product of phenylalanine oxidation by IL4I1, is elevated in endometrial and ovarian tumor samples relative to matched adjacent tissue from the same patients. Furthermore, accumulation of detectable phenylpyruvic acid in the tumor samples is dependent on the presence of IL4I1 itself.

Currently there are no specific inhibitors are available against IL4I1. Some molecules have been shown to inhibit the related LAAOs found in snake venom, but they are generally non-selective and have little activity. Therefore there is a need for specific inhibitors of IL4I1. More specifically there is a need for compounds that specifically inhibit IL4I1 and can be useful for the treatment of indications where IL4I1 is most expressed and/or active, including endometrial, ovarian and triple negative breast cancers.

BRIEF SUMMARY OF THE INVENTION

Described herein are compounds of Formula I:

I

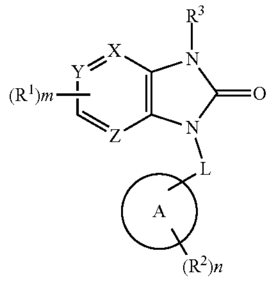

and pharmaceutically acceptable salts thereof, wherein X, Y, Z, A, L, $R^1$, $R^2$ and $R^3$ are described below.

The compounds described herein are IL4I1 inhibitors, which can be useful in the prevention, treatment or amelioration of IL4I1-related diseases.

Also described herein are methods of preventing, treating or ameliorating the symptoms of cancer comprising administering to a patient in need thereof a compound described herein, or a pharmaceutically acceptable salt thereof.

Also described herein are uses of a compound described herein, or a pharmaceutically acceptable salt thereof, to prevent, treat or ameliorate the conditions of cancer in a patient in need thereof.

Also described herein are pharmaceutical compositions comprising a compound described herein, or a pharmaceutically acceptable salt thereof and a pharmaceutically acceptable carrier.

Also described herein are pharmaceutical compositions comprising a compound described herein and a pharmaceutically acceptable carrier.

Also described herein are methods of preventing, treating or ameliorating the symptoms of cancer comprising administering to a patient in need thereof a compound described herein, or a pharmaceutically acceptable salt thereof and another therapeutic agent.

Also described herein are uses of a compound described herein, or a pharmaceutically acceptable salt thereof, in combination with another therapeutic agent to prevent, treat or ameliorate the conditions of cancer in a patient in need thereof.

Also described herein are pharmaceutical compositions comprising a compound described herein, or a pharmaceutically acceptable salt thereof, another therapeutic agent and a pharmaceutically acceptable carrier.

Also described herein are pharmaceutical compositions comprising a compound described herein, another therapeutic agent and a pharmaceutically acceptable carrier.

DETAILED DESCRIPTION OF THE INVENTION

Described herein are compounds of Formula I:

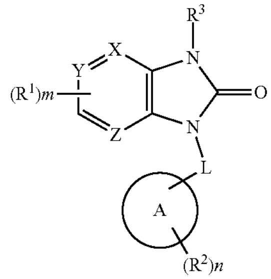

I or a pharmaceutically acceptable salt thereof, wherein:

X is CH or S, wherein when X is S, Z is CH;

Y is CH or a bond;

Z is CH or S, wherein when Z is S, X is CH;

A is aryl, $C_3$-$C_{10}$cycloalkyl, heteroaryl or cycloheteroalkyl;

L is a straight or branched ($C_1$-$C_5$) alkylenyl, wherein one or more —$CH_2$— groups in L are optionally and independently replaced with a moiety selected from the group consisting of O, and NH;

each occurrence of $R^1$ is halogen, $C_1$-$C_6$alkyl, or cycloheteroalkyl;

each occurrence of $R^2$ is independently selected from —$C_1$-$C_6$alkylNR$^4$COC$_3$-$C_6$cycloalkyl, —$C_1$-$C_6$alkylNR$^4$COC$_1$-$C_6$alkyl, —$C_1$-$C_6$alkylCONR$^4$C$_1$-$C_6$alkyl, halogen, alkoxy, —$C_1$-$C_6$alkylcycloheteroalkyl, —$C_1$-$C_6$alkylCONR$^4$aryl, $C_1$-$C_6$alkyl, —$C_1$-$C_6$alkylCOcycloheteroalkyl, —$C_1$-$C_6$alkylCONR$^4$heteroaryl, —$C_1$-$C_6$alkylNR$^4$SO$_2$C$_1$-$C_6$alkyl, —$C_1$-$C_6$alkylNR$^4$SO$_2$C$_3$-$C_6$cycloalkyl, $C_3$-$C_6$cycloalkyl, —$C_1$-$C_6$alkylCONR$^4$C$_3$-$C_6$cycloalkyl, cycloheteroalkyl, halo$C_1$-$C_6$alkyl, —CONR$^4$haloalkyl, —COcycloheteroalkyl, CN, —CONR$^4$C$_1$-$C_6$alkyl, —CONR$^4$C$_3$-$C_6$cycloalkyl, heteroaryl, aryl, haloalkoxy, —$C_1$-$C_6$alkylC$_3$-$C_{10}$cycloalkyl, oxo, —$C_1$-$C_6$alkylheteroaryl, —NR$^4$COC$_1$-$C_6$alkyl, wherein the —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkylC$_3$-$C_{10}$cycloalkyl, is unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl and $C_3$-$C_6$cycloalkyl;

$R^3$ is hydrogen, $C_1$-$C_6$alkyl or halo$C_1$-$C_6$alkyl;

$R^4$ is $C_1$-$C_6$alkyl or hydrogen;

m is 0, 1 or 2; and n is 0, 1, 2 or 3.

With regard to the compounds described herein, X is CH or S. In certain embodiments, X is CH. In other embodiments, X is S. In certain embodiments, wherein when X is S, Z is CH.

With regard to the compounds described herein, Y is CH or a bond. In certain embodiments, Y is CH. In other embodiments, Y is a bond.

With regard to the compounds described herein, Z is CH or S. In certain embodiments, Z is CH. In other embodiments, Z is S. In certain embodiments, wherein when Z is S, X is CH.

With regard to the compounds described herein, A is aryl, $C_3$-$C_{10}$cycloalkyl, heteroaryl or cycloheteroalkyl. In certain embodiments, A is aryl. In certain embodiments, A is a monocyclic aryl. In other embodiments, A is a bicyclic aryl. In other embodiments, A is a multicyclic aryl. Suitable aryls include, but are not limited to, phenyl and naphthyl. In certain embodiments, A is aryl, wherein the aryl is phenyl.

In other embodiments, A is $C_3$-$C_{10}$cycloalkyl. In certain embodiments, A is a monocyclic cycloalkyl. In other embodiments, A is a bicyclic cycloalkyl. In other embodiments, A is a multicyclic cycloalkyl. Suitable cycloalkyls include, but are not limited to, cyclopropyl, cyclobutyl, cyclopentyl, cyclohexyl, cycloheptyl, tetrahydronaphthyl, decahydronaphthyl, indanyl. In certain embodiments, A is $C_3$-$C_{10}$cycloalkyl, wherein the $C_3$-$C_{10}$cycloalkyl is:

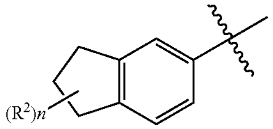
,
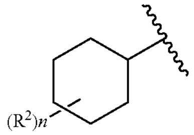
,
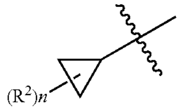
,
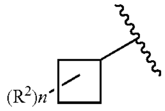
or
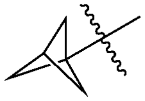
.

In certain embodiments, A is heteroaryl. In certain embodiments, A is a nitrogen-containing heteroaryl. In certain embodiments, A is a monocyclic heteroaryl. In other embodiments, A is a bicyclic heteroaryl. In other embodiments, A is a multicyclic heteroaryl. Suitable heteroaryls include, but are not limited to, pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, and isoquinolyl. In certain embodiments, A is heteroaryl, wherein the heteroaryl is:

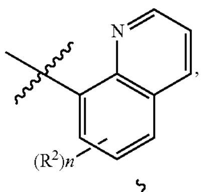
,
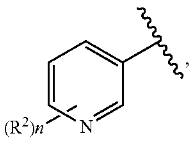
,
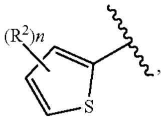
,
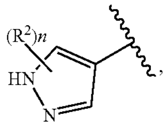
,
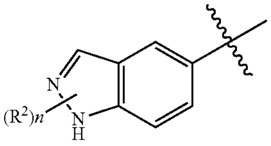
or
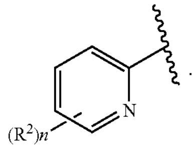
.

In certain embodiments, A is cycloheteroalkyl. In certain embodiments, A is a monocyclic cycloheteroalkyl. In other embodiments, A is a multicyclic cycloheteroalkyl. In still other embodiments, A is a bicyclic cycloheteroalkyl. In certain embodiments, A is a nitrogen-containing cycloheteroalkyl. In other embodiments, A is an oxygen-containing cycloheteroalkyl. In other embodiments, A is a sulfur-containing cycloheteroalkyl.

Suitable cycloheteroalkyls include, but are not limited to, tetrahydropyranyl, tetrahydrofuranyl, pyrrolidinyl, piperidinyl, piperazinyl, dioxanyl, imidazolidinyl, 2,3-dihydrofuro (2,3-b) pyridyl, benzoxazinyl, benzoxazolinyl, 2-H-phthalazinyl, isoindolinyl, benzoxazepinyl, 5,6-dihydroimidazo [2,1-b]thiazolyl, tetrahydroquinolinyl, morpholinyl, tetrahydroisoquinolinyl, dihydroindolyl, tetrahydropyran, and partially unsaturated monocyclic rings that are not aromatic, such as 2- or 4-pyridones attached through the nitrogen or N-substituted-(1H, 3H)-pyrimidine-2,4-diones (N-substituted uracils). In certain embodiments, A is a cycloheteroalkyl, wherein the cycloheteroalkyl is:

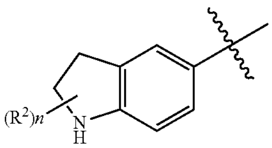
,
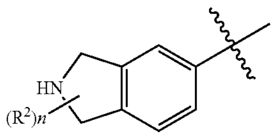
,
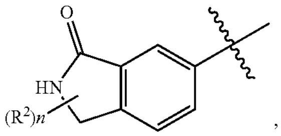
,
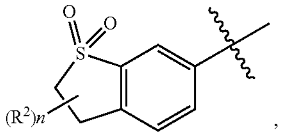
,
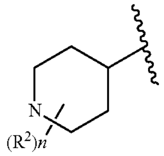
,
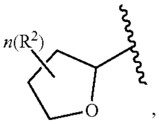
,
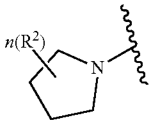
,
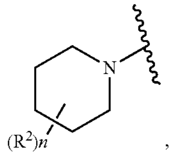
,
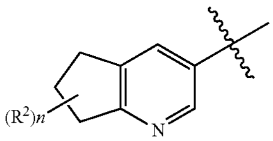
, or
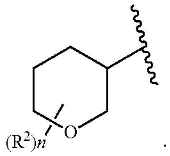
.

With regard to the compounds described herein, L is a straight or branched ($C_1$-$C_5$) alkylenyl, wherein one or more —$CH_2$— groups in L are optionally and independently replaced with a moiety selected from the group consisting of O, and NH. In certain embodiments, L is a straight ($C_1$-$C_5$) alkylenyl, wherein one or more —$CH_2$— groups in L are optionally and independently replaced with a moiety selected from the group consisting of O, and NH. In certain embodiments, L is a branched ($C_1$-$C_5$) alkylenyl, wherein one or more —$CH_2$— groups in L are optionally and independently replaced with a moiety selected from the group consisting of O, and NH. In certain embodiments, L is a ($C_1$-$C_5$) alkylenyl, wherein one or more —$CH_2$— groups in L are independently replaced with a moiety selected from the group consisting of O, and NH. In certain embodiments, L is a ($C_1$-$C_5$) alkylenyl, wherein one or more —$CH_2$— groups in L independently replaced with an O moiety. In certain embodiments, L is a straight ($C_1$-$C_5$) alkylenyl, wherein one or more —$CH_2$— groups in L are independently replaced with a NH moiety. In certain embodiments, L is a straight or branched ($C_1$-$C_5$) alkylenyl.

In certain embodiments, L is —$CH_2$—, —$CH_2CH_2$—, —$CH_2CH_2CH_2CH_2$—, —$CH_2CH_2CH_2O$—, or —$CHCH_3$—.

In certain embodiments, L is

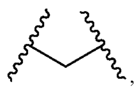
,
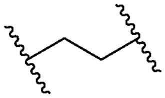
,
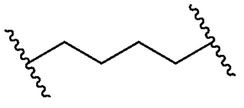
and
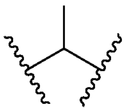
.

In other embodiments, L is

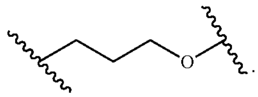 [SMILES: *CCCO*]
.

In certain embodiments, L is

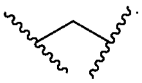 [SMILES: *C*]
.

With regard to the compounds described herein, each occurrence of $R^1$ is halogen, $C_1$-$C_6$alkyl, or cycloheteroalkyl. In certain embodiments, $R^1$ is halogen. Suitable halogens include, but are not limited to, a fluorine, a chlorine, a bromine or an iodine radical. In certain embodiments, $R^1$ is chlorine and fluorine. In certain embodiments, $R^1$ is chlorine. In other embodiments, $R^1$ is fluorine.

In certain embodiments, $R^1$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^1$ is methyl or ethyl. In certain embodiments, $R^1$ is methyl. In certain embodiments, $R^1$ is ethyl.

In certain embodiments, $R^1$ is a cycloheteroalkyl. In certain embodiments, $R^1$ is a monocyclic cycloheteroalkyl. In other embodiments, $R^1$ is a multicyclic cycloheteroalkyl. In still other embodiments, $R^1$ is a bicyclic cycloheteroalkyl. In certain embodiments, $R^1$ is a nitrogen-containing cycloheteroalkyl. In other embodiments, $R^1$ is an oxygen-containing cycloheteroalkyl. In other embodiments, $R^1$ is a sulfur-containing cycloheteroalkyl.

Suitable cycloheteroalkyls include, but are not limited to, tetrahydropyranyl, tetrahydrofuranyl, pyrrolidinyl, piperidinyl, piperazinyl, dioxanyl, imidazolidinyl, 2,3-dihydrofuro (2,3-b) pyridyl, benzoxazinyl, benzoxazolinyl, 2-H-phthalazinyl, isoindolinyl, benzoxazepinyl, 5,6-dihydroimidazo [2,1-b]thiazolyl, tetrahydroquinolinyl, morpholinyl, tetrahydroisoquinolinyl, dihydroindolyl, tetrahydropyran, and partially unsaturated monocyclic rings that are not aromatic, such as 2- or 4-pyridones attached through the nitrogen or N-substituted-(1H, 3H)-pyrimidine-2,4-diones (N-substituted uracils). In certain embodiments, $R^1$ is pyrrolidinyl.

With regard to the compounds described herein, m is 0, 1 or 2. In certain embodiments, m is 0, meaning the compounds of Formula I, Ia, Ib and Ic are not substituted with an $R^1$ substituent. In certain embodiments, m is 1, meaning the compounds of Formula I, Ia, Ib and Ic are substituted with one $R^1$ substituent. In certain embodiments, m is 2, meaning the compounds of Formula I, Ia, Ib and Ic are substituted with two $R^1$ substituents.

In certain embodiments of the compounds described herein, m is 1 or 2 and $R^1$ is fluorine, chlorine, pyrrolidinyl, methyl or ethyl. In certain embodiments of the compounds described herein, m is 1 and $R^1$ is fluorine, chlorine, pyrrolidinyl, methyl or ethyl. In certain embodiments of the compounds described herein, m is 2 and $R^1$ is fluorine, chlorine, pyrrolidinyl, methyl or ethyl. In certain embodiments of the compounds described herein, m is 1 and $R^1$ is fluorine. In certain embodiments of the compounds described herein, m is 1 and $R^1$ is chlorine. In certain embodiments of the compounds described herein, m is 1 and $R^1$ is pyrrolidinyl. In certain embodiments of the compounds described herein, m is 1 and $R^1$ is methyl. In certain embodiments of the compounds described herein, m is 1 and $R^1$ is ethyl.

With regard to the compounds described herein, each occurrence of $R^2$ is independently selected from —$C_1$-$C_6$alkylNR$^4$COC$_3$-$C_6$cycloalkyl, —$C_1$-$C_6$alkylNR$^4$COC$_1$-$C_6$alkyl, —$C_1$-$C_6$alkylCONR$^4$C$_1$-$C_6$alkyl, halogen, alkoxy, —$C_1$-$C_6$alkylcycloheteroalkyl, —$C_1$-$C_6$alkylCONR$^4$aryl, $C_1$-$C_6$alkyl, —$C_1$-$C_6$alkylCOcycloheteroalkyl, —$C_1$-$C_6$alkylCONR$^4$heteroaryl, —$C_1$-$C_6$alkylNR$^4$SO$_2$C$_1$-$C_6$alkyl, —$C_1$-$C_6$alkylNR$^4$SO$_2$C$_3$-$C_6$cycloalkyl, $C_3$-$C_6$cycloalkyl, —$C_1$-$C_6$alkylCONR$^4$C$_3$-$C_6$cycloalkyl, cycloheteroalkyl, halo$C_1$-$C_6$alkyl, —CONR$^4$haloalkyl, —COcycloheteroalkyl, CN, —CONR$^4$C$_1$-$C_6$alkyl, —CONR$^4$C$_3$-$C_6$cycloalkyl, heteroaryl, aryl, haloalkoxy, —$C_1$-$C_6$alkylC$_3$-$C_{10}$cycloalkyl, oxo, —$C_1$-$C_6$alkylheteroaryl, —NR$^4$COC$_1$-$C_6$alkyl, wherein the —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkylC$_3$-$C_{10}$cycloalkyl, is unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl and $C_3$-$C_6$cycloalkyl.

In certain embodiments, each occurrence of $R^2$ is independently selected from —$C_1$-$C_6$alkylNR$^4$COC$_3$-$C_6$cycloalkyl, —$C_1$-$C_6$alkylNR$^4$COC$_1$-$C_6$alkyl, —$C_1$-$C_6$alkylCONR$^4$C$_1$-$C_6$alkyl, halogen, alkoxy, —$C_1$-$C_6$alkylcycloheteroalkyl, —$C_1$-$C_6$alkylCONR$^4$aryl, $C_1$-$C_6$alkyl, —$C_1$-$C_6$alkylCOcycloheteroalkyl, —$C_1$-$C_6$alkylCONR$^4$heteroaryl, —$C_1$-$C_6$alkylNR$^4$SO$_2$C$_1$-$C_6$alkyl, $C_3$-$C_6$cycloalkyl, —$C_1$-$C_6$alkylCONR$^4$C$_3$-$C_6$cycloalkyl, cycloheteroalkyl, halo$C_1$-$C_6$alkyl, —CONR$^4$haloalkyl, —COcycloheteroalkyl, CN, —CONR$^4$C$_1$-$C_6$alkyl, —CONR$^4$C$_3$-$C_6$cycloalkyl, heteroaryl, aryl, haloalkoxy, —$C_1$-$C_6$alkylC$_3$-$C_{10}$cycloalkyl, oxo, —$C_1$-$C_6$alkylheteroaryl, —NR$^4$COC$_1$-$C_6$alkyl, wherein the —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkylC$_3$-$C_{10}$cycloalkyl, is unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl and $C_3$-$C_6$cycloalkyl.

In certain embodiments, $R^2$ is independently selected from —$C_1$-$C_6$alkylNR$^4$COC$_3$-$C_6$cycloalkyl. In certain embodiments, $R^2$ is independently selected from —$C_1$-$C_6$alkylNHCOC$_3$-$C_6$cycloalkyl. In certain embodiments, $R^2$ is

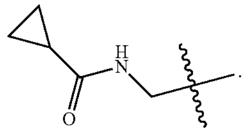 [SMILES: *CNC(=O)C1CC1]

In certain embodiments, $R^2$ is independently selected from —$C_1$-$C_6$alkylNR$^4$COC$_1$-$C_6$alkyl. In certain embodiments, $R^2$ is —$C_1$-$C_6$alkylNHCOC$_1$-$C_6$alkyl. In certain embodiments, $R^2$ is

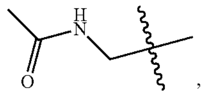 , 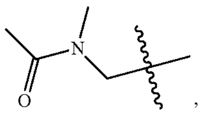 ,

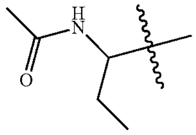 or 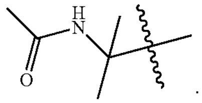 .

In certain embodiments, $R^2$ is independently selected from —$C_1$-$C_6$alkylCONR$^4$C$_1$-$C_6$alkyl. In certain embodiments, $R^2$ is independently selected from —$C_1$-$C_6$alkylCONHC$_1$-$C_6$alkyl. In certain embodiments, $R^2$ is independently selected from —$C_1$-$C_6$alkylCON($C_1$-$C_6$alkyl)$_2$. In certain embodiments, $R^2$ is

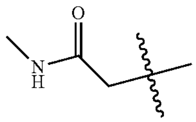 or 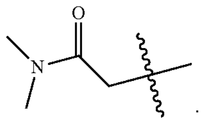 .

In certain embodiments, $R^2$ is independently selected from halogen. Suitable halogens include, but are not limited to, a fluorine, a chlorine, a bromine or an iodine radical. In certain embodiments, $R^2$ is selected from the group consisting of chlorine and fluorine. In certain embodiments, $R^2$ is chlorine. In other embodiments, $R^2$ is fluorine. In certain embodiments, $R^2$ is iodine.

In certain embodiments, $R^2$ is independently selected from alkoxy. Suitable alkoxys include, but are not limited to, methoxy, ethoxy, n-propoxy, isopropoxy and n-butoxy. In certain embodiments, $R^2$ is methoxy.

In certain embodiments, $R^2$ is independently selected from —$C_1$-$C_6$alkylcycloheteroalkyl. In certain embodiments, $R^2$ is independently selected from —$C_1$-

$C_6$alkylcycloheteroalkyl, unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —CO$C_1$-$C_6$alkyl and $C_3$-$C_6$cycloalkyl. In certain embodiments, $R^2$ is

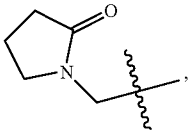, 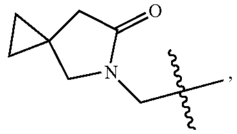, 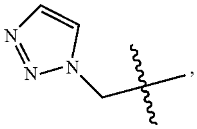, 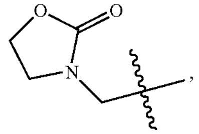, 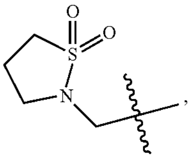, 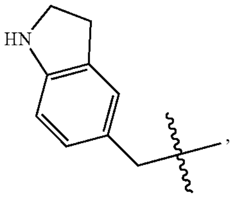, 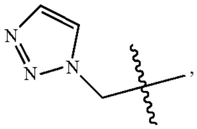, 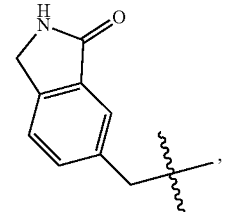, 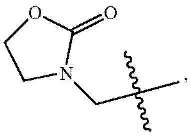, 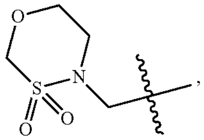, 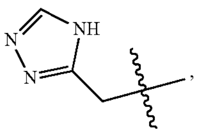, 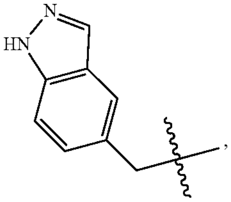, 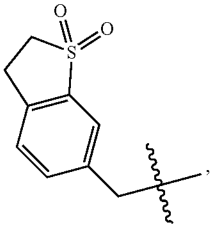, or 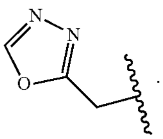.

In certain embodiments, $R^2$ is independently selected from —$C_1$-$C_6$alkylcycloheteroalkyl. In certain embodiments, $R^2$ is independently selected from —$C_1$-$C_6$alkylcycloheteroalkyl, unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —CO$C_1$-$C_6$alkyl and $C_3$-$C_6$cycloalkyl. In certain embodiments, $R^2$ is

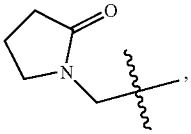, 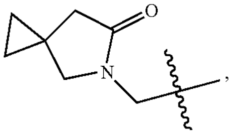, 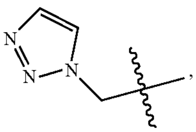, 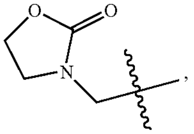, 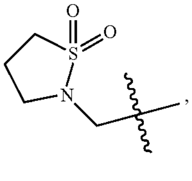, 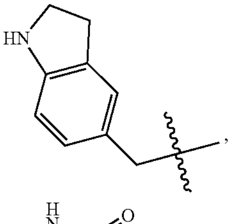, 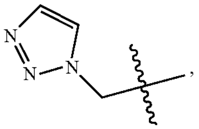, 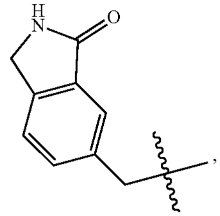, 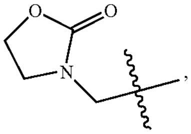, 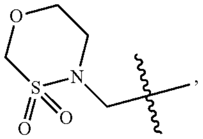, 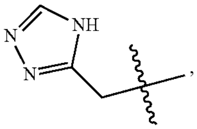, 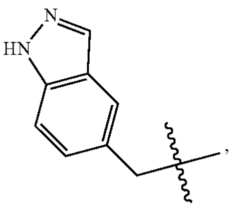, 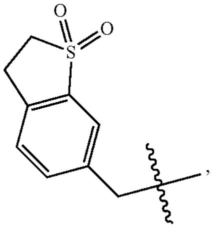, or 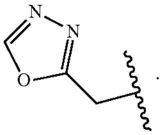.

In certain embodiments, $R^2$ is independently selected from —$C_1$-$C_6$alkylCONR$^4$aryl. In certain embodiments, $R^2$ is independently selected from —$C_1$-$C_6$alkylCONHaryl. In certain embodiments, $R^2$ is

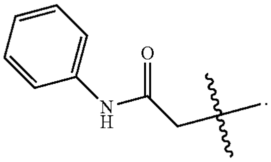 [SMILES: *CC(=O)Nc1ccccc1].

In certain embodiments, $R^2$ is independently selected from $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^2$ is methyl, isobutyl or ethyl. In certain embodiments, $R^2$ is methyl. In certain embodiments, $R^2$ is ethyl. In certain embodiments, $R^2$ is isobutyl.

In certain embodiments, $R^2$ is independently selected from $-C_1$-$C_6$alkylCOcycloheteroalkyl. In certain embodiments, $R^2$ is

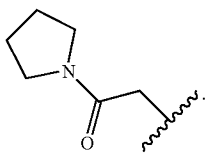 [SMILES: *CC(=O)N1CCCC1]

In certain embodiments, $R^2$ is independently selected from $-C_1$-$C_6$alkylCONR$^4$heteroaryl. In certain embodiments, $R^2$ is

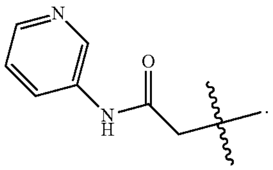 [SMILES: *CC(=O)Nc1cccnc1]

In certain embodiments, $R^2$ is independently selected from $-C_1$-$C_6$alkylNR$^4$SO$_2$C$_1$-C$_6$alkyl. In certain embodiments, $R^2$ is independently selected from $-C_1$-$C_6$alkylNHSO$_2$C$_1$-C$_6$alkyl. In certain embodiments, $R^2$ is

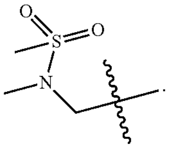 [SMILES: *CN(C)S(C)(=O)=O]

In certain embodiments, $R^2$ is independently selected from $-C_1$-$C_6$alkylNR$^4$SO$_2$C$_3$-C$_6$cycloalkyl. In certain embodiments, $R^2$ is independently selected from $-C_1$-$C_6$alkylNCH$_3$SO$_2$C$_3$-Cocycloalkyl. In certain embodiments, $R^2$ is

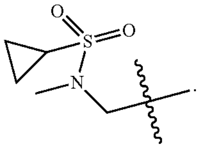 [SMILES: *CN(C)S(=O)(=O)C1CC1]

In certain embodiments, $R^2$ is independently selected from $C_3$-$C_6$cycloalkyl. In certain embodiments, $R^2$ is a monocyclic cycloalkyl. In other embodiments, $R^2$ is a bicyclic cycloalkyl. In other embodiments, $R^2$ is a multicyclic cycloalkyl. Suitable cycloalkyls include, but are not limited to, cyclopropyl, cyclobutyl, cyclopentyl, cyclohexyl, cycloheptyl, tetrahydronaphthyl, decahydronaphthyl, indanyl. In certain embodiments, $R^2$ is $C_3$-$C_{10}$cycloalkyl, wherein the $C_3$-$C_{10}$cycloalkyl is

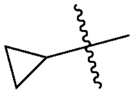
or
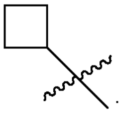
.

In certain embodiments, $R^2$ is independently selected from $-C_1$-$C_6$alkylCONR$^4$C$_3$-C$_6$cycloalkyl. In certain embodiments, $R^2$ is independently selected from $-C_1$-$C_6$alkylCONHC$_3$-C$_6$cycloalkyl. In certain embodiments, $R^2$ is

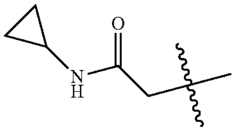
or
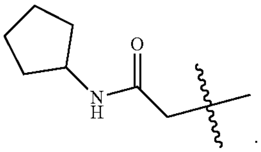
.

In certain embodiments, $R^2$ is independently selected from cycloheteroalkyl. In certain embodiments, $R^2$ is independently selected from cycloheteroalkyl, unsubstituted or substituted with 1 to 3 substituents selected from the group consisting of alkoxy, CN, $-C_1$-$C_6$alkylOH, halogen, $C_1$-$C_6$alkyl, halo$C_1$-$C_6$alkyl, oxo, OH, CN, $-C_1$-$C_6$alkylCN, $-COC_1$-$C_6$alkyl and $C_3$-$C_6$cycloalkyl. In certain embodiments, $R^2$ is a monocyclic cycloheteroalkyl. In other embodiments, $R^2$ is a multicyclic cycloheteroalkyl. In other embodiments, $R^2$ is a multicyclic cycloheteroalkyl, unsubstituted or substituted with 1 to 3 substituents selected from the group consisting of alkoxy, CN, $-C_1$-$C_6$alkylOH, halogen, $C_1$-$C_6$alkyl, halo$C_1$-$C_6$alkyl, oxo, OH, CN, $-C_1$-$C_6$alkylCN, $-COC_1$-$C_6$alkyl and $C_3$-$C_6$cycloalkyl. In still other embodiments, $R^2$ is a bicyclic cycloheteroalkyl. In still other embodiments, $R^2$ is a bicyclic cycloheteroalkyl, unsubstituted or substituted with 1 to 3 substituents selected from the group consisting of alkoxy, CN, $-C_1$-$C_6$alkylOH, halogen, $C_1$-$C_6$alkyl, halo$C_1$-$C_6$alkyl, oxo, OH, CN, $-C_1$-$C_6$alkylCN, $-COC_1$-$C_6$alkyl and $C_3$-$C_6$cycloalkyl. In certain embodiments, $R^2$ is a nitrogen-containing cycloheteroalkyl. In certain embodiments, $R^2$ is a nitrogen-containing cycloheteroalkyl, unsubstituted or substituted with 1 to 3 substituents selected from the group consisting of alkoxy, CN, $-C_1$-$C_6$alkylOH, halogen, $C_1$-$C_6$alkyl, halo$C_1$-$C_6$alkyl, oxo, OH, CN, $-C_1$-$C_6$alkylCN, $-COC_1$-$C_6$alkyl and $C_3$-$C_6$cycloalkyl. In other embodiments, $R^2$ is an oxygen-containing cycloheteroalkyl. In other embodiments, $R^2$ is an oxygen-containing cycloheteroalkyl, unsubstituted or substituted with 1 to 3 substituents selected from the group consisting of alkoxy, CN, $-C_1$-$C_6$alkylOH, halogen, $C_1$-$C_6$alkyl, halo$C_1$-$C_6$alkyl, oxo, OH, CN, $-C_1$-$C_6$alkylCN, $-COC_1$-$C_6$alkyl and $C_3$-$C_6$cycloalkyl. In other embodiments, $R^2$ is a sulfur-containing cycloheteroalkyl. In other embodiments, $R^2$ is a sulfur-containing cycloheteroalkyl, unsubstituted or substituted with 1 to 3 substituents selected from the group consisting of alkoxy, CN, $-C_1$-$C_6$alkylOH, halogen, $C_1$-$C_6$alkyl, halo$C_1$-$C_6$alkyl, oxo, OH, CN, $-C_1$-$C_6$alkylCN, $-COC_1$-$C_6$alkyl and $C_3$-$C_6$cycloalkyl.

Suitable cycloheteroalkyls include, but are not limited to, tetrahydropyranyl, tetrahydrofuranyl, pyrrolidinyl, piperidinyl, piperazinyl, dioxanyl, imidazolidinyl, 2,3-dihydrofuro (2,3-b) pyridyl, benzoxazinyl, benzoxazolinyl, 2-H-phthalazinyl, isoindolinyl, benzoxazepinyl, 5,6-dihydroimidazo [2,1-b]thiazolyl, tetrahydroquinolinyl, morpholinyl, tetrahydroisoquinolinyl, dihydroindolyl, tetrahydropyran, and partially unsaturated monocyclic rings that are not aromatic, such as 2- or 4-pyridones attached through the nitrogen or N-substituted-(1H, 3H)-pyrimidine-2,4-diones (N-substituted uracils). In certain embodiments, $R^2$ is a cycloheteroalkyl, wherein the cycloheteroalkyl is:

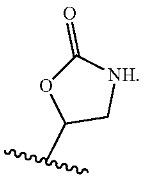

In certain embodiments, $R^2$ is a cycloheteroalkyl, wherein the cycloheteroalkyl is:

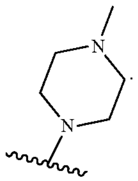

In certain embodiments, $R^2$ is independently selected from halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^2$ is difluoromethyl. In certain embodiments, $R^2$ is trifluoromethyl. In certain embodiments, $R^2$ is difluoromethyl and trifluoromethyl.

In certain embodiments, $R^2$ is independently selected from —CONR$^4$haloalkyl. In certain embodiments, $R^2$ is independently selected from —CONHhaloalkyl. In certain embodiments, $R^2$ is

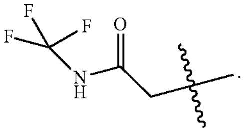 [SMILES: *CC(=O)NC(F)(F)F]

In certain embodiments, $R^2$ is independently selected from —COcycloheteroalkyl. In certain embodiments, $R^2$ is

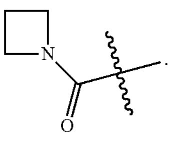 [SMILES: *C(=O)N1CCC1]

In certain embodiments, $R^2$ is independently selected from CN.

In certain embodiments, $R^2$ is independently selected from oxo.

In certain embodiments, $R^2$ is independently selected from —CONR$^4$$C_1$-$C_6$alkyl. In certain embodiments, $R^2$ is independently selected from —CONH$C_1$-$C_6$alkyl. In certain embodiments, $R^2$ is independently selected from —CON($C_1$-$C_6$alkyl)$_2$. In certain embodiments, $R^2$ is

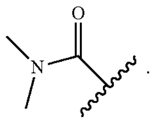 [SMILES: *C(=O)N(C)C]

In certain embodiments, $R^2$ is independently selected from —NR$^4$CO$C_1$-$C_6$alkyl. In certain embodiments, $R^2$ is independently selected from —NHCO$C_1$-$C_6$alkyl. In certain embodiments, $R^2$ is independently selected from —N($C_1$-$C_6$alkyl) CO ($C_1$-$C_6$alkyl). In certain embodiments, $R^2$ is

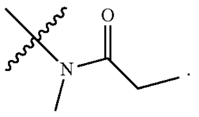 [SMILES: *N(C)C(=O)CC]

In certain embodiments, $R^2$ is independently selected from —CONR$^4$$C_3$-$C_6$cycloalkyl. In certain embodiments, $R^2$ is independently selected from —CONH$C_3$-$C_6$cycloalkyl.

In certain embodiments, $R^2$ is independently selected from heteroaryl. In certain embodiments, $R^2$ is

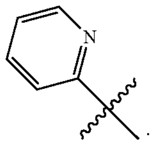 [SMILES: *c1ccccn1]

In certain embodiments, $R^2$ is independently selected from —$C_1$-$C_6$alkylheteroaryl. In certain embodiments, $R^2$ is

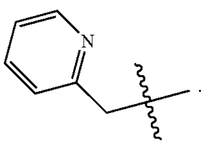 [SMILES: *Cc1ccccn1]

In certain embodiments, $R^2$ is independently selected from aryl. In certain embodiments, $R^2$ is

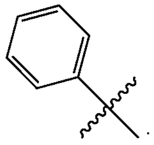 [SMILES: *c1ccccc1]

In certain embodiments, $R^2$ is independently selected from haloalkoxy. Suitable haloalkoxys include, but are not limited to, trifluoromethoxy, difluoromethoxy and monofluoromethoxy. In certain embodiments, $R^2$ is trifluoromethoxy.

In certain embodiments, $R^2$ is independently selected from —$C_1$-$C_6$alkyl$C_3$-$C_{10}$cycloalkyl. In certain embodiments, $R^2$ is

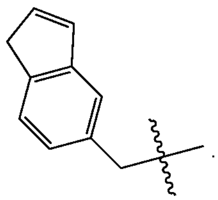 [SMILES: *Cc1ccc2c(c1)C=CC2]

In certain embodiments, $R^2$ is unsubstituted.

In other embodiments, when $R^2$ is —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl, wherein the —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl is substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl. In certain embodiments, the —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl is substituted with 1 substituent selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl.

In other embodiments, the —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl is substituted with 2 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-CoalkylCN, COC$_1$-$C_6$alkyl. In other embodiments, the —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl is substituted with 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl.

In certain embodiments, $R^2$ is chlorine, fluorine, methoxy, isopropoxy, methyl, difluoromethyl, trifluoromethoxy, isobutyl,

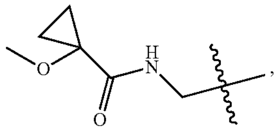

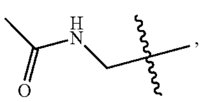

-continued

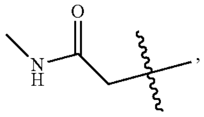

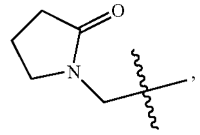

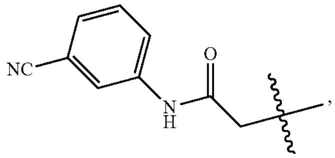

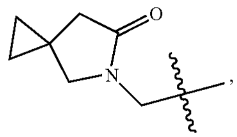

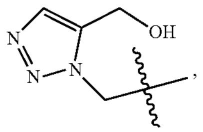

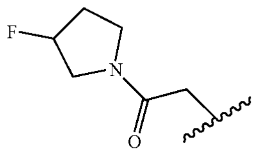

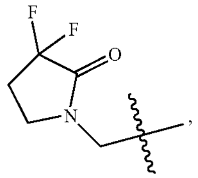

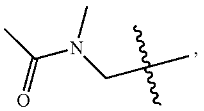

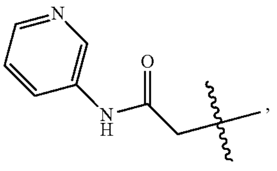

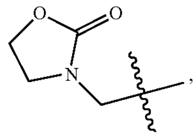

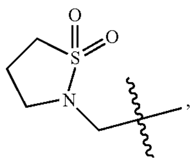

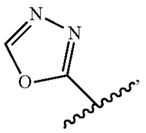

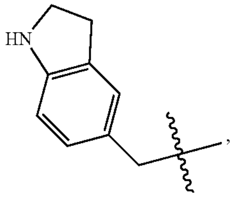

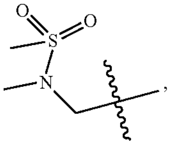

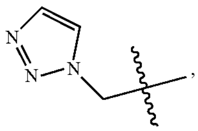

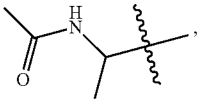

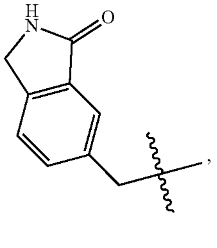

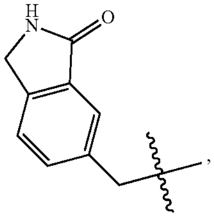

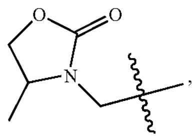

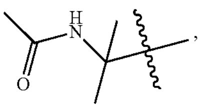

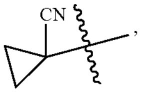

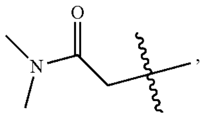

-continued
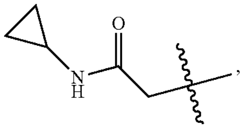
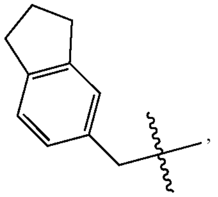
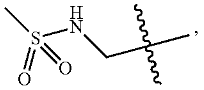
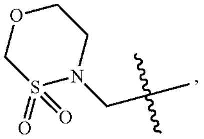
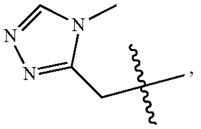
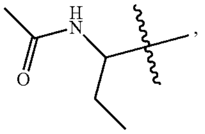
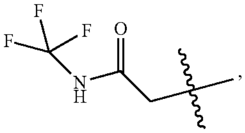
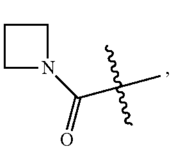
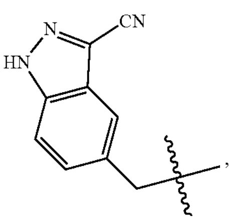
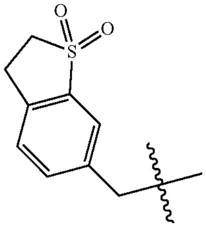
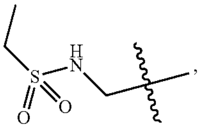
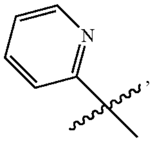
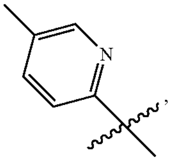
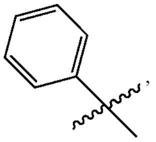
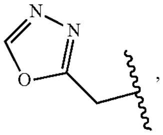
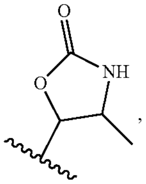
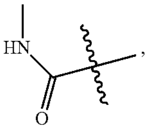
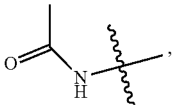
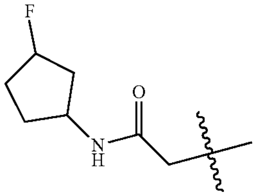
or
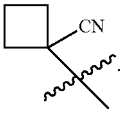
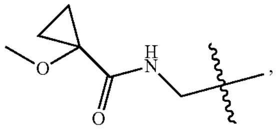
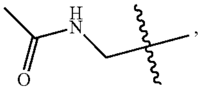
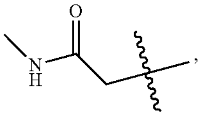
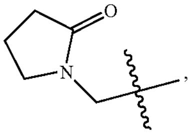
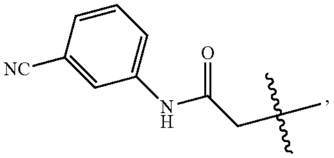
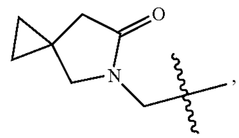
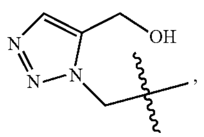
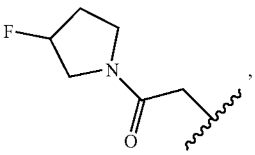
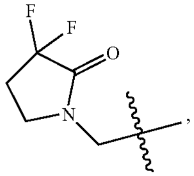
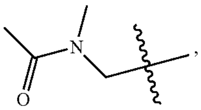
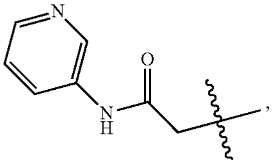
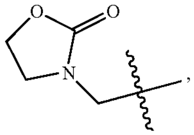
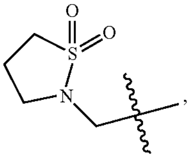
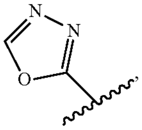
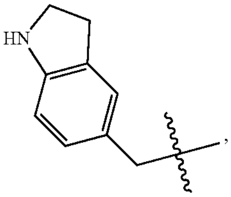
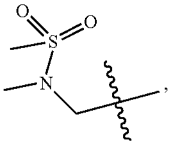
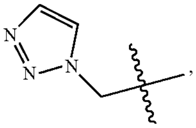
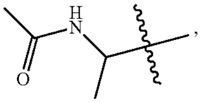
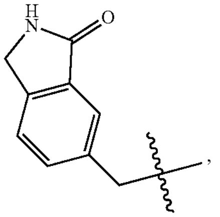
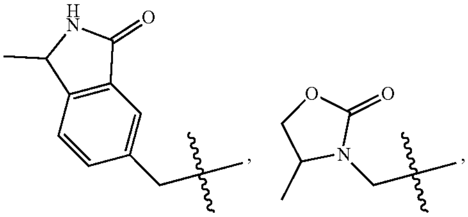
In certain embodiments, n is 1, 2 or 3 and $R^2$ is chlorine, fluorine, methoxy, methyl, difluoromethyl, trifluoromethoxy, isobutyl, -continued

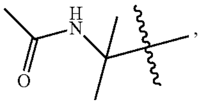,
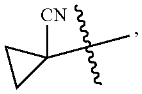,
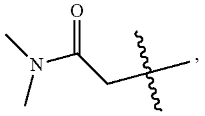,
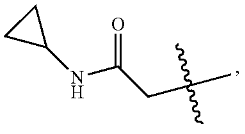,
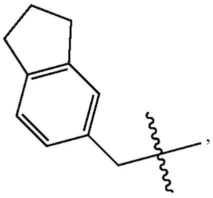,
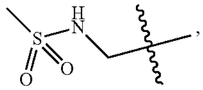,
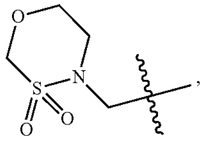,
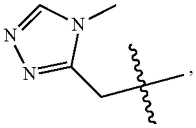,
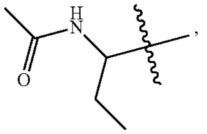,
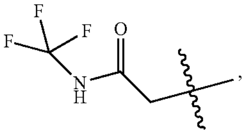,
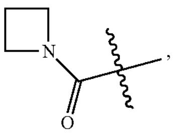,
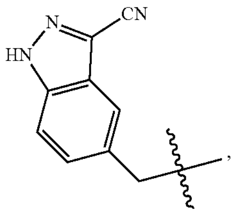,
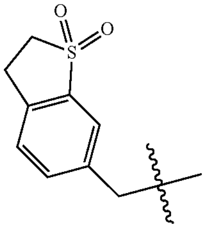
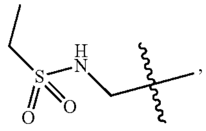,
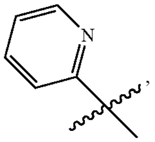,
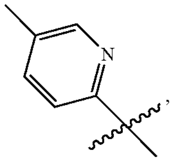,
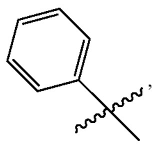,
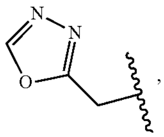,
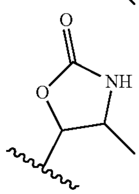
or
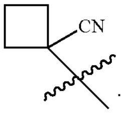.

With regard to the compounds described herein, n is 0, 1, 2 or 3. In certain embodiments, n is 0, meaning A is not substituted with an $R^2$ substituent. In certain embodiments, n is 1, meaning the A is substituted with one $R^2$ substituent. In certain embodiments, n is 2, meaning the A is substituted with two $R^2$ substituents. In certain embodiments, n is 3, meaning the A is substituted with three $R^2$ substituents.

In certain embodiments, $R^2$ is

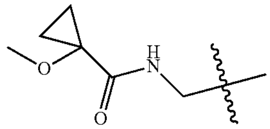,
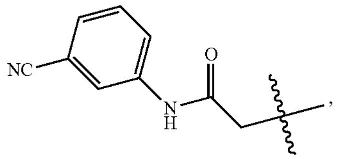,
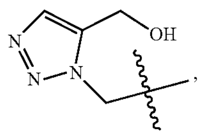,
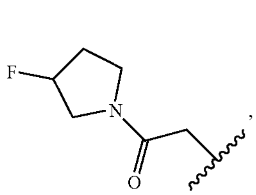,
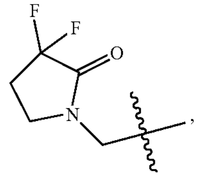,
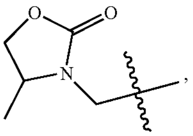,
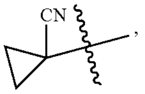,
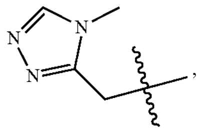,
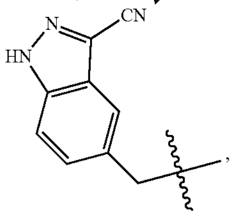,
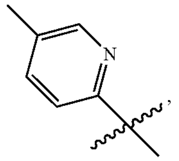,
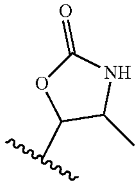
or
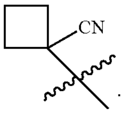.

In certain embodiments, when $R^2$ is —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl, wherein the —$C_1$-$C_6$alkylNR$^4$COC$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl is substituted with 1 to 3 substituents selected from the group consisting of alkoxy, CN, —$C_1$-$C_6$alkylOH, halogen, $C_1$-$C_6$alkyl.

In certain embodiments, when $R^2$ is —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkyl$C_3$-$C_{10}$cycloalkyl, is unsubstituted or substituted with 1 to 3 substituents selected from the group consisting of alkoxy, CN, $C_1$-$C_6$alkylOH, halogen, $C_1$-$C_6$alkyl, halo$C_1$-$C_6$alkyl, oxo, OH, CN, $C_1$-$C_6$alkylCN, COC$_1$-$C_6$alkyl and $C_3$-$C_6$cycloalkyl.

In certain embodiments, $R^2$ is chlorine, fluorine, iodine, methoxy, isopropoxy, methyl, difluoromethyl, trifluoromethoxy, isobutyl,

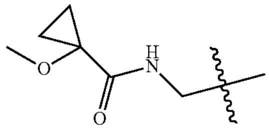, 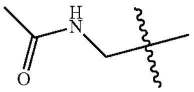,
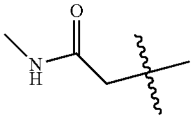, 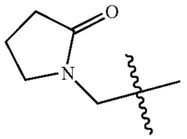,
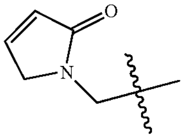, 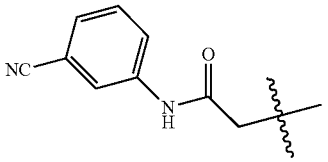,
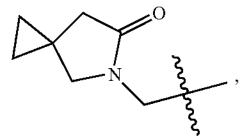, 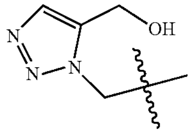,
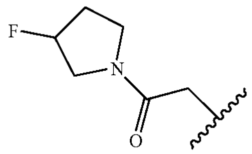, 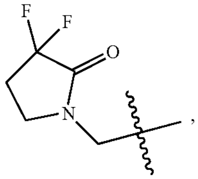,
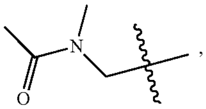, 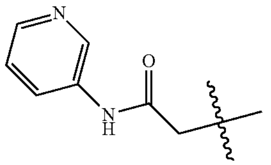,
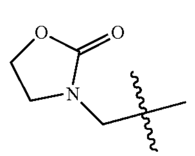, 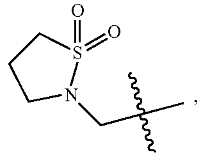,
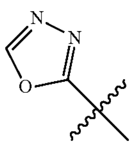, 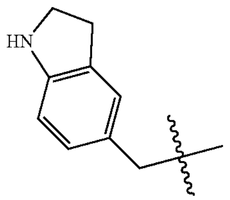,
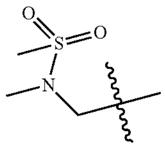, 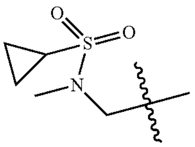,
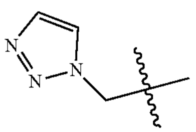, 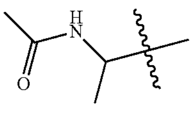,
-continued
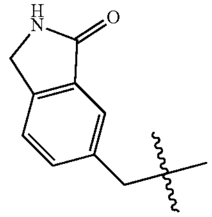, 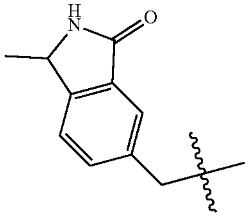,
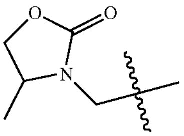, 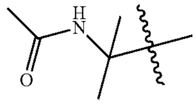,
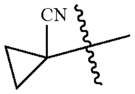, 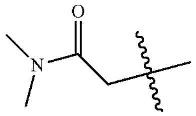,
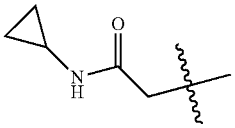, 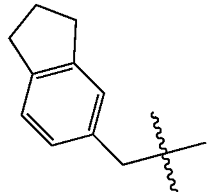,
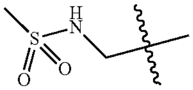, 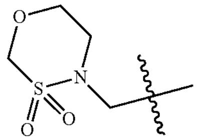,
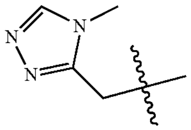, 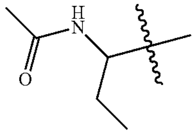,
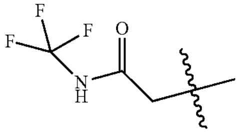, 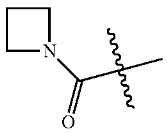,
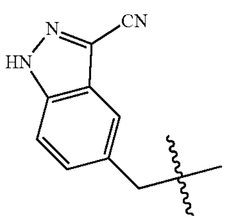, 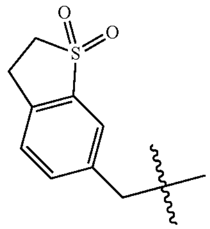,
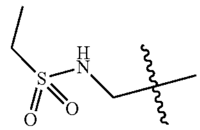, 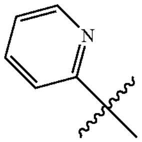,
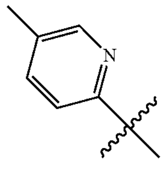, 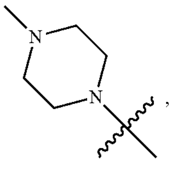, -continued

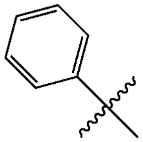, 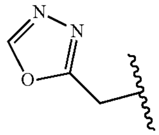,

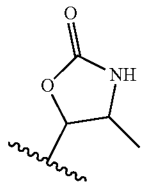, 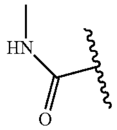,

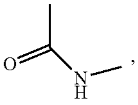, 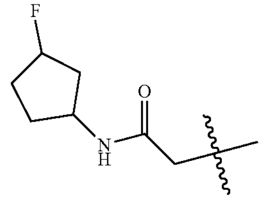 or

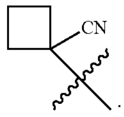.

With regard to the compounds described herein, each occurrence of $R^3$ is hydrogen, $C_1$-$C_6$alkyl, or halo$C_1$-$C_6$alkyl. In certain embodiments, $R^3$ is hydrogen. In certain embodiments, $R^3$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^3$ is methyl.

In certain embodiments, $R^3$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^3$ is difluoromethyl.

In certain embodiments, $R^3$ is hydrogen, methyl or difluoromethyl.

With regard to the compounds described herein, $R^4$ is $C_1$-$C_6$alkyl or hydrogen. In certain embodiments, $R^4$ is hydrogen. In certain embodiments, $R^4$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^4$ is methyl.

Also, described herein are compounds, or a pharmaceutically acceptable salt thereof, having the Formula Ia Ia

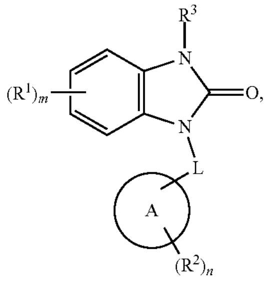

wherein A is aryl, $C_3$-$C_{10}$cycloalkyl, heteroaryl or cycloheteroalkyl;

L is a straight or branched ($C_1$-$C_5$) alkylenyl, wherein one or more —$CH_2$— groups in L are optionally and independently replaced with a moiety selected from the group consisting of O, and NH;

each occurrence of $R^1$ is independently selected from halogen, $C_1$-$C_6$alkyl, or cycloheteroalkyl;

each occurrence of $R^2$ is independently selected from —$C_1$-$C_6$alkylNR$^4$COC$_3$-$C_6$cycloalkyl, —$C_1$-$C_6$alkylNR$^4$COC$_1$-$C_6$alkyl, —$C_1$-$C_6$alkylCONR$^4$C$_1$-$C_6$alkyl, halogen, alkoxy, —$C_1$-$C_6$alkylcycloheteroalkyl, —$C_1$-$C_6$alkylCONR$^4$aryl, $C_1$-$C_6$alkyl, —$C_1$-$C_6$alkylCOcycloheteroalkyl, —$C_1$-$C_6$alkylCONR$^4$heteroaryl, —$C_1$-$C_6$alkylNR$^4$SO$_2$C$_1$-$C_6$alkyl, —$C_1$-$C_6$alkylNR$^4$SO$_2$C$_3$-$C_6$cycloalkyl, $C_3$-$C_6$cycloalkyl, —$C_1$-$C_6$alkylCONR$^4$C$_3$-$C_6$cycloalkyl, cycloheteroalkyl, halo$C_1$-$C_6$alkyl, —CONR$^4$haloalkyl, —COcycloheteroalkyl, CN, —CONR$^4$C$_1$-$C_6$alkyl, —CONR$^4$C$_3$-$C_6$cycloalkyl, heteroaryl, aryl, haloalkoxy, —$C_1$-$C_6$alkylC$_3$-$C_{10}$cycloalkyl, oxo, —$C_1$-$C_6$alkylheteroaryl, —NR$^4$COC$_1$-$C_6$alkyl, wherein the —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkylC$_3$-$C_{10}$cycloalkyl, is unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, $C_1$-$C_6$alkylCN, —COC$_1$-$C_6$alkyl and $C_3$-$C_6$cycloalkyl;

$R^3$ is $C_1$-$C_6$alkyl or halo$C_1$-$C_6$alkyl;

$R^4$ is $C_1$-$C_6$alkyl or hydrogen;

m is 0, 1 or 2; and n is 0, 1, 2 or 3.

Also described herein are compounds, or a pharmaceutically acceptable salt thereof, having the Formula Ib Ib

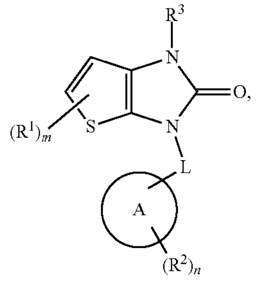

wherein A is aryl, $C_3$-$C_{10}$cycloalkyl, heteroaryl or cycloheteroalkyl;

L is a straight or branched ($C_1$-$C_5$) alkylenyl, wherein one or more —$CH_2$— groups in L are optionally and independently replaced with a moiety selected from the group consisting of O, and NH;

each occurrence of $R^1$ is independently selected from halogen, $C_1$-$C_6$alkyl, or cycloheteroalkyl;

each occurrence of $R^2$ is independently selected from —$C_1$-$C_6$alkylNR$^4$COC$_3$-$C_6$cycloalkyl, —$C_1$-$C_6$alkylNR$^4$COC$_1$-$C_6$alkyl, —$C_1$-$C_6$alkylCONR$^4$C$_1$-$C_6$alkyl, halogen, alkoxy, —$C_1$-$C_6$alkylcycloheteroalkyl, —$C_1$-$C_6$alkylCONR$^4$aryl, $C_1$-$C_6$alkyl, —$C_1$-$C_6$alkylCOcycloheteroalkyl, —$C_1$-$C_6$alkylCONR$^4$heteroaryl, —$C_1$-$C_6$alkylNR$^4$SO$_2$C$_1$-$C_6$alkyl, —$C_1$-$C_6$alkylNR$^4$SO$_2$C$_3$-$C_6$cycloalkyl, $C_3$-$C_6$cycloalkyl, —$C_1$-$C_6$alkylCONR$^4$C$_3$-$C_6$cycloalkyl, cycloheteroalkyl, halo$C_1$-$C_6$alkyl, —CONR$^4$haloalkyl, —COcycloheteroalkyl, CN, —CONR$^4$C$_1$-$C_6$alkyl, —CONR$^4$C$_3$-$C_6$cycloalkyl, heteroaryl, aryl, haloalkoxy, —$C_1$-$C_6$alkylC$_3$-$C_{10}$cycloalkyl, oxo, —$C_1$-$C_6$alkylheteroaryl, —NR$^4$COC$_1$-$C_6$alkyl, wherein the —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, —$C_1$-$C_6$alkylcycloheteroalkyl, —$C_1$-$C_6$alkylCOcycloheteroalkyl, $C_3$-$C_6$cycloalkyl, cycloheteroalkyl, heteroaryl, —$C_1$-$C_6$alkylC$_3$-$C_{10}$cycloalkyl, is unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, COC$_1$-$C_6$alkyl and $C_3$-$C_6$cycloalkyl;

$R^3$ is $C_1$-$C_6$alkyl or halo$C_1$-$C_6$alkyl;

$R^4$ is $C_1$-$C_6$alkyl or hydrogen;

m is 0, 1 or 2; and n is 0, 1, 2 or 3.

Also described herein, are compounds, or a pharmaceutically acceptable salt thereof, having the Formula Ic Ib

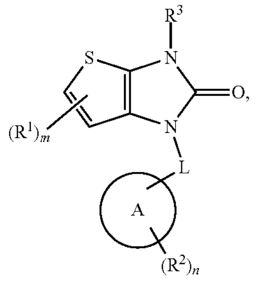

wherein A is aryl, $C_3$-$C_{10}$cycloalkyl, heteroaryl or cycloheteroalkyl;

L is a straight or branched ($C_1$-$C_5$) alkylenyl, wherein one or more —$CH_2$— groups in L are optionally and independently replaced with a moiety selected from the group consisting of O, and NH;

each occurrence of $R^1$ is independently selected from halogen, $C_1$-$C_6$alkyl, or cycloheteroalkyl;

each occurrence of $R^2$ is independently selected from —$C_1$-$C_6$alkylNR$^4$COC$_3$-$C_6$cycloalkyl, —$C_1$-$C_6$alkylNR$^4$COC$_1$-$C_6$alkyl, —$C_1$-$C_6$alkylCONR$^4$C$_1$-$C_6$alkyl, halogen, alkoxy, —$C_1$-$C_6$alkylcycloheteroalkyl, —$C_1$-$C_6$alkylCONR$^4$aryl, $C_1$-$C_6$alkyl, —$C_1$-$C_6$alkylCOcycloheteroalkyl, —$C_1$-$C_6$alkylCONR$^4$heteroaryl, —$C_1$-$C_6$alkylNR$^4$SO$_2$C$_1$-$C_6$alkyl, —$C_1$-$C_6$alkylNR$^4$SO$_2$C$_3$-$C_6$cycloalkyl, $C_3$-$C_6$cycloalkyl, —$C_1$-$C_6$alkylCONR$^4$C$_3$-$C_6$cycloalkyl, cycloheteroalkyl, halo$C_1$-$C_6$alkyl, —CONR$^4$haloalkyl, —COcycloheteroalkyl, CN, —CONR$^4$C$_1$-$C_6$alkyl, —CONR$^4$C$_3$-$C_6$cycloalkyl, heteroaryl, aryl, haloalkoxy, —$C_1$-$C_6$alkylC$_3$-$C_{10}$cycloalkyl, oxo, —$C_1$-$C_6$alkylheteroaryl, —NR$^4$COC$_1$-$C_6$alkyl, wherein the —$C_1$-$C_6$alkylNR$^4$COC$_3$-$C_6$cycloalkyl, —$C_1$-$C_6$alkylCONR$^4$C$_3$-$C_6$cycloalkyl, —$C_1$-$C_6$alkylCONR$^4$aryl, $C_1$-$C_6$alkylcycloheteroalkyl, $C_1$-$C_6$alkylCOcycloheteroalkyl, $C_3$-$C_6$cycloalkyl, cycloheteroalkyl, heteroaryl, —$C_1$-$C_6$alkylC$_3$-$C_{10}$cycloalkyl, is unsubstituted or substituted with 1 to 3 substituents selected from the group consisting of alkoxy, CN, —$C_1$-$C_6$alkylOH, halogen, $C_1$-$C_6$alkyl, halo$C_1$-$C_6$alkyl, oxo, OH, CN, —$C_1$-$C_6$alkylCN, —COC$_1$-$C_6$alkyl and $C_3$-$C_6$cycloalkyl;

$R^3$ is $C_1$-$C_6$alkyl or halo$C_1$-$C_6$alkyl;

$R^4$ is $C_1$-$C_6$alkyl or hydrogen;

m is 0, 1 or 2; and n is 0, 1, 2 or 3.

Also described herein are compounds having the following structure:

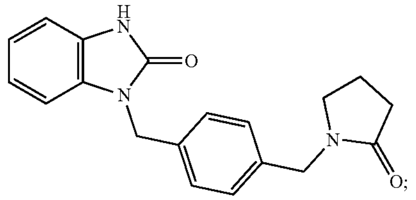 [SMILES: O=C1CCCN1Cc1ccc(Cn2c(=O)[nH]c3ccccc32)cc1]

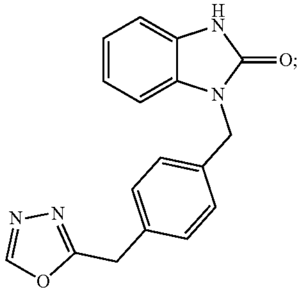 [SMILES: O=c1[nH]c2ccccc2n1Cc1ccc(Cc2nnco2)cc1]

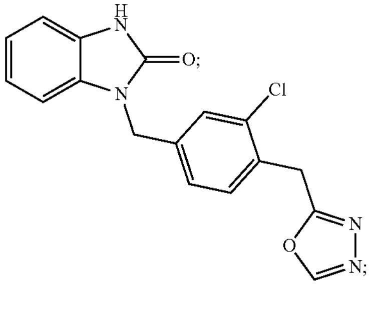 [SMILES: O=c1[nH]c2ccccc2n1Cc1ccc(Cc2nnco2)c(Cl)c1]

-continued
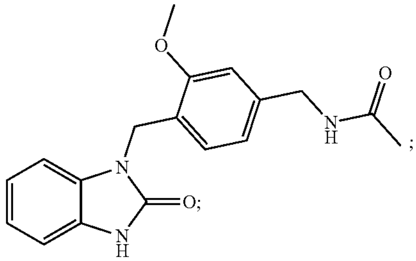 [SMILES: COc1cc(CNC(C)=O)ccc1Cn1c(=O)[nH]c2ccccc21]
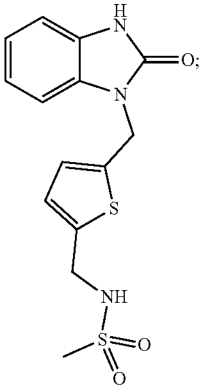 [SMILES: CS(=O)(=O)NCc1ccc(Cn2c(=O)[nH]c3ccccc32)s1]
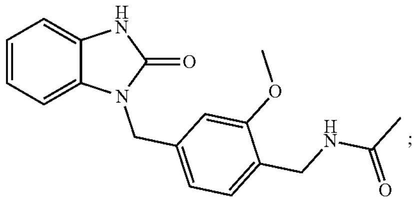 [SMILES: COc1cc(Cn2c(=O)[nH]c3ccccc32)ccc1CNC(C)=O]
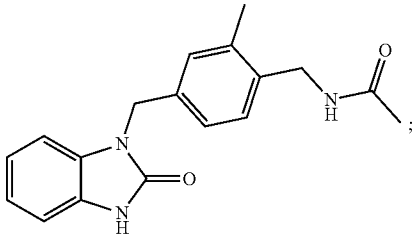 [SMILES: CC(=O)NCc1ccc(Cn2c(=O)[nH]c3ccccc32)cc1C]
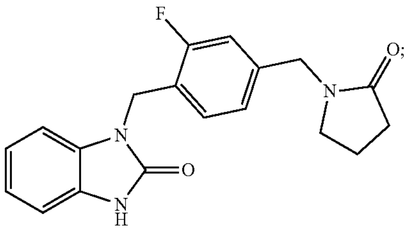 [SMILES: O=C1CCCN1Cc1ccc(Cn2c(=O)[nH]c3ccccc32)c(F)c1]
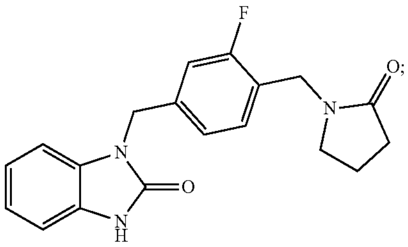
-continued
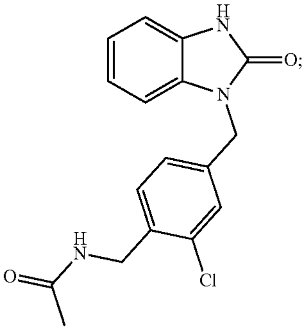 [SMILES: CC(=O)NCc1ccc(Cn2c(=O)[nH]c3ccccc32)cc1Cl]
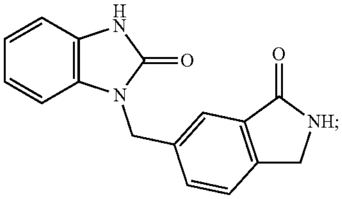 [SMILES: O=C1NCc2ccc(Cn3c(=O)[nH]c4ccccc43)cc21]
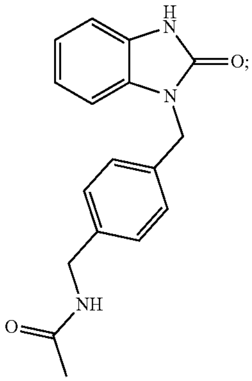 [SMILES: CC(=O)NCc1ccc(Cn2c(=O)[nH]c3ccccc32)cc1]
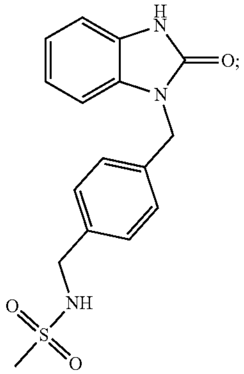 [SMILES: CS(=O)(=O)NCc1ccc(Cn2c(=O)[nH]c3ccccc32)cc1]
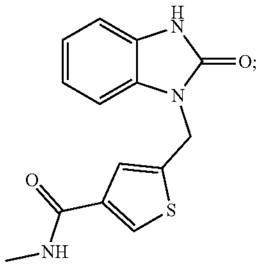 [SMILES: CNC(=O)c1csc(Cn2c(=O)[nH]c3ccccc32)c1]

-continued
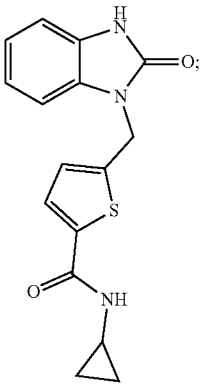 [SMILES: O=C(NC1CC1)c1ccc(Cn2c(=O)[nH]c3ccccc32)s1]
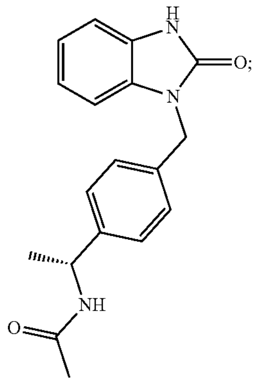 [SMILES: CC(=O)N[C@H](C)c1ccc(Cn2c(=O)[nH]c3ccccc32)cc1]
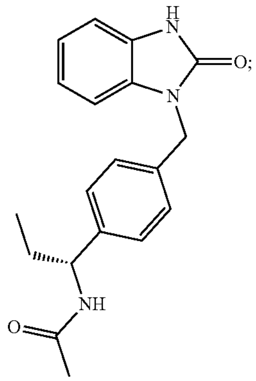 [SMILES: CC[C@@H](NC(C)=O)c1ccc(Cn2c(=O)[nH]c3ccccc32)cc1]
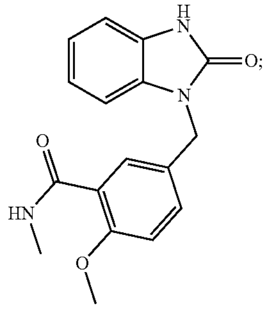 [SMILES: CNC(=O)c1cc(Cn2c(=O)[nH]c3ccccc32)ccc1OC]
-continued
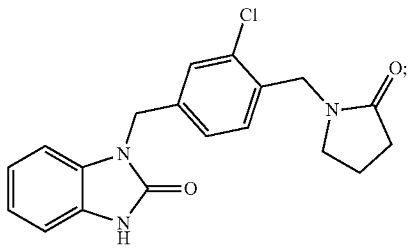
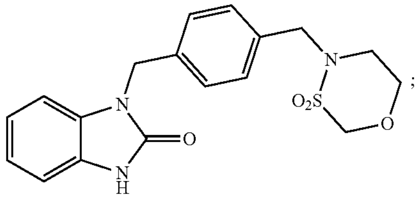 [SMILES: O=c1[nH]c2ccccc2n1Cc1ccc(CN2CCOCS2(=O)=O)cc1]
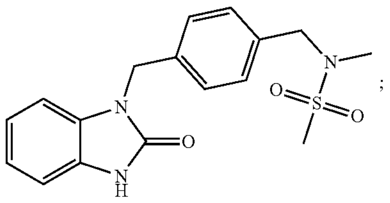 [SMILES: CN(Cc1ccc(Cn2c(=O)[nH]c3ccccc32)cc1)S(C)(=O)=O]
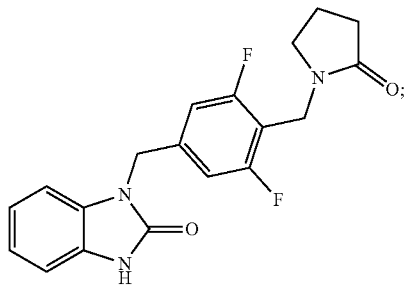 [SMILES: O=C1CCCN1Cc1c(F)cc(Cn2c(=O)[nH]c3ccccc32)cc1F]
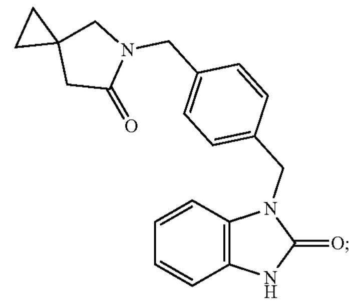 [SMILES: O=C1CC2(CC2)CN1Cc1ccc(Cn2c(=O)[nH]c3ccccc32)cc1]
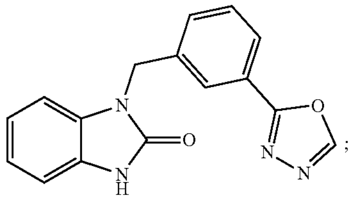 [SMILES: O=c1[nH]c2ccccc2n1Cc1cccc(-c2nnco2)c1]

-continued
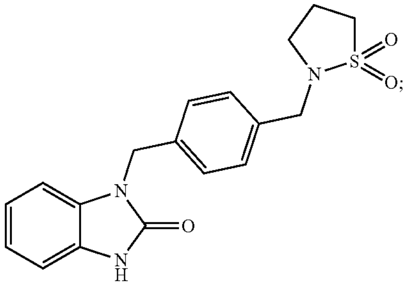 [SMILES: O=c1[nH]c2ccccc2n1Cc1ccc(CN2CCCS2(=O)=O)cc1]
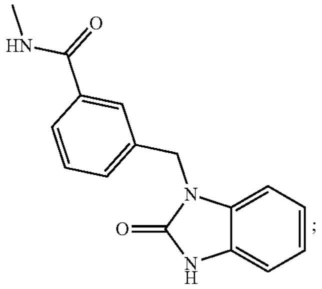 [SMILES: CNC(=O)c1cccc(Cn2c(=O)[nH]c3ccccc32)c1]
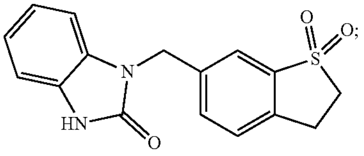 [SMILES: O=c1[nH]c2ccccc2n1Cc1ccc2c(c1)S(=O)(=O)CC2]
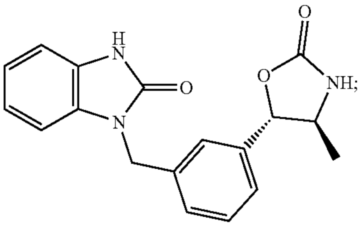 [SMILES: C[C@@H]1NC(=O)O[C@H]1c1cccc(Cn2c(=O)[nH]c3ccccc32)c1]
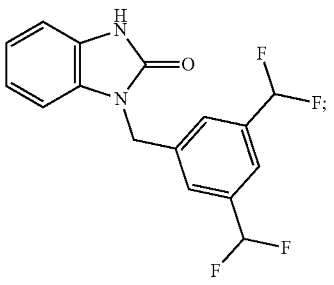 [SMILES: O=c1[nH]c2ccccc2n1Cc1cc(C(F)F)cc(C(F)F)c1]
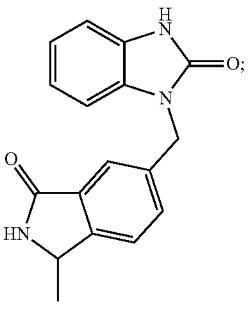 [SMILES: CC1NC(=O)c2cc(Cn3c(=O)[nH]c4ccccc43)ccc21]
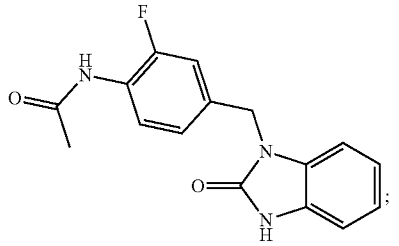 [SMILES: CC(=O)Nc1ccc(Cn2c(=O)[nH]c3ccccc32)cc1F]
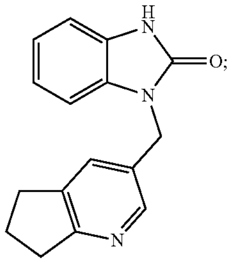 [SMILES: O=c1[nH]c2ccccc2n1Cc1cnc2c(c1)CCC2]
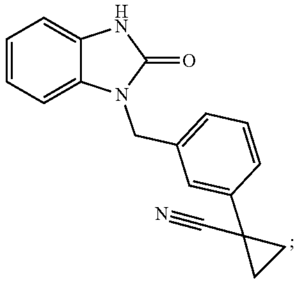 [SMILES: N#CC1(c2cccc(Cn3c(=O)[nH]c4ccccc43)c2)CC1]
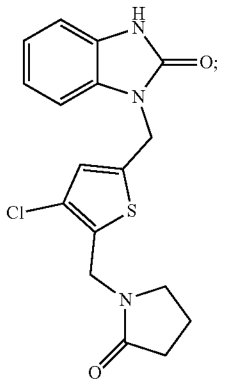 [SMILES: O=C1CCCN1Cc1sc(Cn2c(=O)[nH]c3ccccc32)cc1Cl]
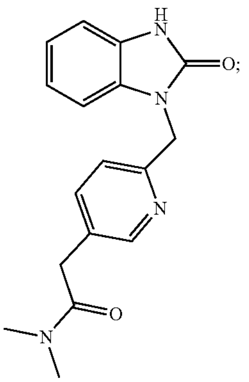 [SMILES: CN(C)C(=O)Cc1ccc(Cn2c(=O)[nH]c3ccccc32)nc1]

-continued
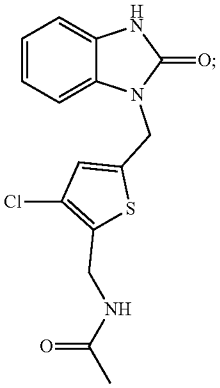 [SMILES: CC(=O)NCc1sc(Cn2c(=O)[nH]c3ccccc32)cc1Cl]
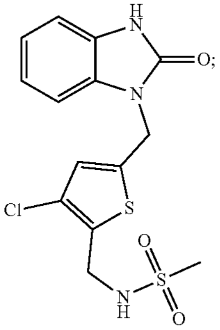 [SMILES: CS(=O)(=O)NCc1sc(Cn2c(=O)[nH]c3ccccc32)cc1Cl]
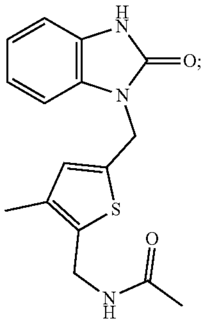 [SMILES: CC(=O)NCc1sc(Cn2c(=O)[nH]c3ccccc32)cc1C]
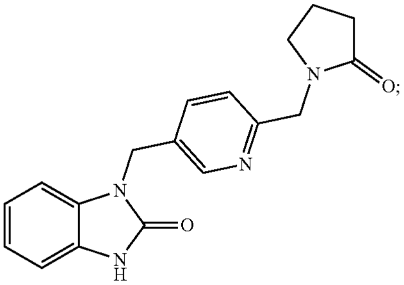 [SMILES: O=C1CCCN1Cc1ccc(Cn2c(=O)[nH]c3ccccc32)cn1]
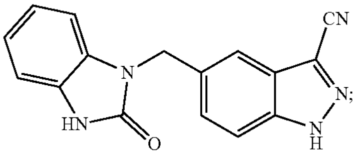 [SMILES: N#Cc1n[nH]c2ccc(Cn3c(=O)[nH]c4ccccc43)cc12]
-continued
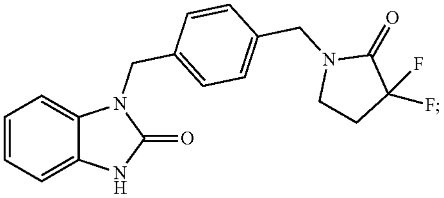 [SMILES: O=C1N(Cc2ccc(Cn3c(=O)[nH]c4ccccc43)cc2)CCC1(F)F]
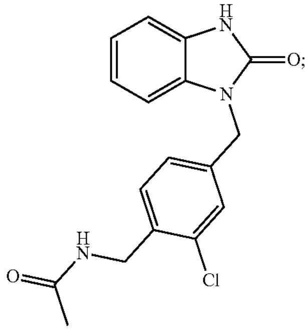 [SMILES: CC(=O)NCc1ccc(Cn2c(=O)[nH]c3ccccc32)cc1Cl]
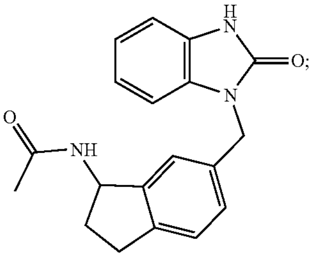 [SMILES: CC(=O)NC1CCc2ccc(Cn3c(=O)[nH]c4ccccc43)cc21]
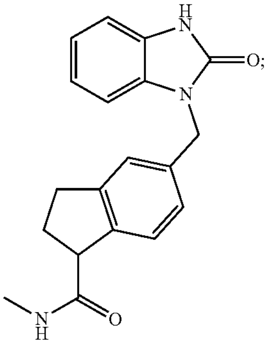 [SMILES: CNC(=O)C1CCc2cc(Cn3c(=O)[nH]c4ccccc43)ccc21]
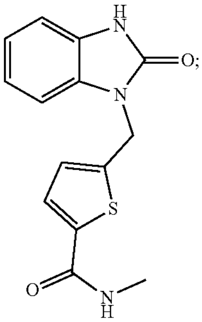 [SMILES: CNC(=O)c1ccc(Cn2c(=O)[nH]c3ccccc32)s1]

-continued
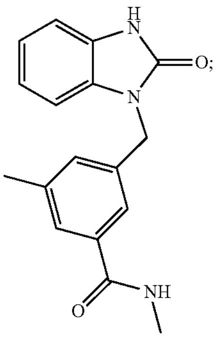 [SMILES: CNC(=O)c1cc(C)cc(Cn2c(=O)[nH]c3ccccc32)c1]
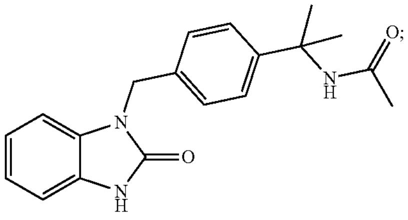 [SMILES: CC(=O)NC(C)(C)c1ccc(Cn2c(=O)[nH]c3ccccc32)cc1]
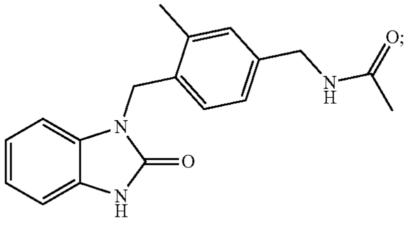 [SMILES: CC(=O)NCc1ccc(Cn2c(=O)[nH]c3ccccc32)c(C)c1]
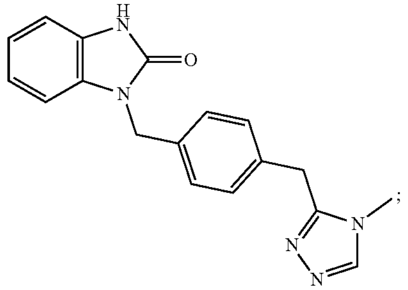 [SMILES: Cn1cnnc1Cc1ccc(Cn2c(=O)[nH]c3ccccc32)cc1]
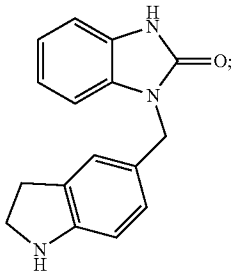 [SMILES: O=c1[nH]c2ccccc2n1Cc1ccc2c(c1)CCN2]
-continued
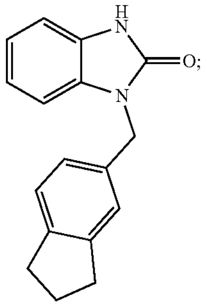 [SMILES: O=c1[nH]c2ccccc2n1Cc1ccc2c(c1)CCC2]
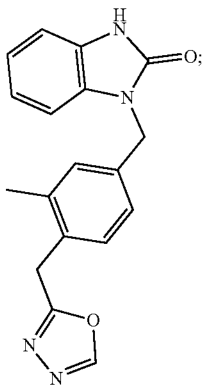 [SMILES: Cc1cc(Cn2c(=O)[nH]c3ccccc32)ccc1Cc1nnco1]
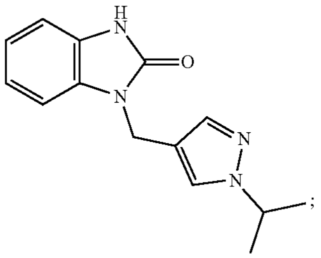 [SMILES: CC(C)n1cc(Cn2c(=O)[nH]c3ccccc32)cn1]
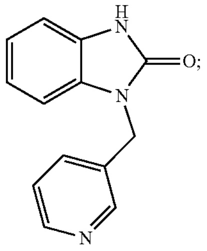 [SMILES: O=c1[nH]c2ccccc2n1Cc1cccnc1]
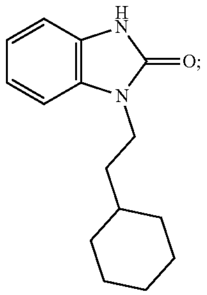 [SMILES: O=c1[nH]c2ccccc2n1CCC1CCCCC1]

-continued
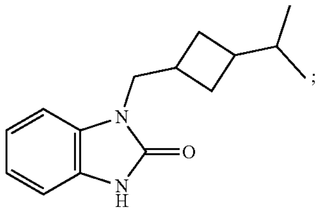 [SMILES: CC(C)C1CC(Cn2c(=O)[nH]c3ccccc32)C1]
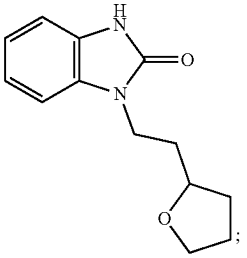 [SMILES: O=c1[nH]c2ccccc2n1CCC1CCCO1]
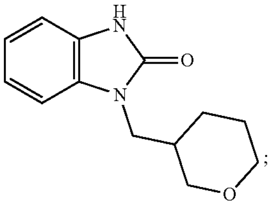 [SMILES: O=c1[nH]c2ccccc2n1CC1CCCOC1]
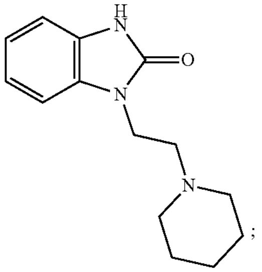 [SMILES: O=c1[nH]c2ccccc2n1CCN1CCCCC1]
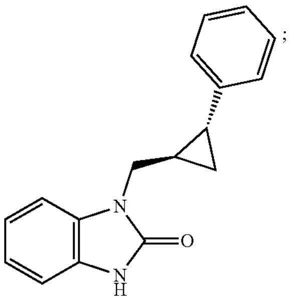 [SMILES: O=c1[nH]c2ccccc2n1C[C@@H]1C[C@H]1c1ccccc1]
-continued
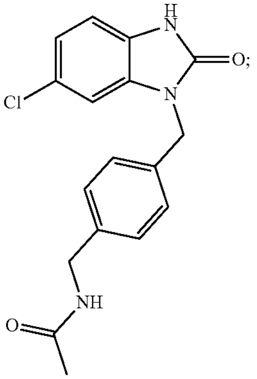 [SMILES: CC(=O)NCc1ccc(Cn2c(=O)[nH]c3ccc(Cl)cc32)cc1]
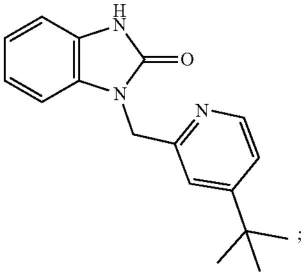 [SMILES: CC(C)(C)c1ccnc(Cn2c(=O)[nH]c3ccccc32)c1]
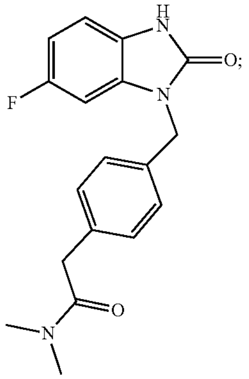 [SMILES: CN(C)C(=O)Cc1ccc(Cn2c(=O)[nH]c3ccc(F)cc32)cc1]
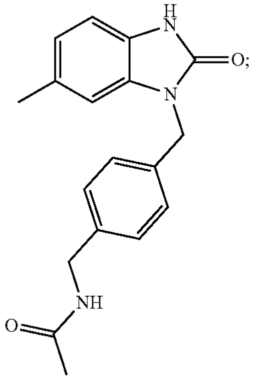 [SMILES: CC(=O)NCc1ccc(Cn2c(=O)[nH]c3ccc(C)cc32)cc1]

-continued
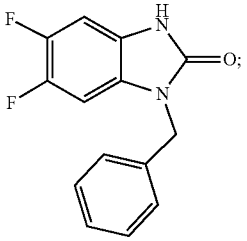 [SMILES: O=c1[nH]c2cc(F)c(F)cc2n1Cc1ccccc1]
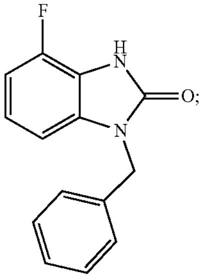 [SMILES: O=c1[nH]c2c(F)cccc2n1Cc1ccccc1]
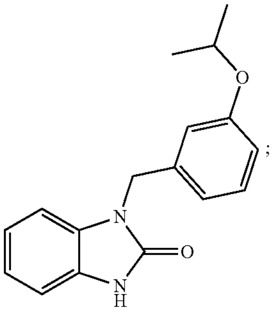 [SMILES: CC(C)Oc1cccc(Cn2c(=O)[nH]c3ccccc32)c1]
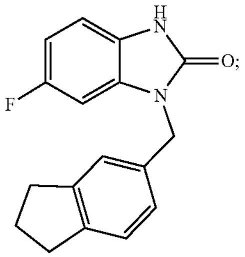 [SMILES: O=c1[nH]c2ccc(F)cc2n1Cc1ccc2c(c1)CCC2]
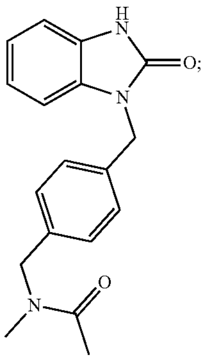 [SMILES: CC(=O)N(C)Cc1ccc(Cn2c(=O)[nH]c3ccccc32)cc1]
-continued
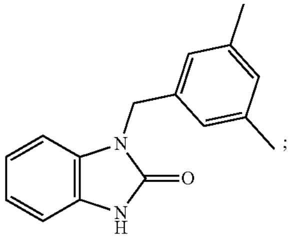 [SMILES: Cc1cc(C)cc(Cn2c(=O)[nH]c3ccccc32)c1]
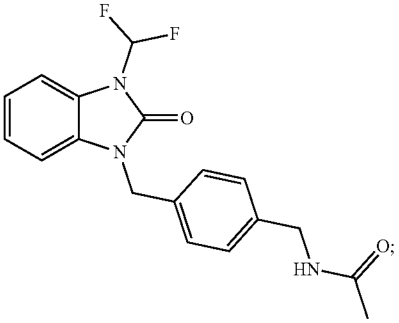 [SMILES: CC(=O)NCc1ccc(Cn2c(=O)n(C(F)F)c3ccccc32)cc1]
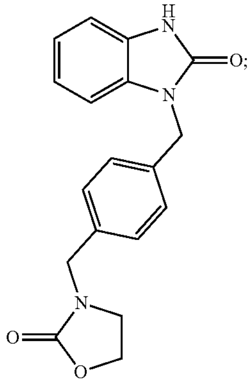 [SMILES: O=C1OCCN1Cc1ccc(Cn2c(=O)[nH]c3ccccc32)cc1]
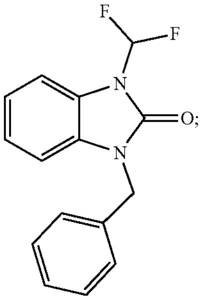 [SMILES: O=c1n(Cc2ccccc2)c2ccccc2n1C(F)F]

-continued
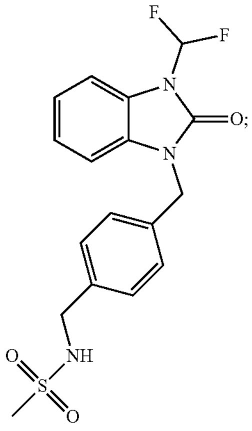 [SMILES: CS(=O)(=O)NCc1ccc(Cn2c(=O)n(C(F)F)c3ccccc32)cc1]
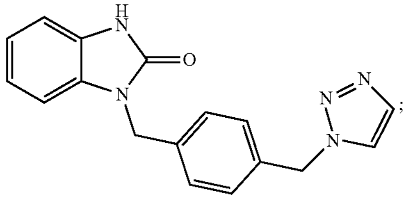 [SMILES: O=c1[nH]c2ccccc2n1Cc1ccc(Cn2ccnn2)cc1]
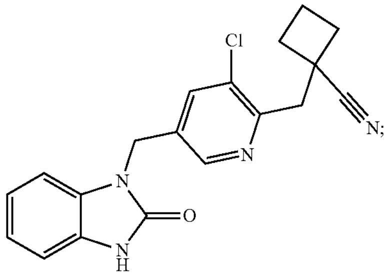 [SMILES: N#CC1(Cc2ncc(Cn3c(=O)[nH]c4ccccc43)cc2Cl)CCC1]
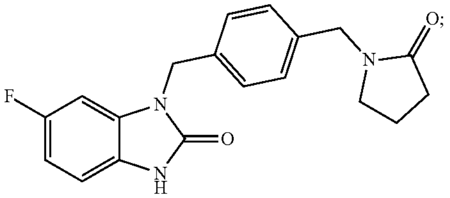 [SMILES: O=C1CCCN1Cc1ccc(Cn2c(=O)[nH]c3ccc(F)cc32)cc1]
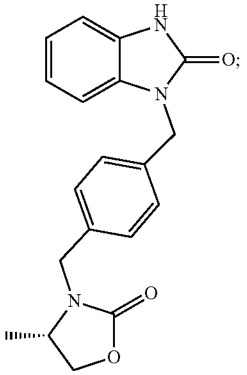 [SMILES: C[C@H]1COC(=O)N1Cc1ccc(Cn2c(=O)[nH]c3ccccc32)cc1]
-continued
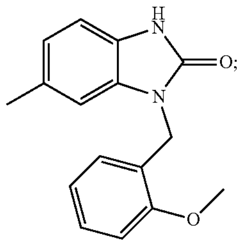 [SMILES: COc1ccccc1Cn1c(=O)[nH]c2ccc(C)cc21]
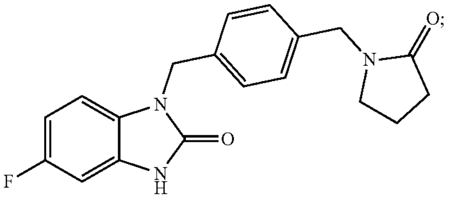 [SMILES: O=C1CCCN1Cc1ccc(Cn2c(=O)[nH]c3cc(F)ccc32)cc1]
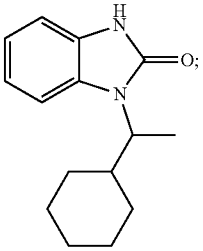 [SMILES: CC(C1CCCCC1)n1c(=O)[nH]c2ccccc21]
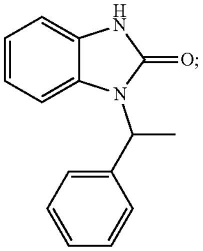 [SMILES: CC(c1ccccc1)n1c(=O)[nH]c2ccccc21]
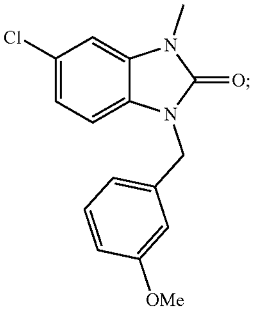 [SMILES: COc1cccc(Cn2c(=O)n(C)c3cc(Cl)ccc32)c1]

-continued
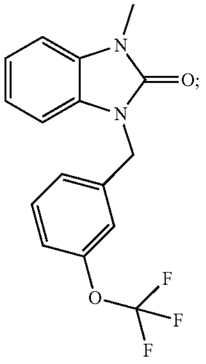 [SMILES: Cn1c(=O)n(Cc2cccc(OC(F)(F)F)c2)c2ccccc21]
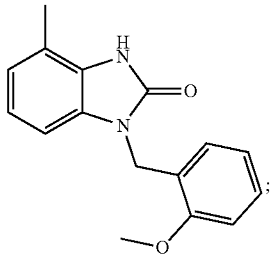 [SMILES: COc1ccccc1Cn1c(=O)[nH]c2c(C)cccc21]
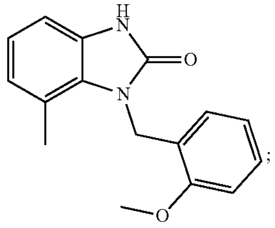 [SMILES: COc1ccccc1Cn1c(=O)[nH]c2cccc(C)c21]
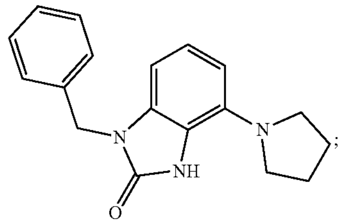 [SMILES: O=c1[nH]c2c(N3CCCC3)cccc2n1Cc1ccccc1]
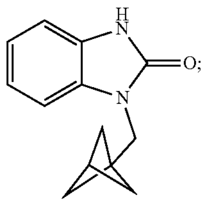 [SMILES: O=c1[nH]c2ccccc2n1CC12CC(C1)C2]
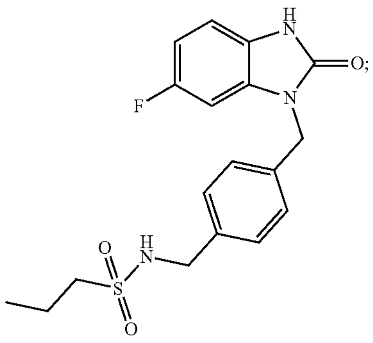 [SMILES: CCCS(=O)(=O)NCc1ccc(Cn2c(=O)[nH]c3ccc(F)cc32)cc1]
-continued
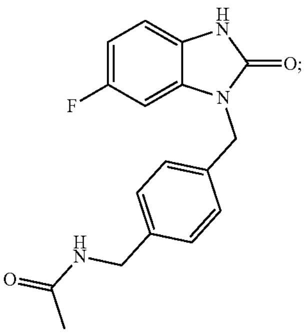 [SMILES: CC(=O)NCc1ccc(Cn2c(=O)[nH]c3ccc(F)cc32)cc1]
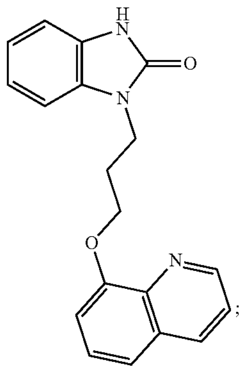 [SMILES: O=c1[nH]c2ccccc2n1CCCOc1cccc2cccnc12]
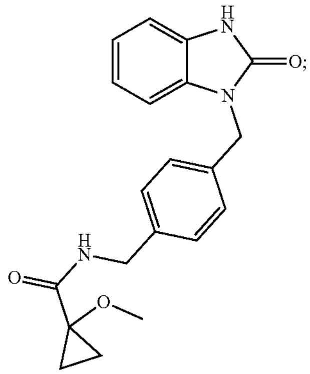 [SMILES: COC1(C(=O)NCc2ccc(Cn3c(=O)[nH]c4ccccc43)cc2)CC1]
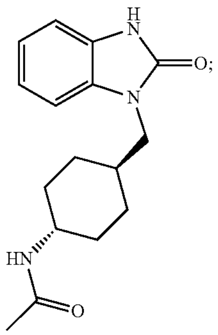

-continued
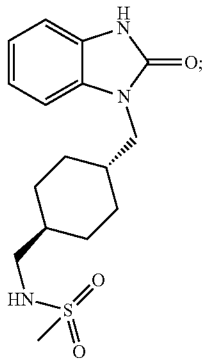
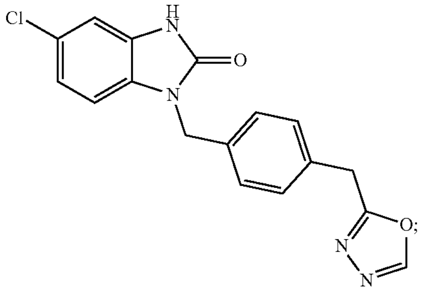
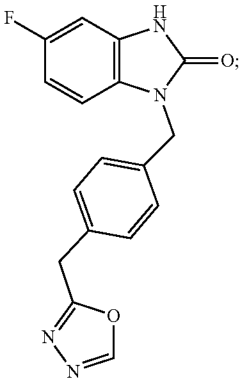 [SMILES: O=c1[nH]c2cc(F)ccc2n1Cc1ccc(Cc2nnco2)cc1]
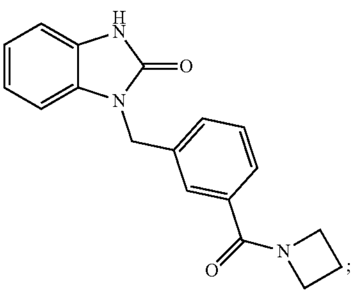 [SMILES: O=C(c1cccc(Cn2c(=O)[nH]c3ccccc32)c1)N1CCC1]
-continued
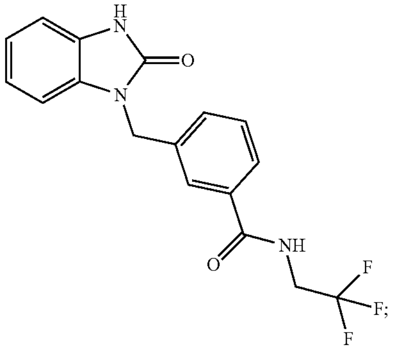 [SMILES: O=C(NCC(F)(F)F)c1cccc(Cn2c(=O)[nH]c3ccccc32)c1]
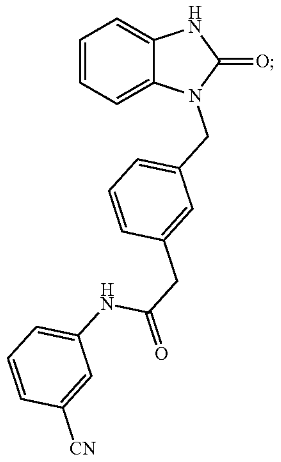 [SMILES: N#Cc1cccc(NC(=O)Cc2cccc(Cn3c(=O)[nH]c4ccccc43)c2)c1]
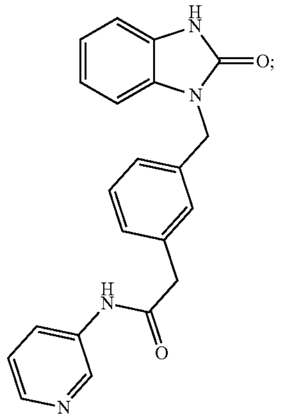 [SMILES: O=C(Cc1cccc(Cn2c(=O)[nH]c3ccccc32)c1)Nc1cccnc1]
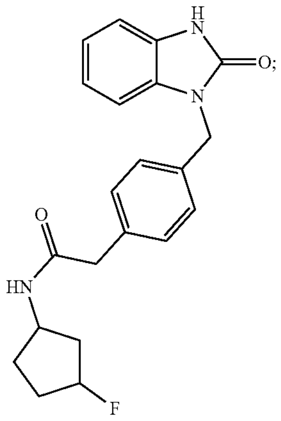 [SMILES: O=C(Cc1ccc(Cn2c(=O)[nH]c3ccccc32)cc1)NC1CCC(F)C1]

-continued
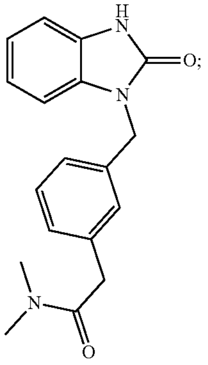 [SMILES: CN(C)C(=O)Cc1cccc(Cn2c(=O)[nH]c3ccccc32)c1]
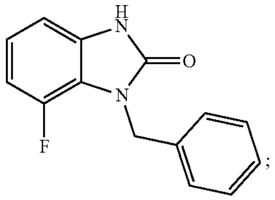 [SMILES: O=c1[nH]c2cccc(F)c2n1Cc1ccccc1]
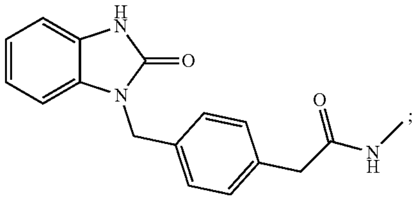 [SMILES: CNC(=O)Cc1ccc(Cn2c(=O)[nH]c3ccccc32)cc1]
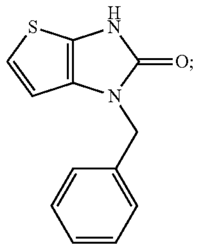 [SMILES: O=c1[nH]c2sccc2n1Cc1ccccc1]
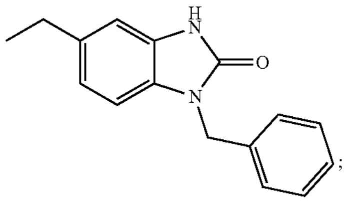 [SMILES: CCc1ccc2c(c1)[nH]c(=O)n2Cc1ccccc1]
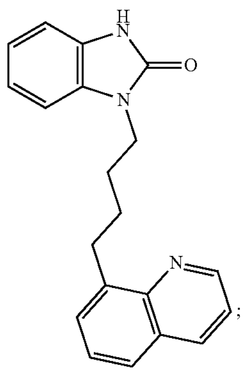
-continued
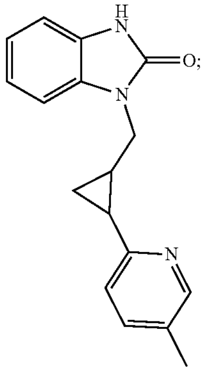 [SMILES: Cc1ccc(C2CC2Cn2c(=O)[nH]c3ccccc32)nc1]
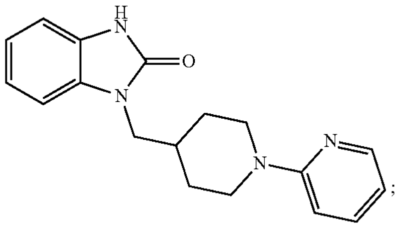 [SMILES: O=c1[nH]c2ccccc2n1CC1CCN(c2ccccn2)CC1]
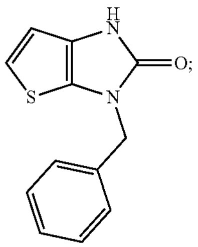 [SMILES: O=c1[nH]c2ccsc2n1Cc1ccccc1]
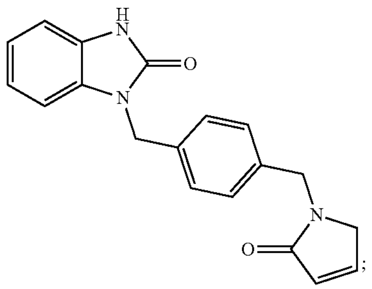 [SMILES: O=C1C=CCN1Cc1ccc(Cn2c(=O)[nH]c3ccccc32)cc1]
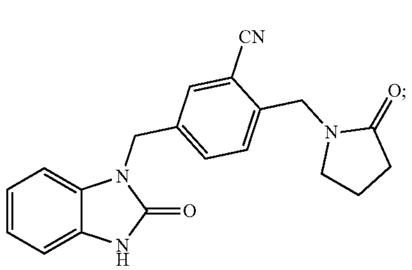 [SMILES: N#Cc1cc(Cn2c(=O)[nH]c3ccccc32)ccc1CN1CCCC1=O]

-continued

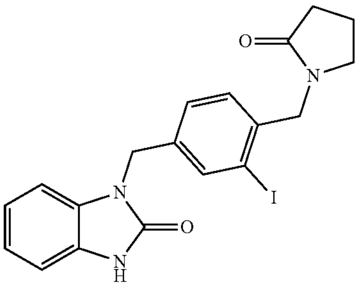
;

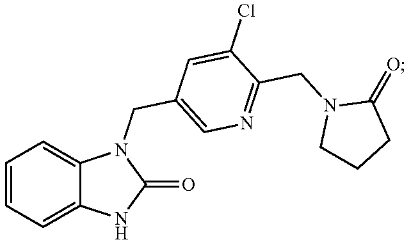 [SMILES: O=C1CCCN1Cc1ncc(Cn2c(=O)[nH]c3ccccc32)cc1Cl]
;

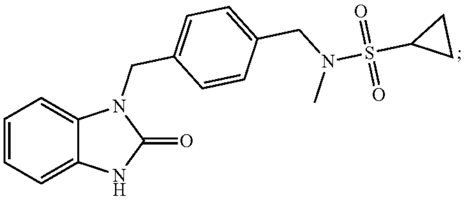 [SMILES: CN(Cc1ccc(Cn2c(=O)[nH]c3ccccc32)cc1)S(=O)(=O)C1CC1]
;

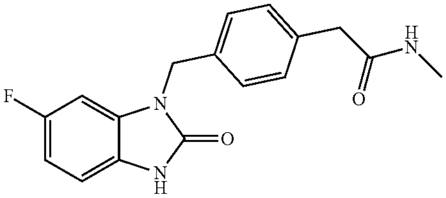
;

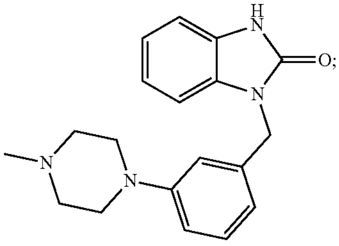
; or

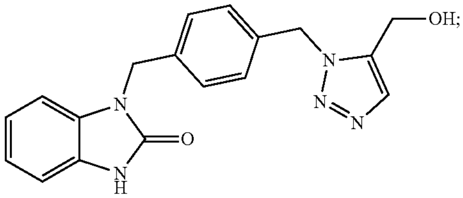 [SMILES: O=c1[nH]c2ccccc2n1Cc1ccc(Cn2nncc2CO)cc1]
;

or pharmaceutically acceptable salts thereof.

Definitions

The term "alkylene," or "alkylenyl" by itself or as part of another substituent means a divalent straight or branched chain hydrocarbon radical having the stated number of carbon atoms. For example, —($C_1$-$C_5$) alkylenyl, would include, e.g., —$CH_2$—, —$CH_2CH_2$—, —$CH_2CH_2CH_2$—, —$CH_2CH_2CH_2CH_2$—, —$CH_2CH(CH_3)CH_2$— or —$CH_2CH_2CH_2CH_2CH_2$—.

The term "halogen" includes a fluorine, a chlorine, a bromine or an iodine radical.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_3$-$C_6$cycloalkyl" encompasses bridged, saturated or unsaturated cycloalkyl groups having 3 to 6 carbons. Examples of cycloalkyl include cyclopropyl, cyclobutyl, cyclopentyl and cyclohexyl.

The term "$C_3$-$C_{10}$cycloalkyl" encompasses bridged, saturated or unsaturated cycloalkyl groups having 3 to 10 carbons. "Cycloalkyl" also includes non-aromatic rings as well as monocyclic, non-aromatic rings fused to a saturated cycloalkyl group and aromatic rings fused to a saturated cycloalkyl group. Examples of cycloalkyl include cyclopropyl, cyclobutyl, cyclopentyl, cyclohexyl, cycloheptyl, tetrahydronaphthyl, decahydronaphthyl, indanyl and the like. Examples described by structure include:

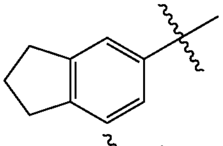
,
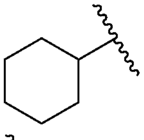
,
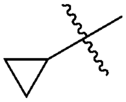
,
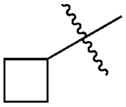
and
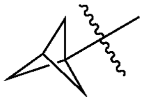
.

The term "heteroaryl" means an aromatic cycloheteroalkyl that contains at least one ring heteroatom selected from O, S and N. Examples of heteroaryl groups include pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl, and the like.

The term "cycloheteroalkyl" means mono- or bicyclic or bridged partially unsaturated or saturated rings containing at least one heteroatom selected from N, S and O, each of said rings having from 3 to 10 atoms in which the point of attachment may be carbon or nitrogen. Examples include tetrahydropyranyl, tetrahydrofuranyl, pyrrolidinyl, piperidinyl, piperazinyl, dioxanyl, imidazolidinyl, 2,3-dihydrofuro (2,3-b) pyridyl, benzoxazinyl, benzoxazolinyl, 2-H-phthalazinyl, isoindolinyl, benzoxazepinyl, 5,6-dihydroimidazo [2,1-b]thiazolyl, tetrahydroquinolinyl, morpholinyl, tetrahydroisoquinolinyl, dihydroindolyl, and tetrahydropyran. The term also includes partially unsaturated monocyclic rings that are not aromatic, such as 2- or 4-pyridones attached through the nitrogen or N-substituted-(1H, 3H)-pyrimidine- 2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl. Examples described by structure include:

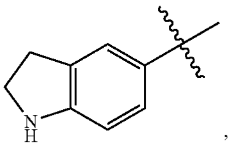
,
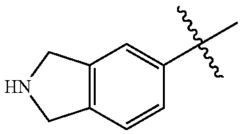
,
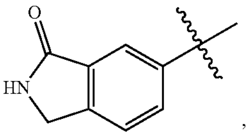
,
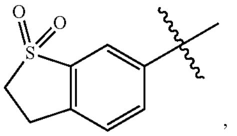
,
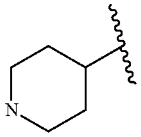
,
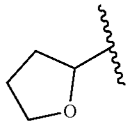
,
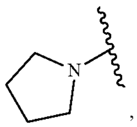
,
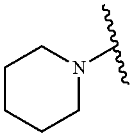
,
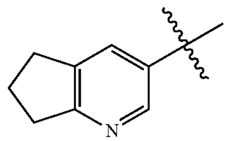
or
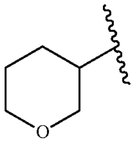
.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropylamine, tromethamine, and the like.

The term "patient" refers to a mammalian patient, including a human, canine, feline, bovine, or porcine patient, preferably a human patient, receiving or about to receive medical treatment.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that the present invention is meant to include the pharmaceutically acceptable salts, and also salts that are not pharmaceutically acceptable, of the compounds described herein, when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the Schemes and Examples herein using appropriate isotopically-enriched reagents or Intermediates.

It should be noted that chemically unstable compounds are excluded from the embodiments contained herein.

Methods of Treatment

Also encompassed by the present invention are methods of preventing, treating or ameliorating IL4I1-related diseases. The compounds described herein can be effective in preventing, treating or ameliorating various IL4I1-related diseases, such as cancer. Described herein are methods for treatment of cancer displaying IL4I1-expressing cells in a patient. Described herein are methods for prevention of cancer displaying IL4I1-expressing cells in a patient. Described herein are methods for ameliorating of cancer displaying IL4I1-expressing cells in a patient.

In one embodiment described herein, the cancer to be treated is selected from the group consisting of cancers displaying IL4I1-expressing cells and lymphomas displaying IL4I1-expressing cells. In certain embodiment, the cancers to be treated are solid tumors. In certain embodiments, the cancers to be treated are typically selected from carcinomas, sarcomas, mesotheliomas, blastomas and germ cell tumors. In another particular embodiment, cancers to be treated are typically selected from the group consisting of mesotheliomas, non-small-cell lung carcinomas, colon carcinoma, breast carcinoma, thyroid carcinoma, testicular germ cell tumors and ovarian carcinoma, displaying IL4I1-expressing cells.

In another specific embodiment, the cancer to be treated is selected from the group consisting of lymphomas displaying IL4I1-expressing cells typically selected from B-cell lymphomas displaying IL4I1-expressing cells.

In certain embodiments, the cancer to be treated is selected from the group consisting of PMBL (Primary Mediastinal large B-cell Lymphoma), classical Hodgkin lymphomas (cHL), NLPHL (Nodular lymphocyte predominant Hodgkin's lymphoma), non-mediastinal Diffuse Large B-Cell Lymphoma (DLBCL) and SLL/CLL (Small Lymphocytic Lymphoma/Chronic Lymphocytic Leukemia), displaying IL4I1-expressing cells. In another specific embodiment, the cancer to be treated is selected from the group consisting of lymphomas displaying IL4I1-expressing cells.

In one embodiment described herein, the cancer to be prevented is selected from the group consisting of cancers displaying IL4I1-expressing cells and lymphomas displaying IL4I1-expressing cells. In certain embodiment, the cancers to be prevented are solid tumors. In certain embodiments, the cancers to be prevented are typically selected from carcinomas, sarcomas, mesotheliomas, blastomas and germ cell tumors. In another particular embodiment, cancers to be prevented are typically selected from the group consisting of mesotheliomas, non-small-cell lung carcinomas, colon carcinoma, breast carcinoma, thyroid carcinoma, testicular germ cell tumors and ovarian carcinoma, displaying IL4I1-expressing cells.

In another specific embodiment, the cancer to be prevented is selected from the group consisting of lymphomas displaying IL4I1-expressing cells typically selected from B-cell lymphomas displaying IL4I1-expressing cells.

In certain embodiments, the cancer to be prevented is selected from the group consisting of PMBL (Primary Mediastinal large B-cell Lymphoma), classical Hodgkin lymphomas (cHL), NLPHL (Nodular lymphocyte predominant Hodgkin's lymphoma), non-mediastinal Diffuse Large B-Cell Lymphoma (DLBCL) and SLL/CLL (Small Lymphocytic Lymphoma/Chronic Lymphocytic Leukemia), displaying IL4I1-expressing cells. In another specific embodiment, the cancer to be treated is selected from the group consisting of lymphomas displaying IL4I1-expressing cells.

In one embodiment described herein, the cancer to be ameliorated is selected from the group consisting of cancers displaying IL4I1-expressing cells and lymphomas displaying IL4I1-expressing cells. In certain embodiment, the cancers to be ameliorated are solid tumors. In certain embodiments, the cancers to be ameliorated are typically selected from carcinomas, sarcomas, mesotheliomas, blastomas and germ cell tumors. In another particular embodiment, cancers to be ameliorated are typically selected from the group consisting of mesotheliomas, non-small-cell lung carcinomas, colon carcinoma, breast carcinoma, thyroid carcinoma, testicular germ cell tumors and ovarian carcinoma, displaying IL4I1-expressing cells.

In another specific embodiment, the cancer to be ameliorated is selected from the group consisting of lymphomas displaying IL4I1-expressing cells typically selected from B-cell lymphomas displaying IL4I1-expressing cells.

In certain embodiments, the cancer to be ameliorated is selected from the group consisting of PMBL (Primary Mediastinal large B-cell Lymphoma), classical Hodgkin lymphomas (cHL), NLPHL (Nodular lymphocyte predominant Hodgkin's lymphoma), non-mediastinal Diffuse Large B-Cell Lymphoma (DLBCL) and SLL/CLL (Small Lymphocytic Lymphoma/Chronic Lymphocytic Leukemia), displaying IL4I1-expressing cells. In another specific embodiment, the cancer to be ameliorated is selected from the group consisting of lymphomas displaying IL4I1-expressing cells Pharmaceutical Compositions Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day, or from about 0.001 to about 50 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Examples of other active ingredients that may be administered in combination with a compound of any of the Formulas described herein or a pharmaceutically acceptable salt thereof and either administered separately or in the same pharmaceutical composition, include, but are not limited to pain relieving agents, anti-angiogenic agents, anti-neoplastic agents, anti-diabetic agents, anti-infective agents, or gastrointestinal agents, or combinations thereof.

Suitable compounds that may be used in combination with a compound according to the present invention include without limitation sildenafil, vardenafil, tadalafil and alprostadil, epoprostenol, iloprost, bosentan, amlodipine, diltiazem, nifedipine, ambrisentan and warfarin, fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn, atorvastatin, lovastatin, simvastatin, pravastatin, fluvastatin, rosuvastatin, gemfibrozil, fenofibrate, nicotinic acid, clopidogrel and pharmaceutically acceptable salts thereof.

Additionally, a compound of any of the Formulas disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

PD-1 is recognized as having an important role in immune regulation and the maintenance of peripheral tolerance. PD-1 is moderately expressed on naive T-cells, B-cells and NKT-cells and up-regulated by T-cell and B-cell receptor signaling on lymphocytes, monocytes and myeloid cells (Sharpe et al., Nature Immunology (2007); 8:239-245).

Two known ligands for PD-1, PD-L1 (B7-H1) and PD-L2 (B7-DC) are expressed in human cancers arising in various tissues. In large sample sets of, for example, ovarian, renal, colorectal, pancreatic, and liver cancers, and in melanoma, it was shown that PD-L1 expression correlated with poor prognosis and reduced overall survival irrespective of subsequent treatment. (Dong et al., Nat Med. 8 (8): 793-800 (2002); Yang et al., Invest Ophthamol Vis Sci. 49:2518-2525 (2008); Ghebeh et al., Neoplasia 8:190-198 (2006); Hamanishi et al., Proc. Natl. Acad. Sci. USA 104:3360-3365 (2007); Thompson et al., Cancer 5:206-211 (2006); Nomi et al., Clin. Cancer Research 13:2151-2157 (2007); Ohigashi et al., Clin. Cancer Research 11:2947-2953; Inman et al., Cancer 109:1499-1505 (2007); Shimauchi et al., Int. J. Cancer 121:2585-2590 (2007); Gao et al., Clin. Cancer Research 15:971-979 (2009); Nakanishi J., Cancer Immunol Immunother. 56:1173-1182 (2007); and Hino et al., Cancer 00:1-9 (2010)).

Similarly, PD-1 expression on tumor infiltrating lymphocytes was found to mark dysfunctional T-cells in breast cancer and melanoma (Ghebeh et al., BMC Cancer. 2008 8:5714-15 (2008); and Ahmadzadeh et al., Blood 114:1537-1544 (2009)) and to correlate with poor prognosis in renal cancer (Thompson et al., Clinical Cancer Research 15:1757-1761 (2007)). Thus, it has been proposed that PD-L1 expressing tumor cells interact with PD-1 expressing T-cells to attenuate T-cell activation and to evade immune surveillance, thereby contributing to an impaired immune response against the tumor.

Immune checkpoint therapies targeting the PD-1 axis have resulted in groundbreaking improvements in clinical response in multiple human cancers (Brahmer, et al., N Engl J Med 2012, 366:2455-65; Garon et al., N Engl J Med 2015, 372:2018-28; Hamid et al., N Engl J Med 2013, 369:134-44; Robert et al., Lancet 2014, 384:1109-17; Robert et al., N Engl J Med 2015, 372:2521-32; Robert et al., N Engl J Med 2015, 372:320-30; Topalian et al., N Engl J Med 2012, 366:2443-54; Topalian et al., J Clin Oncol 2014, 32:1020-30; and Wolchok et al., N Engl J Med 2013, 369:122-33).

"PD-1 antagonist" means any chemical compound or biological molecule that blocks binding of PD-L1 expressed on a cancer cell to PD-1 expressed on an immune cell (T-cell, B-cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCDIL1, PDL1, B7H1, B7-4, CD274 and B7-H for PD-L1; and PDCD1L2, PDL2, B7-DC, Btdc and CD273 for PD-L2. In any of the treatment methods, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP 054862 and NP_079515, respectively.

PD-1 antagonists useful in any of the treatment methods, medicaments and uses of the present invention include a monoclonal antibody (mAb), or antigen binding fragment thereof, which specifically binds to PD-1 or PD-L1, and preferably specifically binds to human PD-1 or human PD-Ll. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments. Examples of PD-1 antagonists include, but are not limited to, pembrolizumab (KEYTRUDA®, Merck and Co., Inc., Kenilworth, NJ, USA). "Pembrolizumab" (formerly known as MK-3475, SCH 900475 and lambrolizumab and sometimes referred to as "pembro") is a humanized IgG4 mAb with the structure described in WHO Drug Information, Vol. 27, No. 2, pages 161-162 (2013). Additional examples of PD-1 antagonists include nivolumab (OPDIVO®, Bristol-Myers Squibb Company, Princeton, NJ, USA), atezolizumab (MPDL3280A; TECENTRIQ®, Genentech, San Francisco, CA, USA), durvalumab (IMFINZI®, Astra Zeneca Pharmaceuticals, LP, Wilmington, DE, and avelumab (BAVENCIO®, Merck KGAA, Darmstadt, Germany and Pfizer, Inc., New York, NY).

Examples of monoclonal antibodies (mAbs) that bind to human PD-1, and useful in the treatment methods, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment methods, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906. Other PD-1 antagonists useful in any of the treatment methods, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment methods, medicaments and uses of the present invention include AMP-224 (also known as B7-DCIg), which is a PD-L2-FC fusion protein that binds to human PD-1. Thus, one embodiment provides for a method of treating cancer comprising administering an effective amount of a compound of the invention, or a pharmaceutically acceptable salt thereof, in combination with a PD-1 antagonist to a subject in need thereof. In such embodiments, the compounds of the invention, or a pharmaceutically acceptable salt thereof, and PD-1 antagonist are administered concurrently or sequentially.

Specific non-limiting examples of such cancers in accordance with this embodiment include melanoma (including unresectable or metastatic melanoma), head & neck cancer (including recurrent or metastatic head and neck squamous cell cancer (HNSCC)), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, and salivary cancer.

In one embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma. In one such embodiment, the agent is a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

Pembrolizumab is approved by the U.S. FDA for the treatment of patients with unresectable or metastatic melanoma and for the treatment of certain patients with recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma, as described in the Prescribing Information for KEYTRUDA™ (Merck & Co., Inc., Whitehouse Station, NJ USA; initial U.S. approval 2014, updated November 2018). In another embodiment, there is provided a method of treating cancer comprising administering an effective amount of a compound of the invention, or a pharmaceutically acceptable salt thereof, to a person in need thereof, in combination with pembrolizumab, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, head and neck squamous cell cancer (HNSCC), Hodgkin lymphoma, primary mediastinal large B-cell lymphoma, urothelial carcinoma, microsatellite instability-high cancer, gastric cancer, Merkel cell carcinoma, hepatocellular carcinoma, esophageal cancer and cervical cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab. In other such embodiment, the agent is durvalumab or avelumab.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, small cell lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab. In other such embodiment, the agent is durvalumab or avelumab.

In one embodiment, there is provided a method of treating unresectable or metastatic melanoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating recurrent or metastatic head and neck squamous cell cancer (HNSCC) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating classical Hodgkin lymphoma (cHL) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating urothelial carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating gastric cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating cervical cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating primary mediastinal large-B-cell lymphoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating microsatellite instability-high (MSI-H) cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating non-small cell lung cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

In one embodiment, there is provided a method of treating hepatocellular carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab. In other such embodiment, the agent is durvalumab or avelumab.

Examples of vascular endothelial growth factor (VEGF) receptor inhibitors include, but are not limited to, bevacizumab (sold under the trademark AVASTIN by Genentech/Roche), axitinib, (N-methyl-2-[3-[([E])-2-pyridin-2-ylethenyl]-1 H-indazol-6-yl]sulfanyl]benzamide, also known as AG013736, and described in PCT Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethy)amino]-3-pyridinecarboxamide. and described in PCT Publication No. WO 02/068470), pasireotide (also known as SO 230, and described in PCT Publication No. WO02/010192), and sorafenib (sold under the tradename NEXAVAR).

Examples of topoisomerase II inhibitors include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUB EX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.

ACN=$CH_3CN$=MeCN=acetonitrile

AcOH=acetic acid

APhos-Pd-G3=Palladium G3-(4-(N,N-Dimethylamino)phenyl)di-tert-butylphosphine=[4-(Di-tert-butylphosphino)-N,N-dimethylaniline-2-(2'-aminobiphenyl)]palladium(II) methanesulfonate APhos-Pd-G4=4-Ditert-butylphosphanyl-N,N-dimethylaniline; methanesulfonic acid; N-methyl-2-phenylaniline; palladium $Boc_2O$=di-tert-butyl dicarbonate Boc-Ser (Bzl)-OH=N-(tert-Butoxycarbonyl)-O-benzyl-L-serine CDI=1,1'-carbonyldiimidazole CELITE=diatomaceous earth $CF_3CH_2OH$=2,2,2-trifluoroethanol Conc.=concentrated $CO_2$=carbon dioxide Cp*RuCl$(PPh_3)_2$=pentamethylcyclopentadienylbis(triphenylphosphine)ruthenium(II) chloride DCM=dichloromethane DIEA=DIPEA=N,N-diisopropylethylamine=Hünig's base DMA=Dimethylacetamide DMAP=4-Dimethylaminopyridine DMF=N,N-dimethylformamide DMSO=dimethyl sulfoxide DPPE=1,2-bis(diphenylphosphino)ethane EDCI=1-ethyl-3-(3-dimethylaminopropyl)carbodiimide EtOAc=ethyl acetate h=hours $H_2$=hydrogen $H_2O$=water HATU=1-[bis(dimethylamino)methylene]-1H-1,2,3-triazolo[4,5-b]pyridinium 3-oxid hexafluorophosphate HBr=hydrogen bromide HCl=hydrochloric acid HFBA=heptafluorobutyric acid HOBT=hydroxybenzotriazole $K_2CO_3$=potassium carbonate LCMS=liquid chromatography-mass spectrometry LHMDS=LiHMDS=lithium bis(trimethylsilyl)amide $LiAlH_4$=lithium aluminum hydride LiF=lithium fluoride LiOH=lithium hydroxide min=minutes MeOH=methanol $MgSO_4$=magnesium sulfate $NaBH_4$=sodium borohydride NaCl=sodium chloride $NaHCO_3$=sodium bicarbonate NaOH=sodium hydroxide $Na_2SO_4$=sodium sulfate NaH=sodium hydride $NH_4Cl$=ammonium chloride $NH_4OH$=ammonium hydroxide $Pd(OH)_2$/C=Pearlman's catalysts=palladium hydroxide on carbon Pd(dtbpf)$Cl_2$=1,1'-Bis (di-t-butylphosphino) ferrocene palladium dichloride SFC=supercritical fluid chromatography sSPhos Pd G2=chloro (sodium-2-dicyclohexylphosphino-2',6'-dimethoxy-1,1'-biphenyl-3'-sulfonate) [2-(2'-amino-1,1'-biphenyl)]palladium(II)

TEA=triethylamine

TFA=trifluoroacetic acid

THF=tetrahydrofuran

1 Standard atmosphere [atm]=101325 pascal [Pa]=14.6959488 psi

The meanings of the abbreviations in the nuclear magnetic resonance spectra are shown below:

s=singlet, d=doublet, dd=double doublet, dt=double triplet, ddd=double double doublet, Sept =septet, t=triplet, m=multiplet, br=broad, brs=broad singlet, q=quartet J=coupling constant and Hz=hertz.

Compounds of this invention can be prepared using the intermediates and processes outlined below. The various starting materials used are commercially available or are readily made by Scheme 1

Certain compounds of Formula I were synthesized by converting alkyl boronate 1 to 2 under palladium catalyzed Suzuki conditions with the corresponding aryl bromide. Then a deprotection completed the synthesis.

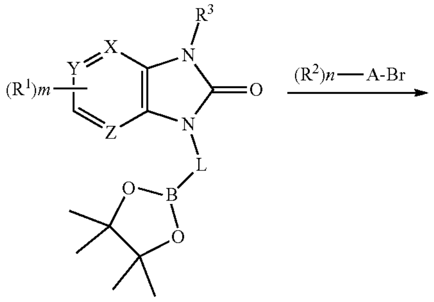

1

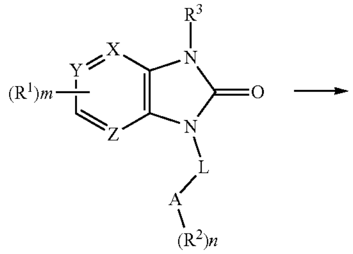

2

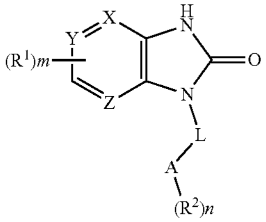

Scheme 2

Certain compounds of Formula I were synthesized from diamino 3 in the presence of CDI.

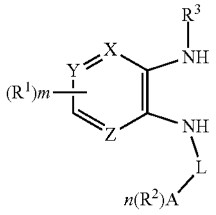

3

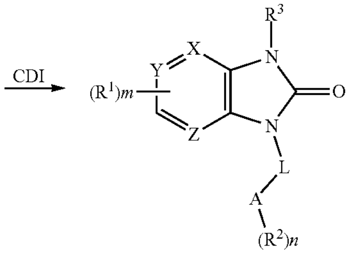

Scheme 3

Certain compounds of Formula I were synthesized by converting diamino 4 to 5 in the presence of CDI. Then 5 was converted to 6 via a deprotection. Coupling with the corresponding acid, acid anhydride, sulfonyl chloride or sulfonic anhydride completed the synthesis.

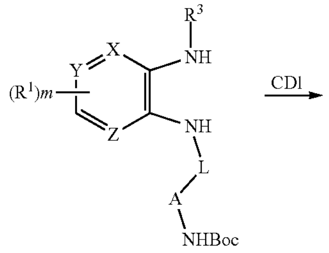

4

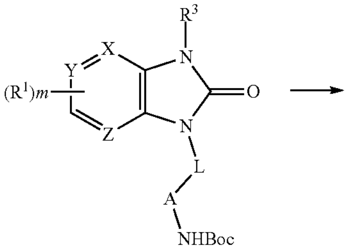

5

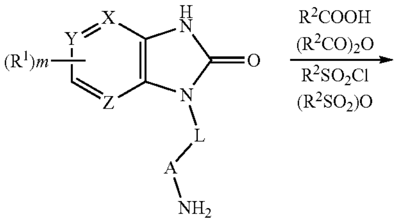

6

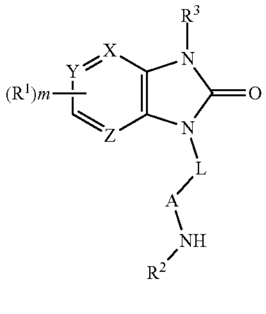

Scheme 4

Certain compounds of Formula I were synthesized by converting alkyl acid 7 to 8 under iridium and nickel catalyzed decarboxylative coupling conditions with the corresponding aryl bromide. If needed, a deprotection completed the synthesis.

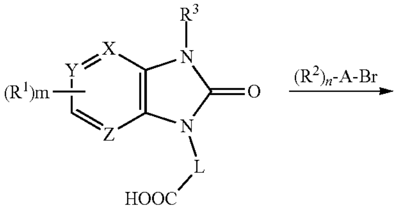

7

-continued

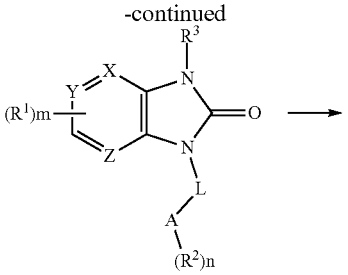

8

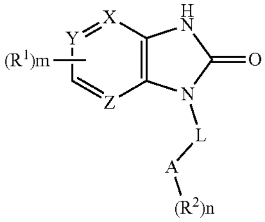

Scheme 5

Certain compounds of Formula I were synthesized by converting alkyl acid 9 to 10 under iridium and nickel catalyzed decarboxylative coupling conditions with the corresponding aryl bromide. Deprotection of 10 afforded compound 11. Coupling with the corresponding acid completed the synthesis.

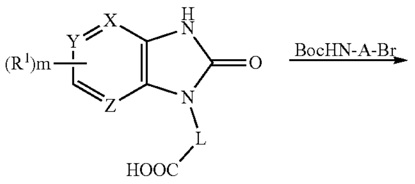

9

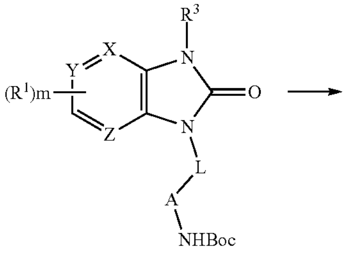

10

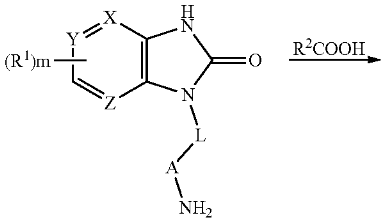

11

-continued

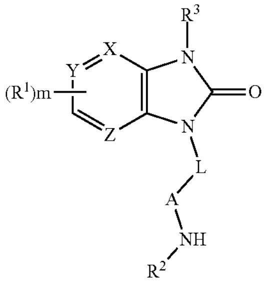

Scheme 6

Certain compounds of Formula I were synthesized from amine 12 in the presence of base and an alkyl halide.

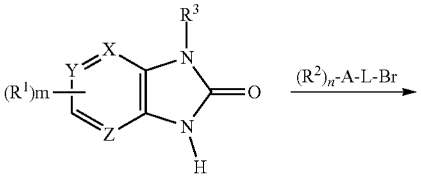

12

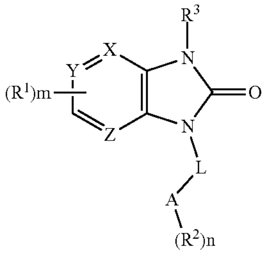

Scheme 7

Certain compounds of Formula I were synthesized by converting amine 13 to 14 in the presence of base and an alkyl halide. A deprotection completed the synthesis.

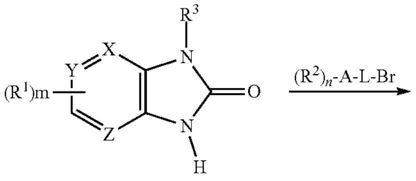

13

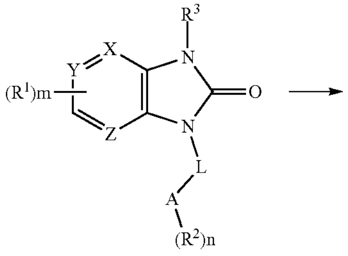

14

-continued

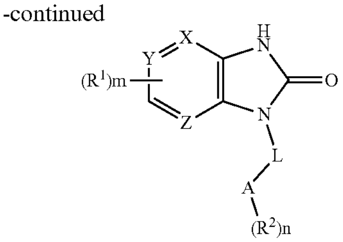

Scheme 8

Certain compounds of Formula I were synthesized from amine 15 via a Mitsunobu reaction.

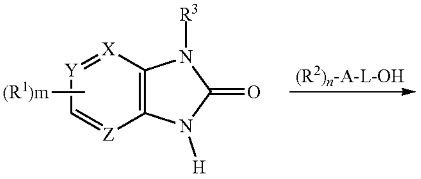

15

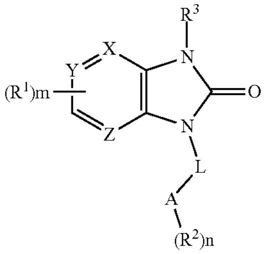

Scheme 9

Certain compounds of Formula I were synthesized by converting amine 16 to 17 via a Mitsunobu reaction. A deprotection completed the synthesis.

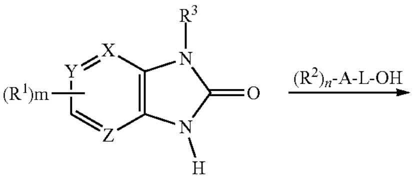

16

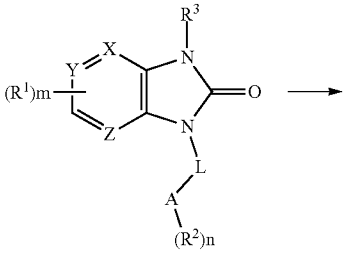

17

-continued

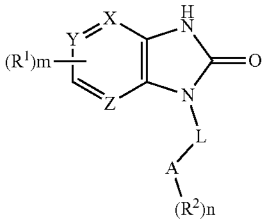

Scheme 10

Certain compounds of Formula I were synthesized from carbamate 18 using a copper catalyzed aryl amination reaction followed by an intramolecular cyclization.

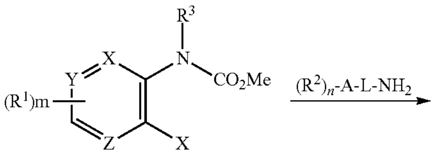

18

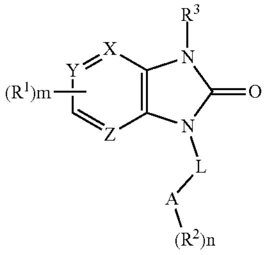

Scheme 11

Certain compounds of Formula I were synthesized by converting carbamate 19 to 20 using a copper catalyzed aryl amination reaction followed by an intramolecular cyclization. A deprotection of 20 afforded 21. The synthesis was completed with an amide coupling.

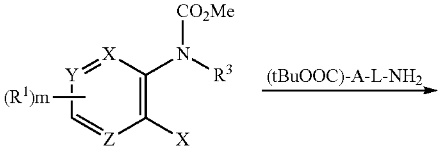

19

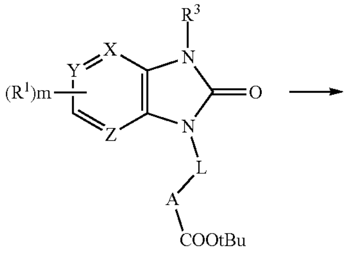

20

-continued

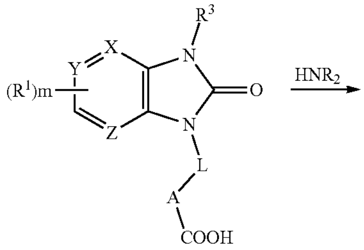

21

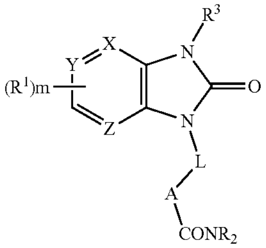

Scheme 12

Certain compounds of Formula I were synthesized from aryl halide 22 with a urea via a palladium catalyzed aryl amination reaction.

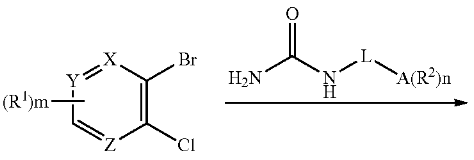

22

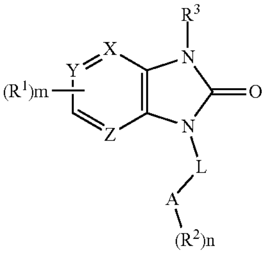

Scheme 13

Certain compounds of Formula I were synthesized by converting aryl azide 23 to 24 via a ruthenium catalyzed reaction. A deprotection completed the synthesis.

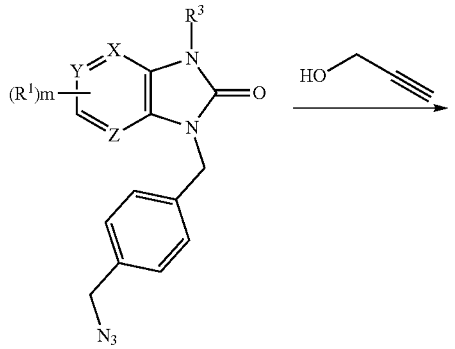

23

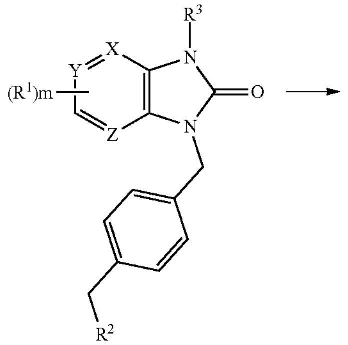

24

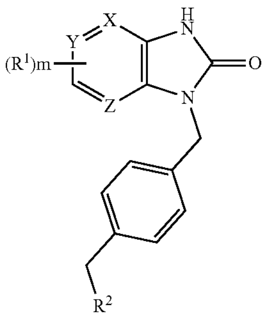

Scheme 14

Certain compounds of Formula I were synthesized by converting boronate 25 to 26 via a palladium catalyzed Suzuki reaction. 26 was converted to 27 via a palladium catalyzed cyclopropanation reaction. A deprotection completed the synthesis.

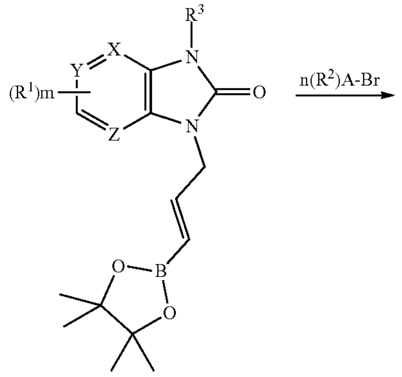

25

-continued

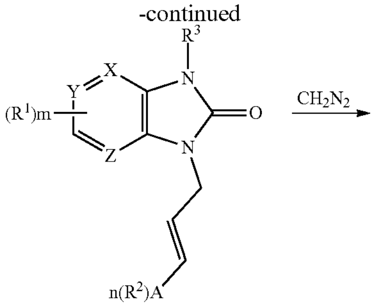

26

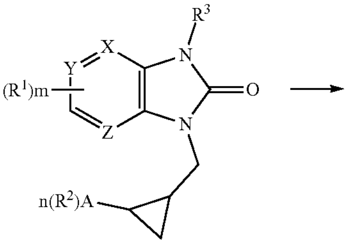

27

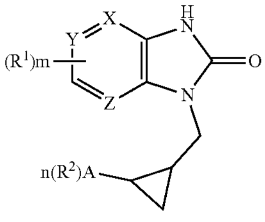

Scheme 15

Certain compounds of Formula I were synthesized by converting acid 28 to 29 in the presence of triphosgene. 29 was converted to 30 in the presence of sodium azide. A Curtius rearrangement followed by intramolecular cyclization completed the synthesis.

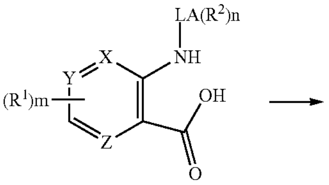

28

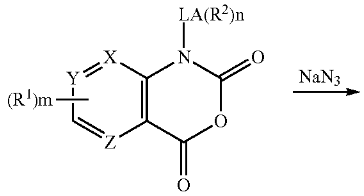

29

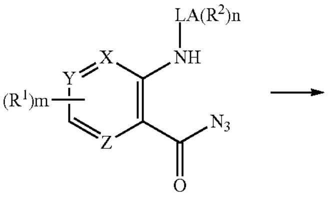

30

-continued

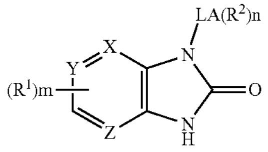

Scheme 16

Certain compounds of Formula I were synthesized by converting amine 31 to 32 in via alkylation with a benzyl halide. 32 was converted to 33 via an alkylation with an amine. A deprotection completed the synthesis.

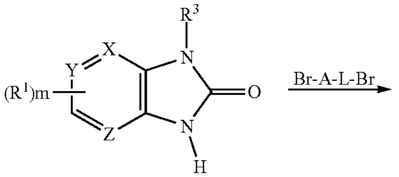

31

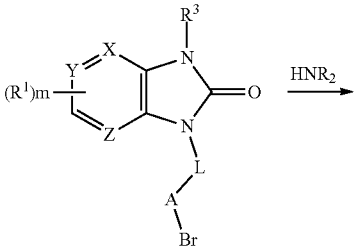

32

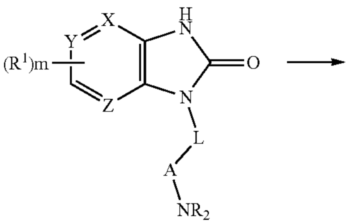

33

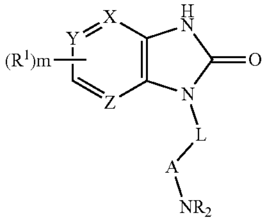

Scheme 17

Certain compounds of Formula I were synthesized by converting amine 34 to 35 in via an alkylation with a di-iodo alkyl compound. 35 was converted to 36 via an alkylation with triphenylphosphine. 36 was converted to 37 via a Wittig reaction. 37 was converted to 38 via a deprotection. The synthesis was completed via a palladium catalyzed hydrogenation reaction.

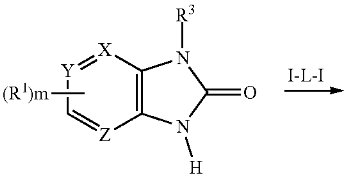

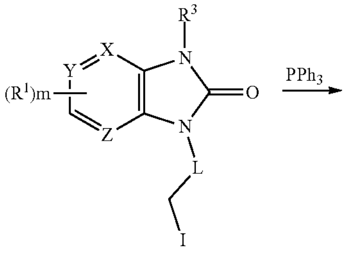

35

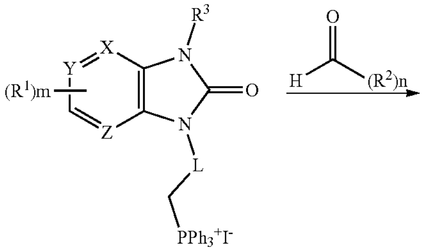

36

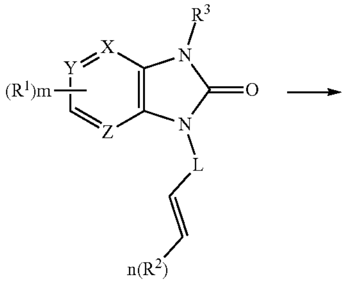

37

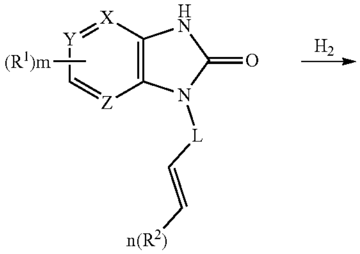

38

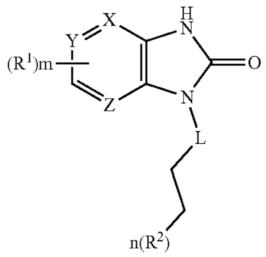

Scheme 18

Certain compounds of Formula I were synthesized by converting amine 39 to 40 via alkylation with a benzyl halide. 40 was converted to 41 via a nickel catalyzed reductive coupling. A deprotection completed the synthesis.

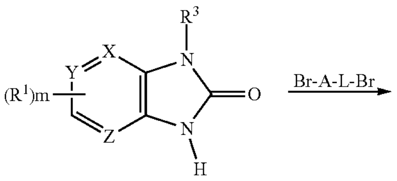

39

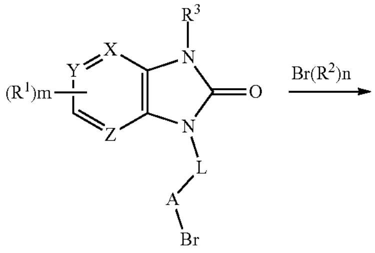

40

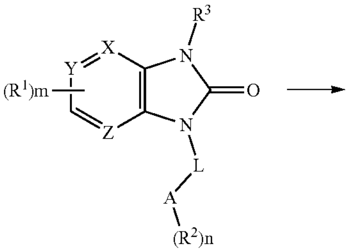

41

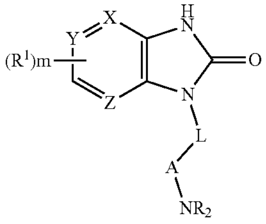

Intermediate 1:

tert-butyl 2-oxo-3-((4,4,5,5-tetramethyl-1,3,2-dioxaborolan-2-yl)methyl)-2,3-dihydro-1H-benzo[d]imidazole-1-carboxylate

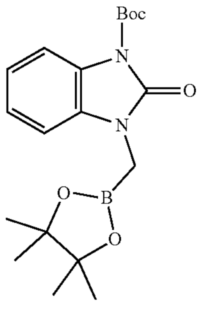 [SMILES: CC(C)(C)OC(=O)n1c(=O)n(CB2OC(C)(C)C(C)(C)O2)c2ccccc21]

Tert-butyl 2-oxo-2,3-dihydro-1H-benzo[d]imidazole-1-carboxylate (194.0 g, 0.83 mol, 1 equiv), THF (3.8 L) and NaH (36.40 g, 0.91 mol, 1.10 equiv) were added to a round bottom flask. This reaction mixture was stirred for 30 minutes at 0° C. 2-(bromomethyl)-4,4,5,5-tetramethyl-1,3,2-dioxaborolane (228.6 g, 1.08 mol) was then added at 0° C., and the reaction mixture was stirred overnight at 30° C. Water was added to quench the reaction, and then it was extracted with ethyl acetate. The organics were concentrated under reduced pressure and then slurried with MTBE to afford a solid. $^1$HNMR (400 MHZ, $CDCl_3$): δ 7.80 (dd, J=7.8, 1.3 Hz, 1H), 7.13 (dtd, J=24.0, 7.7, 1.3 Hz, 2H), 6.87 (dd, J=7.5, 1.4 Hz, 1H), 3.43 (s, 2H), 1.63 (s, 9H), 1.27 (s, 12H).

Intermediate 2:

2-(3-(tert-butoxycarbonyl)-2-oxo-2,3-dihydro-1H-benzo[d]imidazol-1-yl)acetic acid

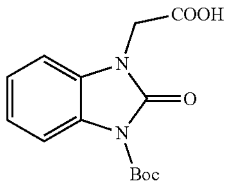 [SMILES: CC(C)(C)OC(=O)n1c(=O)n(CC(=O)O)c2ccccc21]

Step A: tert-butyl 3-(2-ethoxy-2-oxoethyl)-2-oxo-2,3-dihydro-1H-benzo[d]imidazole-1-carboxylate

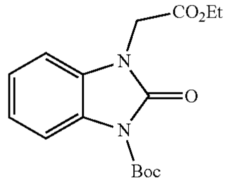 [SMILES: CCOC(=O)Cn1c(=O)n(C(=O)OC(C)(C)C)c2ccccc21]

Tert-butyl 2-oxo-2,3-dihydro-1H-benzo[d]imidazole-1-carboxylate (0.275 g, 1.174 mmol) and potassium carbonate (0.324 g, 2.348 mmol) were added to an 8 ml vial, then acetonitrile (2 ml) followed by ethyl bromoacetate (0.261 ml, 2.348 mmol) was added. The reaction mixture was then heated to 60° C. for 3 hours. When the reaction was done the reaction mixture was evaporated under reduced pressure and then purified by silica gel column chromatography with hexanes and ethyl acetate as eluent. LC/MS (m/z): 265 (M+H)+(observed as loss of/Bu).

Step B: 2-(3-(tert-butoxycarbonyl)-2-oxo-2,3-dihydro-1H-benzo[d]imidazol-1-yl)acetic acid

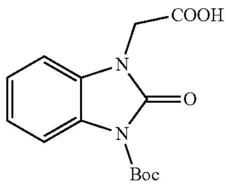 [SMILES: CC(C)(C)OC(=O)n1c(=O)n(CC(=O)O)c2ccccc21]

Tert-butyl 3-(2-ethoxy-2-oxoethyl)-2-oxo-2,3-dihydro-1H-benzo[d]imidazole-1-carboxylate (340 mg, 1.061 mmol) and lithium hydroxide (50.8 mg, 2.123 mmol) were added to a 20 ml vial. Then dioxane and water (1:1) 1 ml were added and the reaction mixture was stirred for 1 hour at room temperature. Water was added and the reaction mixture was extracted with ethyl acetate. The water layer was then made acidic with 1 M HCl, extracted with ethyl acetate and the combined organics were dried with magnesium sulfate, filtered and evaporated in vacuo to afforded the desired product which was used as is without further purification. LC/MS (m/z): 237 (M+H)+(observed as loss of/Bu).

Intermediate 3:

1-(difluoromethyl)-1,3-dihydro-2H-benzo[d]imidazol-2-one

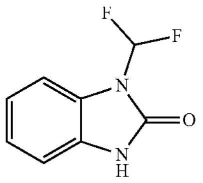 [SMILES: O=c1[nH]c2ccccc2n1C(F)F]

Step A: 2-chloro-1-(difluoromethyl)-1H-benzo[d]imidazole

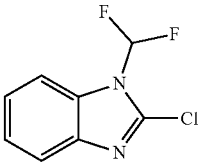 [SMILES: FC(F)n1c(Cl)nc2ccccc21]

2-chloro-1H-benzo[d]imidazole (0.63 g, 4.13 mmol) was dissolved in ACN (10 ml) and diethyl (bromodifluoromethyl)phosphonate (1.1 g, 4.12 mmol) and potassium fluoride (0.48 g, 8.26 mmol) were added at room temperature. The reaction mixture was stirred at room temperature for 15 hours. Then the solvent was removed under reduced pressure, and the residue was dissolved in water (30 ml) and EtOAc (20 ml). The organic layer was separated, the aqueous was re-extracted with EtOAc (20 ml×2), and the combined organic layers were washed with brine (10 ml), dried over anhydrous $Na_2SO_4$, filtered and concentrated under reduced pressure. The residue was purified by silica gel chromatography with ethyl acetate and petroleum ether as eluent. It was isolated as a solid. LCMS (ESI) m/z: 203 $[M+H]^+$.

Step B: 1-(difluoromethyl)-1,3-dihydro-2H-benzo[d]imidazol-2-one

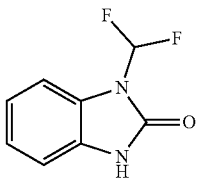 [SMILES: O=c1[nH]c2ccccc2n1C(F)F]

2-chloro-1-(difluoromethyl)-1H-benzo[d]imidazole (263 mg, 1.298 mmol) was dissolved in acetic acid (5 ml) and the mixture was stirred at 100° C. for 1 hour. After this time, the mixture was concentrated under reduced pressure to afford a crude solid, which was used directly in the next step without any further purification. LCMS (ESI) m/z: 185 $[M+H]^+$.

Intermediate 4:

3-((2-oxo-2,3-dihydro-1H-benzo[d]imidazol-1-yl)methyl)benzoic acid

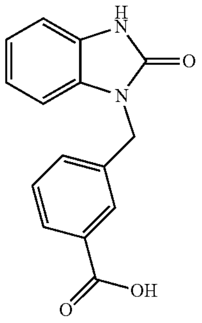 [SMILES: O=C(O)c1cccc(Cn2c(=O)[nH]c3ccccc32)c1]

Step A: methyl 3-((2-oxo-3-(prop-1-en-2-yl)-2,3-dihydro-1H-benzo[d]imidazol-1-yl)methyl)benzoate

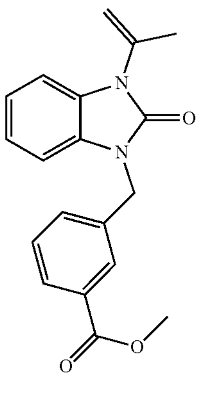 [SMILES: C=C(C)n1c(=O)n(Cc2cccc(C(=O)OC)c2)c2ccccc21]

Potassium carbonate (3173 mg, 22.96 mmol) and 1-(prop-1-en-2-yl)-1,3-dihydro-2H-benzo[d]imidazol-2-one (2000 mg, 11.48 mmol) were added to a 250 mL round bottom flask. Acetonitrile (25 ml) and methyl 3-(bromomethyl)benzoate (2630 mg, 11.48 mmol) were added portion wise over 5 minutes and the reaction mixture was stirred at room temperature for 15 hours. Then, the reaction mixture was filtered through CELITE and evaporated in vacuo. LCMS (ESI) m/z: 323 $[M+H]^+$.

Step B: methyl 3-((2-oxo-2,3-dihydro-1H-benzo[d]imidazol-1-yl)methyl)benzoate

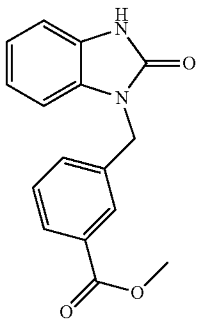 [SMILES: COC(=O)c1cccc(Cn2c(=O)[nH]c3ccccc32)c1]

Methyl 3-((2-oxo-3-(prop-1-en-2-yl)-2,3-dihydro-1H-benzo[d]imidazol-1-yl)methyl)benzoate (3700 mg, 11.48 mmol) was dissolved in methanol (25 ml). Water (5 ml) was added, and the reaction mixture was placed into an ice bath. Next, hydrochloric acid (4 M in dioxanes, 8.61 ml, 34.4 mmol) was added slowly, and the reaction mixture was stirred at room temperature for 1 hour. 6M $HCl_{aq}$ (1 ml) was added and the reaction mixture was heated to 50° C. for 2 hours. Then, the solvent was evaporated in vacuo. The residue was purified by silica gel chromatography with hexanes and ethyl acetate as the eluent. LCMS (ESI) m/z: 283 $[M+H]^+$.

Step C: 3-((2-oxo-2,3-dihydro-1H-benzo[d]imidazol-1-yl)methyl)benzoic acid

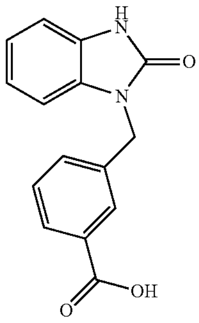 [SMILES: O=C(O)c1cccc(Cn2c(=O)[nH]c3ccccc32)c1]

Methyl 3-((2-oxo-2,3-dihydro-1H-benzo[d]imidazol-1-yl)methyl)benzoate (1400 mg, 4.96 mmol) was added to a 20 ml vial and dissolved in THF: water (3:1) (10 ml). Lithium hydroxide (178 mg, 7.44 mmol) was added portionwise over five minutes, and the mixture was allowed to stir for 2 hours at room temperature. The resulting reaction was evaporated in vacuo. 10 ml of DCM was added followed by 5 ml of 0.5 M NaOH. The organics were removed, and then the aqueous layer was acidified with 6M HCl until a pH of around 2-3. The formed solid was filtered and washed with DCM and used as is. LCMS (ESI) m/z: 269 $[M+H]^+$.

Intermediate 5:

2-(3-((2-oxo-2,3-dihydro-1H-benzo[d]imidazol-1-yl)methyl)phenyl)acetic acid

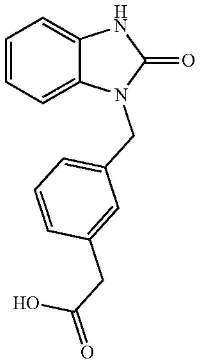 [SMILES: O=C(O)Cc1cccc(Cn2c(=O)[nH]c3ccccc32)c1]

Step A: tert-butyl 2-(3-((2-oxo-2,3-dihydro-1H-benzo[d]imidazol-1-yl)methyl)phenyl)acetate

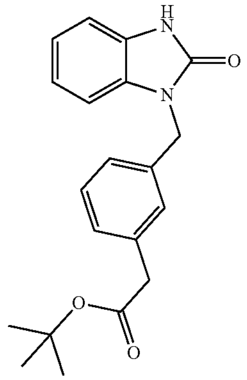 [SMILES: CC(C)(C)OC(=O)Cc1cccc(Cn2c(=O)[nH]c3ccccc32)c1]

Cuprous iodide (166 mg, 0.869 mmol), L-hydroxyproline (228 mg, 1.739 mmol), potassium phosphate (1845 mg, 8.69 mmol), and methyl (2-bromophenyl)carbamate (1000 mg, 4.35 mmol) were added to a vial under nitrogen. DMSO (11 ml) was added followed by tert-butyl 2-(3-(aminomethyl)phenyl)acetate (962 mg, 4.35 mmol). The reaction mixture was purged with nitrogen, sealed and heated to 130° C. After 18 hours, the reaction mixture was cooled to room temperature and filtered over CELITE, rinsing with ethyl acetate. The combined organics were concentrated under reduced pressure, washed with brine, dried over magnesium sulfate, filtered, and concentrated under reduced pressure. The residue was purified by silica gel chromatography with hexanes and ethyl acetate as eluent. LCMS (ESI) m/z: 361 $[M+Na]^+$.

Step B: 2-(3-((2-oxo-2,3-dihydro-1H-benzo[d]imidazol-1-yl)methyl)phenyl)acetic acid

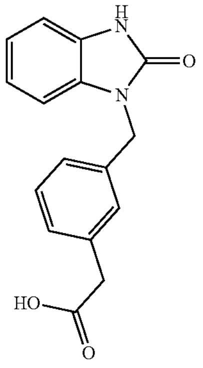 [SMILES: O=C(O)Cc1cccc(Cn2c(=O)[nH]c3ccccc32)c1]

tert-butyl 2-(3-((2-oxo-2,3-dihydro-1H-benzo[d]imidazol-1-yl)methyl)phenyl)acetate (451.4 mg, 1.334 mmol), TFA (2.00 ml), and dioxane (2.00 ml) were added to a vial. The vial was sealed and stirred and heated to 60° C. for 24 hours. DCM was added and the mixture was washed with brine, and the combined organics were were dried over magnesium sulfate, filtered, and concentrated under reduced pressure. LCMS (ESI) m/z: 283 $[M+H]^+$.

Intermediate 6:

2-(4-((2-oxo-2,3-dihydro-1H-benzo[d]imidazol-1-yl)methyl)phenyl)acetic acid

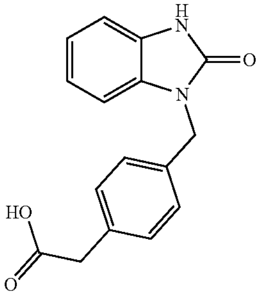 [SMILES: O=C(O)Cc1ccc(Cn2c(=O)[nH]c3ccccc32)cc1]

Step A: ethyl 2-(4-(((2-nitrophenyl)amino)methyl)phenyl)acetate

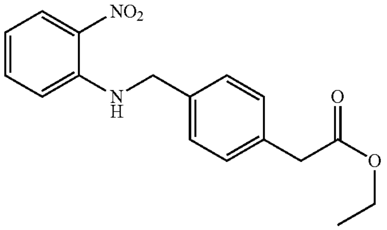

Ethyl 2-(4-(aminomethyl)phenyl)acetate, HCl was added to a 250 ml round bottom flask followed by DMF (15 ml), and the mixture was placed in a water bath. Potassium carbonate (4.04 g, 29.3 mmol) was added to the flask followed by the dropwise addition of 1-fluoro-2-nitrobenzene (1.371 ml, 13 mmol). The reaction was filtered and evaporated in vacuo to afford the crude material which was taken on to the next step. LCMS (ESI) m/z: 315 $[M+H]^+$.

Step B: ethyl 2-(4-(((2-aminophenyl)amino)methyl)phenyl)acetate

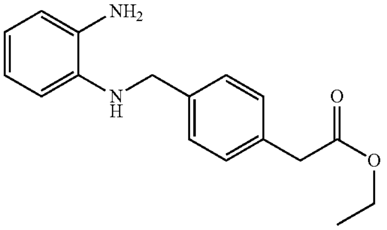 [SMILES: CCOC(=O)Cc1ccc(CNc2ccccc2[N+](=O)[O-])cc1]

Zinc (4.67 g, 71.5 mmol) was added to a 500 ml round bottom flask followed by 75 ml of ethanol. The mixture was cooled to 0° C. and acetic acid (4.09 ml, 71.5 mmol) was added. After 5 minutes, ethyl 2-(4-(((2-nitrophenyl)amino)methyl)phenyl)acetate (4.09 g, 13 mmol) was added in 15 ml of ethanol and the reaction was allowed to stir at room temperature under nitrogen. After 1 hour, additional zinc (500 mgs) was added along with 1 ml of acetic acid. The reaction mixture was then heated to 35° C. for 5 hours, filtered through CELITE and evaporated in vacuo. The product was dissolved in ethyl acetate and washed with sodium bicarbonate. The combined organics were then dried with magnesium sulfate, filtered, and evaporated in vacuo. The product was taken on crude. LCMS (ESI) m/z: 285 $[M+H]^+$.

Step C: ethyl 2-(4-((2-oxo-2,3-dihydro-1H-benzo[d]imidazol-1-yl)methyl)phenyl)acetate

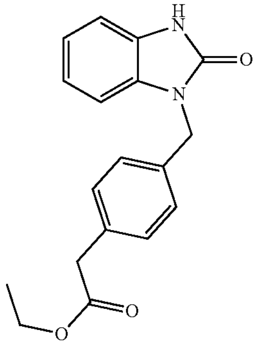 [SMILES: CCOC(=O)Cc1ccc(Cn2c(=O)[nH]c3ccccc32)cc1]

Ethyl 2-(4-(((2-aminophenyl)amino)methyl)phenyl)acetate (3.5 g, 12.31 mmol) was dissolved in 25 ml of DCM. CDI (1.996 g, 12.31 mmol) was added along with an additional 20 ml of DCM, a water bath was placed under the flask, and it was stirred at room temperature overnight. Next, the reaction was washed with 1 M HCl and brine. The organics were dried with magnesium sulfate, filtered and evaporated in vacuo to give the desired crude material. The crude residue was purified by silica gel chromatography with hexanes and ethyl acetate as eluent. LCMS (ESI) m/z: 311 $[M+H]^+$.

Step D: 2-(4-((2-oxo-2,3-dihydro-1H-benzo[d]imidazol-1-yl)methyl)phenyl)acetic acid

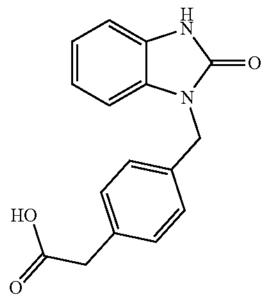 [SMILES: O=C(O)Cc1ccc(Cn2c(=O)[nH]c3ccccc32)cc1]

Ethyl 2-(4-((2-oxo-2,3-dihydro-1H-benzo[d]imidazol-1-yl)methyl)phenyl)acetate (530 mg, 1.708 mmol), NaOH (1708 μl, 3.42 mmol), and dioxane (3.4 ml) were added to a vial. The vial was sealed and heated to 65° C. overnight. After this time, the reaction mixture was cooled to room temperature, and concentrated under reduced pressure. The residue was dissolved in ethyl acetate and acidified to pH 1 using 4M HCl in dioxane. The solvents were then removed in vacuo, and the solid was further dried on the lyophylizer to afford the product. LCMS (ESI) m/z: 283 $[M+H]^+$.

Example 1

Preparation of 1-(4-((2-oxopyrrolidin-1-yl)methyl)benzyl)-1,3-dihydro-2H-benzo[d]imidazol-2-one

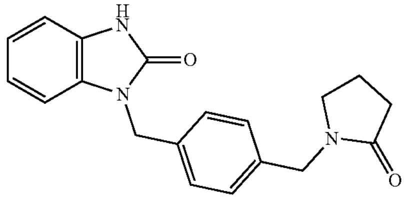 [SMILES: O=C1CCCN1Cc1ccc(Cn2c(=O)[nH]c3ccccc32)cc1]

Step A: 1-(4-bromobenzyl)pyrrolidin-2-one

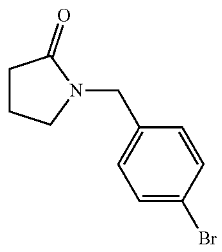 [SMILES: O=C1CCCN1Cc1ccc(Br)cc1]

Sodium hydride (2.376 g, 59.4 mmol) was added to a 500 ml round bottom flask with a stir bar and purged with nitrogen. THF (80 ml) was added, and the mixture was cooled to 0° C. with an ice bath. The reaction mixture was stirred for 5 minutes. Pyrrolidin-2-one (4.10 ml, 54 mmol) was added slowly, and the reaction mixture was stirred for 30 minutes. 1-bromo-4-(bromomethyl)benzene (13.50 g, 54.0 mmol) was added slowly as a solution in THF (40 ml). The reaction mixture was slowly warmed to room temperature and then stirred for 3 days. The reaction mixture was slowly quenched with water while the mixture was cooled by a water bath. The reaction mixture was added to a separatory funnel and extracted 3 times with ethyl acetate. The combined organics were dried over magnesium sulfate, filtered and then concentrated under reduced pressure. The crude material was purified by silica gel column chromatography with methanol in dichloromethane as the eluent. LC/MS (m/z): 254 (M+H)+

Step B: tert-butyl 2-oxo-3-(4-((2-oxopyrrolidin-1-yl)methyl)benzyl)-2,3-dihydro-1H-benzo[d]imidazole-1-carboxylate

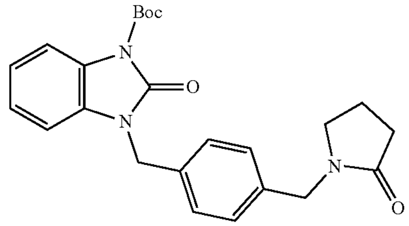 [SMILES: CC(C)(C)OC(=O)n1c(=O)n(Cc2ccc(CN3CCCC3=O)cc2)c2ccccc21]

Tert-butyl 2-oxo-3-((4,4,5,5-tetramethyl-1,3,2-dioxaborolan-2-yl)methyl)-2,3-dihydro-1H-benzo[d]imidazole-1-carboxylate (14.97 g, 40 mmol) (Intermediate 1), 1-(4-bromobenzyl)pyrrolidin-2-one (10.67 g, 42.0 mmol), cesium carbonate (39.1 g, 120 mmol), APhos Pd G3 (0.635 g, 1.000 mmol), and APhos Pd G4 (0.649 g, 1.000 mmol) were added to 500 ml round bottom flask with stir bar. The flask was evacuated and back-filled with nitrogen twice. Dioxane (180 ml) and water (18 ml) were added. The reaction mixture was then sealed and heated to 75° C. for 15 hours. When finished, the reaction mixture was cooled to room temperature and diluted with water. The mixture was then extracted 3 times with ethyl acetate, and the organics were combined, dried with magnesium sulfate, filtered and evaporated under reduced pressure. The crude material was purified on silica gel with methanol in dichloromethane as the eluent. LC/MS (m/z): 444 (M+Na)+

Step C: 1-(4-((2-oxopyrrolidin-1-yl)methyl)benzyl)-1,3-dihydro-2H-benzo[d]imidazol-2-one

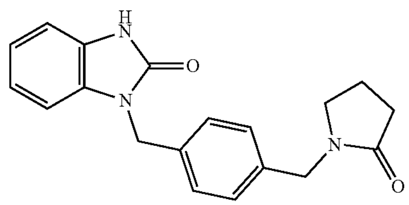 [SMILES: O=C1CCCN1Cc1ccc(Cn2c(=O)[nH]c3ccccc32)cc1]

tert-butyl 2-oxo-3-(4-((2-oxopyrrolidin-1-yl)methyl)benzyl)-2,3-dihydro-1H-benzo[d]imidazole-1-carboxylate (7.72 g, 18.32 mmol) was added to 40 ml vial with stir bar. Formic acid (14.05 ml, 366 mmol) was then added to the vial. The reaction mixture was stirred at room temperature for 3 hours (alternatively TFA could be used for this deprotection as well) and diluted with water. The mixture was then extracted 3 times with dichloromethane, and the organics were combined, dried with magnesium sulfate, filtered and evaporated under reduced pressure. The crude material was purified on silica gel with methanol in dichloromethane as the eluent. $^1$H NMR (600 MHz, DMSO-$d_6$) δ 10.94 (s, 1H), 7.28 (d, J=8.1 Hz, 2H), 7.16 (d, J=8.1 Hz, 2H), 7.05-6.91 (m, 4H), 4.97 (s, 2H), 4.31 (s, 2H), 3.18 (t, J=7.0 Hz, 2H), 2.25 (t, J=8.1 Hz, 2H), 1.93-1.85 (m, 2H). LC/MS (m/z): 322 (M+H)+

Example 2

Preparation of 1-(4-((2-oxo-2,5-dihydro-1H-pyrrol-1-yl)methyl)benzyl)-1,3-dihydro-2H-benzo[d]imidazol-2-one

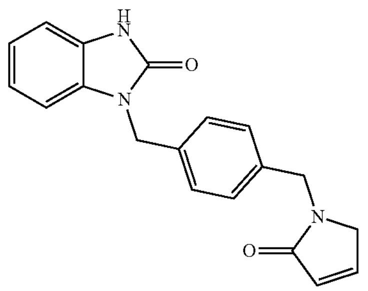 [SMILES: O=C1C=CCN1Cc1ccc(Cn2c(=O)[nH]c3ccccc32)cc1]

Step A: N-(4-bromobenzyl) prop-2-en-1-amine

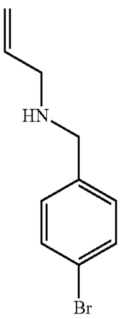

3-chloroprop-1-ene (0.823 g, 10.75 mmol) was added to a mixture of (4-bromophenyl)methanamine (2 g, 10.75 mmol) and $Cs_2CO_3$ (5.25 g, 16.12 mmol) in DMF (15 mL) at 20° C. The resulting mixture was stirred at 50° C. for 12 hours. After 12 hours the reaction mixture was dried over $Na_2SO_4$ and filtered. LC/MS (m/z): 228 (M+H)+.

Step B: N-allyl-N-(4-bromobenzyl)acrylamide

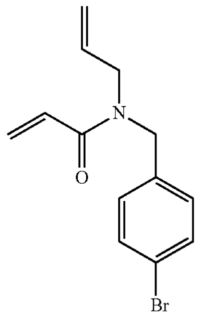 [SMILES: C=CCN(Cc1ccc(Br)cc1)C(=O)C=C]

A mixture of N-(4-bromobenzyl) prop-2-en-1-amine (800 mg, 3.54 mmol), DIEA (1.236 mL, 7.08 mmol) and acryloyl chloride (0.288 mL, 3.54 mmol) in DMF (15 mL) was stirred at 20° C. for 12 hours. After 12 hours the reaction mixture was extracted with water (200 mL) and EtOAc (100 mL). The organic layer was dried over $Na_2SO_4$ and concentrated in vacuo. The residue was purified by flash silica gel chromatography (ISCO®; 12 g SepaFlash® Silica Flash Column, eluent of 0-35% ethyl acetate/pet. ether gradient @ 40 mL/min) to afford N-allyl-N-(4-bromobenzyl) acrylamide. LC/MS (m/z): 280 (M+H)+.

Step C: 1-(4-bromobenzyl)-1,5-dihydro-2H-pyrrol-2-one

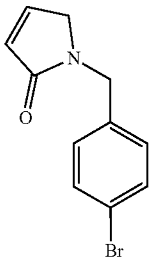 [SMILES: O=C1C=CCN1Cc1ccc(Br)cc1]

A mixture of (1,3-bis(2,4,6-trimethylphenyl)-2-imidazolidinylidene)dichloro-(phenylmethylene)(tricyclohexylphosphine)ruthenium (0.909 g, 1.071 mmol), and N-allyl-N-(4-bromobenzyl) acrylamide (2 g, 7.14 mmol) in DCM (60 ml) was degassed and backfilled with $N_2$ (three times). The mixture was heated to 25° C. for 16 hours. After 16 hours the solvent was removed under reduced pressure, and the residue was dissolved in water (10 mL) and EtOAc (10 mL). The organic layer was separated and the aqueous was re-extracted with EtOAc (10 mL*3) and the combined organic layers were washed with brine (10 mL), dried over anhydrous $Na_2SO_4$, filtered and concentrated under reduced pressure. The residue was purified by flash silica gel chromatography (ISCO®; 12 g SepaFlash® Silica Flash Column, eluent of [0~30]% ethyl acetate/pet. ether gradient @ 35 mL/min) to afford 1-(4-bromobenzyl)-1,5-dihydro-2H-pyrrol-2-one. LC/MS (m/z): 254 (M+H)+.

Step D: 1-(4-((2-oxo-2,5-dihydro-1H-pyrrol-1-yl)methyl)benzyl)-1,3-dihydro-2H-benzo[d]imidazol-2-one

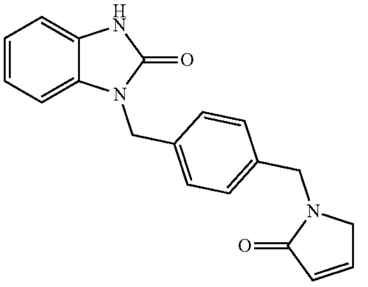 [SMILES: O=C1C=CCN1Cc1ccc(Cn2c(=O)[nH]c3ccccc32)cc1]

A mixture of tert-butyl 2-oxo-3-((4,4,5,5-tetramethyl-1,3,2-dioxaborolan-2-yl)methyl)-2,3-dihydro-1H-benzo[d]imidazole-1-carboxylate (742 mg, 1.983 mmol), $K_3PO_4$ (1052 mg, 4.96 mmol), 1-(4-bromobenzyl)-1,5-dihydro-2H-pyrrol-2-one (500 mg, 1.983 mmol) and Pd(dtbpf)$Cl_2$ (129 mg, 0.198 mmol) in 1,4-Dioxane (5 ml) and water (1 ml) was degassed and backfilled with $N_2$ (three times). The mixture was heated to 90° C. for 12 hours. After 12 hours the solvent was removed under reduced pressure, and the residue was dissolved in water (10 mL) and EtOAc (10 mL). The organic layer was separated, and the aqueous layer was re-extracted with EtOAc (10 mL*3). The combined organic layers were washed with brine (10 mL), dried over anhydrous $Na_2SO_4$, filtered and concentrated under reduced pressure to afford crude product. The residue was purified by normal-phase chromatography. Using heptane (solvent A) and ethanol (solvent B) as mobile phases, a gradient of 0% to 5% solvent B was run at 25 mL/min for 9 minutes to afford 1-(4-((2-oxo-2,5-dihydro-1H-pyrrol-1-yl)methyl)benzyl)-1,3-dihydro-2H-benzo[d]imidazol-2-one. $^1H$ NMR (400 MHZ, METHANOL-d4) δ=7.31 (d, J=8.1 Hz, 2H), 7.27-7.19 (m, 3H), 7.09-6.95 (m, 4H), 6.15 (br d, J=5.9 Hz, 1H), 5.07 (s, 2H), 4.61 (s, 2H), 3.98 (s, 2H). LC/MS (m/z): 320 (M+H)+.

Example 3

Preparation of 1-(4-((1,3,4-oxadiazol-2-yl)methyl)benzyl)-1,3-dihydro-2H-benzo[d]imidazol-2-one

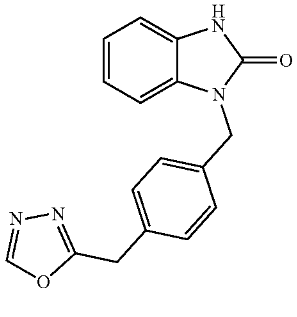 [SMILES: O=c1[nH]c2ccccc2n1Cc1ccc(Cc2nnco2)cc1]

Step A: 2-(4-bromophenyl)acetohydrazide

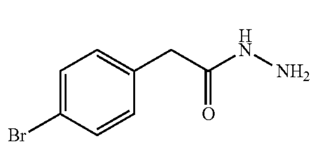 [SMILES: NNC(=O)Cc1ccc(Br)cc1]

Ethyl 2-(4-bromophenyl)acetate (15.25 g, 62.7 mmol) in ethanol (150 ml) was added to a round bottom flask under nitrogen. Hydrazine (35% in water) (11.25 ml, 125 mmol) was added, and the reaction mixture was stirred at room temp under nitrogen overnight. Then the reaction mixture was evaporated in vacuo, and the precipitate was filtered off and washed with diethyl ether and dried. LC/MS (m/z): 229 (M+H)+

Step B: 2-(4-bromobenzyl)-1,3,4-oxadiazole

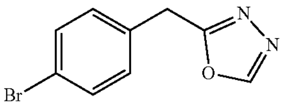 [SMILES: Brc1ccc(Cc2nnco2)cc1]

Ts-OH (0.673 g, 3.54 mmol) and 2-(4-bromophenyl)acetohydrazide (8.1 g, 35.4 mmol) were added to a 500 ml round bottom flask. Toluene (100 ml) and triethoxymethane (14.72 ml, 88 mmol) were added, and the reaction mixture was heated to 100° C. for 2 hours with a reflux condenser attached and under nitrogen. The reaction mixture was then cooled to room temperature, evaporated in vacuo, dry loaded onto a cartridge with silica gel and purified via silica gel column chromatography using a gradient of hexanes and ethyl acetate. LC/MS (m/z): 239 (M+H)+

Utilizing the procedures outlined in Steps B-C in Example 1, 2-(4-bromobenzyl)-1,3,4-oxadiazole was elaborated to the final product 1-(4-((1,3,4-oxadiazol-2-yl)methyl)benzyl)-1,3-dihydro-2H-benzo[d]imidazol-2-one in Steps C and D below.

Step C: tert-butyl 3-(4-((1,3,4-oxadiazol-2-yl)methyl)benzyl)-2-oxo-2,3-dihydro-1H-benzo[d]imidazole-1-carboxylate. LC/MS (m/z): 429 (M+Na)+

Step D: 1-(4-((1,3,4-oxadiazol-2-yl)methyl)benzyl)-1,3-dihydro-2H-benzo[d]imidazol-2-one. 1H NMR (600 MHZ, DMSO-$d_6$) δ 10.94 (s, 1H), 9.10 (s, 1H), 7.31-7.22 (m, 4H), 7.03-6.90 (m, 4H), 4.97 (s, 2H), 4.25 (s, 2H). LC/MS (m/z): 306 (M+H)+

Example 4

Preparation of 1-(4-((1,3,4-oxadiazol-2-yl)methyl)-3-chlorobenzyl)-1,3-dihydro-2H-benzo[d]imidazol-2-one

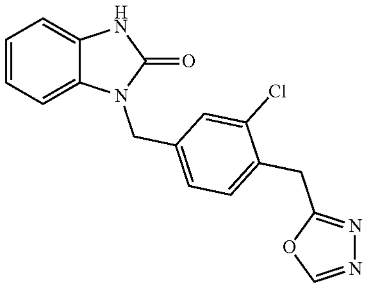 [SMILES: O=c1[nH]c2ccccc2n1Cc1ccc(Cc2nnco2)c(Cl)c1]

Utilizing the procedures outlined in Steps A-D in Example 3, ethyl-2-(4-bromo-2-chlorophenyl)acetate was elaborated to the final product 1-(4-((1,3,4-oxadiazol-2-yl)methyl)-3-chlorobenzyl)-1,3-dihydro-2H-benzo[d]imidazol-2-one.

Step A: 2-(4-bromo-2-chlorophenyl)acetohydrazide. LC/MS (m/z): 265 (M+H)+

Step B: 2-(4-bromo-2-chlorobenzyl)-1,3,4-oxadiazole. LC/MS (m/z): 275 (M+H)+

Step C: tert-butyl 3-(4-((1,3,4-oxadiazol-2-yl)methyl)-3-chlorobenzyl)-2-oxo-2,3-dihydro-1H-benzo[d]imidazole-1-carboxylate. LC/MS (m/z): 341 (M+H)+(observe as loss of Boc)

Step D: 1-(4-((1,3,4-oxadiazol-2-yl)methyl)-3-chlorobenzyl)-1,3-dihydro-2H-benzo[d]imidazol-2-one. $^{1}$H NMR (600 MHZ, DMSO-$d_6$) δ 10.98 (s, 1H), 9.11 (s, 1H), 7.46-7.40 (m, 2H), 7.27 (d, J=7.9 Hz, 1H), 7.08 (d, J=7.8 Hz, 1H), 7.03-6.92 (m, 3H), 5.01 (s, 2H), 4.36 (s, 2H). LC/MS (m/z): 341 (M+H)+

Example 5

Preparation of N-(3-methoxy-4-((2-oxo-2,3-dihydro-1H-benzo[d]imidazol-1-yl)methyl)benzyl)acetamide

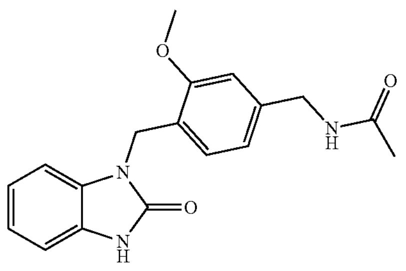 [SMILES: COc1cc(CNC(C)=O)ccc1Cn1c(=O)[nH]c2ccccc21]

Step A: N-(4-bromo-3-methoxybenzyl)acetamide

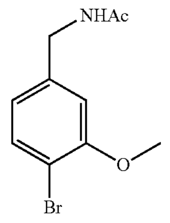

4-bromo-3-methoxybenzonitrile (1 g, 4.72 mmol) and acetic anhydride (0.667 ml, 7.07 mmol) were added to a dried round bottom flask and dissolved in THF (20 ml) under a nitrogen atmosphere. Raney nickel (0.554 g, 4.72 mmol) was then added to the flask. The mixture was degassed and backfilled with hydrogen (three times). The resulting mixture was stirred under hydrogen (Pressure: 30 psi) at 25° C. for 12 hours. The mixture was filtered and the filtrate was concentrated under reduced pressure. The residue was purified by flash silica gel chromatography with ethyl acetate and petroleum ether as eluent. Material was isolated as a solid. LCMS (ESI) m/z: 258 $[M+H]^{+}$.

Utilizing the procedures outlined in Steps B-C in Example 1, N-(4-bromo-3-methoxybenzyl)acetamide was elaborated to the final product N-(3-methoxy-4-((2-oxo-2,3-dihydro-1H-benzo[d]imidazol-1-yl)methyl)benzyl)acetamide.

Step B: tert-butyl 3-(4-(acetamidomethyl)-2-methoxybenzyl)-2-oxo-2,3-dihydro-1H-benzo[d]imidazole-1-carboxylate. LC/MS (m/z): 326 (M+H)+ (observe as loss of Boc)

Step C: N-(3-methoxy-4-((2-oxo-2,3-dihydro-1H-benzo[d]imidazol-1-yl)methyl)benzyl)acetamide. $^{1}$H NMR (400 MHZ, MeOH-d4) δ 7.10-7.05 (m, 1H), 7.05-7.00 (m, 1H), 7.00-6.90 (m, 4H), 6.78 (d, J=6.7 Hz, 1H), 5.04 (s, 2H), 4.31 (s, 2H), 3.89 (s, 3H), 1.97 (s, 3H). LCMS (ESI) m/z: 326 [M+H]+.

Example 6

Preparation of N-((5-((2-oxo-2,3-dihydro-1H-benzo[d]imidazol-1-yl)methyl)thiophen-2-yl)methyl)methanesulfonamide

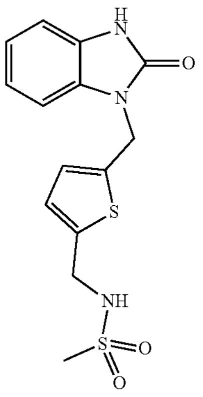 [SMILES: CS(=O)(=O)NCc1ccc(Cn2c(=O)[nH]c3ccccc32)s1]

Step A: N-(thiophen-2-ylmethyl)methanesulfonamide

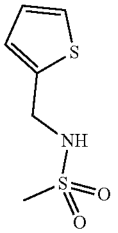

Thiophen-2-ylmethanamine (5.0 g, 44.2 mmol) was dissolved in DCM (50 ml). Pyridine (5.34 ml, 66.3 mmol) was added followed by methanesulfonyl chloride (6.05 g, 52.8 mmol) at 0° C. After stirring the mixture at room temperature for 15 hours, the reaction was quenched by the addition of 1M HCl solution (100 ml). The reaction mixture was extracted with DCM (50 ml×2), washed with brine (30 ml), dried over anhydrous $Na_2SO_4$, filtered and concentrated under reduced pressure. The residue was purified by flash silica gel chromatography with ethyl acetate and petroleum ether as eluent. $^1H$ NMR (500 MHz, $CDCl_3$) § 7.29 (d, J=5.0 Hz, 1H), 7.05 (d, J=2.9 Hz, 1H), 6.99 (dd, J=3.6, 5.0 Hz, 1H), 4.80 (br s, 1H), 4.53 (d, J=6.0 Hz, 2H), 2.88 (s, 3H).

Step B: N-((5-bromothiophen-2-yl)methyl)methanesulfonamide

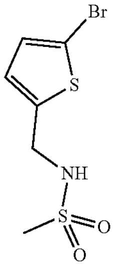

N-(thiophen-2-ylmethyl)methanesulfonamide (1 g, 5.23 mmol) was dissolved in DCM (10 ml). N-bromosuccinimide (1.02 g, 5.73 mmol) was added at room temperature, and the mixture was stirred for 1 hour. The reaction was quenched with saturated aqueous $Na_2SO_3$ solution (20 ml). The mixture was extracted with DCM (50 ml×2), and the combined organic layers were washed with brine (20 ml), dried over anhydrous $Na_2SO_4$, filtered and concentrated under reduced pressure. The residue was purified by flash silica gel chromatography with ethyl acetate and petroleum ether as eluent. $^1H$ NMR (400 MHZ, $CDCl_3$) δ 6.93 (d, J=3.5 Hz, 1H), 6.81 (d, J=3.9 Hz, 1H), 4.83 (br s, 1H), 4.44 (d, J=5.5 Hz, 2H), 2.91 (s, 3H).

Utilizing the procedures outlined in Steps B-C in Example 1 N-((5-bromothiophen-2-yl)methyl)methanesulfonamide was elaborated to the final product N-((5-((2-oxo-2,3-dihydro-1H-benzo[d]imidazol-1-yl)methyl)thiophen-2-yl)methyl)methanesulfonamide in Steps C-D below.

Step C: tert-butyl 3-((5-(methylsulfonamidomethyl)thiophen-2-yl)methyl)-2-oxo-2,3-dihydro-1H-benzo[d]imidazole-1-carboxylate LCMS (ESI) m/z: 338 $[M+H]^+$ (observed as loss of Boc).

Step D: N-((5-((2-oxo-2,3-dihydro-1H-benzo[d]imidazol-1-yl)methyl)thiophen-2-yl)methyl)methanesulfonamide. $^1H$ NMR (400 MHZ, MeOH-d4) δ 7.15-7.09 (m, 1H), 7.08-7.02 (m, 3H), 7.00 (d, J=3.4 Hz, 1H), 6.88 (d, J=3.4 Hz, 1H), 5.21 (s, 2H), 4.34 (s, 2H), 2.77 (s, 3H). LCMS (ESI) m/z: 338 $[M+H]^+$ The Examples in Table 1 were synthesized according to the methods described in Example 1, Steps B-C, employing the appropriate aryl bromide starting materials.

TABLE 1

| Example No. | Structure | Name | Observed |
|---|---|---|---|
| Example 7 | 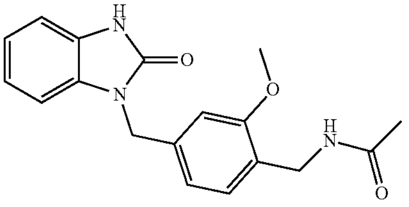 [SMILES: COc1cc(Cn2c(=O)[nH]c3ccccc32)ccc1CNC(C)=O] | N-({2-methoxy-4-[(2-oxo-2,3-dihydro-1H-benzimidazol-1-yl)methyl]phenyl}methyl)acetamide | 326 [M + H]+ |
| Example 8 | 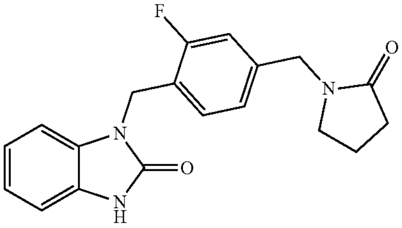 [SMILES: O=C1CCCN1Cc1ccc(Cn2c(=O)[nH]c3ccccc32)c(F)c1] | 1-({2-fluoro-4-[(2-oxopyrrolidin-1-yl)methyl]phenyl}methyl)-1,3-dihydro-2H-benzimidazol-2-one | 340 [M + H]+ |

TABLE 1-continued

| Example No. | Structure | Name | Observed |
|---|---|---|---|
| Example 9 | 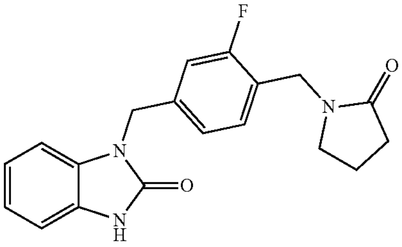 [SMILES: O=C1CCCN1Cc1ccc(Cn2c(=O)[nH]c3ccccc32)cc1F] | 1-({3-fluoro-4-[(2-oxopyrrolidin-1-yl)methyl]phenyl}methyl)-1,3-dihydro-2H-benzimidazol-2-one | 340 [M + H]+ |
| Example 10 | 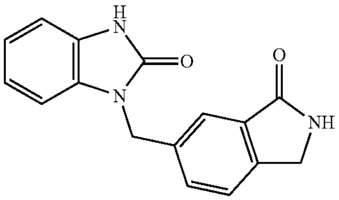 [SMILES: O=C1NCc2ccc(Cn3c(=O)[nH]c4ccccc43)cc21] | 1-[(3-oxo-2,3-dihydro-1H-isoindol-5-yl)methyl]-1,3-dihydro-2H-benzimidazol-2-one | 280 [M + H]+ |

Example 11

Preparation N-(4-((2-oxo-2,3-dihydro-1H-benzo[d]imidazol-1-yl)methyl)benzyl)acetamide

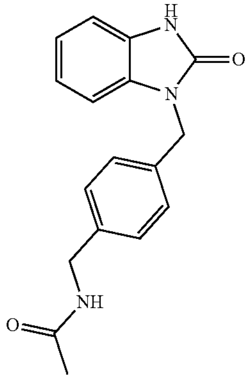 [SMILES: CC(=O)NCc1ccc(Cn2c(=O)[nH]c3ccccc32)cc1]

Step A: N-(4-((2-oxo-2,3-dihydro-1H-benzo[d]imidazol-1-yl)methyl)benzyl)acetamide

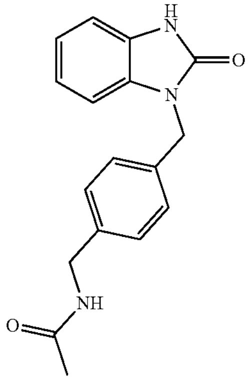 [SMILES: CC(=O)NCc1ccc(Cn2c(=O)[nH]c3ccccc32)cc1]

N-(4-bromobenzyl)acetamide (6.09 g, 26.7 mmol), cesium carbonate (26.1 g, 80 mmol), sSPhos Pd G2 (2.198 g, 2.67 mmol), and tert-butyl 2-oxo-3-((4,4,5,5-tetramethyl-1,3,2-dioxaborolan-2-yl)methyl)-2,3-dihydro-1H-benzo[d]imidazole-1-carboxylate (10 g, 26.7 mmol) (Intermediate 1) were added to a round bottom flask equipped with a stir bar. The mixture was purged with nitrogen for 5 minutes. After 5 minutes, dioxane (81 ml) and water (8.10 ml) were added to the mixture. The reaction mixture was heated to 80° C. for 17 hours, while stirring. After 17 hours, the mixture was cooled to room temperature and concentrated under reduced pressure. Ethyl acetate was added, and the reaction mixture was washed with water. The combined organics were dried over magnesium sulfate, filtered, and concentrated under reduced pressure. The material was dissolved in THF (40 ml), HCl (4 M in dioxane) (40 ml, 160 mmol) was added dropwise to the solution. The mixture was heated to 45° C. for 45 minutes. After 45 minutes, the material was filtered, to afford the title compound. LC/MS (m/z): 296 (M+H)+.

Step B: N-(4-((2-oxo-2,3-dihydro-1H-benzo[d]imidazol-1-yl)methyl)benzyl)acetamide

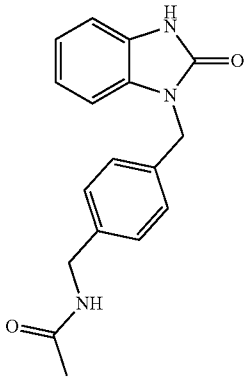 [SMILES: CC(=O)NCc1ccc(Cn2c(=O)[nH]c3ccccc32)cc1]

N-(4-((2-oxo-2,3-dihydro-1H-benzo[d]imidazol-1-yl)methyl)benzyl)acetamide (17.7 g, 59.9 mmol) was added to a round bottom flask. Acetonitrile (144 ml)/water (55.4 ml) were added to the flask. A condenser was attached to the flask, and the flask was heated to 80° C. for 30 minutes. After 30 minutes, the temperature was increased to 95° C. and stirring was resumed. After 15 minutes, ACN (36 ml) and water (14 ml) were added, and the temperature was increased to 105° C. After 1 hour, the mixture was allowed to cool slowly to room temperature, while stirring for 16 hours. After 16 hours, the mixture was filtered. The collected solids were rinsed with cold ACN (cooled to 0° C. with ice bath). The collected solid was dried on the lyopholizer for 16 hours to afford the title compound. LC/MS (m/z): 296 (M+H)+. $^1$H NMR (600 MHZ, DMSO-d6) δ 10.94 (s, 1H), 8.28 (t, J=5.6 Hz, 1H), 7.32-7.16 (m, 4H), 7.05-6.87 (m, 4H), 4.96 (s, 2H), 4.18 (d, J=5.9 Hz, 2H), 1.83 (s, 3H).

Example 12

Preparation of N-(4-((2-oxo-2,3-dihydro-1H-benzo[d]imidazol-1-yl)methyl)benzyl)methanesulfonamide

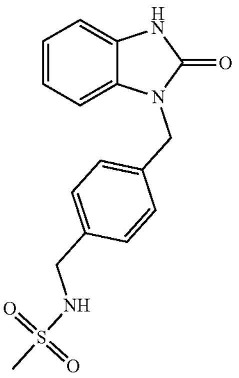 [SMILES: CS(=O)(=O)NCc1ccc(Cn2c(=O)[nH]c3ccccc32)cc1]

Step A: N-(4-bromobenzyl)methanesulfonamide

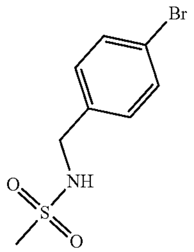

(4-bromophenyl)methanamine (5 g, 26.9 mmol), TEA (9.36 ml, 67.2 mmol) and DCM (100 ml) was added to a vial equipped with a stir bar. Methanesulfonic anhydride (5.62 g, 32.2 mmol) was added at 20° C. in portions, and the mixture was stirred at 20° C. for 2 hours. After 2 hours, water (100 ml) was added, and the reaction mixture was washed with DCM (100 ml×3). The resulting organic phases were washed with brine (20 ml), dried over anhydrous $Na_2SO_4$, filtered, and concentrated under reduced pressure. The residue was purified by flash silica gel chromatography with ethyl acetate and petroleum ether as eluent to afford the title compound. LCMS (ESI) m/z: 286 $[M+Na]^+$.

Step B: tert-butyl 3-(4-(methylsulfonamidomethyl)benzyl)-2-oxo-2,3-dihydro-1H-benzo[d]imidazole-1-carboxylate

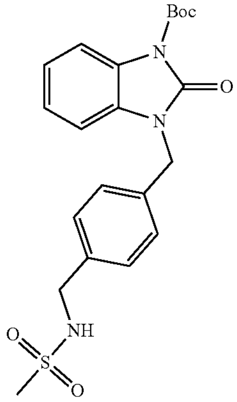 [SMILES: CC(C)(C)OC(=O)n1c(=O)n(Cc2ccc(CNS(C)(=O)=O)cc2)c2ccccc21]

Tert-butyl 2-oxo-3-((4,4,5,5-tetramethyl-1,3,2-dioxaborolan-2-yl)methyl)-2,3-dihydro-1H-benzo[d]imidazole-1-carboxylate (3.18 g, 8.50 mmol), sSPhos Pd G2 (0.137 g, 0.167 mmol), cesium carbonate (5.43 g, 16.66 mmol)), dioxane (30 mL) and water (3 mL) were added to a flask equipped with a stir bar, at 20° C. The reaction mixture was bubbled with a stream of nitrogen for 2 minutes. After 2 minutes, the flask was sealed and heated to 80° C. for 12 hours. After 12 hours, the reaction mixture was diluted with water (100 mL) and washed with ethyl acetate (100 mL*3). The combined organic phases were washed with brine (200 mL), dried over anhydrous $Na_2SO_4$, filtered, and concentrated under reduced pressure. The residue was purified by flash silica gel chromatography with ethyl acetate and petroleum ether as eluent to afford the title compound. LCMS (ESI) m/z: 376 $[M+H]^+$. (observe as loss of Bu)

Step C: N-(4-((2-oxo-2,3-dihydro-1H-benzo[d]imidazol-1-yl)methyl)benzyl)methanesulfonamide

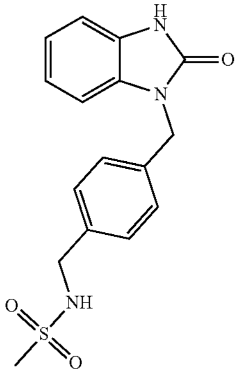 [SMILES: CS(=O)(=O)NCc1ccc(Cn2c(=O)[nH]c3ccccc32)cc1]

Tert-butyl 3-(4-(methylsulfonamidomethyl)benzyl)-2-oxo-2,3-dihydro-1H-benzo[d]imidazole-1-carboxylate (3 g, 6.95 mmol), TFA (2.68 mL, 34.8 mmol), and DCM (15 mL) was added to a vial equipped with a stir bar. The reaction mixture was stirred at 20° C. for 2 hours. After 2 hours, the reaction mixture was concentrated in vaccuo. The resulting material was dissolved in water and $CH_3CN$, and the material was dried on the lyopholizer to afford the title compound. LCMS (ESI) m/z: 332 $[M+H]^+$. $^1H$ NMR (500 MHz, $MeOH-d_4$) δ 7.44-7.27 (m, 4H), 7.20-6.90 (m, 4H), 5.10 (s, 2H), 4.23 (s, 2H), 2.83 (s, 3H).

Example 13

Preparation of: N-methyl-5-((2-oxo-2,3-dihydro-1H-benzo[d]imidazol-1-yl)methyl)thiophene-3-carboxamide

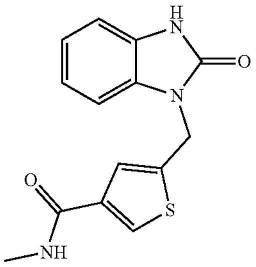 [SMILES: CNC(=O)c1csc(Cn2c(=O)[nH]c3ccccc32)c1]

Step A: 5-bromo-N-methylthiophene-3-carboxamide

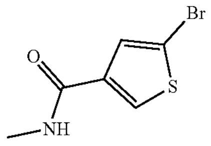

5-bromothiophene-3-carboxylic acid (100 mg, 0.483 mmol), 1-methyl-1H-imidazole (139 mg, 1.690 mmol), methanamine (0.966 mL, 1.932 mmol, 2 M in THF), N-(chloro (dimethylamino)methylene)-N-methylmethanaminium hexafluorophosphate (V) (163 mg, 0.580 mmol), and DCM (3 mL) were added to a vial equipped with a stir bar. The reaction mixture was allowed to stir at 20° C. for 2 hours. After 2 hours, the reaction mixture was filtered. The collected filtrate was concentrated under reduced pressure to afford the crude product. This material was purified by HPLC (water and ACN mobile phase modified with TFA) to afford the title compound. MS (ESI) m/z: 222 $[M+H]^+$.

Step B: tert-butyl 3-((4-(methylcarbamoyl)thiophen-2-yl)methyl)-2-oxo-2,3-dihydro-1H-benzo[d]imidazole-1-carboxylate

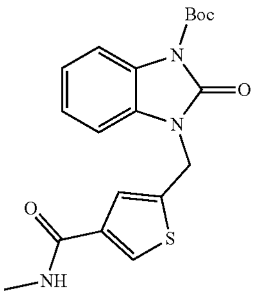 [SMILES: CNC(=O)c1csc(Cn2c(=O)n(C(=O)OC(C)(C)C)c3ccccc32)c1]

Utilizing the procedure in Example 12, 5-bromo-N-methylthiophene-3-carboxamide was elaborated to the title compound. LCMS (ESI) m/z: 288 $[M+H]^+$. (observe as loss of/Bu)

Step C: N-methyl-5-((2-oxo-2,3-dihydro-1H-benzo[d]imidazol-1-yl)methyl)thiophene-3-carboxamide

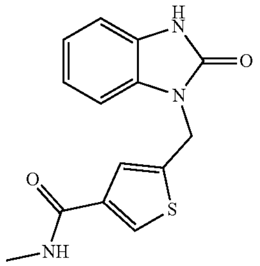 [SMILES: CNC(=O)c1csc(Cn2c(=O)[nH]c3ccccc32)c1]

Tert-butyl 3-((4-(methylcarbamoyl)thiophen-2-yl)methyl)-2-oxo-2,3-dihydro-1H-benzo[d]imidazole-1-carboxylate (20 mg, 0.052 mmol), TFA (1 mL, 12.98 mmol), and DCM (4 mL) were added to a vial equipped with a stir bar. The resulting mixture was stirred at 20° C. for 2.2 hours. After 2.2 hours, the reaction mixture was concentrated under reduced pressure to afford the crude product. This material was purified by HPLC (eluting acetonitrile/water gradient with TFA modifier) to afford the title compound. LCMS (ESI) m/z: 288 $[M+H]^+$.

$^1H$ NMR (500 MHz, MeOH-d4) δ 7.89 (d, J=1.2 Hz, 1H), 7.46 (s, 1H), 7.17-7.12 (m, 1H), 7.10-7.02 (m, 3H), 5.24 (s, 2H), 2.85 (s, 3H).

The Examples in Table 2 were synthesized according to the methods described in Example 13, Step B, employing the appropriate Br starting materials.

TABLE 2

| Example No. | Structure | Name | Observed Mass [M+H]+ |
|---|---|---|---|
| Example 14 | 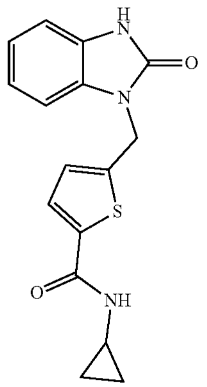 | N-cclopropyl-5-((2-oxo-2,3-dihydro-1H-benzo[d]imidazol-1-yl)methyl)thiophene-2-carboxamide | 314 [M + H]+ |

Example 15

Preparation of (R)—N-(1-(4-((2-oxo-2,3-dihydro-1H-benzo[d]imidazol-1-yl)methyl)phenyl)ethyl) acetamide

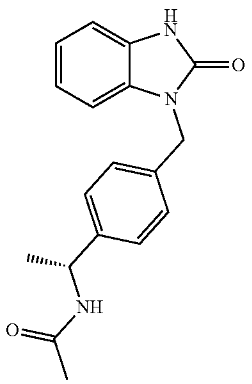 [SMILES: CC(=O)N[C@H](C)c1ccc(Cn2c(=O)[nH]c3ccccc32)cc1]

Step A: (R)—N-(1-(4-bromophenyl)ethyl)acetamide

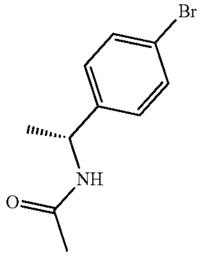

(R)-1-(4-bromophenyl) ethan-1-amine (250 mg, 1.250 mmol), acetyl chloride (89 μl, 1.250 mmol) and DMA (1000 μl) were added to a vial equipped with a stir bar. The reaction mixture was allowed to stir for 18 hours. After 18 hours, the material was dry loaded onto silica. The material was loaded onto a 25 g column, and the column was run from 100% hexanes to 100% ethyl acetate/ethanol. The desired product eluted and fractions were collected and concentrated under reduced pressure to afford the title compound. LC/MS (m/z): 242 (M+H)+.

Step B: (R)—N-(1-(4-((2-oxo-2,3-dihydro-1H-benzo[d]imidazol-1-yl)methyl)phenyl)ethyl)acetamide

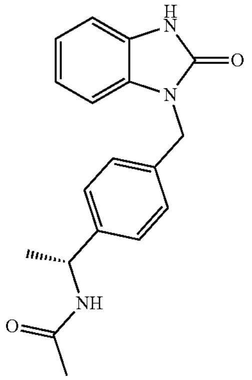 [SMILES: CC(=O)N[C@H](C)c1ccc(Cn2c(=O)[nH]c3ccccc32)cc1]

Utilizing the procedure from Example 12 with the corresponding Bromide in Step A, (R)—N-(1-(4-bromophenyl) ethyl)acetamide was elaborated to the title compound. LC/MS (m/z): 310 (M+H)+. $^1$H NMR (600 MHZ, DMSO-d6) δ 10.93 (s, 1H), 8.21 (d, J=8.0 Hz, 1H), 7.31-7.18 (m, 4H), 7.04-7.00 (m, 1H), 7.00-6.91 (m, 3H), 4.95 (s, 2H), 4.83 (p, J=7.1 Hz, 1H), 1.79 (s, 3H), 1.27 (d, J=7.0 Hz, 3H).

The Examples in Table 3 were synthesized according to the methods described in Example 15 employing the appropriate substituted (4-bromophenyl)methanamine starting materials in Step A, using conditions therein described above, or standard amide coupling conditions (for example HATU/DIEA).

TABLE 3

| Example No. | Structure | Name | Observed Mass [M + H]+ |
|---|---|---|---|
| Example 16 | 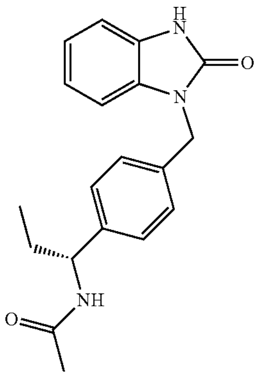 | (R)-N-(1-(4-((2-oxo-2,3-dihydro-1H-benzo[d]imidazol-1-yl)methyl)phenyl) propyl)acetamide | 324 [M + H]+ |

TABLE 3-continued

| Example No. | Structure | Name | Observed Mass [M + H]+ |
|---|---|---|---|
| Example 17 | 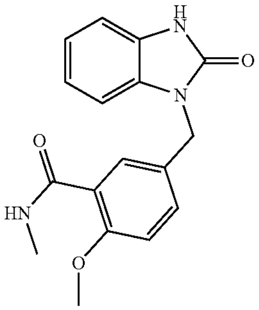 [SMILES: CNC(=O)c1cc(Cn2c(=O)[nH]c3ccccc32)ccc1OC] | 2-methoxy-N-methyl-5-((2-oxo-2,3-dihydro-1H-benzo[d]imidazol-1-yl)methyl)benzamide | 312 [M + H]+ |

Example 18

Preparation of 1-(3-chloro-4-((2-oxopyrrolidin-1-yl)methyl)benzyl)-1,3-dihydro-2H-benzo[d]imidazol-2-one

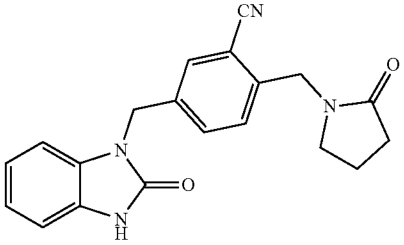 [SMILES: N#Cc1cc(Cn2c(=O)[nH]c3ccccc32)ccc1CN1CCCC1=O]

Sodium hydride (7.60 mg, 0.19 mmol) and 4-bromo-1-(bromomethyl)-2-chlorobenzene (48.3 mg, 0.17 mmol) and pyrrolidin-2-one (15.19 mg, 0.179 mmol) were added to a 8 mL vial and then DMA (0.75 ml) was added. The resulting reaction mixture was stirred at room temperature for 60 mins. The solution was kept for the next step. 4,4'-di-tert-butyl-2,2'-bipyridine (4.56 mg, 0.017 mmol), nickel (II) chloride ethylene glycol dimethyl ether complex (3.74 mg, 0.017 mmol), $Ir[dF(CF_3)ppy]_2(dtbbpy)PF_6$ (1.717 mg, 1.700 μmol), 2-(2-oxo-2,3-dihydro-1H-benzo[d]imidazol-1-yl) acetic acid (44.1 mg, 0.230 mmol) and cesium carbonate (74.8 mg, 0.230 mmol) were added to a separate 8 mL vial. Then 1 mL of DMA was added, and this mixture was added to the alkylated pyrrolidinone from above, and the mixture was sealed and purged with argon for 2 minutes and then stirred under blue LED light for 18 hours. After this time, the crude material was filtered and purified by HPLC (eluting acetonitrile/water gradient with $NH_4OH$ modifier). $^1H$ NMR (600 MHZ, DMSO-$d_6$) δ 10.98 (s, 1H), 7.42 (s, 1H), 7.26 (d, J=7.9 Hz, 1H), 7.21 (d, J=7.9 Hz, 1H), 7.08 (d, J=6.9 Hz, 1H), 7.03-6.92 (m, 3H), 5.00 (s, 2H), 4.40 (s, 2H), 3.23 (t, J=6.9 Hz, 2H), 2.28 (t, J=8.0 Hz, 2H), 1.97-1.89 (m, 2H). LCMS (ESI) m/z: 356 [M+H]+.

Example 19

Preparation of 1-(3-iodo-4-((2-oxopyrrolidin-1-yl)methyl)benzyl)-1,3-dihydro-2H-benzo[d]imidazol-2-one

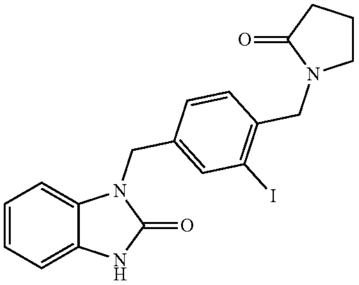 [SMILES: O=C1CCCN1Cc1ccc(Cn2c(=O)[nH]c3ccccc32)cc1I]

Step A: 1,4-bis(bromomethyl)-2-iodobenzene

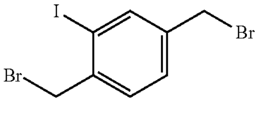 [SMILES: BrCc1ccc(CBr)c(I)c1]

Triphenylphosphine (2295 mg, 8.75 mmol) was added to a mixture of (2-iodo-1,4-phenylene)dimethanol (770 mg, 2.92 mmol) and carbon tetrabromide (2901 mg, 8.75 mmol) in DCM (25 mL) at 25° C. The resulting mixture was stirred at 25° C. for 16 hours under $N_2$. After 16 hours the mixture was filtered and the filtrate was concentrated under reduced pressure to afford the crude product. The residue was purified by flash silica gel chromatography (ISCO®; 4 g SepaFlash® Silica Flash Column, eluent of 0~20% ethyl acetate/pet. ether gradient @ 40 mL/min) to afford 1,4-bis(bromomethyl)-2-iodobenzene.

Step B: 1-(4-(bromomethyl)-2-iodobenzyl)pyrrolidin-2-one

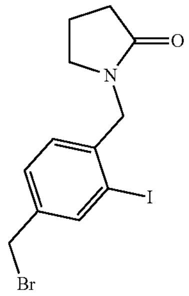 [SMILES: O=C1CCCN1Cc1ccc(CBr)cc1I]

NaH (111 mg, 2.77 mmol) was added to a stirred solution of pyrrolidin-2-one (0.264 mL, 3.46 mmol) in DMF (25 mL) at 0° C. After the addition was finished, the reaction was stirred at 0° C. for 0.5 hours. After 0.5 hours 1,4-bis (bromomethyl)-2-iodobenzene (900 mg, 2.309 mmol) was added. The reaction was stirred at 25° C. for 4 hours. After 4 hours, saturated $NH_4Cl$ (200 mL) was added and the material was washed with EtOAc (200 mL). The separated organic layer was dried over $Na_2SO_4$, filtered and concentrated in vacuo. The residue was purified by flash silica gel chromatography (ISCO®; 40 g SepaFlash® Silica Flash Column, eluent of 45% ethyl acetate/pet. ether gradient @ 35 mL/min) to afford 1-(4-(bromomethyl)-3-iodobenzyl) pyrrolidin-2-one and 1-(4-(bromomethyl)-2-iodobenzyl) pyrrolidin-2-one and 1-(4-(bromomethyl)-2-iodobenzyl) pyrrolidin-2-one-1-(4-(bromomethyl)-3-iodobenzyl) pyrrolidin-2-one. LCMS (ESI) m/z: 394 [M+H]+.

Step C: 1-(4-((2-chloro-1H-benzo[d]imidazol-1-yl) methyl)-2-iodobenzyl)pyrrolidin-2-one

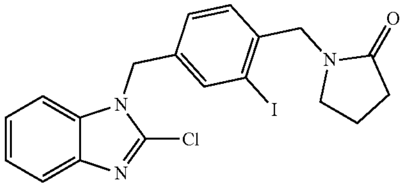 [SMILES: O=C1CCCN1Cc1ccc(Cn2c(Cl)nc3ccccc32)cc1I]

NaH (18.27 mg, 0.457 mmol) was added to a stirred solution of 2-chloro-1H-benzo[d]imidazole (55.8 mg, 0.365 mmol) in DMF (5 mL) at 0° C. After the addition was complete, the reaction was stirred at 0° C. for 0.5 hours. After 0.5 hours, 1-(4-(bromomethyl)-2-iodobenzyl)pyrrolidin-2-one (120 mg, 0.305 mmol) was added. The reaction was stirred at 25° C. for 3.5 hours. After 3.5 hours water (20 mL) was added. The material was washed with DCM (20 mL). The separated organic layer was dried over $Na_2SO_4$, filtered and concentrated in vacuo. The residue was purified by HPLC (eluting acetonitrile/water gradient with $NH_4HCO_3$ modifier) to afford 1-(4-((2-chloro-1H-benzo[d] imidazol-1-yl)methyl)-2-iodobenzyl)pyrrolidin-2-one. LCMS (ESI) m/z: 466 [M+H]+.

Step D: 1-(3-iodo-4-((2-oxopyrrolidin-1-yl)methyl) benzyl)-1,3-dihydro-2H-benzo[d]imidazol-2-one

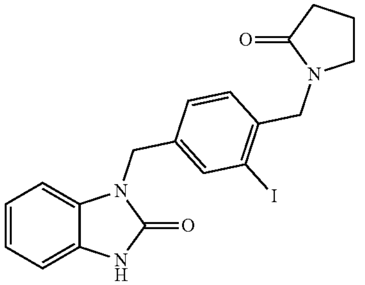 [SMILES: O=C1CCCN1Cc1ccc(Cn2c(=O)[nH]c3ccccc32)cc1I]

A mixture of 1-(4-((2-chloro-1H-benzo[d]imidazol-1-yl) methyl)-2-iodobenzyl)pyrrolidin-2-one (105 mg, 0.225 mmol)) in AcOH (3 mL) was stirred at 80° C. for 6 hours. After 6 hours the solvent was filtered and concentrated under reduced pressure. The residue was diluted with toluene (10 mL) and concentrated to reduced pressure (2 times) to afford 1-(3-iodo-4-((2-oxopyrrolidin-1-yl)methyl)benzyl)-1,3-dihydro-2H-benzo[d]imidazol-2-one. $^1H$ NMR (500 MHz, DMSO-d6) δ=10.98 (s, 1H), 7.84 (s, 1H), 7.29 (d, J=7.9 Hz, 1H), 7.11-7.03 (m, 2H), 7.01-6.93 (m, 3H), 4.96 (s, 2H), 4.28 (s, 2H), 3.22 (t, J=7.0 Hz, 2H), 2.28 (t, J=8.0 Hz, 2H), 1.99-1.98 (m, 1H), 1.99-1.89 (m, 1H). LCMS (ESI) m/z: 448 [M+H]+.

Example 20

Preparation of 1-(4-((3,3-dioxido-1,3,4-oxathiazinan-4-yl)methyl)benzyl)-1,3-dihydro-2H-benzo[d] imidazol-2-one

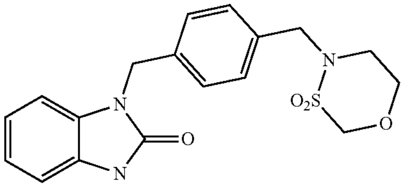 [SMILES: O=c1[nH]c2ccccc2n1Cc1ccc(CN2CCOCS2(=O)=O)cc1]

Utilizing the procedures outlined in Example 18, 1-bromo-4-(bromomethyl)benzene and 1,3,4-oxathiazinane 3,3-dioxide were elaborated to the final product 1-(4-((3,3-dioxido-1,3,4-oxathiazinan-4-yl)methyl)benzyl)-1,3-dihydro-2H-benzo[d]imidazol-2-one. 1H NMR (600 MHZ, DMSO-$d_6$) δ 10.94 (s, 1H), 7.34-7.28 (m, 4H), 7.04-6.91 (m, 4H), 4.99 (s, 2H), 4.83 (s, 2H), 4.26 (s, 2H), 3.81-3.76 (m, 2H), 3.31-3.28 (m, 2H). LCMS (ESI) m/z: 374 [M+H]+.

The Examples in Table 4 were synthesized according to the methods described in Example 18 using the appropriate aryl bromide starting materials; alternatively it can be done stepwise with column chromatography after the formation of the desired aryl bromide.

TABLE 4

| Example No. | Structure | Name | Exact Mass [M + H]+ |
|---|---|---|---|
| Example 21 | 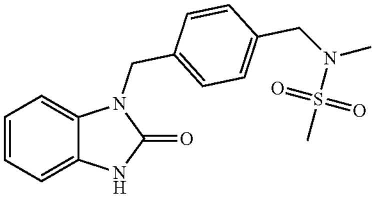 | N-methyl-N-({4-[(2-oxo-2,3-dihydro-1H-benzimidazol-1-yl)methyl]phenyl}methyl)methanesulfonamide | 346 [M + H]+ |
| Example 22 | 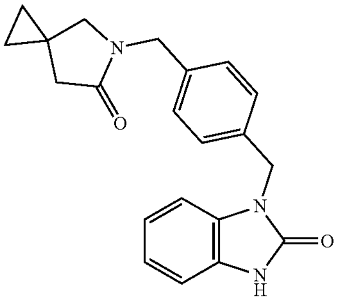 [SMILES: O=C1CC2(CC2)CN1Cc1ccc(Cn2c(=O)[nH]c3ccccc32)cc1] | 1-({4-[(6-oxo-5-azaspiro[2.4]heptan-5-yl)methyl]phenyl}methyl)-1,3-dihydro-2H-benzimidazol-2-one | 348 [M + H]+ |
| Example 23 | 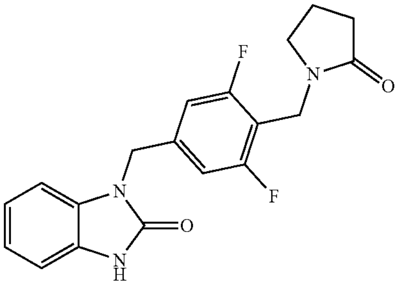 [SMILES: O=C1CCCN1Cc1c(F)cc(Cn2c(=O)[nH]c3ccccc32)cc1F] | 1-({3,5-difluoro-4-[(2-oxopyrrolidin-1-yl)methyl]phenyl}methyl)-1,3-dihydro-2H-benzimidazol-2-one | 358 [M + H]+ |
| Example 24 | 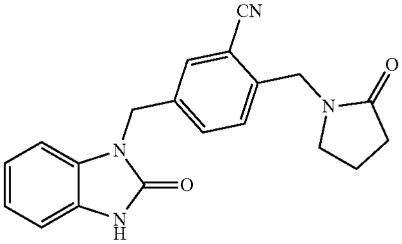 [SMILES: N#Cc1cc(Cn2c(=O)[nH]c3ccccc32)ccc1CN1CCCC1=O] | 5-((2-oxo-2,3-dihydro-1H-benzo[d]imidazol-1-yl)methyl)-2-((2-oxopyrrolidin-1-yl)methyl)benzonitrile | 347 [M + H]+ |
| Example 25 | 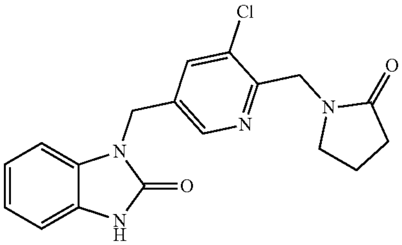 [SMILES: O=C1CCCN1Cc1ncc(Cn2c(=O)[nH]c3ccccc32)cc1Cl] | 1-((5-chloro-6-((2-oxopyrrolidin-1-yl)methyl)pyridin-3-yl)methyl)-1,3-dihydro-2H-benzo[d]imidazol-2-one | 357 [M + H]+ |

Example 26

Preparation of 1-(4-((1,1-dioxidoisothiazolidin-2-yl) methyl)benzyl)-1,3-dihydro-2H-benzo[d]imidazol-2-one

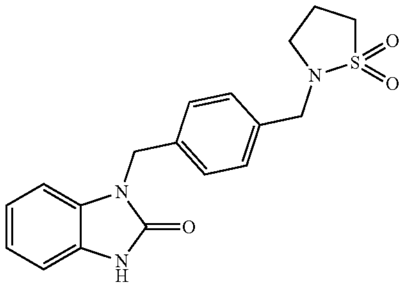 [SMILES: O=c1[nH]c2ccccc2n1Cc1ccc(CN2CCCS2(=O)=O)cc1]

4,4'-di-tert-butyl-2,2'-bipyridine (3.75 mg, 0.014 mmol), nickel (II) chloride ethylene glycol dimethyl ether complex (3.07 mg, 0.014 mmol), Ir[dF($CF_3$)ppy]$_2$(dtbbpy)$PF_6$ (0.940 mg, 0.930 μmol), 2-(3-(tert-butoxycarbonyl)-2-oxo-2,3-dihydro-1H-benzo[d]imidazol-1-yl)acetic acid (0.037 g, 0.126 mmol) (Intermediate 2), 2-(4-bromobenzyl)isothiazolidine 1,1-dioxide (0.027 g, 0.093 mmol) and cesium carbonate (0.041 g, 0.13 mmol) were added to a 8 ml vial with stir bar. Then the 1 mL of DMA was added, and the reaction mixture was purged with argon for 2 minutes and then sealed. The reaction mixture was then placed in the photoreator and irradiated with blue LED light for 4 hours, filtered, evaporated under reduced pressure, then DCM: TFA (1:1) 2 mL was added, and the reaction mixture was stirred for 3 hours. The reaction mixture was evaporated under reduced pressure and purified by HPLC (eluting acetonitrile/water gradient with TFA modifier). Isolated as a solid. $^1$H NMR (600 MHz, DMSO-d$_6$) δ 10.94 (s, 1H), 7.32-7.26 (m, 4H), 7.05-6.90 (m, 4H), 4.98 (s, 2H), 4.03 (s, 2H), 3.24-3.19 (m, 2H), 3.03 (t, J=6.8 Hz, 2H), 2.21-2.14 (m, 2H). LCMS (ESI) m/z: 358 [M+H]+. (Alternatively 2-tert-Butyl-1,1,3,3-tetramethyl-guanidine could be used as a base).

Example 27

Preparation of 1-(3-(1,3,4-oxadiazol-2-yl)benzyl)-1, 3-dihydro-2H-benzo[d]imidazol-2-one

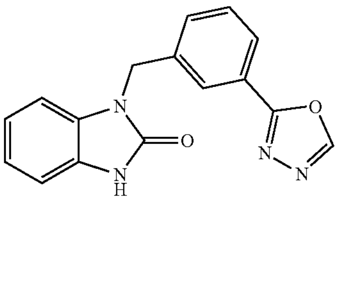 [SMILES: O=c1[nH]c2ccccc2n1Cc1cccc(-c2nnco2)c1]

4,4'-di-tert-butyl-2,2'-bipyridine (7.16 mg, 0.027 mmol), nickel (II) chloride ethylene glycol dimethyl ether complex (5.86 mg, 0.027 mmol), Ir[dF($CF_3$)ppy]$_2$(dtbbpy)$PF_6$ (1.795 mg, 1.777 μmol), 2-(2-oxo-2,3-dihydro-1H-benzo[d]imidazol-1-yl)acetic acid (0.046 g, 0.240 mmol), 2-(3-bromophenyl)-1,3,4-oxadiazole (0.0400 g, 0.178 mmol) and cesium carbonate (0.078 g, 0.24 mmol) were added to an 8 ml vial with stir bar. Then the 1.5 ml of DMA was added, and the reaction vial was purged with argon for 2 minutes and then sealed. The reaction mixture was then irradiated with blue LED for 18 hours. When done, the reaction mixture was evaporated under reduced pressure and then purified by silica gel column chromatography with hexanes and a 3:1 blend of EtOAc:EtOH as eluent. $^1$H NMR (600 MHZ, DMSO-d$_6$) δ 11.01 (s, 1H), 9.32 (s, 1H), 7.98 (s, 1H), 7.95-7.90 (m, 1H), 7.60-7.56 (m, 2H), 7.09 (d, J=7.1 Hz, 1H), 7.04-6.94 (m, 3H), 5.13 (s, 2H). LCMS (ESI) m/z: 293 [M+H]+. (Alternatively 2-tert-Butyl-1,1,3,3-tetramethyl-guanidine could be used as a base in these procedures too, and it could be purified by HPLC eluting acetonitrile/water gradient with TFA modifier).

Example 28

Preparation of 1-((1,1-dioxido-2,3-dihydrobenzo[b] thiophen-6-yl)methyl)-1,3-dihydro-2H-benzo[d] imidazol-2-one

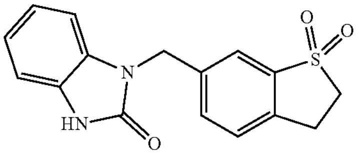 [SMILES: O=c1[nH]c2ccccc2n1Cc1ccc2c(c1)S(=O)(=O)CC2]

Utilizing the procedure outlined in Example 27, 6-bromo-2,3-dihydrobenzo[b]thiophene 1,1-dioxide was elaborated to 1-((1,1-dioxido-2,3-dihydrobenzo[b]thiophen-6-yl) methyl)-1,3-dihydro-2H-benzo[d]imidazol-2-one. $^1$H NMR (500 MHz, DMSO-d$_6$) δ 11.01 (s, 1H), 7.65 (s, 1H), 7.61 (d, J=8.0 Hz, 1H), 7.50 (d, J=8.0 Hz, 1H), 7.15-7.07 (m, 1H), 7.04-6.91 (m, 3H), 5.11 (s, 2H), 3.58 (t, J=6.9 Hz, 2H), 3.32-3.26 (m, 2H). LCMS (ESI) m/z: 315 [M+H]+.

The Examples in Table 5 were synthesized according to the methods described in Example 27 employing the appropriate aryl bromide starting materials.

TABLE 5

| Example No. | Structure | Name | Exact Mass [M + H]+ |
|---|---|---|---|
| Example 29 | 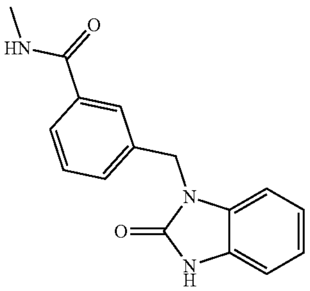 [SMILES: CNC(=O)c1cccc(Cn2c(=O)[nH]c3ccccc32)c1] | N-methyl-3-[(2-oxo-2,3-dihydro-1H-benzimidazol-1-yl)methyl]benzamide | 282 [M + H]+ |
| Example 30 | 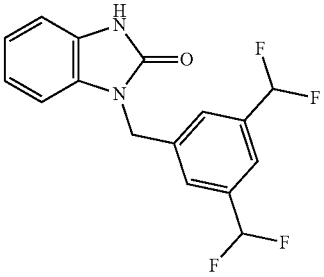 [SMILES: O=c1[nH]c2ccccc2n1Cc1cc(C(F)F)cc(C(F)F)c1] | 1-{[3,5-bis(difluoromethyl)phenyl]methyl}-1,3-dihydro-2H-benzimidazol-2-one | 325 [M + H]+ |
| Example 31 | 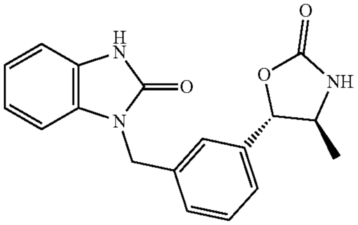 [SMILES: C[C@@H]1NC(=O)O[C@H]1c1cccc(Cn2c(=O)[nH]c3ccccc32)c1] | 1-({3-[(4S,5S)-4-methyl-2-oxo-1,3-oxazolidin-5-yl]phenyl }methyl)-1,3-dihydro-2H-benzimidazol-2-one | 324 [M + H]+ |
| Example 32 | 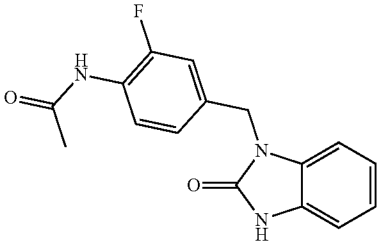 [SMILES: CC(=O)Nc1ccc(Cn2c(=O)[nH]c3ccccc32)cc1F] | N-{2-fluoro-4-[(2-oxo-2,3-dihydro-1H-benzimidazol-1-yl)methyl]phenyl } acetamide | 300 [M + H]+ |
| Example 33 | 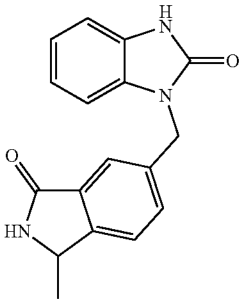 [SMILES: CC1NC(=O)c2cc(Cn3c(=O)[nH]c4ccccc43)ccc21] | 1-[(1-methyl-3-oxo-2,3-dihydro-1H-isoindol-5-yl)methyl]-1,3-dihydro-2H-benzimidazol-2-one | 294 [M + H]+ |

TABLE 5-continued

| Example No. | Structure | Name | Exact Mass [M + H]+ |
| --- | --- | --- | --- |
| Example 34 | 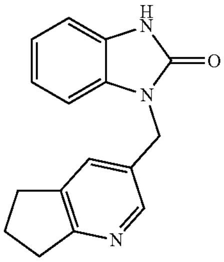 [SMILES: O=c1[nH]c2ccccc2n1Cc1cnc2c(c1)CCC2] | 1-[(6,7-dihydro-5H-cyclopenta[b]pyridin-3-yl)methyl]-1,3-dihydro-2H-benzimidazol-2-one | 266 [M + H]+ |
| Example 35 | 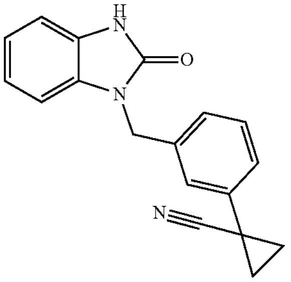 [SMILES: N#CC1(c2cccc(Cn3c(=O)[nH]c4ccccc43)c2)CC1] | 1-{3-[(2-oxo-2,3-dihydro-1H-benzimidazol-1-yl)methyl]phenyl}cyclopropane-1-carbonitrile | 290 [M + H]+ |

Example 36

Preparation of 1-((4-chloro-5-((2-oxopyrrolidin-1-yl)methyl)thiophen-2-yl)methyl)-1,3-dihydro-2H-benzo[d]imidazol-2-one

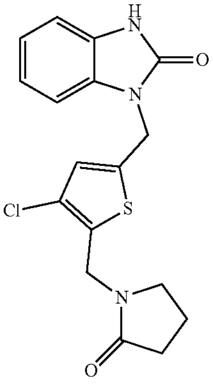 [SMILES: O=C1CCCN1Cc1sc(Cn2c(=O)[nH]c3ccccc32)cc1Cl]

Step A: (3-chlorothiophen-2-yl)methanol

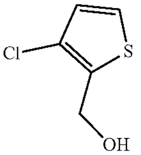

$LiAlH_4$ (0.350 g, 9.23 mmol) was added to a mixture of 3-chlorothiophene-2-carboxylic acid (1 g, 6.15 mmol) in 20 mL of THE under nitrogen at 25° C. and the reaction was stirred at 25° C. for 2 h. The reaction mixture was quenched with 20 mL of saturated $NH_4Cl$ and extracted with ethyl acetate (15 mL×3). The combined organic phases were washed with brine, dried with $Na_2SO_4$, filtered and concentrated under reduced pressure. The residue was purified by silica gel chromatography with ethyl acetate and petroleum ether as eluent. $^1H$ NMR (500 MHz, $CDCl_3$) δ 7.25 (d, J=5.5 Hz, 1H), 6.91 (d, J=5.3 Hz, 1H), 4.81 (d, J=5.8 Hz, 2H), 2.03 (t, J=6.2 Hz, 1H).

Step B: 5-bromo-2-(bromomethyl)-3-chlorothiophene

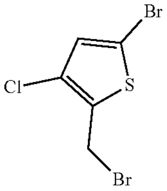

Bromine (0.416 mL, 8.07 mmol) was added to a mixture of (3-chlorothiophen-2-yl)methanol (800 mg, 5.38 mmol) in AcOH (10 mL) and the mixture was stirred at 25° C. for 12 hours. The reaction mixture was quenched with brine (30 mL) and extracted with ethyl acetate (15 mL×3). The combined organic phases were washed with brine (15 mL), dried over anhydrous $Na_2SO_4$, filtered and concentrated under reduced pressure. The residue was purified by silica gel chromatography with petroleum ether as eluent. $^1H$ NMR (400 MHZ, $CDCl_3$) δ 6.86 (s, 1H), 4.58 (s, 2H).

Step C: 1-((5-bromo-3-chlorothiophen-2-yl)methyl) pyrrolidin-2-one

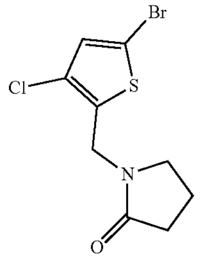 [SMILES: O=C1CCCN1Cc1sc(Br)cc1Cl]

NaH (188 mg, 4.70 mmol, 60% in oil) was added to a solution of pyrrolidin-2-one (200 mg, 2.350 mmol) in THF (10 mL) under nitrogen at 0° C. After stirring for 20 min at 0° C., a solution of 5-bromo-2-(bromomethyl)-3-chlorothiophene (546 mg, 1.880 mmol) in THF (2 mL) was added to the mixture. The resulting mixture was stirred at 20° C. for 2 hours. The reaction mixture was quenched with saturated $NH_4Cl$ (20 mL) and extracted with ethyl acetate (10 mL×3). The combined organic phases were washed with brine (10 mL), dried over anhydrous $Na_2SO_4$, filtered and concentrated under reduced pressure. The residue was purified by silica gel chromatography with ethyl acetate and petroleum ether as eluent. $^1H$ NMR (500 MHz, $CDCl_3$) δ 6.86 (s, 1H), 4.54 (s, 2H), 3.37 (t, J=7.1 Hz, 2H), 2.39 (t, J=8.1 Hz, 2H), 2.05-2.00 (m, 2H).

Utilizing the procedure outlined in Example 27, 1-((5-bromo-3-chlorothiophen-2-yl)methyl)pyrrolidin-2-one was elaborated to the final product 1-((4-chloro-5-((2-oxopyrrolidin-1-yl)methyl)thiophen-2-yl)methyl)-1,3-dihydro-2H-benzo[d]imidazol-2-one.

Step D: 1-((4-chloro-5-((2-oxopyrrolidin-1-yl)methyl) thiophen-2-yl)methyl)-1,3-dihydro-2H-benzo[d]imidazol-2-one. $^1H$ NMR (400 MHZ, MeOH-$d_4$) δ 7.15-7.10 (m, 1H), 7.08-7.06 (m, 3H), 6.99 (s, 1H), 5.16 (s, 2H), 4.53 (s, 2H), 3.35 (t, J=7.0 Hz, 2H), 2.38-2.30 (m, 2H), 2.04-1.92 (m, 2H). LCMS (ESI) m/z: 362 $[M+H]^+$.

Example 37

Preparation of N,N-dimethyl-2-(6-((2-oxo-2,3-dihydro-1H-benzo[d]imidazol-1-yl)methyl)pyridin-3-yl)acetamide

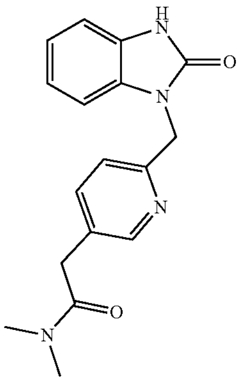 [SMILES: CN(C)C(=O)Cc1ccc(Cn2c(=O)[nH]c3ccccc32)nc1]

Step A: 2-(6-bromopyridin-3-yl)-N,N-dimethylacetamide

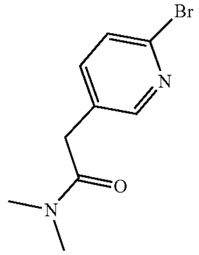

Dimethylamine hydrochloride (75 mg, 0.926 mmol), 2-(6-bromopyridin-3-yl)acetic acid (100 mg, 0.463 mmol), HATU (264 mg, 0.694 mmol) and TEA (0.18 mL, 1.291 mmol) were dissolved in DMF (2.5 mL) and stirred at room temperature for 3 hours. and the reaction mixture was filtered and directly purified by HPLC (eluting acetonitrile/water gradient with TFA modifier).

LCMS (ESI) m/z: 245 $[M+H]^+$

Utilizing the procedure outlined in Example 27, 2-(6-bromopyridin-3-yl)-N,N-dimethylacetamide was elaborated to the final product N,N-dimethyl-2-(6-((2-oxo-2,3-dihydro-1H-benzo[d]imidazol-1-yl)methyl)pyridin-3-yl)acetamide.

Step B: N,N-dimethyl-2-(6-((2-oxo-2,3-dihydro-1H-benzo[d]imidazol-1-yl)methyl)pyridin-3-yl)acetamide. $^1H$ NMR (500 MHZ, MeOH-$d_4$) δ 8.53 (br s, 1H), 8.01-7.99 (m, 1H), 7.51 (d, J=8.0 Hz, 1H), 7.14-7.07 (m, 2H), 7.05-7.00 (m, 2H), 5.32 (s, 2H), 3.91 (s, 2H), 3.14 (s, 3H), 2.95 (s, 3H). LCMS (ESI) m/z: 311 $[M+H]^+$.

Example 38

Preparation of N-((3-chloro-5-((2-oxo-2,3-dihydro-1H-benzo[d]imidazol-1-yl)methyl)thiophen-2-yl) methyl)acetamide

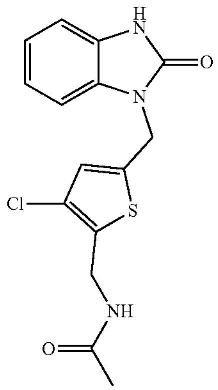 [SMILES: CC(=O)NCc1sc(Cn2c(=O)[nH]c3ccccc32)cc1Cl]

Step A: 3-chlorothiophene-2-carboxamide

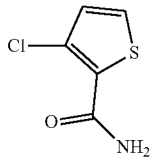

HOBT (1.9 g, 12.3 mmol) was added to a solution of 3-chlorothiophene-2-carboxylic acid (2 g, 12.3 mmol), TEA (5.1 mL, 36.9 mmol) and EDCI (2.8 g, 14.8 mmol) in DMF (50 mL) at room temperature, and the reaction mixture was stirred for 0.5 hours. Then, $NH_4Cl$ (2.0 g, 36.9 mmol) was added, and the reaction mixture was stirred for another 12 hours. The reaction mixture was quenched with $H_2O$ (150 mL) and extracted with EtOAc (25 mL×3). The combined organic phases were dried over anhydrous $Na_2SO_4$, filtered and concentrated under reduced pressure. The residue was purified by silica gel chromatography with petroleum ether and ethyl acetate as eluent. Isolated as a solid. LCMS (ESI) m/z 162 $[M+H]^+$.

Step B: (3-chlorothiophen-2-yl)methanamine

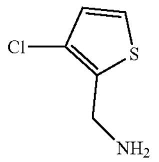

$LiAlH_4$ (188 mg, 4.95 mmol) was added to a mixture of 3-chlorothiophene-2-carboxamide (400 mg, 2.5 mmol) in THF (5 mL) at 0° C. The reaction was stirred at 0° C. for 2 hours. Then 0.5 mL of water and 5 g of $Na_2SO_4$ were added to quench the reaction. The mixture was filtered and the filtrate was concentrated under reduced pressure the product, which was not further purified. LCMS (ESI) m/z 148 $[M+H]^+$.

Step C: N-((3-chlorothiophen-2-yl)methyl)acetamide

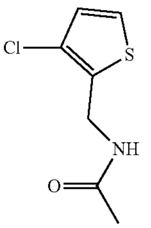

Acetic anhydride (207 mg, 2.0 mmol) was added to a mixture of (3-chlorothiophen-2-yl)methanamine (150 mg, 1.0 mmol) and TEA (0.3 mL, 2.0 mmol) in DCM (3 mL) at 0° C. The reaction was stirred at 0° C. for 1 hour. The reaction mixture was quenched with saturated $NH_4Cl$ (15 mL) and extracted with EtOAc (15 mL×3). The combined organic phases were dried over anhydrous $Na_2SO_4$, filtered and concentrated under reduced pressure. The residue was purified by silica gel chromatography with petroleum ether as eluent. LCMS (ESI) m/z 190 $[M+H]^+$.

Step D: N-((5-bromo-3-chlorothiophen-2-yl)methyl)acetamide

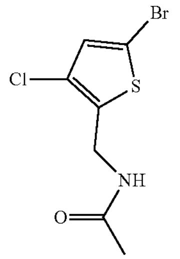

N-bromosuccinimide (90 mg, 0.5 mmol) was added to mixture of N-((3-chlorothiophen-2-yl)methyl)acetamide (80 mg, 0.4 mmol) in DCM (3 mL). The reaction was stirred at 20° C. for 1.5 hours. 4 mL of saturated $NaHCO_3$ was added to quench the reaction. The reaction was extracted with EtOAc (15 mL×3). The combined organic phases were dried over anhydrous $Na_2SO_4$, filtered and concentrated under reduced pressure. The residue was purified by silica gel chromatography with petroleum ether as eluent. LCMS (ESI) m/z 270 $[M+H]^+$.

Step E: N-((3-chloro-5-((2-oxo-2,3-dihydro-1H-benzo[d]imidazol-1-yl)methyl)thiophen-2-yl)methyl)acetamide

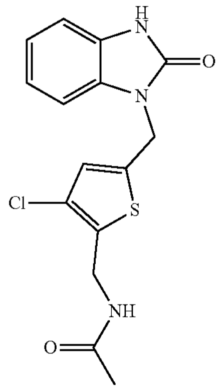 [SMILES: CC(=O)NCc1sc(Cn2c(=O)[nH]c3ccccc32)cc1Cl]

Utilizing the procedure outlined in Example 27, N-((5-bromo-3-chlorothiophen-2-yl)methyl)acetamide was elaborated to the title compound. $^1H$ NMR (500 MHZ, MeOH-$d_4$) δ 7.17-7.13 (m, 1H), 7.11-7.07 (m, 3H), 6.99 (s, 1H), 5.18 (s, 2H), 4.43 (s, 2H), 1.93 (s, 3H). LCMS (ESI) m/z 336 $[M+H]^+$.

Example 39

N-((3-chloro-5-((2-oxo-2,3-dihydro-1H-benzo[d]imidazol-1-yl)methyl)thiophen-2-yl)methyl)methanesulfonamide

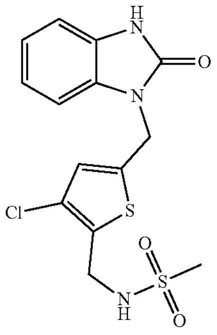 [SMILES: CS(=O)(=O)NCc1sc(Cn2c(=O)[nH]c3ccccc32)cc1Cl]

Step A: 5-bromo-3-chlorothiophene-2-carboxamide

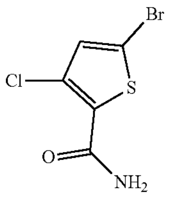

HOBT (317 mg, 2.070 mmol) was added to a solution of 5-bromo-3-chlorothiophene-2-carboxylic acid (500 mg, 2.070 mmol), TEA (0.866 mL, 6.21 mmol) and EDC (476 mg, 2.485 mmol) in DMF (3 mL) at 20° C. The reaction was allowed to stir for 0.5 h. After 0.5 hours, $NH_4Cl$ (554 mg, 10.35 mmol) was added, and the mixture was stirred for 12 hours. After 12 hours, water (30 mL) was added, and the mixture was washed with EtOAc (25 mL×3). The combined organic phases were dried over anhydrous $Na_2SO_4$, filtered, and concentrated under reduced pressure. The residue was purified by silica gel chromatography with petroleum ether and ethyl acetate as eluent to afford the title compound. LCMS (ESI) m/z 283 $[M+H+CH_3CN]^+$.

Step B: (5-bromo-3-chlorothiophen-2-yl)methanamine

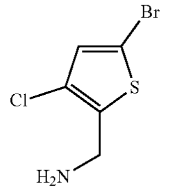

$BH_3 \cdot THF$ (5 mL, 5.00 mmol, 1 M in THF) was added to a stirred solution of 5-bromo-3-chlorothiophene-2-carboxamide (200 mg, 0.832 mmol) in THF (5 mL). The reaction was stirred at 75° C. for 16 hours. After 16 hours, MeOH (2 mL) was added to the mixture, and the reaction mixture was concentrated under reduced pressure to afford the title compound. LCMS (ESI) m/z: 211 $[M+H-NH_2]^+$.

Step D: N-((5-bromo-3-chlorothiophen-2-yl)methyl)methanesulfonamide

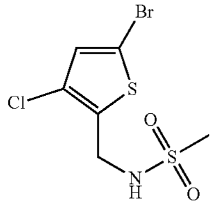

(5-bromo-3-chlorothiophen-2-yl)methanamine (200 mg, 0.883 mmol), TEA (0.369 mL, 2.65 mmol) and DCM (3 mL) were added to a vial equipped with a stir bar. Methanesulfonyl chloride (0.138 mL, 1.766 mmol) was added, and the reaction mixture was stirred at 20° C. for 2 hours. After 2 hours, saturated $NH_4Cl$ (15 mL) was added and the mixture was washed with EtOAc (15 mL×3). The combined organic phases were dried over anhydrous $Na_2SO_4$, filtered and concentrated under reduced pressure. The residue was purified by silica gel chromatography with petroleum ether and ethyl acetate as eluent to afford the title compound. $^1H$ NMR (500 MHz, $CDCl_3$) δ 6.89 (s, 1H), 5.06 (br s, 1H), 4.41 (s, 2H), 2.95 (s, 3H).

Step E: N-((3-chloro-5-((2-oxo-2,3-dihydro-1H-benzo[d]imidazol-1-yl)methyl)thiophen-2-yl)methyl)methanesulfonamide

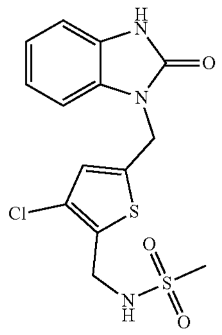 [SMILES: CS(=O)(=O)NCc1sc(Cn2c(=O)[nH]c3ccccc32)cc1Cl]

Utilizing the procedure in Example 27, N-((5-bromo-3-chlorothiophen-2-yl)methyl)methanesulfonamide was elaborated to the title compound. LCMS (ESI) m/z: 372 $[M+H]^+$. $^1H$ NMR (400 MHZ, DMSO-d6) δ 10.97 (s, 1H), 7.68 (t, J=6.3 Hz, 1H), 7.22-7.17 (m, 1H), 7.10 (s, 1H), 7.03-6.95 (m, 3H), 5.11 (s, 2H), 4.19 (d, J=6.3 Hz, 2H), 2.88 (s, 3H).

Example 40

N-((3-methyl-5-((2-oxo-2,3-dihydro-1H-benzo[d]imidazol-1-yl)methyl)thiophen-2-yl)methyl)acetamide

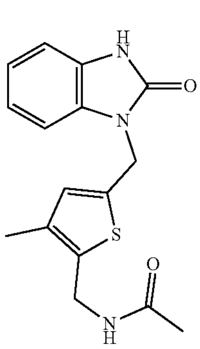 [SMILES: CC(=O)NCc1sc(Cn2c(=O)[nH]c3ccccc32)cc1C]

Step A: (E)-5-bromo-3-methylthiophene-2-carbaldehyde oxime

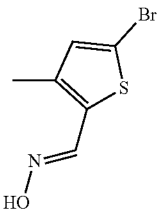

5-bromo-3-methylthiophene-2-carbaldehyde (100 mg, 0.488 mmol) and EtOH (5 mL) was added to a vial equipped with a stir bar. Hydroxylamine hydrochloride (65 mg, 0.935 mmol) and sodium acetate (88 mg, 1.073 mmol) were added, and the reaction was stirred at 30° C. for 16 hours.

After 16 hours, the mixture was diluted with water (30 mL) and washed with ethyl acetate (20 mL×3). The combined organic layers were collected, washed with brine (10 mL), dried over $Na_2SO_4$, and filtered. The collected filtrate was concentrated in vacuo. The residue was purified by prep-TLC (pet. ether/ethyl acetate=2:1) to afford the title compound. LCMS (ESI) m/z: 220 $[M+H]^+$.

Step B: (5-bromo-3-methylthiophen-2-yl)methanamine

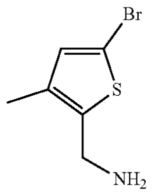

(E)-5-bromo-3-methylthiophene-2-carbaldehyde oxime (90 mg, 0.409 mmol) and AcOH (1 mL) were added to a vial equipped with a stir bar. Zinc (107 mg, 1.636 mmol) was added, and the vial was sealed and heated to 70° C. for 30 minutes. After 30 minutes, the reaction mixture was cooled to room temperature. Aq. HCl (5 mL, 2M) was added, and the mixture was washed with ethyl acetate (5 mL×2). The combined aqueous phase was basified with aq. NaOH (5 mL, 4M), and washed with ethyl acetate (10 mL×3). The resulting organic layers were collected, dried over $Na_2SO_4$, filtered, and concentrated in vacuo to afford the title compound. LCMS (ESI) m/z 206 $[M+H]^+$.

Step C: N-((5-bromo-3-methylthiophen-2-yl)methyl)acetamide

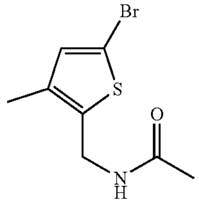

(5-bromo-3-methylthiophen-2-yl)methanamine (70 mg, 0.340 mmol) in DCM (1.5 mL) was added to a vial equipped with a stir bar. TEA (0.104 mL, 0.747 mmol), DMAP (4 mg, 0.033 mmol) and acetic anhydride (42 mg, 0.411 mmol) were added and the reaction mixture was stirred at 15° C. (room temperature) for 16 hours. After 16 hours, the mixture was diluted with water (5 mL), extracted with ethyl acetate (5 mL×3), and the organic layers were collected, dried over $Na_2SO_4$, and filtered. The collected filtrate was concentrated in vacuo. The resulting residue was purified by prep-TLC (pet.ether/ethyl acetate=2:1) to afford the title compound. LCMS (ESI) m/z 248 $[M+H]^+$.

Step D: N-((3-methyl-5-((2-oxo-2,3-dihydro-1H-benzo[d]imidazol-1-yl)methyl)thiophen-2-yl)methyl) acetamide

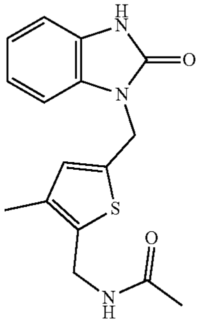 [SMILES: CC(=O)NCc1sc(Cn2c(=O)[nH]c3ccccc32)cc1C]

Utilizing the procedure from Example 27, N-((5-bromo-3-methylthiophen-2-yl)methyl)acetamide was elaborated to the title compound. LCMS (ESI) m/z: 316 $[M+H]^+$. $^1H$ NMR (500 MHz, MeOH-d4) δ 7.18-7.11 (m, 1H), 7.09-7.05 (m, 3H), 6.86 (s, 1H), 5.15 (s, 2H), 4.37 (s, 2H), 2.16 (s, 3H), 1.94-1.86 (m, 3H).

Example 41

Preparation of 1-((6-((2-oxopyrrolidin-1-yl)methyl) pyridin-3-yl)methyl)-1,3-dihydro-2H-benzo[d]imidazol-2-one

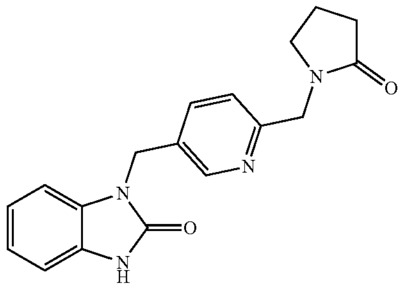 [SMILES: O=C1CCCN1Cc1ccc(Cn2c(=O)[nH]c3ccccc32)cn1]

Step A: 1-((5-bromopyridin-2-yl)methyl)pyrrolidin-2-one

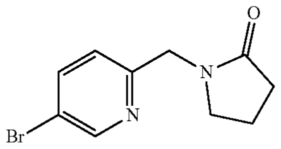 [SMILES: O=C1CCCN1Cc1ccc(Br)cn1]

Pyrrolidin-2-one (68.1 μL, 0.89 mmol) was dissolved in 1.5 mL of THF at 0° C., and to this was added sodium hydride (40.6 mg, 1.016 mmol). The resulting solution was stirred at 0° C. for 15 min followed by addition of a solution of 5-bromo-2-(bromomethyl)pyridine (150 mg, 0.59 mmol) in 1.5 mL of THF, then allowed to stir at room temperature for 2 hours. The reaction mixture was then quenched with saturated $NH_4Cl$ solution and extracted with EtOAc (3×). The combined organic layers were washed with brine, dried over magnesium sulfate, filtered and concentrated in vacuo.

The residue was purified by silica gel chromatography with hexanes and 3 EtOAc: 1 EtOH as eluent. LCMS (ESI) m/z 257 $[M+H]^+$.

Step B: 1-((6-((2-oxopyrrolidin-1-yl)methyl)pyridin-3-yl)methyl)-1,3-dihydro-2H-benzo[d]imidazol-2-one

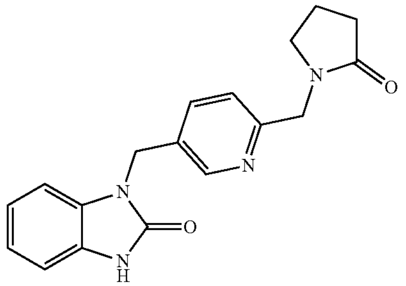 [SMILES: O=C1CCCN1Cc1ccc(Cn2c(=O)[nH]c3ccccc32)cn1]

Utilizing the procedure outlined in Example 27, 1-((5-bromopyridin-2-yl)methyl)pyrrolidin-2-one was elaborated to the title compound. $^1$H NMR (500 MHZ, DMSO-$d_6$) δ 11.01 (s, 1H), 8.61 (d, J=1.8 Hz, 1H), 7.82 (dd, J=8.1, 2.1 Hz, 1H), 7.33 (d, J=8.1 Hz, 1H), 7.14 (dt, J=6.3, 3.4 Hz, 1H), 7.02-6.90 (m, 4H), 5.07 (s, 2H), 4.48 (s, 2H), 3.32 (t, J=7.0 Hz, 2H), 2.28 (t, J=8.1 Hz, 2H), 1.95 (p, J=7.5 Hz, 2H). LCMS (ESI) m/z 323 $[M+H]^+$.

Example 42

Preparation of 5-((2-oxo-2,3-dihydro-1H-benzo[d] imidazol-1-yl)methyl)-1H-indazole-3-carbonitrile

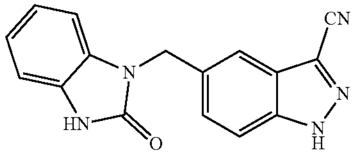 [SMILES: N#Cc1n[nH]c2ccc(Cn3c(=O)[nH]c4ccccc43)cc12]

Step A: tert-butyl 5-bromo-3-cyano-1H-indazole-1-carboxylate

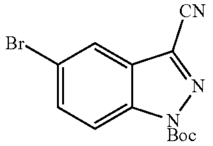 [SMILES: CC(C)(C)OC(=O)n1nc(C#N)c2cc(Br)ccc21]

5-bromo-1H-indazole-3-carbonitrile (2 g, 9.01 mmol) and di-tert-butyl-dicarbonate (3.14 mL, 13.51 mmol) were dissolved in acetonitrile (20 mL), and then DMAP (0.055 g, 0.45 mmol) was added. The mixture was stirred for 2 hours. The solvents were evaporated. To the residue was added hexanes (30 mL), and it was stirred vigorously for 10 minutes. The solids were collected by filtration to afford the title compound. LCMS (ESI) m/z 344 $[M+Na]^+$.

Step B: 5-((2-oxo-2,3-dihydro-1H-benzo[d]imidazol-1-yl)methyl)-1H-indazole-3-carbonitrile

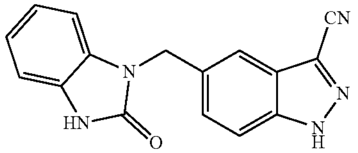 [SMILES: N#Cc1n[nH]c2ccc(Cn3c(=O)[nH]c4ccccc43)cc12]

Utilizing the procedure outlined in Example 27, tert-butyl 5-bromo-3-cyano-1H-indazole-1-carboxylate was elaborated to the title compound. $^1$H NMR (500 MHZ, DMSO-$d_6$) δ 10.99 (s, 1H), 7.91 (s, 1H), 7.74 (d, J=8.7 Hz, 1H), 7.51 (dd, J=8.8, 1.3 Hz, 1H), 7.18-7.08 (m, 1H), 7.06-6.89 (m, 3H), 5.16 (s, 2H). LCMS (ESI) m/z 290 $[M+H]^+$.

Example 43

Preparation of 1-(4-((3,3-difluoro-2-oxopyrrolidin-1-yl)methyl)benzyl)-1,3-dihydro-2H-benzo[d]imidazol-2-one

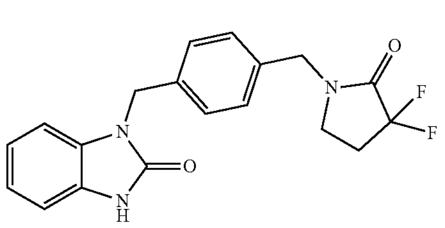 [SMILES: O=C1N(Cc2ccc(Cn3c(=O)[nH]c4ccccc43)cc2)CCC1(F)F]

Step A: 1-(4-bromobenzyl)-3,3-difluoropyrrolidin-2-one

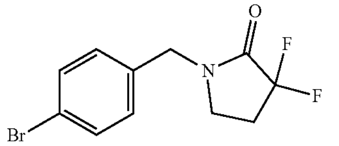 [SMILES: O=C1N(Cc2ccc(Br)cc2)CCC1(F)F]

Sodium bis(trimethylsilyl)amide (200 μl, 0.20 mmol, 1M in THF) was added to a solution of 3,3-difluoropyrrolidin-2-one (36 mg, 0.30 mmol) in THF (0.6 mL) at room temperature. The solution was allowed to stir at room temperature for 15 minutes, after which 1-bromo-4-(bromomethyl)benzene (50 mg, 0.20 mmol) was added as a solution in THF (0.6 mL). The resulting solution was stirred overnight. The reaction was quenched by the addition of hydrochloric acid (200 μl, 0.20 mmol, IN solution) dropwise. The reaction was then concentrated under reduced pressure, and the residue was dissolved in DMSO. The compound was purified by HPLC (eluting acetonitrile/water gradient with $NH_4OH$ modifier). LC/MS (m/z): 290 $(M+H)^+$

Step B: 1-(4-((3,3-difluoro-2-oxopyrrolidin-1-yl)methyl)benzyl)-1,3-dihydro-2H-benzo[d]imidazol-2-one

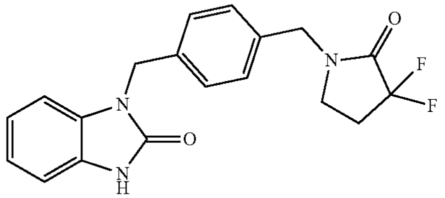 [SMILES: O=C1N(Cc2ccc(Cn3c(=O)[nH]c4ccccc43)cc2)CCC1(F)F]

Utilizing the procedure outlined in Example 27, 1-(4-bromobenzyl)-3,3-difluoropyrrolidin-2-one was elaborated to the title compound. $^1H$ NMR (600 MHZ, DMSO-$d_6$) δ 10.95 (s, 1H), 7.32 (d, J=8.1 Hz, 2H), 7.21 (d, J=8.1 Hz, 2H), 7.04 (d, J=7.3 Hz, 1H), 7.02-6.92 (m, 3H), 4.99 (s, 2H), 4.45 (s, 2H), 3.34-3.29 (m, 2H), 2.59-2.49 (m, 2H). LC/MS (m/z): 358 $(M+H)^+$

Example 44

Preparation of N-(2-chloro-4-((2-oxo-2,3-dihydro-1H-benzo[d]imidazol-1-yl)methyl)benzyl)acetamide

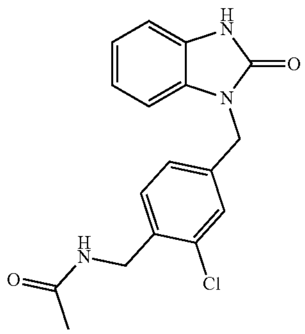 [SMILES: CC(=O)NCc1ccc(Cn2c(=O)[nH]c3ccccc32)cc1Cl]

Step A: tert-butyl (2-chloro-4-((2-oxo-2,3-dihydro-1H-benzo[d]imidazol-1-yl)methyl)benzyl)carbamate

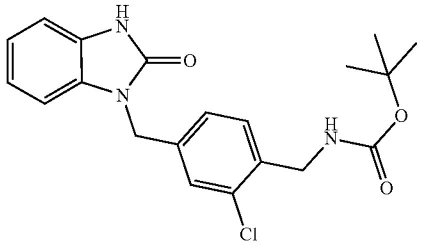 [SMILES: CC(C)(C)OC(=O)NCc1ccc(Cn2c(=O)[nH]c3ccccc32)cc1Cl]

Utilizing the procedure outlined in Example 27, 1-(4-bromobenzyl)-3,3-difluoropyrrolidin-2-one was elaborated to the title compound. LC/MS (m/z): 332 (M+H)+ (observe the loss of the tert-butyl group).

Step B: 1-(4-(aminomethyl)-3-chlorobenzyl)-1,3-dihydro-2H-benzo[d]imidazol-2-one

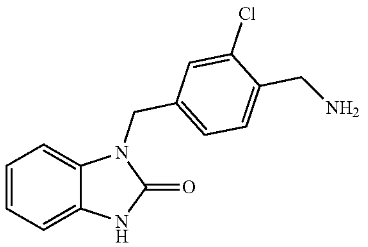 [SMILES: NCc1ccc(Cn2c(=O)[nH]c3ccccc32)cc1Cl]

Tert-butyl (2-chloro-4-((2-oxo-2,3-dihydro-1H-benzo[d]imidazol-1-yl)methyl)benzyl)carbamate (58 mg, 0.150 mmol), HCl (299 μl, 1.196 mmol), and THF (1000 μl) were added to a vial equipped with a stir bar. The reaction mixture was stirred at rt for 20 minutes. After 20 minutes, the reaction mixture was heated to 40° C. for 4 hours. After 4 hours, the reaction mixture was cooled to room temperature and concentrated under reduced pressure. The material was carried onto the following step without further purification. LC/MS (m/z): 288 (M+H)+.

Step C: Preparation of N-(2-chloro-4-((2-oxo-2,3-dihydro-1H-benzo[d]imidazol-1-yl)methyl)benzyl) acetamide

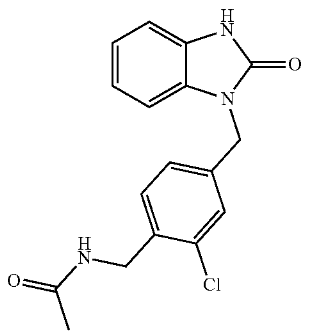 [SMILES: CC(=O)NCc1ccc(Cn2c(=O)[nH]c3ccccc32)cc1Cl]

Acetic acid (8.55 μl, 0.149 mmol), HATU (85 mg, 0.224 mmol) and DMF (1494 μl) were stirred at room temperature for 5 minutes. After 5 minutes, 1-(4-(aminomethyl)-3-chlorobenzyl)-1,3-dihydro-2H-benzo[d]imidazol-2-one (43 mg, 0.149 mmol) was added, followed by DIEA (78 μl, 0.448 mmol). The reaction mixture was allowed to stir at room temperature for 30 minutes. After 30 minutes, the reaction mixture was filtered and submitted directly for HPLC purification (purified by HPLC, eluting acetonitrile/water gradient with basic modifier, linear gradient) to afford the title compound. LC/MS (m/z): 330 (M+H)+. $^1H$ NMR (600 MHz, DMSO-d6) δ 10.97 (s, 1H), 8.29 (t, J=5.6 Hz, 1H), 7.40-7.34 (m, 1H), 7.32-7.21 (m, 2H), 7.09-7.03 (m, 1H), 7.02-6.95 (m, 3H), 4.98 (s, 2H), 4.24 (d, J=5.7 Hz, 2H), 1.86 (s, 3H).

Example 45

Preparation of N-(6-((2-oxo-2,3-dihydro-1H-benzo[d]imidazol-1-yl)methyl)-2,3-dihydro-1H-inden-1-yl)acetamide

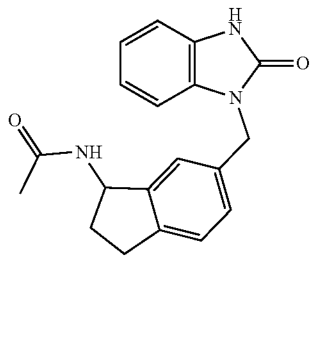 [SMILES: CC(=O)NC1CCc2ccc(Cn3c(=O)[nH]c4ccccc43)cc21]

Step A: tert-butyl (6-((2-oxo-2,3-dihydro-1H-benzo[d]imidazol-1-yl)methyl)-2,3-dihydro-1H-inden-1-yl)carbamate

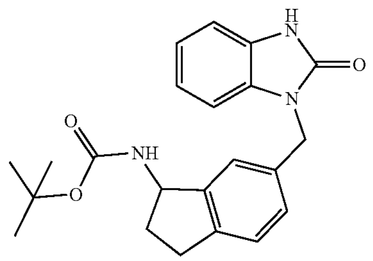 [SMILES: CC(C)(C)OC(=O)NC1CCc2ccc(Cn3c(=O)[nH]c4ccccc43)cc21]

Utilizing the procedure outlined in Example 27, tert-butyl (6-bromo-2,3-dihydro-1H-inden-1-yl)carbamate elaborated to the title compound. LC/MS (m/z): 324 (M+H)+ (observe loss of t-butyl).

Step B: 1-((3-amino-2,3-dihydro-1H-inden-5-yl)methyl)-1,3-dihydro-2H-benzo[d]imidazol-2-one

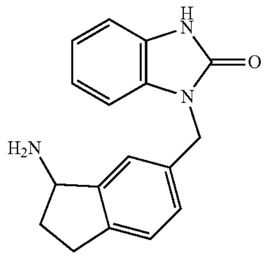 [SMILES: NC1CCc2ccc(Cn3c(=O)[nH]c4ccccc43)cc21]

Tert-butyl (6-((2-oxo-2,3-dihydro-1H-benzo[d]imidazol-1-yl)methyl)-2,3-dihydro-1H-inden-1-yl)carbamate (427.8 mg, 1.127 mmol), HCl (4 M in dioxane) (4.23 ml, 16.91 mmol), and dioxane (5 ml) were added to a vial equipped with a stir bar. The reaction mixture was allowed to stir at room temperature for 1 hour. After 1 hour, the reaction mixture was concentrated under reduced pressure to afford the title compound. LC/MS (m/z): 302 (M+H)+ (observe M+22).

Step C: N-(6-((2-oxo-2,3-dihydro-1H-benzo[d]imidazol-1-yl)methyl)-2,3-dihydro-1H-inden-1-yl)acetamide

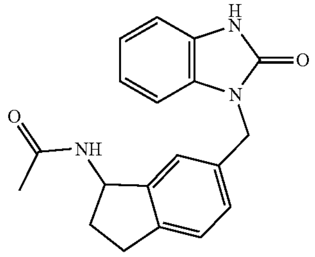 [SMILES: CC(=O)NC1CCc2ccc(Cn3c(=O)[nH]c4ccccc43)cc21]

Acetic acid (16.39 μl, 0.286 mmol), HATU (82 mg, 0.215 mmol), and DMF (1432 μl) were added to a vial equipped with a stir bar. The reaction mixture was allowed to stir at room temperature for 5 minutes. After 5 minutes, 1-((3-amino-2,3-dihydro-1H-inden-5-yl)methyl)-1,3-dihydro-2H-benzo[d]imidazol-2-one (40 mg, 0.143 mmol) was added, followed by DIEA (75 μl, 0.430 mmol). The reaction mixture was allowed to stir at room temperature for 18 hours. After 18 hours, the crude material was dissolved in 3 ml DMSO, filtered, and submitted directly for HPLC purification (purified by HPLC, eluting acetonitrile/water gradient with TFA modifier, linear gradient) to afford the title compound. LC/MS (m/z): 322 (M+H)+.

Step D: N-(6-((2-oxo-2,3-dihydro-1H-benzo[d]imidazol-1-yl)methyl)-2,3-dihydro-1H-inden-1-yl)acetamide

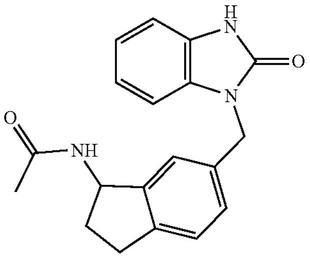 [SMILES: CC(=O)NC1CCc2ccc(Cn3c(=O)[nH]c4ccccc43)cc21]

Preparative resolution of N-(6-((2-oxo-2,3-dihydro-1H-benzo[d]imidazol-1-yl)methyl)-2,3-dihydro-1H-inden-1-yl) acetamide was performed using supercritical fluid chromatography on a Sepiatec Prep 100. A Chiral Technologies IG column (5 μm, 21 mm×250 mm, Chiral Tech., West Chester, PA) was used as the chiral stationary phase. The compound mixture was dissolved in a 1:1 mixture of methanol and acetonitrile. Injection and collection were carried out using the following isocratic SFC conditions: 55% carbon dioxide and 45% methanol with 0.1% ammonium hydroxide as the mobile phase, 220 nm UV wavelength, 100 bar outlet pressure, 40° C. column compartment temperature, 70 mL/min total flow rate. Retention times for peak collection were as follows: first eluting peak, 3.9 min; second eluting peak, 5.4 min.

LC/MS (m/z): 322 (M+H)+. $^{1}$H NMR (600 MHz, DMSO-d6) δ 10.92 (s, 1H), 8.14 (d, J=8.2 Hz, 1H), 7.19-7.11 (m, 2H), 7.02-6.90 (m, 3H), 5.19 (q, J=7.8 Hz, 1H), 4.96 (s, 2H), 2.89-2.81 (m, 1H), 2.77-2.68 (m, 1H), 2.37-2.28 (m, 1H), 1.82 (s, 3H), 1.75-1.66 (m, 1H).

Example 46

N-methyl-5-((2-oxo-2,3-dihydro-1H-benzo[d]imidazol-1-yl)methyl)-2,3-dihydro-1H-indene-1-carboxamide

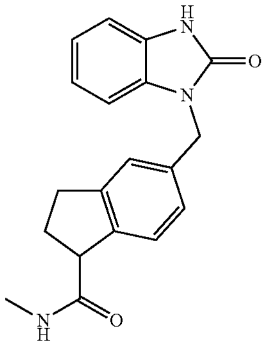 [SMILES: CNC(=O)C1CCc2cc(Cn3c(=O)[nH]c4ccccc43)ccc21]

Step A: 5-bromo-N-methyl-2,3-dihydro-1H-indene-1-carboxamide

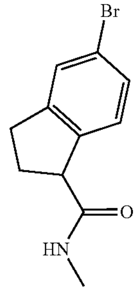

5-bromo-2,3-dihydro-1H-indene-1-carboxylic acid (200 mg, 0.830 mmol), HATU (473 mg, 1.244 mmol), and DMF (4148 μl) were added to a vial equipped with a stir bar. The mixture was stirred at room temperature for 5 minutes. After 5 minutes, methanamine (129 μl, 1.659 mmol) was added, followed by DIEA (435 μl, 2.489 mmol). The reaction mixture was allowed to stir at room temperature for 1 hour. After 1 hour, the crude was washed with ethyl acetate and water. The combined organics were dried over magnesium sulfate, filtered, and concentrated under reduced pressure. The material was dissolved in DCM, and loaded directly onto a 40 g column. The column was run from 100% hexanes to 100% ethyl acetate. The desired product eluted and fractions were collected and concentrated under reduced pressure to afford the title compound. LC/MS (m/z): 254 (M+H)+.

Step B: N-methyl-5-((2-oxo-2,3-dihydro-1H-benzo[d]imidazol-1-yl)methyl)-2,3-dihydro-1H-indene-1-carboxamide

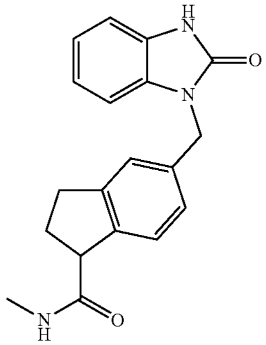 [SMILES: CNC(=O)C1CCc2cc(Cn3c(=O)[nH]c4ccccc43)ccc21]

Utilizing the procedure in Example 27, 5-bromo-N-methyl-2,3-dihydro-1H-indene-1-carboxamide was elaborated to the title compound. LC/MS (m/z): 322 (M+H)+.

Step C: N-methyl-5-((2-oxo-2,3-dihydro-1H-benzo[d]imidazol-1-yl)methyl)-2,3-dihydro-1H-indene-1-carboxamide

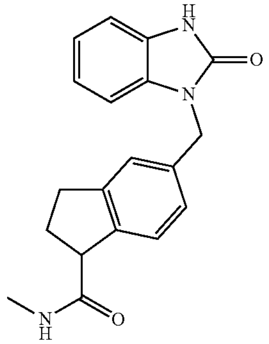 [SMILES: CNC(=O)C1CCc2cc(Cn3c(=O)[nH]c4ccccc43)ccc21]

Preparative resolution of N-methyl-5-((2-oxo-2,3-dihydro-1H-benzo[d]imidazol-1-yl)methyl)-2,3-dihydro-1H-indene-1-carboxamide was performed using supercritical fluid chromatography on a Sepiatec Prep 100. A Chiral Technologies IG column (5 μm, 21 mm×250 mm, Chiral Tech, West Chester, PA) was used as the chiral stationary phase. The compound mixture was dissolved in a 1:1 mixture of methanol and DMSO. Injection and collection were carried out using the following isocratic SFC conditions: 60% carbon dioxide and 40% methanol with 0.1% ammonium hydroxide as the mobile phase, 220 nm UV wavelength, 100 bar outlet pressure, 40° C. column compartment temperature, 70 mL/min total flow rate. Retention times for peak collection were as follows: first eluting peak, 3.9 min; second eluting peak, 5.9 min.

LC/MS (m/z): 322 (M+H)+. $^1$H NMR (600 MHz, DMSO-d6) δ 10.97-10.86 (m, 1H), 8.04-7.92 (m, 1H), 7.21-7.05 (m, 3H), 7.05-6.87 (m, 4H), 4.94 (s, 2H), 3.77 (t, J=7.5 Hz, 1H), 2.98-2.87 (m, 1H), 2.81-2.72 (m, 1H), 2.60 (d, J=4.6 Hz, 3H), 2.26-2.08 (m, 2H).

The Examples in Table 6 were synthesized according to the methods described in Example 46 employing the appropriate substituted bromide starting material and amine starting material in Step A.

TABLE 6

| Example No. | Structure | Name | Exact Mass [M + H]+ |
|---|---|---|---|
| Example 47 | 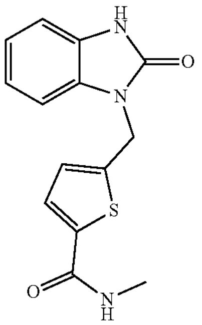 [SMILES: CNC(=O)c1ccc(Cn2c(=O)[nH]c3ccccc32)s1] | N-methyl-5-[(2-oxo-2,3-dihydro-1H-benzimidazol-1-yl)methyl]thiophene-2-carboxamide | 288 [M + H]+ |
| Example 48 | 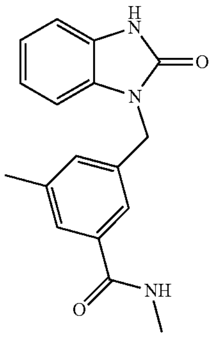 [SMILES: CNC(=O)c1cc(C)cc(Cn2c(=O)[nH]c3ccccc32)c1] | N,3-dimethyl-5-((2-oxo-2,3-dihydro-1H-benzo[d]imidazol-1-yl)methyl)benzamide | 296 [M + H]+ |

Example 49

Preparation of N-(2-methyl-4-((2-oxo-2,3-dihydro-1H-benzo[d]imidazol-1-yl)methyl)benzyl)acetamide

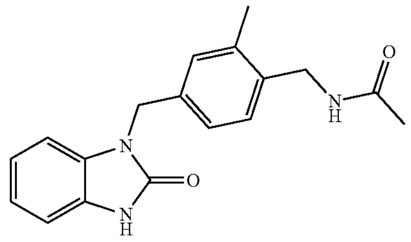 [SMILES: CC(=O)NCc1ccc(Cn2c(=O)[nH]c3ccccc32)cc1C]

Step A: N-(2-methyl-4-((2-oxo-2,3-dihydro-1H-benzo[d]imidazol-1-yl)methyl)benzyl)acetamide

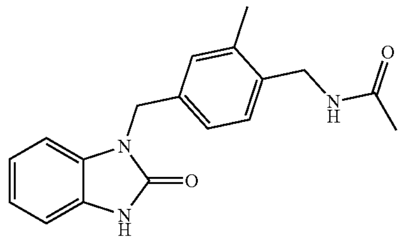 [SMILES: CC(=O)NCc1ccc(Cn2c(=O)[nH]c3ccccc32)cc1C]

Acetyl chloride (35.7 μl, 0.500 mmol), (4-bromo-2-methylphenyl)methanamine (100 mg, 0.500 mmol), TEA (139 μl, 1.000 mmol), and DMA (1250 μl) were added to a vial equipped with a stir bar. The mixture was stirred at room temperature for 96 hours. After 96 hours, acetyl chloride (53.3 μl, 0.750 mmol) was added, and the reaction mixture was allowed to stir for 72 hours. After 72 hours, 4,4'-di-tert-butyl-2,2'-bipyridine (20.12 mg, 0.075 mmol), nickel (II) chloride ethylene glycol dimethyl ether complex (16.47 mg, 0.075 mmol), $Ir[dF(CF_3)ppy]_2(dtbbpy)PF_6$ (5.61 mg, 5.00 μmol), and 2-(2-oxo-2,3-dihydro-1H-benzo[d]imidazol-1-yl)acetic acid (130 mg, 0.675 mmol) were added to a second vial. This vial was purged with nitrogen for 5 minutes. After 5 minutes, DMA (1.0 ml) was added, and the vial was purged with nitrogen for 10 minutes. After 10 minutes, the contents of vial 2 were added to the contents of vial 1. Lastly, 2-(tert-butyl)-1,1,3,3-tetramethylguanidine (118 μl, 1.000 mmol) was added to the combined reaction mixture. The mixture was sealed and placed in the Penn Optic photoreactor for 5 hours (fan speed 5200 rpm; Stir 700 rpm; LED 70%). After 5 hours, the crude reaction mixture was washed with ethyl acetate and water. The combined organics were dried over magnesium sulfate, filtered, and concentrated under reduced pressure. The reaction mixture was submitted directly for HPLC purification (purified by HPLC, eluting acetonitrile/water gradient with basic modifier, linear gradient) to afford the title compound. LC/MS (m/z): 310 (M+H)+. $^1H$ NMR (600 MHZ, DMSO-d6) δ 10.91 (s, 1H), 8.11 (t, J=5.3 Hz, 1H), 7.18-7.06 (m, 3H), 7.02-6.88 (m, 4H), 4.92 (s, 2H), 4.15 (d, J=5.6 Hz, 2H), 2.20 (s, 3H), 1.82 (s, 3H).

The Examples in Table 7 were synthesized according to the methods described in Example 49 employing the appropriate substituted (4-bromophenyl)methanamine starting materials.

Table 7

| Example No. | Structure | Name | Observed Mass [M + H]+ |
|---|---|---|---|
| Example 50 | 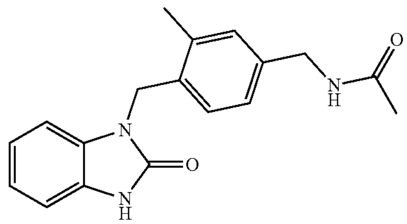 [SMILES: CC(=O)NCc1ccc(Cn2c(=O)[nH]c3ccccc32)c(C)c1] | N-({3-methyl-4-[(2-oxo-2,3-dihydro-1H-benzimidazol-1-yl)methyl]phenyl}methyl)acetamide | 310 [M + H]+ |
| Example 51 | 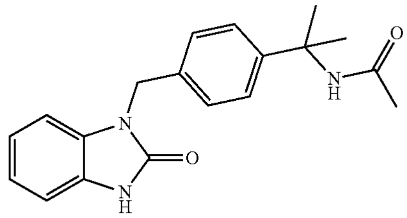 [SMILES: CC(=O)NC(C)(C)c1ccc(Cn2c(=O)[nH]c3ccccc32)cc1] | N-(2-{4-[(2-oxo-2,3-dihydro-1H-benzimidazol-1-yl)methyl]phenyl}propan-2-yl)acetamide | 324 [M + H]+ |

Example 52

Preparation of 1-(indolin-5-ylmethyl)-1,3-dihydro-2H-benzo[d]imidazol-2-one

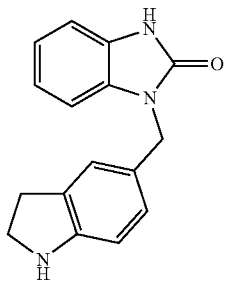 [SMILES: O=c1[nH]c2ccccc2n1Cc1ccc2c(c1)CCN2]

Step A: tert-butyl 5-((2-oxo-2,3-dihydro-1H-benzo[d]imidazol-1-yl)methyl)indoline-1-carboxylate

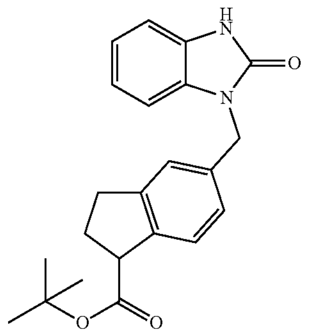 [SMILES: CC(C)(C)OC(=O)C1CCc2cc(Cn3c(=O)[nH]c4ccccc43)ccc21]

Utilizing the procedure in Example 27, tert-butyl 5-bromoindoline-1-carboxylate was elaborated to the title compound. LC/MS (m/z): 310 (M+H)+ (observe loss of the tert-butyl group).

Step B: 1-(indolin-5-ylmethyl)-1,3-dihydro-2H-benzo[d]imidazol-2-one

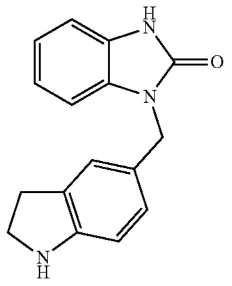 [SMILES: O=c1[nH]c2ccccc2n1Cc1ccc2c(c1)CCN2]

Tert-butyl 5-((2-oxo-2,3-dihydro-1H-benzo[d]imidazol-1-yl)methyl)indoline-1-carboxylate (74.8 mg, 0.205 mmol), dioxane (3000 μl), and HCl (4.0 M in Dioxane) (512 μl, 2.047 mmol) were added to a vial equipped with a stir bar. The vial was sealed and stirred at room temperature for 22.5 hours. After 22.5 hours, the reaction mixture was heated to 50° C. for 1.5 hours. After 1.5 hours, the reaction mixture was cooled to room temperature, and concentrated under reduced pressure. The mixture was dissolved in ACN/water, and was frozen and dried on the lyophilizer for 16 hours to afford the title compound. LC/MS (m/z): 266 (M+H)+. $^{1}H$ NMR (600 MHZ, DMSO-d6) δ 10.95 (s, 1H), 7.29 (s, 1H), 7.23 (d, J=7.6 Hz, 1H), 7.20-7.07 (m, 1H), 7.06-7.02 (m, 1H), 7.02-6.91 (m, 2H), 4.98 (s, 2H), 3.61 (t, J=7.9 Hz, 2H), 3.08 (t, J=7.9 Hz, 2H).

Example 53

Preparation of 1-(4-((4-methyl-4H-1,2,4-triazol-3-yl)methyl)benzyl)-1,3-dihydro-2H-benzo[d]imidazol-2-one

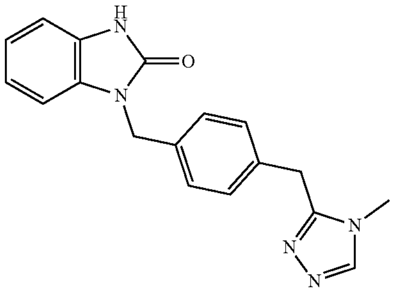 [SMILES: Cn1cnnc1Cc1ccc(Cn2c(=O)[nH]c3ccccc32)cc1]

Step A: 3-(4-bromobenzyl)-4-methyl-4H-1,2,4-triazole

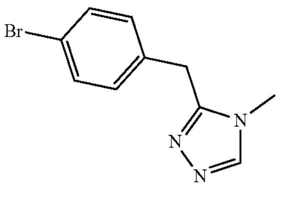

2-(4-bromobenzyl)-1,3,4-oxadiazole (700 mg, 2.93 mmol) and dioxane (8 mL) were added to a vial equipped with a stir bar. Methanamine (4 mL, 39.5 mmol, 30% in EtOH) and AcOH (0.12 mL, 2.096 mmol) were added, and the vial was sealed and heated to 130° C. for 16 hours. After 16 hours, the reaction mixture was cooled to room temperature. The reaction was concentrated under reduced pressure and purified by flash silica gel chromatography with methanol and DCM as eluent to afford the title compound. MS (ESI) m/z: 252 [M+H$^{+}$]

Step B: 1-(4-((4-methyl-4HI-1,2,4-triazol-3-yl) methyl)benzyl)-1/-benzo[d]imidazol-2 (3H)-one

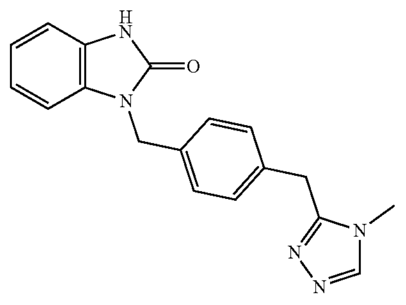 [SMILES: Cn1cnnc1Cc1ccc(Cn2c(=O)[nH]c3ccccc32)cc1]

Utilizing the procedure from Example 27, 3-(4-bromobenzyl)-4-methyl-4H-1,2,4-triazole was elaborated to the title compound. MS (ESI) m/z: 320 $[M+H^+]$. $^1H$ NMR (500 MHZ, $CD_3OD$) δ 8.85 (s, 1H), 7.37 (d, J=8.0 Hz, 2H), 7.28 (d, J=8.0 Hz, 2H), 7.14-6.97 (m, 4H), 5.10 (s, 2H), 4.34 (s, 2H), 3.70 (s, 3H).

Example 54

Preparation of: 1-(4-((1,3,4-oxadiazol-2-yl)methyl)-3-methylbenzyl)-1,3-dihydro-2H-benzo[d]imidazol-2-one

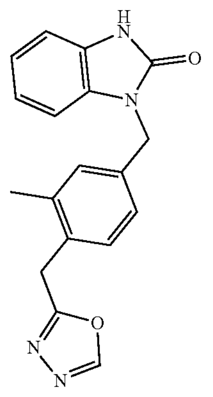 [SMILES: Cc1cc(Cn2c(=O)[nH]c3ccccc32)ccc1Cc1nnco1]

Step A: (E)-5-bromo-3-chlorothiophene-2-carbaldehyde oxime

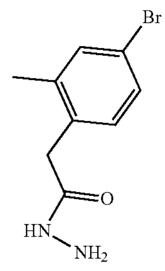

Methyl 2-(4-bromo-2-methylphenyl)acetate (1.0 g, 4.11 mmol) and MeOH (10 mL) were added to a vial equipped with a stir bar. Hydrazine (0.538 g, 16.45 mmol) (98%) was added at room temperature (26° C.). After the addition was complete, the reaction was stirred at 65° C. The reaction was then heated to 75° C. and allowed to stir for 16 hours. After 16 hours, the reaction mixture was cooled to room temperature. The solvent was evaporated under reduced pressure to afford the title compound.

Step B: 2-(4-bromo-2-methylbenzyl)-1,3,4-oxadiazole

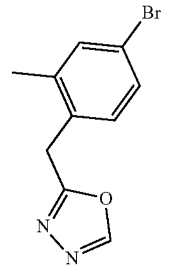

2-(4-bromo-2-methylphenyl)acetohydrazide (0.5 g, 2.057 mmol), Xylene (12 mL), and AcOH (2 mL) were added to a vial equipped with a stir bar. Triethoxymethane (1.219 g, 8.23 mmol) was added at 26° C. (room temperature), and the reaction was stirred at 150° C. for 2 hours. After 2 hours, the reaction mixture was cooled to room temperature. Water (30 mL) was added to the mixture, and the mixture was washed with EtOAc (30 mL×2). The combined organics layers were collected, washed with brine (10 mL), dried over $Na_2SO_4$, and filtered. The collected filtrate was concentrated in vacuo. The resulting residue was purified by flash silica gel chromatography with petroleum ether and ethyl acetate as eluent to afford the title compound. LCMS (ESI) m/z: 255 $[M+H]^+$.

Step C: 1-(4-((1,3,4-oxadiazol-2-yl)methyl)-3-methylbenzyl)-1,3-dihydro-2H-benzo[d]imidazol-2-one

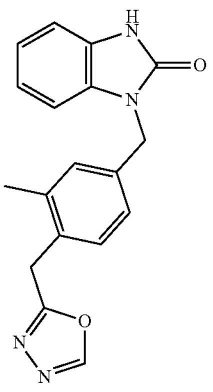 [SMILES: Cc1cc(Cn2c(=O)[nH]c3ccccc32)ccc1Cc1nnco1]

Utilizing the procedure from Example 27, 2-(4-bromo-2-methylbenzyl)-1,3,4-oxadiazole was elaborated to the title compound. LC/MS (ESI) m/z: 321 $[M+H]^+$. $^1H$ NMR (500 MHZ, MeOH-d4) δ 8.83 (s, 1H), 7.23-7.00 (m, 7H), 5.05 (s, 2H), 4.28 (s, 2H), 2.32 (s, 3H).

Example 55

Preparation of 1-((2,3-dihydro-1H-inden-5-yl) methyl)-1,3-dihydro-2H-benzo[d]imidazol-2-one

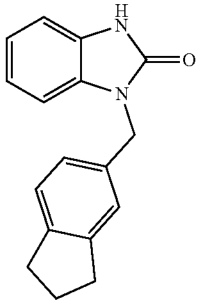 [SMILES: O=c1[nH]c2ccccc2n1Cc1ccc2c(c1)CCC2]

Copper iodide (15.24 mg, 0.080 mmol), L-hydroxyproline (20.98 mg, 0.160 mmol), potassium phosphate (0.066 ml, 0.8 mmol), and methyl (2-bromophenyl)carbamate (92 mg, 0.4 mmol) were added to a vial and placed under nitrogen. DMSO (1 ml) and (2,3-dihydro-1H-inden-5-yl) methanamine (0.050 ml, 0.400 mmol) were added to the vial, and the vial was heated to 70° C. for 2 hours. Then the heat was increased to 130° C. for 12 hours. After this time the reaction mixture was cooled to room temperature and then filtered through a syringe filter and purified by HPLC (eluting acetonitrile/water gradient with TFA modifier). $^1$H NMR (500 MHZ, DMSO-$d_6$) δ 10.95 (s, 1H), 7.17-7.10 (m, 2H), 7.06 (d, J=8.6 Hz, 1H), 7.01-6.91 (m, 4H), 4.92 (s, 2H), 2.77 (t, J=7.4 Hz, 4H), 1.98-1.90 (m, 2H). LCMS (ESI) m/z: 265 $[M+H]^+$.

Example 56

Preparation of 1-(pyridin-3-ylmethyl)-1,3-dihydro-2H-benzo[d]imidazol-2-one

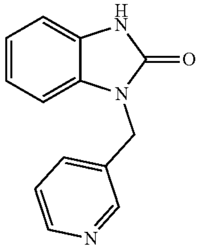 [SMILES: O=c1[nH]c2ccccc2n1Cc1cccnc1]

Utilizing the procedure from Example 55, pyridin-3-ylmethanamine was elaborated to the final product 1-(pyridin-3-ylmethyl)-1,3-dihydro-2H-benzo[d]imidazol-2-one. $^1$H NMR (500 MHZ, DMSO-$d_6$) δ 11.04 (s, 1H), 8.84 (br s, 1H), 7.87 (d, J=6.9 Hz, 1H), 7.65-7.54 (m, 1H), 7.10 (d, J=7.1 Hz, 1H), 7.03-6.93 (m, 4H), 5.10 (s, 2H). LCMS (ESI) m/z: 226 $[M+H]^+$.

The Examples in Table 8 were synthesized according to the methods described in Example 55 employing the appropriate amine starting materials.

TABLE 8

| Example No. | Structure | Name | Exact Mass [M + H]+ |
|---|---|---|---|
| Example 57 | 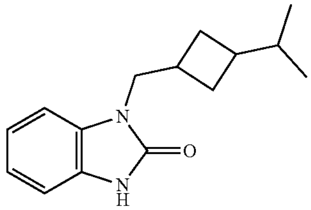 [SMILES: CC(C)C1CC(Cn2c(=O)[nH]c3ccccc32)C1] | 1-{[3-(propan-2-yl)cyclobutyl]methyl}-1,3-dihydro-2H-benzimidazol-2-one | 245 [M + H]+ |
| Example 58 | 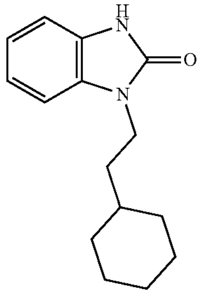 [SMILES: O=c1[nH]c2ccccc2n1CCC1CCCCC1] | 1-(2-cyclohexylethyl)-1,3-dihydro-2H-benzimidazol-2-one | 245 [M + H]+ |
| Example 59 | 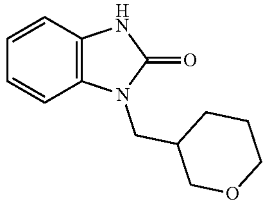 [SMILES: O=c1[nH]c2ccccc2n1CC1CCCOC1] | 1-[(oxan-3-yl)methyl]-1,3-dihydro-2H-benzimidazol-2-one | 233 [M + H]+ |

TABLE 8-continued
| Example No. | Structure | Name | Exact Mass [M + H]+ |
| --- | --- | --- | --- |
| Example 60 | 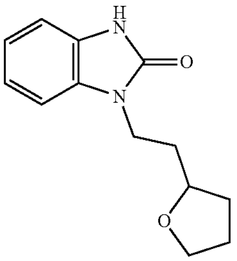 [SMILES: O=c1[nH]c2ccccc2n1CCC1CCCO1] | 1-[2-(oxolan-2-yl)ethyl]-1,3-dihydro-2H-benzimidazol-2-one | 233 [M + H]+ |
| Example 61 | 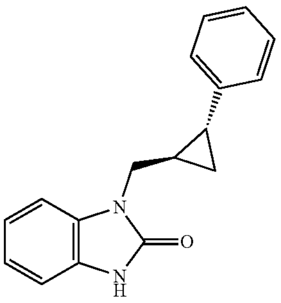 [SMILES: O=c1[nH]c2ccccc2n1C[C@@H]1C[C@H]1c1ccccc1] | 1-{[(1R,2R)-2-phenylcyclopropyl]methyl}-1,3-dihydro-2H-benzimidazol-2-one | 265 [M + H]+ |
| Example 62 | 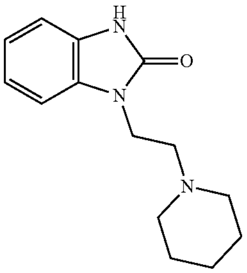 [SMILES: O=c1[nH]c2ccccc2n1CCN1CCCCC1] | 1-[2-(piperidin-1-yl)ethyl]-1,3-dihydro-2H-benzimidazol-2-one | 246 [M + H]+ |
| Example 63 | 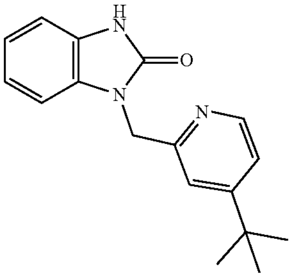 [SMILES: CC(C)(C)c1ccnc(Cn2c(=O)[nH]c3ccccc32)c1] | 1-[(4-tert-butylpyridin-2-yl)methyl]-1,3-dihydro-2H-benzimidazol-2-one | 282 [M + H]+ |

Example 64

Preparation of N-(4-((6-chloro-2-oxo-2,3-dihydro-1H-benzo[d]imidazol-1-yl)methyl)benzyl)acetamide

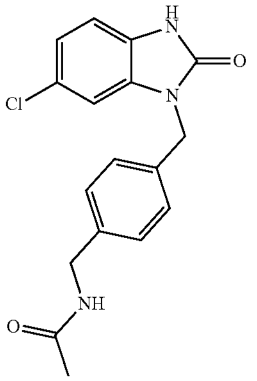

Step A: tert-butyl (4-((6-chloro-2-oxo-2,3-dihydro-1H-benzo[d]imidazol-1-yl)methyl)benzyl)carbamate

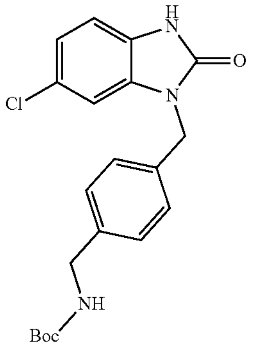 [SMILES: CC(C)(C)OC(=O)NCc1ccc(Cn2c(=O)[nH]c3ccc(Cl)cc32)cc1]

Utilizing the procedure for Example 55, tert-butyl (4-(aminomethyl)benzyl)carbamate and methyl (2-bromo-4-chlorophenyl)carbamate were elaborated to the title compound. $^1$H NMR (500 MHz, DMSO-$d_6$) δ 11.12 (br s, 1H), 7.25 (br d, J=8.2 Hz, 2H), 7.18 (br d, J=8.2 Hz, 3H), 7.02-6.96 (m, 2H), 4.96-4.70 (m, 2H), 4.07 (br d, J=5.8 Hz, 2H), 1.37 (s, 9H).

Step B: 1-(4-(aminomethyl)benzyl)-6-chloro-1,3-dihydro-2H-benzo[d]imidazol-2-one

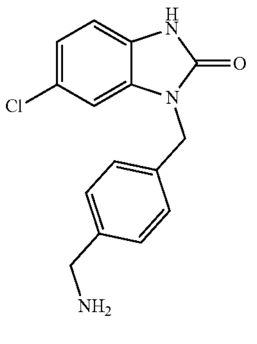 [SMILES: NCc1ccc(Cn2c(=O)[nH]c3ccc(Cl)cc32)cc1]

A mixture of tert-butyl 4-((6-chloro-2-oxo-2,3-dihydro-1H-benzo[d]imidazol-1-yl)methyl)benzylcarbamate (90.0 mg, 0.232 mmol) and TFA (0.018 mL, 0.232 mmol) in DCM (5 mL) was stirred at 25° C. for 3 hours. The mixture was concentrated under reduced pressure. The compound was used as is for the next step. LCMS (ESI) m/z: 288 [M+H]$^+$.

Step C: N-(4-((3-acetyl-6-chloro-2-oxo-2,3-dihydro-1H-benzo[d]imidazol-1-yl)methyl)benzyl)acetamide

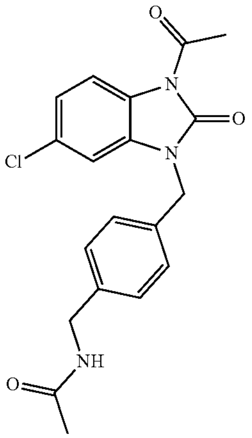 [SMILES: CC(=O)NCc1ccc(Cn2c(=O)n(C(C)=O)c3ccc(Cl)cc32)cc1]

1-(4-(aminomethyl)benzyl)-6-chloro-1,3-dihydro-2H-benzo[d]imidazol-2-one (50.0 mg, 0.174 mmol), $Ac_2O$ (0.016 mL, 0.174 mmol) and triethylamine (0.097 mL, 0.695 mmol) in DCM (2 mL) were stirred at 25° C. for 16 hours. The reaction mixture was filtered and concentrated under reduced pressure to afford the crude product, which was used directly in the next step. LCMS (ESI) m/z: 394 [M+Na]$^+$.

Step D: N-(4-((6-chloro-2-oxo-2,3-dihydro-1H-benzo[d]imidazol-1-yl)methyl)benzyl)acetamide

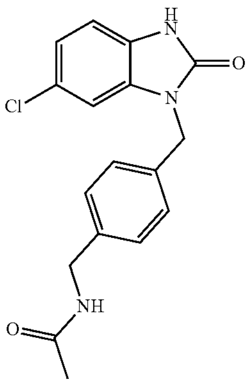 [SMILES: CC(=O)NCc1ccc(Cn2c(=O)[nH]c3ccc(C)cc32)cc1]

N-(4-((3-acetyl-6-chloro-2-oxo-2,3-dihydro-1H-benzo[d]imidazol-1-yl)methyl)benzyl)acetamide (50.0 mg, 0.134 mmol) and 2M HCl (0.067 mL, 0.134 mmol) in 1,4-dioxane (4 mL) was stirred at 25° C. for 2 hours. After this, the mixture was poured into saturated $NaHCO_3$ solution (5 mL). The reaction mixture was diluted with water (10 mL) and extracted with EtOAc (10 mL×3). The combined organic phases were washed with brine (10 mL), dried over anhydrous $Na_2SO_4$, filtered and concentrated under reduced pressure to give crude product. It was purified by HPLC (eluting acetonitrile/water gradient with TFA modifier). Isolated as a solid. $^1H$ NMR (500 MHz, MeOH-$d_4$) δ 7.30-7.25 (m, 4H), 7.04-7.01 (m, 2H), 6.97 (s, 1H), 5.04 (s, 2H), 4.38 (s, 2H), 1.96 (s, 3H). LCMS (ESI) m/z: 330 $[M+H]^+$.

Example 65

Preparation of N-(4-((6-methyl-2-oxo-2,3-dihydro-1H-benzo[d]imidazol-1-yl)methyl)benzyl)acetamide

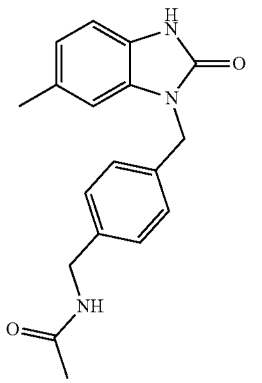

Step A: tert-butyl (4-((6-methyl-2-oxo-2,3-dihydro-1H-benzo[d]imidazol-1-yl)methyl)benzyl)carbamate

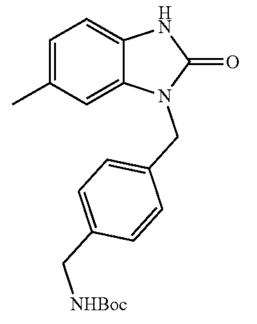 [SMILES: Cc1ccc2[nH]c(=O)n(Cc3ccc(CNC(=O)OC(C)(C)C)cc3)c2c1]

Utilizing the procedure for Example 55, tert-butyl (4-(aminomethyl)benzyl)carbamate and methyl (2-bromo-4-methylphenyl)carbamate were elaborated to the title compound. LCMS (ESI) m/z: 368 $[M+H]^+$.

Step B: 1-(4-(aminomethyl)benzyl)-6-methyl-1,3-dihydro-2H-benzo[d]imidazol-2-one

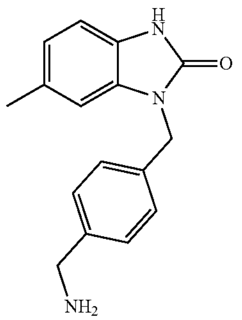 [SMILES: Cc1ccc2[nH]c(=O)n(Cc3ccc(CN)cc3)c2c1]

A mixture of tert-butyl 4-((6-methyl-2-oxo-2,3-dihydro-1H-benzo[d]imidazol-1-yl)methyl)benzylcarbamate (50 mg, 0.136 mmol) and TFA (1 mL, 12.98 mmol) in DCM (5 mL) was stirred at room temperature for 4 hours. Then, it was concentrated under reduced pressure to give the material as a solid, which was used in next step directly. $^1H$ NMR (400 MHZ, MeOH-$d_4$) δ 7.44-7.37 (m, 4H), 6.98-6.94 (m, 1H), 6.90-6.85 (m, 1H), 6.78 (s, 1H), 5.09 (s, 2H), 4.08 (s, 2H), 2.29 (s, 3H).

Step C: N-(4-((6-methyl-2-oxo-2,3-dihydro-1H-benzo[d]imidazol-1-yl)methyl)benzyl)acetamide

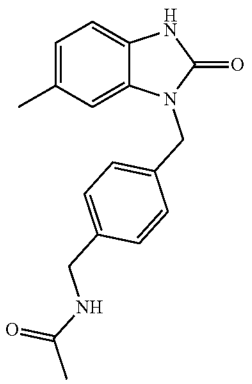 [SMILES: CC(=O)NCc1ccc(Cn2c(=O)[nH]c3ccc(C)cc32)cc1]

A mixture of 1-(4-(aminomethyl)benzyl)-6-methyl-1H-benzo[d]imidazol-2 (3H)-one (30 mg, 0.112 mmol), TEA (0.063 mL, 0.449 mmol) and N-Acetoxysuccinimide (17.63 mg, 0.112 mmol) in DCM (3 mL) was stirred at room temperature for 16 h. The reaction mixture was dissolved with water (10 mL) and extracted with DCM (10 mL×3). The combined organic phases were washed with brine (10 mL), dried over anhydrous $Na_2SO_4$, filtered and concentrated under reduced pressure to give crude product, which was purified by HPLC (eluting acetonitrile/water gradient with TFA modifier). Isolated as a solid. $^1H$ NMR (500 MHz, DMSO-$d_6$) δ 10.80 (s, 1H), 8.32-8.23 (m, 1H), 7.26-7.23 (m, 2H), 7.21-7.17 (m, 2H), 6.86 (d, J=8.0 Hz, 1H), 6.83 (s, 1H), 6.77 (d, J=7.8 Hz, 1H), 4.93 (s, 2H), 4.18 (d, J=6.0 Hz, 2H), 2.25 (s, 3H), 1.83 (s, 3H). LCMS (ESI) m/z: 310 $[M+H]^+$.

Example 66

Preparation of 2-(4-((6-fluoro-2-oxo-2,3-dihydro-1H-benzo[d]imidazol-1-yl)methyl)phenyl)-N,N-dimethylacetamide

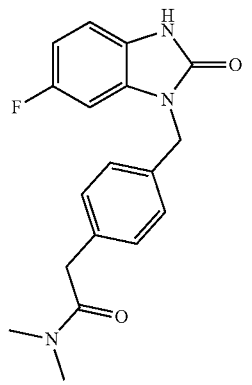 [SMILES: CN(C)C(=O)Cc1ccc(Cn2c(=O)[nH]c3ccc(F)cc32)cc1]

Step A: methyl (2-bromo-4-fluorophenyl)carbamate

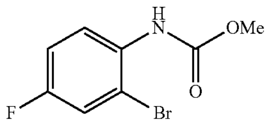 [SMILES: COC(=O)Nc1ccc(F)cc1Br]

2-bromo-4-fluoroaniline (5.0 g, 26.3 mmol) was dissolved in DCM (37.6 ml). Pyridine (5.32 ml, 65.8 mmol) was added to the mixture. The mixture was cooled to 0° C. in an ice bath, and methyl chloroformate (2.446 ml, 31.6 mmol) was added dropwise via an addition funnel. Once the addition was complete, the reaction mixture was allowed to stir at 0° C. for 75 minutes. After 75 minutes, the reaction mixture was washed with 100 ml of 0.5 M HCl. The aqueous layer was extracted 2 more times with DCM (100 ml). The combined organics were washed with brine, dried with magnesium sulfate, filtered, and concentrated under reduced pressure. Diethyl ether was added, and the mixture was stirred. The resulting material was filtered, and afforded the title compound as a solid. The remaining filtrate was purified via silica gel column chromatography with hexanes and ethyl acetate as eluent to afford the title compound. LC/MS (m/z): 248 (M+H)+.

Step B: tert-butyl 2-(4-((6-fluoro-2-oxo-2,3-dihydro-1H-benzo[d]imidazol-1-yl)methyl)phenyl) acetate

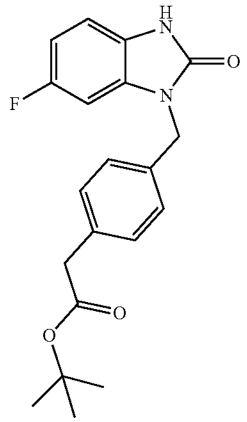 [SMILES: CC(C)(C)OC(=O)Cc1ccc(Cn2c(=O)[nH]c3ccc(F)cc32)cc1]

In the glove box, bis[(tetrabutylammonium iodide)copper (I) iodide] (0.448 g, 0.400 mmol) and 1,10-phenanthroline (0.144 g, 0.800 mmol) were added to a 40 mL vial with a stir bar. DMSO (5 mL) was added and the mixture was stirred for 10 minutes. Methyl (2-bromo-4-fluorophenyl)carbamate (0.992 g, 4 mmol), tert-butyl 2-(4-(aminomethyl)phenyl) acetate, oxalic acid (1.308 g, 4.20 mmol), and potassium phosphate (2.55 g, 12.00 mmol) were added to a second vial. The Cu/Ligand solution was added to the reagent solution and rinsed with DMSO (15 mL). The vial was sealed, removed from the glove box, and heated to 100° C. for 22 hours. After 22 hours, the reaction mixture was cooled to room temperature, and filtered through CELITE, rinsing with EtOAc. The mixture was washed with water and the organic layer was dried over $MgSO_4$, filtered, and concentrated under reduced pressure. The material was purified via column chromatography, eluting 30-60% EtOAc in hexanes to afford the title compound. LC/MS (m/z): 379 (M+Na)+

Step C: 2-(4-((6-fluoro-2-oxo-2,3-dihydro-1H-benzo[d]imidazol-1-yl)methyl)phenyl)acetic acid

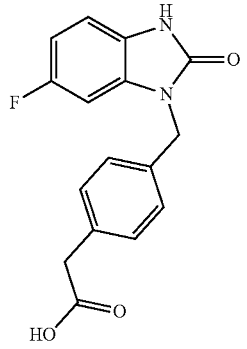 [SMILES: O=C(O)Cc1ccc(Cn2c(=O)[nH]c3ccc(F)cc32)cc1]

Tert-butyl 2-(4-((6-fluoro-2-oxo-2,3-dihydro-1H-benzo[d]imidazol-1-yl)methyl)phenyl)acetate (828.8 mg, 2.325 mmol) was added to a 40 mL vial equipped with stir bar. Dioxane (5814 µl) was added, followed by trifluoroacetic acid (3583 µl, 46.5 mmol). The vial was sealed and heated to 60° C. for 24 hours. After 24 hours, the reaction mixture was cooled to room temperature. Trifluoroacetic acid (500 μl, 6.49 mmol) was added and stirring was resumed at 60° C. for 68 hours. After 68 hours, the material was filtered and rinsed with ethyl acetate and water. The collected solids afforded the title compound. The collected filtrate was washed with ethyl acetate, dried over $MgSO_4$, filtered, and concentrated under reduced pressure to afford the title compound. LC/MS (m/z): 301 (M+H)+.

Step D: 2-(4-((6-fluoro-2-oxo-2,3-dihydro-1H-benzo[d]imidazol-1-yl)methyl)phenyl)-N,N-dimethylacetamide

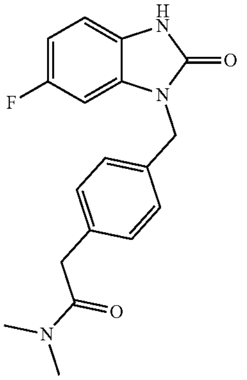 [SMILES: CN(C)C(=O)Cc1ccc(Cn2c(=O)[nH]c3ccc(F)cc32)cc1]

2-(4-((6-fluoro-2-oxo-2,3-dihydro-1H-benzo[d]imidazol-1-yl)methyl)phenyl)acetic acid (485.7 mg, 1.617 mmol), HATU (923 mg, 2.426 mmol), and DMF (8087 μl) were added to a vial equipped with a stir bar. The reaction mixture was allowed to stir at room temperature for 5 minutes. After 5 minutes, dimethylamine (2 M in THF) (1617 μl, 3.23 mmol) and DIEA (847 μl, 4.85 mmol) were added. The reaction mixture was stirred at 45° C. for 3 hours. After 3 hours, the crude material was washed with ethyl acetate and saturated $NaHCO_3$. The combined organics were dried over magnesium sulfate, filtered, and concentrated under reduced pressure. The residue was dissolved in DCM, and loaded directly onto an 80 g column. The column was run from 100% hexanes to 100% ethyl acetate. The column was then flushed from 100% DCM to 30% methanol. The desired product eluted and fractions were collected and concentrated under reduced pressure. The material was then dissolved in ACN/water and heated to 80° C. while stirring for 20 minutes. After 20 minutes, the mixture was allowed to cool to room temperature while stirring for 48 hours. After 48 hours, the material was filtered, rinsing with acetonitrile. The collected solid afforded the title compound. LC/MS (m/z): 328 (M+H)+. $^1H$ NMR (600 MHZ, DMSO-d6) δ 10.98 (s, 1H), 7.21 (dd, J=54.7, 8.1 Hz, 3H), 7.02 (dd, J=9.1, 2.4 Hz, 1H), 6.98-6.91 (m, 1H), 6.84-6.71 (m, 1H), 4.95 (s, 2H), 3.63 (s, 2H), 2.97 (s, 3H), 2.79 (s, 3H).

Example 67

Preparation of 2-(4-((6-fluoro-2-oxo-2,3-dihydro-1H-benzo[d]imidazol-1-yl)methyl)phenyl)-N-methylacetamide

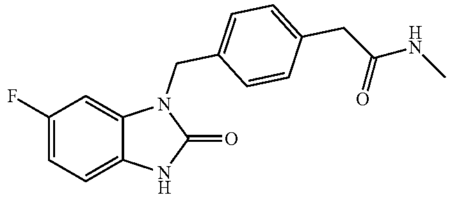 [SMILES: CNC(=O)Cc1ccc(Cn2c(=O)[nH]c3ccc(F)cc32)cc1]

Step A: 5-fluoro-1,3-dihydro-2H-benzo[d]imidazol-2-one

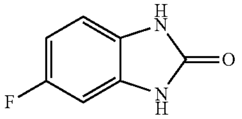 [SMILES: O=c1[nH]c2ccc(F)cc2[nH]1]

Triethylamine (33.2 mL, 238 mmol) and 1,1'-carbonyldiimidazole (CDI) (19.28 g, 119 mmol) were added to a stirred solution of 4-fluorobenzene-1,2-diamine (5.0 g, 39.6 mmol) in THF (100 mL) at 30° C. After the addition was finished, the reaction was stirred at 80° C. for 15 hours. After 15 hours the reaction was cooled to room temperature. Water (50 mL) was added and the mixture was extracted with EtOAc (50 mL*2). The organic layers were collected, washed with brine, dried over $Na_2SO_4$, and filtered. The filtrate was concentrated in vacuo. The residue was purified by flash silica gel chromatography (ISCO®; Agela® Flash Column Silica-CS (12 g), Eluent of 0~70% Ethyl acetate/Petroleum ether gradient @ 30 mL/min) to afford 5-fluoro-1H-benzo[d]imidazol-2 (3H)-one. LC/MS (m/z): 153 (M+H)+.

Step B: tert-butyl 5-fluoro-2-oxo-2,3-dihydro-1H-benzo[d]imidazole-1-carboxylate

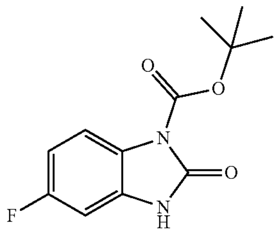 [SMILES: CC(C)(C)OC(=O)n1c(=O)[nH]c2cc(F)ccc21]

NaH (67 mg, 1.675 mmol) (60% in oil) was added dropwise to a stirred solution of 5-fluoro-1H-benzo[d]imidazol-2 (3H)-one (240 mg, 1.578 mmol) in DMF (5 mL) at 0° C. The reaction was stirred for 1 hour, after which $BOC_2O$ (0.366 mL, 1.578 mmol) in DMF (2 mL) was added dropwise. After the addition was finished, the reaction was stirred at 15° C. for 2 hours. After 2 hours, the mixture was concentrated and extracted with EtOAc (300 mL*3). The combined organic layers were collected, washed with brine (100 mL), and dried over $Na_2SO_4$. The mixture was filtered and concentrated in vacuo. The crude product was purified by flash silica gel chromatography (ISCO®; Agela® Flash Column Silica-CS (12 g) Eluent of 0~30% Ethyl acetate/Petroleum ether gradient @ 90 mL/min) to afford tert-butyl 5-fluoro-2-oxo-2,3-dihydro-1H-benzo[d]imidazole-1-carboxylate. LC/MS (m/z): 197 (M+H)+.

Step C: tert-butyl 5-fluoro-3-(4-(2-methoxy-2-oxoethyl)benzyl)-2-oxo-2,3-dihydro-1H-benzo[d]imidazole-1-carboxylate

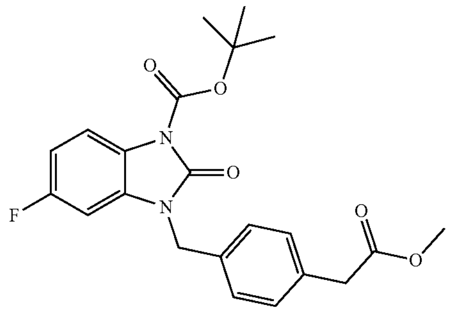 [SMILES: COC(=O)Cc1ccc(Cn2c(=O)n(C(=O)OC(C)(C)C)c3ccc(F)cc32)cc1]

Methyl 2-(4-(hydroxymethyl)phenyl)acetate (89 mg, 0.492 mmol), (E)-di-tert-butyl diazene-1,2-dicarboxylate (170 mg, 0.737 mmol) and diphenyl (p-tolyl) phosphine (204 mg, 0.737 mmol) were added to a stirred solution of tert-butyl 5-fluoro-2-oxo-2,3-dihydro-1H-benzo[d]imidazole-1-carboxylate (124 mg, 0.492 mmol) in THF (3 mL) at 0° C. After the addition was finished, the reaction was stirred at 80° C. for 15 hours. After 15 hours, the mixture was concentrated and purified by HPLC (eluting acetonitrile/water gradient with TFA modifier) to afford tert-butyl 5-fluoro-3-(4-(2-methoxy-2-oxoethyl)benzyl)-2-oxo-2,3-dihydro-1H-benzo[d]imidazole-1-carboxylate. LC/MS (m/z): 437 (M+H)+.

Step D: 2-(4-((6-fluoro-2-oxo-2,3-dihydro-1H-benzo[d]imidazol-1-yl)methyl)phenyl)acetic acid

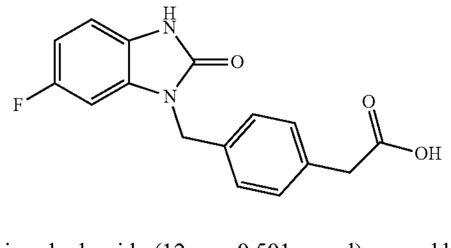

Lithium hydroxide (12 mg, 0.501 mmol) was added to a stirred solution of tert-butyl 5-fluoro-3-(4-(2-methoxy-2-oxoethyl)benzyl)-2-oxo-2,3-dihydro-1H-benzo[d]imidazole-1-carboxylate (42 mg, 0.101 mmol) in MeOH (5 mL), THF (5 mL) and water (2.5 mL) at 30° C. After the addition was finished, the reaction was stirred at 30° C. for 2 hours. After 2 hours the reaction was adjusted to pH~5 with HCl (2 N, in water) and concentrated in vacuo. The residue was purified by HPLC (eluting acetonitrile/water gradient with TFA modifier) to afford 2-(4-((6-fluoro-2-oxo-2,3-dihydro-1H-benzo[d]imidazol-1-yl)methyl)phenyl)acetic acid. LC/MS (m/z): 323 (M+H)+.

Step E: 2-(4-((6-fluoro-2-oxo-2,3-dihydro-1H-benzo[d]imidazol-1-yl)methyl)phenyl)-N-methylacetamide

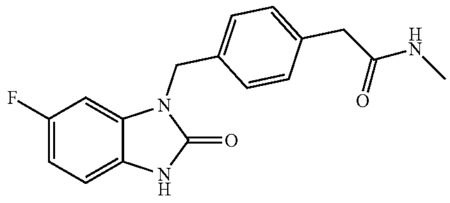 [SMILES: CNC(=O)Cc1ccc(Cn2c(=O)[nH]c3ccc(F)cc32)cc1]

Methanamine hydrochloride (17 mg, 0.252 mmol), triethylamine (0.07 mL, 0.502 mmol) and HATU (82 mg, 0.216 mmol) were added to a stirred solution of 2-(4-((6-fluoro-2-oxo-2,3-dihydro-1H-benzo[d]imidazol-1-yl)methyl)phenyl)acetic acid (50 mg, 0.167 mmol) in DMF (2 mL) at 30° C. After the addition was finished, the reaction was stirred at 30° C. for 5 hours. The reaction mixture was then filtered and purified by HPLC (eluting acetonitrile/water gradient with TFA modifier) to afford 2-(4-((6-fluoro-2-oxo-2,3-dihydro-1H-benzo[d]imidazol-1-yl)methyl)phenyl)-N-methylacetamide. $^1$H NMR (400 MHZ, METHANOL-d4) δ=7.22-7.32 (m, 4H) 6.97-7.05 (m, 1H) 6.73-6.83 (m, 2H) 5.03 (s, 2H) 3.46 (s, 2H) 2.66-2.71 (m, 2H) 2.66-2.71 (m, 1H). LC/MS (m/z): 314 (M+H)+.

Example 68

Preparation of 1-benzyl-4-fluoro-1,3-dihydro-2H-benzo[d]imidazol-2-one

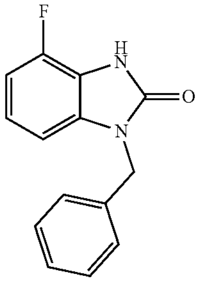 [SMILES: O=c1[nH]c2c(F)cccc2n1Cc1ccccc1]

Step A: 1-benzyl-4-fluoro-1,3-dihydro-2H-benzo[d]imidazol-2-one

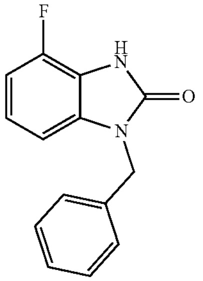 [SMILES: O=c1[nH]c2c(F)cccc2n1Cc1ccccc1]

Potassium phosphate (339 mg, 1.595 mmol), phenylmethanamine (87 μl, 0.797 mmol), methyl (2-bromo-6-fluorophenyl)carbamate (197.8 mg, 0.797 mmol), cuprous iodide (30.4 mg, 0.159 mmol), and L-hydroxyproline (41.8 mg, 0.319 mmol) were added to a vial equipped with a stir bar. The vial was purged with nitrogen for 5 minutes. After 5 minutes, DMSO (2658 μl) was added. The vial was sealed and heated to 40° C. for 3 hours. After 3 hours, the reaction mixture was heated to 130° C. for 16 hours. After 16 hours, the crude reaction mixture was filtered over CELITE, rinsing with ethyl acetate. The material was concentrated under reduced pressure, and the resulting residue was washed with ethyl acetate and brine. The resulting material was concentrated under reduced pressure. The resulting material was dissolved in DCM, and loaded onto a 25 g silca gel column. The column was run from 100% hexanes to 100% ethyl acetate. The desired product eluted, and fractions were collected and concentrated under reduced pressure. The material was dissolved in ACN/water; was frozen and dried on the lyopholizer for 48 hours to afford the title compound. LC/MS (m/z): 243 (M+H)+. 1H NMR (600 MHz, DMSO-d6) δ 11.52 (s, 1H), 7.36-7.28 (m, 4H), 7.28-7.21 (m, 1H), 6.99-6.91 (m, 1H), 6.91-6.84 (m, 2H), 5.01 (s, 2H).

The Examples in Table 9 were synthesized according to the methods described in Example 68 employing the appropriate substituted methyl (2-bromophenyl)carbamate starting materials in Step A and the appropriate substituted methanamine.

TABLE 9

| Example No. | Structure | Name | Observed Mass [M + H]+ |
|---|---|---|---|
| Example 69 | 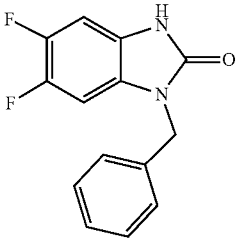 [SMILES: O=c1[nH]c2cc(F)c(F)cc2n1Cc1ccccc1] | 1-benzyl-5,6-difluoro-1,3-dihydro-2H-benzo[d]imidazol-2-one | 261 [M + H]+ |
| Example 70 | 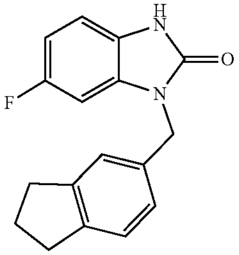 [SMILES: O=c1[nH]c2ccc(F)cc2n1Cc1ccc2c(c1)CCC2] | 1-((2,3-dihydro-1H-inden-5-yl)methyl)-6-fluoro-1,3-dihydro-2H-benzo[d]imidazol-2-one | 283 [M + H]+ |

Example 71

Preparation of 1-(3-isopropoxybenzyl)-1,3-dihydro-2H-benzo[d]imidazol-2-one

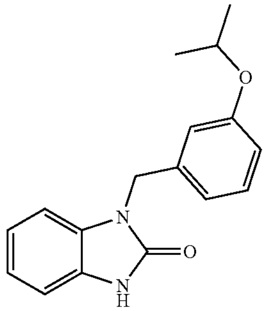 [SMILES: CC(C)Oc1cccc(Cn2c(=O)[nH]c3ccccc32)c1]

Sodium hydride (10 mgs, 0.25 mmol) was added to an 8 mL vial and placed under nitrogen. 0.50 mL of DMF was added, and then 1,3-dihydro-2H-benzo[d]imidazol-2-one (33 mgs, 0.25 mmol) was added as a solution in 0.50 mL of DMF, and the reaction mixture was allowed to stir for 1 hour. Then, 1-(bromomethyl)-3-isopropoxybenzene (57 mgs, 0.25 mmol) was added, and it was allowed to stir for 15 hours at room temperature. After this time, the reaction mixture was filtered and purified by HPLC (eluting acetonitrile/water gradient with TFA modifier). $^{1}H$ NMR (500 MHZ, DMSO-$d_6$) δ 10.97 (s, 1H), 7.20 (t, J=7.7 Hz, 1H), 7.07-6.90 (m, 4H), 6.85-6.76 (m, 3H), 4.93 (s, 2H), 4.56-4.48 (m, 1H), 1.20 (d, J=6.0 Hz, 6H). LCMS (ESI) m/z: 283 $[M+H]^+$.

The Example in Table 10 was synthesized according to the methods described in Example 71 employing the appropriate benzyl bromide starting materials.

TABLE 1010

| Example No. | Structure | Name | Exact Mass [M + H]+ |
|---|---|---|---|
| Example 72 | 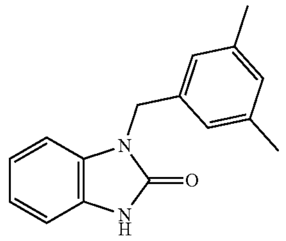 [SMILES: Cc1cc(C)cc(Cn2c(=O)[nH]c3ccccc32)c1] | 1-[(3,5-dimethylphenyl) methyl]-1,3-dihydro-2H-benzimidazol-2-one | 253 [M + H]+ |

Example 73

N-methyl-N-(4-((2-oxo-2,3-dihydro-1H-benzo[d]imidazol-1-yl)methyl)benzyl)acetamide

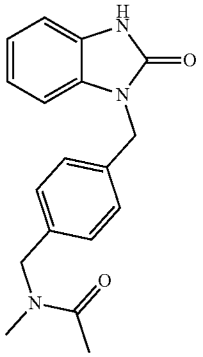 [SMILES: CC(=O)N(C)Cc1ccc(Cn2c(=O)[nH]c3ccccc32)cc1]

Step A: N-(4-(bromomethyl)benzyl)-N-methylacetamide

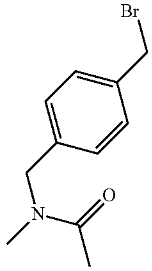

N-methylacetamide (200 mg, 2.74 mmol) and DMF (5 mL) was added to a vial equipped with a stir bar. The mixture was cooled to 0° C., and NaH (120 mg, 3.01 mmol) (60% in oil) was added. The mixture was allowed to stir at 0° C. for 30 minutes. After 30 minutes, this mixture was added to a solution of 1,4-bis(bromomethyl)benzene (1083 mg, 4.10 mmol) in DMF (5 mL). After the addition, the reaction was stirred at 30° C. for 16 hours. After 16 hours, the reaction mixture was diluted with water (50 mL) and extracted with ethyl acetate (30 mL×3). The organic layers were collected, washed with brine, and dried over $Na_2SO_4$. The resulting material was filtered, and concentrated in vacuo. The resulting residue was purified by flash silica gel chromatography with ethyl acetate and petroleum ether as eluent to afford the title compound. MS (ESI) m/z: 256 [M+H$^+$].

Step B: tert-butyl 3-(4-((N-methylacetamido)methyl)benzyl)-2-oxo-2,3-dihydro-1H-benzo[d]imidazole-1-carboxylate

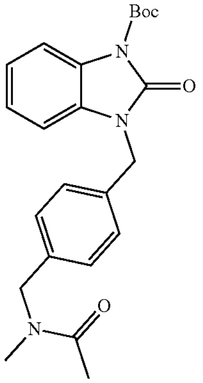 [SMILES: CC(=O)N(C)Cc1ccc(Cn2c(=O)n(C(=O)OC(C)(C)C)c3ccccc32)cc1]

Tert-butyl 2-oxo-2,3-dihydro-1H-benzo[d]imidazole-1-carboxylate (0.1 g, 0.427 mmol) and DMF (3 mL) were added to a vial equipped with a stir bar. $K_2CO_3$ (0.118 g, 0.854 mmol) and N-(4-(bromomethyl)benzyl)-N-methylacetamide (0.120 g, 0.470 mmol) were added, and the reaction mixture was stirred at 30° C. for 16 hours. After 16 hours, the reaction mixture was washed with water (30 mL) and ethyl acetate (30 mL×2). The resulting organic layers were collected, washed with brine (10 mL), dried over $Na_2SO_4$, and filtered. The resulting filtrate was concentrated in vacuo to afford the title compound. MS (ESI) m/z: 432 [observe M+22$^+$].

Step C: N-methyl-N-(4-((2-oxo-2,3-dihydro-1H-benzo[d]imidazol-1-yl)methyl) benzyl)acetamide

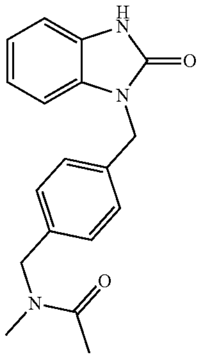 [SMILES: CC(=O)N(C)Cc1ccc(Cn2c(=O)[nH]c3ccccc32)cc1]

Tert-butyl 3-(4-((N-methylacetamido) methyl)benzyl)-2-oxo-2,3-dihydro-1H-benzo[d]imidazole-1-carboxylate (175 mg, 0.427 mmol) and DCM (2 mL) were added to a vial equipped with a stir bar. TFA (2 mL, 26.0 mmol) was added, and the reaction mixture was allowed to stir at 30° C. for 16 hours. After 16 hours, the reaction mixture was concentrated in vacuo. The resulting residue was purified by prep-HPLC (Method Column Phenomenex Synergi C18 150*30 mm*4 μm Condition water (0.1% TFA)-ACN Begin B 26 End B 46 Gradient Time (min) 10 100% B Hold Time (min) 2 Flow-Rate (mL/min) 25 Injections 3) to afford the title compound. MS (ESI) m/z: 310 [M+H$^+$] $^1$HNMR (500 MHZ, $CD_3OD$) δ 7.39-7.28 (m, 2H), 7.26-7.17 (m, 2H), 7.13-6.95 (m, 4H), 5.14-5.05 (m, 2H), 4.62-4.51 (m, 2H), 2.99-2.86 (m, 3H), 2.17-2.12 (m, 3H).

The Examples in Table 11 were synthesized according to the methods described in Example 73 employing the appropriate amide (or lactam) starting materials.

TABLE 11

| Example No. | Structure | IUPAC Name | Observed Mass [M + H]+ |
|---|---|---|---|
| Example 74 | 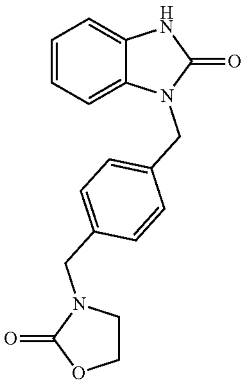 [SMILES: O=C1OCCN1Cc1ccc(Cn2c(=O)[nH]c3ccccc32)cc1] | 3-(4-((2-oxo-2,3-dihydro-1H-benzo[d] imidazol-1-yl)methyl) benzyl) oxazolidin-2-one | 324 [M + H]+ |

Example 75

Preparation of N-methyl-N-(4-((2-oxo-2,3-dihydro-1H-benzo[d]imidazol-1-yl)methyl)benzyl)cyclopropanesulfonamide

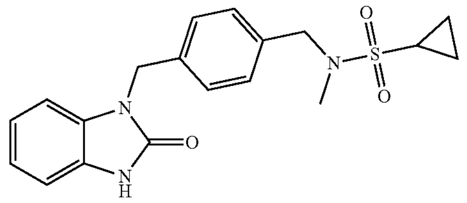 [SMILES: CN(Cc1ccc(Cn2c(=O)[nH]c3ccccc32)cc1)S(=O)(=O)C1CC1]

Step A: methyl 4-((2-chloro-1H-benzo[d]imidazol-1-yl)methyl)benzoate

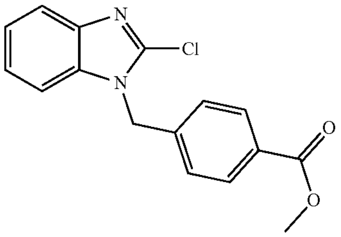 [SMILES: COC(=O)c1ccc(Cn2c(Cl)nc3ccccc32)cc1]

NaH in oil (0.849 g, 21.23 mmol) was added to a mixture of 2-chloro-1H-benzo[d]imidazole (3 g, 19.66 mmol) and DMF (40 mL) at 0° C., and stirred at 20° C. for 30 minutes. After 30 minutes, methyl 4-(bromomethyl)benzoate (4.95 g, 21.63 mmol) was added and the reaction was stirred at 20° C. for 12 h. After 12 hours the reaction mixture was added to saturated aqueous ammonium chloride solution (200 mL), and extracted with ethyl acetate (30 mL*3). The organic phase was washed with saturated saline (30 mL), dried over anhydrous magnesium sulfate, and concentrated in vacuo. The residue was purified by flash silica gel chromatography (ISCO®; 40 g SepaFlash® Silica Flash Column, eluent of [0~30] % ethyl acetate/pet. ether gradient @ 40 mL/min) to afford methyl 4-((2-chloro-1H-benzo[d]imidazol-1-yl) methyl)benzoate. MS (ESI) m/z: 302 [M+H$^+$].

Step B: methyl 4-((2-oxo-2,3-dihydro-1H-benzo[d] imidazol-1-yl)methyl)benzoate

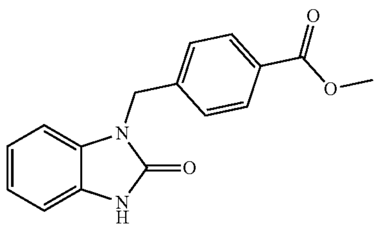 [SMILES: COC(=O)c1ccc(Cn2c(=O)[nH]c3ccccc32)cc1]

A mixture of methyl 4-((2-chloro-1H-benzo[d]imidazol-1-yl)methyl)benzoate (300 mg, 0.998 mmol) in acetic acid (3 ml) was degassed and backfilled with $N_2$ (three times).

The mixture was stirred at 80° C. for 16 hours. After 16 hours the mixture was concentrated under reduced pressure to afford methyl 4-((2-oxo-2,3-dihydro-1H-benzo[d]imidazol-1-yl)methyl)benzoate. MS (ESI) m/z: 283 [M+H$^+$].

Step C: 4-((2-oxo-2,3-dihydro-1H-benzo[d]imidazol-1-yl)methyl)benzoic acid

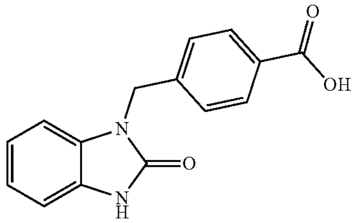 [SMILES: O=C(O)c1ccc(Cn2c(=O)[nH]c3ccccc32)cc1]

A mixture of methyl 4-((2-oxo-2,3-dihydro-1H-benzo[d]imidazol-1-yl)methyl)benzoate (240 mg, 0.850 mmol) and lithium hydroxide (61.1 mg, 2.55 mmol) in water (1 ml) and THF (5) and MeOH (5 ml) was degassed and backfilled with $N_2$ (three times) and stirred at 60° C. for 1 hour. After 1 hour the mixture was concentrated under reduced pressure and adjusted to pH=3-6 by aqueous HCl (2M), and filtered. The filtrate was concentrated under reduced pressure to afford 4-((2-oxo-2,3-dihydro-1H-benzo[d]imidazol-1-yl)methyl)benzoic acid. MS (ESI) m/z: 269 [M+H$^+$].

Step D: N-methyl-4-((2-oxo-2,3-dihydro-1H-benzo[d]imidazol-1-yl)methyl)benzamide

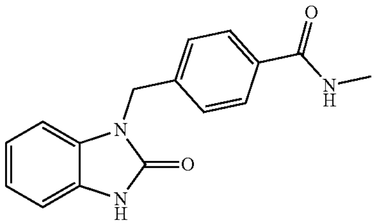 [SMILES: CNC(=O)c1ccc(Cn2c(=O)[nH]c3ccccc32)cc1]

Triethylamine (9.43 mg, 0.093 mmol) and HATU (17.01 mg, 0.045 mmol) was added to a solution of 4-((2-oxo-2,3-dihydro-1H-benzo[d]imidazol-1-yl)methyl)benzoic acid (10 mg, 0.037 mmol) in DMF (2 ml) at 25° C. The reaction mixture was stirred at 25° C. for 30 min. After 30 minutes, methanamine (1.273 mg, 0.041 mmol) was added to the mixture. The mixture was stirred at 25° C. for 2 hours. After 2 hours the mixture was filtered and concentrated under reduced pressure to afford N-methyl-4-((2-oxo-2,3-dihydro-1H-benzo[d]imidazol-1-yl)methyl)benzamide. MS (ESI) m/z: 282 [M+H$^+$].

Step E: 1-(4-((methylamino)methyl)benzyl)-1,3-dihydro-2H-benzo[d]imidazol-2-one

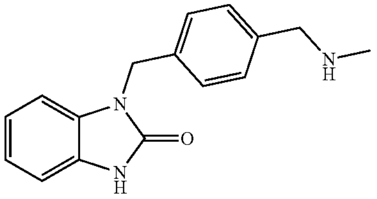 [SMILES: CNCc1ccc(Cn2c(=O)[nH]c3ccccc32)cc1]

A mixture of N-methyl-4-((2-oxo-2,3-dihydro-1H-benzo[d]imidazol-1-yl)methyl)benzamide (130 mg, 0.462 mmol) and $LiAlH_4$ (26.3 mg, 0.693 mmol) in THF (40 ml) was degassed and backfilled with $N_2$ (three times) and stirred at 70° C. for 16 h. After 16 hours $Na_2SO_4$. $H_2O$ (130 mg) was added to the reaction and stirred for 30 min at 25° C. After 30 minutes the mixture was filtered and the filtrate was concentrated under reduced pressure and purified by HPLC (with TFA modifier) to afford 1-(4-((methylamino)methyl)benzyl)-1,3-dihydro-2H-benzo[d]imidazol-2-one. MS (ESI) m/z: 268 [M+H$^+$]

Step F: N-methyl-N-(4-((2-oxo-2,3-dihydro-1H-benzo[d]imidazol-1-yl)methyl)benzyl)cyclopropanesulfonamide

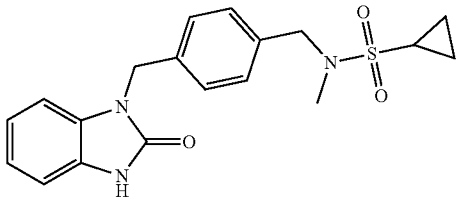 [SMILES: CN(Cc1ccc(Cn2c(=O)[nH]c3ccccc32)cc1)S(=O)(=O)C1CC1]

A mixture of 1-(4-((methylamino)methyl)benzyl)-1,3-dihydro-2H-benzo[d]imidazol-2-one (30 mg, 0.112 mmol), TEA (0.031 ml, 0.224 mmol) and cyclopropanesulfonyl chloride (12.62 mg, 0.090 mmol) in DCM (10 ml) was degassed and backfilled with $N_2$ (three times). The mixture was stirred at 25° C. for 16 h. After 16 hours, the mixture was concentrated under reduced pressure and purified by HPLC (with TFA modifer) to afford N-methyl-N-(4-((2-oxo-2,3-dihydro-1H-benzo[d]imidazol-1-yl)methyl)benzyl)cyclopropanesulfonamide. $^1$H NMR (400 MHZ, MeOD): δ 7.97-7.88 (m, 4H), 7.71-7.53 (m, 4H), 5.67 (s, 2H), 4.91 (s, 2H), 3.31 (s, 3H), 3.13-3.03 (m, 1H), 1.73-1.53 (m, 4H). MS (ESI) m/z: 372 [M+H$^+$].

Example 76

Preparation of N-(4-((3-(difluoromethyl)-2-oxo-2,3-dihydro-1H-benzo[d]imidazol-1-yl)methyl)benzyl) acetamide

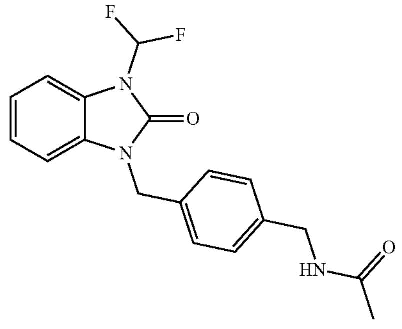 [SMILES: CC(=O)NCc1ccc(Cn2c(=O)n(C(F)F)c3ccccc32)cc1]

Step A: tert-butyl (4-((3-(difluoromethyl)-2-oxo-2,3-dihydro-1H-benzo[d]imidazol-1-yl)methyl)benzyl)carbamate

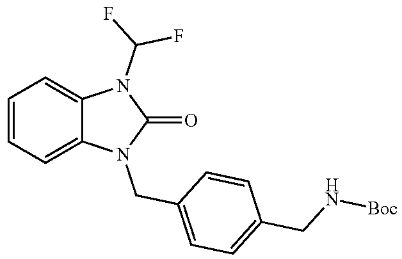 [SMILES: CC(C)(C)OC(=O)NCc1ccc(Cn2c(=O)n(C(F)F)c3ccccc32)cc1]

1-(difluoromethy yl)-1H-benzo[d]imidazol-2 (3H)-one (47 mg, 0.255 mmol) and $K_2CO_3$ (65 mg, 0.470 mmol) in DMF (3 mL) was added to a vial equipped with a stir bar. Tert-butyl 4-(bromomethyl)benzylcarbamate (70 mg, 0.233 mmol) was added at 20° C. The resulting mixture was stirred at 20° C. for 15 hours. After 15 hours, the mixture was filtered and the filtrate was purified by HPLC (eluting acetonitrile/water gradient with TFA modifier). The desired product was isolated as a solid. LCMS (ESI) m/z: 426 $[M+Na]^+$.

Step B: (4-((3-(difluoromethyl)-2-oxo-2,3-dihydro-1H-benzo[d]imidazol-1-yl)methyl)phenyl)methanaminium chloride

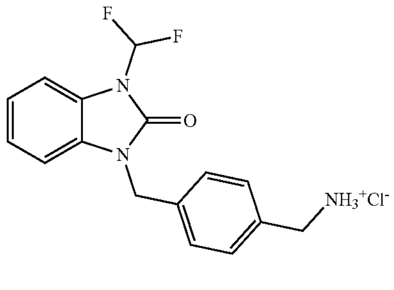

Tert-butyl 4-((3-(difluoromethyl)-2-oxo-2,3-dihydro-1H-benzo[d]imidazol-1-yl)methyl)benzylcarbamate (53 mg, 0.131 mmol) was dissolved in hydrogen chloride (2 mL, 8.00 mmol) (4 M, in dioxane) and the mixture was stirred at 20° C. for 2 hours. After 2 hours, the mixture was concentrated under reduced pressure to give the crude material, which was used directly in the next step without further purification. LCMS (ESI) m/z: 345 $[M+MeCN]^+$.

Step C: N-(4-((3-(difluoromethyl)-2-oxo-2,3-dihydro-1H-benzo[d]imidazol-1-yl)methyl)benzyl) acetamide

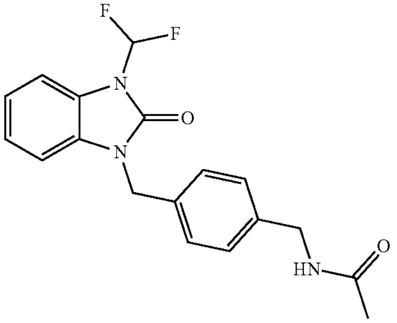 [SMILES: CC(=O)NCc1ccc(Cn2c(=O)n(C(F)F)c3ccccc32)cc1]

Triethylamine (0.06 mL, 0.430 mmol) and acetic anhydride (0.02 mL, 0.212 mmol) were added to a solution of (4-((3-(difluoromethyl)-2-oxo-2,3-dihydro-1H-benzo[d] imidazol-1-yl)methyl)phenyl)methanaminium chloride (44 mg, 0.130 mmol) in DCM (5 mL) at 20° C. and the mixture was stirred at 20° C. for 2 hours. After 2 hours, the mixture was concentrated in vacuo and purified by HPLC (eluting acetonitrile/water gradient with TFA modifier). LCMS (ESI) m/z: 346 $[M+H]^+$. $^1H$ NMR (500 MHZ, $CD_3OD$) δ 7.61-7.38 (t, J=58.5, 1H), 7.49 (s, 1H), 7.40-7.37 (m, 1H), 7.34-7.29 (m, 2H), 7.29-7.24 (m, 2H), 7.18-7.13 (m, 2H), 7.11-7.05 (m, 1H), 5.08 (s, 2H), 4.32 (s, 2H), 1.96 (s, 3H).

Example 77

Preparation of N-(4-((3-(difluoromethyl)-2-oxo-2,3-dihydro-1H-benzo[d]imidazol-1-yl)methyl)benzyl) methanesulfonamide

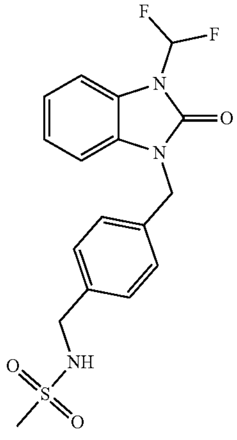 [SMILES: CS(=O)(=O)NCc1ccc(Cn2c(=O)n(C(F)F)c3ccccc32)cc1]

Utilizing the procedure outlined in Example 76, using methanesulfonyl chloride in Step C, the title compound was afforded. $^{1}H$ NMR (400 MHZ, $CDCl_3$) δ 7.45-7.08 (m, 1H), 7.36-7.32 (m, 1H), 7.29 (br s, 2H), 7.22-7.20 (m, 1H), 7.16 (s, 1H), 7.12-7.02 (m, 2H), 6.87-6.81 (m, 1H), 4.99 (s, 2H), 4.58 (br s, 1H), 4.24 (d, J=5.9 Hz, 2H), 2.82 (s, 3H). LCMS (ESI) m/z: 382 $[M+H]^+$.

Example 78

Preparation of 1-benzyl-3-(difluoromethyl)-1,3-dihydro-2H-benzo[d]imidazol-2-one

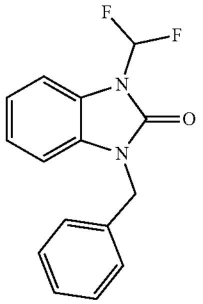 [SMILES: O=c1n(Cc2ccccc2)c2ccccc2n1C(F)F]

1-(difluoromethyl)-1H-benzo[d]imidazol-2 (3H)-one (90 mg, 0.489 mmol) and DMF (2 mL) were added to a vial equipped with a stir bar. $K_2CO_3$ (101 mg, 0.733 mmol) and (bromomethyl)benzene (84 mg, 0.489 mmol) were added and the reaction mixture was stirred at 20° C. (room temperature) under nitrogen atmosphere. The reaction mixture was allowed to stir for 2 hours. After 2 hours, the reaction mixture was concentrated in vacuo. The resulting residue was purified by Pre-HPLC (Column Boston Green ODS 150*30 mm*5 μm, Condition water (0.1% TFA)-MeCN Begin B 59, End B 79 Gradient Time (min) 10 100% B Hold Time (min) 2 Flow Rate (mL/min) 25) to afford the title compound. LCMS (ESI) m/z: 275 $[M+H]^+$. $^{1}H$ NMR (500 MHZ, MeOH-d4) δ 7.65-7.40 (m, 1H), 7.39-7.37 (m, 1H), 7.36-7.32 (m, 4H), 7.32-7.26 (m, 1H), 7.20-7.14 (m, 2H), 7.12-7.10 (m, 1H), 5.10 (s, 2H).

Example 79

Preparation of 1-((3-chloro-5-((2-oxo-2,3-dihydro-1H-benzo[d]imidazol-1-yl)methyl)pyridin-2-yl)methyl)cyclobutane-1-carbonitrile

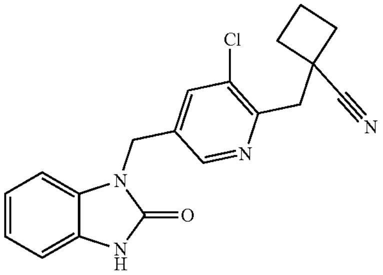 [SMILES: N#CC1(Cc2ncc(Cn3c(=O)[nH]c4ccccc43)cc2Cl)CCC1]

Step A: tert-butyl 3-((6-bromo-5-chloropyridin-3-yl)methyl)-2-oxo-2,3-dihydro-1H-benzo[d]imidazole-1-carboxylate

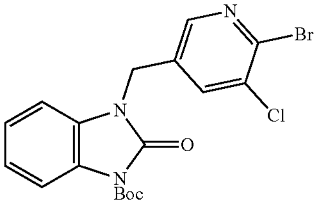 [SMILES: CC(C)(C)OC(=O)n1c(=O)n(Cc2cnc(Br)c(Cl)c2)c2ccccc21]

Tert-butyl 2-oxo-2,3-dihydro-1H-benzo[d]imidazole-1-carboxylate (164 mg, 0.70 mmol) and 2-bromo-5-(bromomethyl)-3-chloropyridine (210 mg, 0.74 mmol) was dissolved in DMF (3.8 mL) and potassium carbonate (203 mg, 1.47 mmol) was added. The resulting reaction mixture was stirred at room temperature for 1.5 hours. After 1.5 hours, saturated $NaHCO_3$ was added, and the mixture was extracted with EtOAc (3×). The combined organic layers were washed with water and brine and then dried over magnesium sulfate, and filtered. The solvent was evaporated under reduced pressure. The residue was purified by silica gel chromatography with hexanes and ethyl acetate as eluent. LCMS (ESI) m/z: 338 $[M+H]^+$(observed as loss of Boc).

Step B: tert-butyl 3-((5-chloro-6-((1-cyanocyclobutyl)methyl)pyridin-3-yl)methyl)-2-oxo-2,3-dihydro-1H-benzo[d]imidazole-1-carboxylate

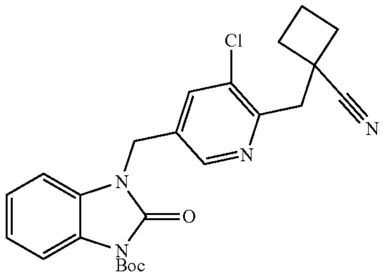 [SMILES: CC(C)(C)OC(=O)n1c(=O)n(Cc2cnc(CC3(C#N)CCC3)c(Cl)c2)c2ccccc21]

1-(bromomethyl) cyclobutane-1-carbonitrile (13.09 mg, 0.075 mmol), nickel (II) chloride ethylene glycol dimethyl ether complex (8.26 mg, 0.038 mmol), picolinimidamide hydrochloride (5.93 mg, 0.038 mmol), zinc (9.84 mg, 0.150 mmol), tetrabutylammonium iodide (41.7 mg, 0.113 mmol), and tert-butyl 3-((6-bromo-5-chloropyridin-3-yl)methyl)-2-oxo-2,3-dihydro-1H-benzo[d]imidazole-1-carboxylate (33 mg, 0.075 mmol) were added to a 4 mL vial. and DMA (0.75 mL) was added. The reaction vial was sealed, degassed and flushed with nitrogen for 1 minute, then the resulting reaction mixture was stirred for 4 hours. After 4 hours, the mixture was filtered through CELITE and purified by HPLC (eluting acetonitrile/water gradient with TFA modifier). LCMS (ESI) m/z: 475 $[M+Na]^+$ Step C: 1-((3-chloro-5-((2-oxo-2,3-dihydro-1H-benzo[d]imidazol-1-yl)methyl)pyridin-2-yl)methyl) cyclobutane-1-carbonitrile

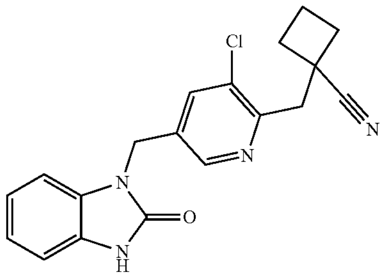 [SMILES: N#CC1(Cc2ncc(Cn3c(=O)[nH]c4ccccc43)cc2Cl)CCC1]

1-((3-chloro-5-((2-oxo-2,3-dihydro-1H-benzo[d]imidazol-1-yl)methyl)pyridin-2-yl)methyl)cyclobutane-1-carbonitrile was dissolved in 1 mL of TFA:DCM (1:1) and stirred at room temperature for 30 minutes. The resulting mixture was concentrated and purified by HPLC (eluting acetonitrile/water gradient with TFA modifier). $^1$H NMR (500 MHZ, DMSO-$d_6$) δ 10.90 (s, 1H), 8.32 (d, J=1.6 Hz, 1H), 7.93 (d, J=1.6 Hz, 1H), 7.06-6.84 (m, 4H), 5.21 (s, 2H), 3.08 (s, 2H), 2.34 (dt, J=11.5, 8.2 Hz, 2H), 2.30-2.21 (m, 2H), 2.09-1.99 (m, 2H). LCMS (ESI) m/z: 353 $[M+H]^+$ Example 80

Preparation of 1-(3-(4-methylpiperazin-1-yl)benzyl)-1,3-dihydro-2H-benzo[d]imidazol-2-one

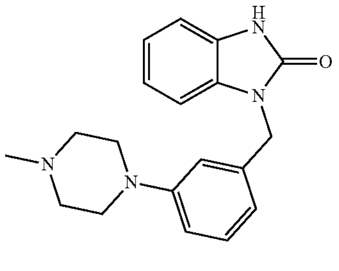 [SMILES: CN1CCN(c2cccc(Cn3c(=O)[nH]c4ccccc43)c2)CC1]

Step A: tert-butyl 3-(3-iodobenzyl)-2-oxo-2,3-dihydro-1H-benzo[d]imidazole-1-carboxylate

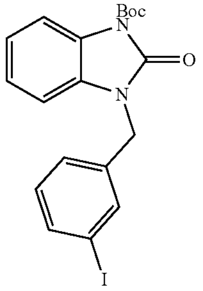 [SMILES: CC(C)(C)OC(=O)n1c(=O)n(Cc2cccc(I)c2)c2ccccc21]

NaH (0.205 g, 5.12 mmol) (60% in oil) was added portionwise to a stirred solution of tert-butyl 2-oxo-2,3-dihydro-1H-benzo[d]imidazole-1-carboxylate (1.0 g, 4.27 mmol) in DMF (10 mL) at 0° C. The reaction was stirred for 1 hour. After 1 hour 1-(bromomethyl)-3-iodobenzene (1.394 g, 4.70 mmol) in DMF (10 mL) was added dropwise. After the addition was complete, the reaction was stirred at 25° C. for 16 hours. After 16 hours Water (50 mL) was added and the mixture was extracted with EtOAc (30 mL*2). The organic layers were collected, washed with brine (10 mL), dried over $Na_2SO_4$, and filtered. The filtrate was concentrated in vacuo to afford tert-butyl 3-(3-iodobenzyl)-2-oxo-2,3-dihydro-1H-benzo[d]imidazole-1-carboxylate. 1H NMR (400 MHZ, CHLOROFORM-d) δ 7.78-7.89 (m, 1H), 7.67 (s, 1H), 7.61 (d, J=7.83 Hz, 1H), 7.28 (br d, J=7.58 Hz, 1H), 6.99-7.15 (m, 3H), 6.78-6.87 (m, 1H), 4.97 (s, 2H), 1.69 (s, 9H). LCMS (ESI) m/z: 287.0 [M−56+H].

Step B: 1-(3-(4-methylpiperazin-1-yl)benzyl)-1,3-dihydro-2H-benzo[d]imidazol-2-one

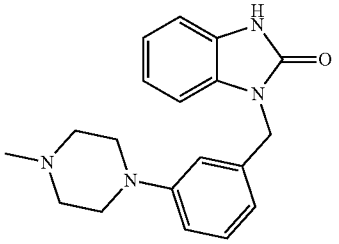 [SMILES: CN1CCN(c2cccc(Cn3c(=O)[nH]c4ccccc43)c2)CC1]

$K_3PO_4$ (283 mg, 1.333 mmol), copper (I) iodide (21.57 mg, 0.113 mmol), (2S,4R)-4-hydroxypyrrolidine-2-carboxylic acid (29.7 mg, 0.227 mmol) and 1-methylpiperazine (66.7 mg, 0.666 mmol) was added to a stirred mixture of tert-butyl 3-(3-iodobenzyl)-2-oxo-2,3-dihydro-1H-benzo[d]imidazole-1-carboxylate (300 mg, 0.666 mmol) in DMSO (6 ml) at 20° C. After the addition was finished, the reaction was stirred at 80° C. for 2.5 hours. After 2.5 hours the reaction was filtered and the residue was purified by HPLC (eluting acetonitrile/water gradient with $NH_4HCO_3$ modifier) to afford 1-(3-(4-methylpiperazin-1-yl)benzyl)-1H-benzo[d]imidazol-2(3H)-one. 1H NMR (400 MHZ, METHANOL-d4) δ=7.27-7.16 (m, 1H), 7.12-7.03 (m, 2H), 7.03-6.98 (m, 2H), 6.96 (s, 1H), 6.90 (br d, J=8.3 Hz, 1H), 6.80 (br d, J=7.5 Hz, 1H), 5.04 (s, 2H), 3.24-3.07 (m, 4H), 2.67-2.53 (m, 4H), 2.35 (s, 3H). LCMS (ESI) m/z: 323 $[M+H]^+$.

Example 81

Preparation of 1-(4-((5-(hydroxymethyl)-1H-1,2,3-triazol-1-yl)methyl)benzyl)-1,3-dihydro-2H-benzo[d]imidazol-2-one

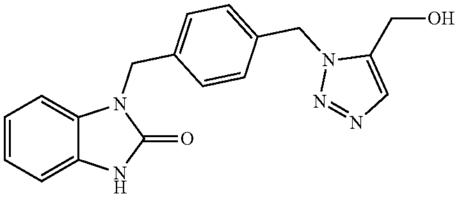 [SMILES: O=c1[nH]c2ccccc2n1Cc1ccc(Cn2nncc2CO)cc1]

Step A: tert-butyl 3-(4-(bromomethyl)benzyl)-2-oxo-2,3-dihydro-1H-benzo[d]imidazole-1-carboxylate

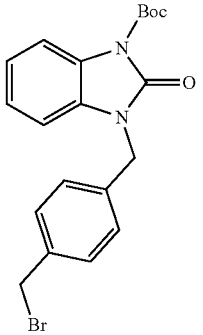 [SMILES: CC(C)(C)OC(=O)n1c(=O)n(Cc2ccc(CBr)cc2)c2ccccc21]

Tert-butyl 2-oxo-2,3-dihydro-1H-benzo[d]imidazole-1-carboxylate (3.0 g, 12.81 mmol) was added slowly to a mixture of 1,4-bis(bromomethyl)benzene (4.06 g, 15.37 mmol) and potassium carbonate (5.31 g, 38.4 mmol) in DMF (60 mL) at 20° C. The resulting mixture was stirred at 20° C. for 15 h. After 15 hours the solvent was removed under reduced pressure and the residue was dissolved in water (30 mL) and EtOAc (30 mL). The organic layer was separated and the aqueous was re-extracted with EtOAc (20 mL*2). The combined organic layers were washed with brine (20 mL), dried over anhydrous $Na_2SO_4$, filtered and concentrated under reduced pressure. The residue was purified by flash silica gel chromatography (ISCO®; 40 g SepaFlash® Silica Flash Column, eluent of 0-30% ethyl acetate/pet. ether gradient @ 35 mL/min) to afford tert-butyl 3-(4-(bromomethyl)benzyl)-2-oxo-2,3-dihydro-1H-benzo[d]imidazole-1-carboxylate. 1H NMR (400 MHZ, CHLOROFORM-d) δ=7.89-7.81 (m, 1H), 7.38-7.30 (m, 4H), 7.16-7.07 (m, 2H), 6.89-6.84 (m, 1H), 5.04 (s, 2H), 4.46 (s, 2H), 1.70 (s, 9H).

Step B: tert-butyl 3-(4-(azidomethyl)benzyl)-2-oxo-2,3-dihydro-1H-benzo[d]imidazole-1-carboxylate

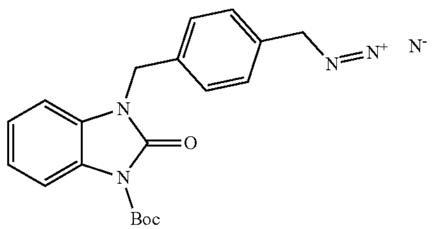

Sodium azide (0.27 g, 4.15 mmol) was added to a solution of tert-butyl 3-(4-(bromomethyl)benzyl)-2-oxo-2,3-dihydro-1H-benzo[d]imidazole-1-carboxylate (1.6 g, 3.83 mmol) in DMF (10 mL) at 0° C. and the mixture was stirred at 25° C. for 2 h. After 2 hours the mixture was adjusted to pH~10 with a $Na_2CO_3$ solution and poured into water (50 mL) and EtOAc (30 mL). The organic layer was separated and the aqueous was re-extracted with EtOAc (20 mL*2). The combined organic layers were washed with brine (20 mL), dried over anhydrous $Na_2SO_4$, filtered and concentrated under reduced pressure. The aqueous layer was poured into saturated Sodium hypochlorite solution (20 mL) and stirred for 15 h. After 15 hours the residue was purified by flash silica gel chromatography (ISCO®; 12 g SepaFlash® Silica Flash Column, eluent of 0-20% ethyl acetate/pet. ether gradient @ 35 mL/min) to afford tert-butyl 3-(4-(azidomethyl)benzyl)-2-oxo-2,3-dihydro-1H-benzo[d]imidazole-1-carboxylate. LCMS (ESI) m/z: 324 [M+H-$C_4H8$]+.

Step C: tert-butyl 3-(4-((4 or 5-(hydroxymethyl)-1H-1,2,3-triazol-1-yl)methyl)benzyl)-2-oxo-2,3-dihydro-1H-benzo[d]imidazole-1-carboxylate

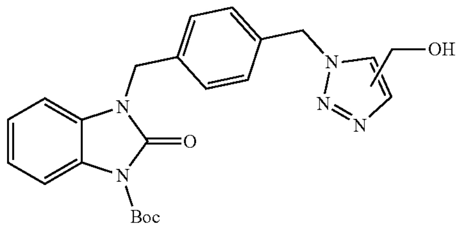

Prop-2-yn-1-ol (0.013 mL, 0.221 mmol) and Cp*RuCl (PPh3)2 (1.469 mg, 1.845 μmol) were added to a solution of tert-butyl 3-(4-(azidomethyl)benzyl)-2-oxo-2,3-dihydro-1H-benzo[d]imidazole-1-carboxylate (70 mg, 0.184 mmol) in THF (10 mL) at 20° C. The reaction mixture was stirred at 80° C. for 60 h. After 60 hours the mixture was filtered and the filtrate was concentrated under reduced pressure to afford crude tert-butyl 3-(4-((4 or 5-(hydroxymethyl)-1H-1,2,3-triazol-1-yl)methyl)benzyl)-2-oxo-2,3-dihydro-1H-benzo[d]imidazole-1-carboxylate. LCMS (ESI) m/z: 336.0 [M+H]+.

Step D: 1-(4-((4 or 5-(hydroxymethyl)-1H-1,2,3-triazol-1-yl)methyl)benzyl)-1,3-dihydro-2H-benzo[d]imidazol-2-one

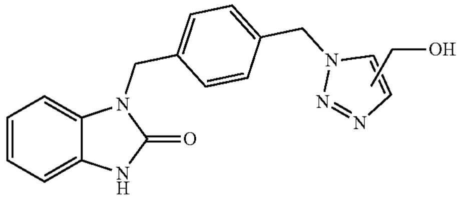

TFA (0.068 mL, 0.886 mmol) was added to a solution of tert-butyl 3-(4-((4 or 5-(hydroxymethyl)-1H-1,2,3-triazol-1-yl)methyl)benzyl)-2-oxo-2,3-dihydro-1H-benzo[d]imidazole-1-carboxylate (80 mg, 0.177 mmol) in DCM (2 mL). The reaction mixture was stirred at 20° C. for 1 h. After 1 hour the solvent was removed under reduced pressure. The residue was purified by HPLC (eluting acetonitrile/water gradient with $NH_4HCO_3$ modifier) to afford 1-(4-((5-(hydroxymethyl)-1H-1,2,3-triazol-1-yl)methyl)benzyl)-1H-benzo[d]imidazol-2 (3H)-one. LCMS (ESI) m/z: 336 $[M+H]^+$ Step E: 1-(4-((5-(hydroxymethyl)-1H-1,2,3-triazol-1-yl)methyl)benzyl)-1,3-dihydro-2H-benzo[d]imidazol-2-one

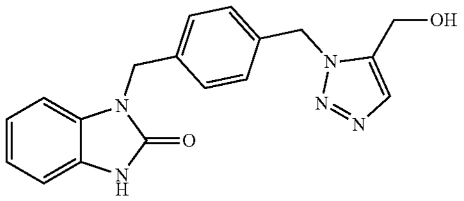 [SMILES: O=c1[nH]c2ccccc2n1Cc1ccc(Cn2nncc2CO)cc1]

Preparative resolution of 1-(4-((4 or 5-(hydroxymethyl)-1H-1,2,3-triazol-1-yl)methyl)benzyl)-1H-benzo[d]imidazol-2 (3H)-one was performed using supercritical fluid chromatography on a MG II preparative SFC. A Chiral Technologies AD-H column (10 μm, 30 mm×250 mm, Chiral Technologies, West Chester, PA) was used as the chiral stationary phase. The compound mixture was dissolved in EtOH. Injection, and collection was carried out using the following isocratic SFC conditions: 45% carbon dioxide and 55% ethanol with 0.1% ammonium hydroxide as the mobile phase, 220 nm UV wavelength, 100 bar outlet pressure, 38° C. column compartment temperature, 70 mL/min total flow rate. Retention times for peak collection were as follows: desired, first eluting peak, 1.040 min; second eluting peak, 2.588 min. 1H NMR (400 MHZ, METHANOL-d4) δ 7.64 (s, 1H), 7.32-7.27 (m, 2H), 7.25-7.18 (m, 2H), 7.11-7.02 (m, 2H), 7.02-6.97 (m, 1H), 6.97-6.92 (m, 1H), 5.62 (s, 2H), 5.05 (s, 2H), 4.55 (s, 2H). LCMS (ESI) m/z: 336.2 [M+H]+.

Example 82

Preparation of 1-(4-((1H-1,2,3-triazol-1-yl)methyl)benzyl)-1H-benzo[d]imidazol-2 (3H)-one

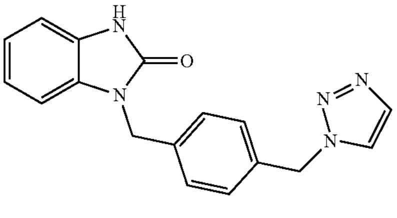 [SMILES: O=c1[nH]c2ccccc2n1Cc1ccc(Cn2ccnn2)cc1]

Step A: tert-butyl 3-(4-(bromomethyl)benzyl)-2-oxo-2,3-dihydro-1H-benzo[d]imidazole-1-carboxylate

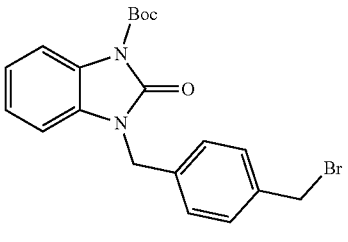 [SMILES: CC(C)(C)OC(=O)n1c(=O)n(Cc2ccc(CBr)cc2)c2ccccc21]

Tert-butyl 2-oxo-2,3-dihydro-1H-benzo[d]imidazole-1-carboxylate (11.7 g, 49.9 mmol) and DMF (300 mL) were added to a vial equipped with a stir bar. 1,4-bis(bromomethyl)benzene (19.5 g, 73.9 mmol) and $K_2CO_3$ (10.35 g, 74.9 mmol) were added, and the vial was stirred at 30° C. for 3 hours. After 3 hours, the reaction was concentrated under reduced pressure and diluted with water (300 mL). The resulting material was washed with ethyl acetate (300 mL×3). The combined organic layers were collected, dried over $Na_2SO_4$, and filtered. The combined filtrate was concentrated in vacuo. The resulting residue was purified by flash silica gel chromatography with ethyl acetate and petroleum ether as eluent to afford the title compound. $^1$H NMR (500 MHZ, CHLOROFORM-d) δ 7.80-7.73 (m, 1H), 7.28-7.25 (m, 2H), 7.25-7.22 (m, 2H), 7.07-7.00 (m, 2H), 6.81-6.75 (m, 1H), 4.99-4.92 (m, 2H), 4.40-4.34 (m, 2H), 1.61 (s, 9H).

Step B: tert-butyl 3-(4-((1H-1,2,3-triazol-1-yl)methyl)benzyl)-2-oxo-2,3-dihydro-1H-benzo[d]imidazole-1-carboxylate

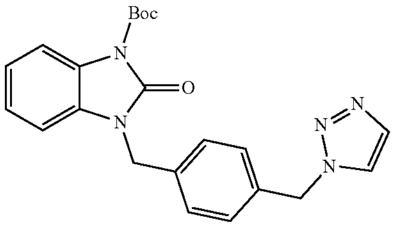 [SMILES: CC(C)(C)OC(=O)n1c(=O)n(Cc2ccc(Cn3ccnn3)cc2)c2ccccc21]

Tert-butyl 3-(4-(bromomethyl)benzyl)-2-oxo-2,3-dihydro-1H-benzo[d]imidazole-1-carboxylate (50 mg, 0.120 mmol) and THF (5 mL) were added to a vial equipped with a stir bar. 1,2,3-Triazole (10 mg, 0.145 mmol) and 1,8-diazabicyclo[5.4. 0] undec-7-ene (0.022 mL, 0.145 mmol) were added while stirring at 0° C. The reaction mixture was allowed to warm to room temperature (28° C.) and was stirred at room temperature for 12 hours. After 12 hours, the solvent was concentrated in vacuo to afford the title compound. LCMS (ESI) m/z: 406 $[M+H]^+$.

Step C: 1-(4-((1H-1,2,3-triazol-1-yl)methyl)benzyl)-1,3-dihydro-2H-benzo[d]imidazol-2-one

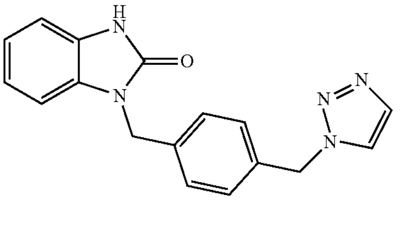 [SMILES: O=c1[nH]c2ccccc2n1Cc1ccc(Cn2ccnn2)cc1]

Tert-butyl 3-(4-((1H-1,2,3-triazol-1-yl)methyl)benzyl)-2-oxo-2,3-dihydro-1H-benzo[d]imidazole-1-carboxylate (100 mg, 0.247 mmol) and DCM (5 mL) were added to a vial equipped with a stir bar. TFA (1 mL, 12.98 mmol) was added, and the mixture was allowed to stir at 28° C. for 12 hours. After 12 hours, the solvent was concentrated in vacuo. The resulting residue was purified by reverse phase HPLC on a GILSON 281 instrument fitted with a YMC-Actus Triart C18 150*30 mm*5 μm using water (0.1% TFA)-MeCN and acetonitrile as eluents followed by lyophilization to afford the title compound. LCMS (ESI) m/z: 306 $[M+H]^+$. $^1$H NMR (500 MHZ, $CD_3OD$) δ 7.94 (d, J=1.0 Hz, 1H), 7.71 (d, J=1.0 Hz, 1H), 7.35-7.30 (m, 2H), 7.30-7.25 (m, 2H), 7.09-6.94 (m, 4H), 5.60 (s, 2H), 5.08 (s, 2H).

The examples in Table 12 were synthesized according to the methods described in Example 82 employing the appropriate substituted starting materials in Step B under the appropriate conditions (for example, $K_2CO_3$/MeCN/70° C./16 hours).

Table 12

| Example No. | Structure | Name | Observed Mass [M + H]+ |
|---|---|---|---|
| Example 83 | 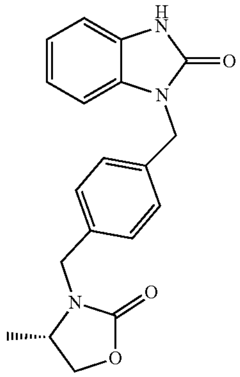 [SMILES: C[C@H]1COC(=O)N1Cc1ccc(Cn2c(=O)[nH]c3ccccc32)cc1] | (S)-4-methyl-3-(4-((2-oxo-2,3-dihydro-1H-benzo[d]imidazol-1-yl)methyl)benzyl)oxazolidin-2-one | 338 [M + H]+ |

Example 84

Preparation of 6-fluoro-1-(4-((2-oxopyrrolidin-1-yl)methyl)benzyl)-1,3-dihydro-2H-benzo[d]imidazol-2-one

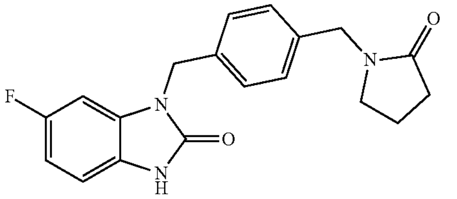 [SMILES: O=C1CCCN1Cc1ccc(Cn2c(=O)[nH]c3ccc(F)cc32)cc1]

Step A: 1-(4-((2-chloro-6-fluoro-1H-benzo[d]imidazol-1-yl)methyl)benzyl)pyrrolidin-2-one

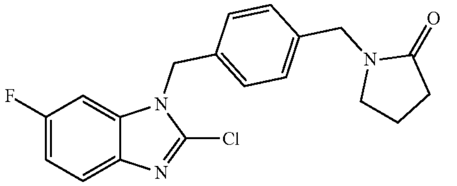 [SMILES: O=C1CCCN1Cc1ccc(Cn2c(Cl)nc3ccc(F)cc32)cc1]

2-chloro-5-fluorobenzimidazole (199 mg, 1.169 mmol) and 1-(4-(hydroxymethyl)benzyl)pyrrolidin-2-one (240 mg, 1.169 mmol) in DCM (2 mL) were added to triphenylphosphine (368 mg, 1.403 mmol) and diisopropyl azodicarboxylate (DIAD) (0.341 mL, 1.754 mmol) at 0° C. The resulting mixture was stirred at 20° C. for 2 h. The reaction was filtered, and the filtrate was concentrated in vacuo. The residue was purified by silica gel chromatography with ethyl acetate and petroleum ether as eluent. The title compound was afforded as a mixture along with its regioisomer, 1-(4-((2-chloro-6-fluoro-1H-benzo[d]imidazol-1-yl)methyl)benzyl)pyrrolidin-2-one. LCMS (ESI) m/z: 358 $[M+H]^+$.

Step B: 6-fluoro-1-(4-((2-oxopyrrolidin-1-yl)methyl)benzyl)-1,3-dihydro-2H-benzo[d]imidazol-2-one

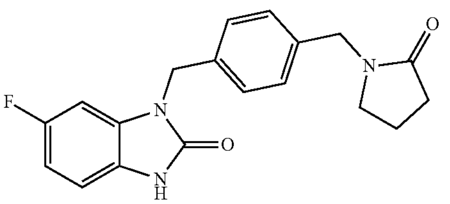 [SMILES: O=C1CCCN1Cc1ccc(Cn2c(=O)[nH]c3ccc(F)cc32)cc1]

The mixture of 1-(4-((2-chloro-5-fluoro-1/-benzo[d]imidazol-1-yl)methyl)benzyl)pyrrolidin-2-one and its regioisomer 1-(4-((2-chloro-6-fluoro-1H-benzo[d]imidazol-1-yl)methyl)benzyl)pyrrolidin-2-one (200 mg (total of mixture), 0.559 mmol) in AcOH (2 mL) was stirred at 80° C. for 12 hours. After 12 hours, the mixture was concentrated under reduced pressure. The residue was purified by HPLC (eluting acetonitrile/water gradient with TFA modifier), then the mixture of regioisomers were separated by SFC (Column DAICEL CHIRALPAK AD-H (250 mm×30 mm, 5 μm) Condition 0.1% $NH_3 \cdot H_2O$ EtOH Begin B 45% End B 45% Gradient Time (min) 100% B Hold Time (min) Flow Rate (mL/min) 50) to give the title compound as the first eluting peak. $^1$H NMR (500 MHZ, MeOH-d4) δ 7.17 (d, J=7.9 Hz, 2H), 7.06 (d, J=8.1 Hz, 2H), 6.86 (dd, J=4.6, 8.4 Hz, 1H), 6.67-6.59 (m, 1H), 6.67-6.59 (m, 1H), 4.89 (s, 2H), 4.25 (s, 2H), 3.11 (t, J=7.1 Hz, 2H), 2.26 (t, J=8.1 Hz, 2H), 1.84-1.78 (m, 2H). LCMS (ESI) m/z: 340 $[M+H]^+$.

Example 85

Preparation of 5-fluoro-1-(4-((2-oxopyrrolidin-1-yl)methyl)benzyl)-1,3-dihydro-2H-benzo[d]imidazol-2-one

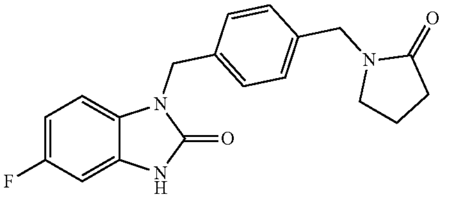 [SMILES: O=C1CCCN1Cc1ccc(Cn2c(=O)[nH]c3cc(F)ccc32)cc1]

The title compound was afforded utilizing the same procedure outlined in Steps A-B in Example 84, except that the $2^{nd}$ peak eluting off of the SFC in Step B was collected. $^1$H NMR (500 MHz, MeOH-d4) δ 7.17 (d, J=7.9 Hz, 2H), 7.08 (d, J=8.1 Hz, 2H), 6.78 (dd, J=4.3, 8.6 Hz, 1H), 6.73

(dd, J=2.4, 8.6 Hz, 1H), 6.64-6.57 (m, 1H), 4.91 (s, 2H), 4.27 (s, 2H), 3.15 (t, J=7.2 Hz, 2H), 2.28 (t, J=8.1 Hz, 2H), 1.87-1.81 (m, 2H). LCMS (ESI) m/z: 340 $[M+H]^+$.

Example 86

Preparation of 1-(2-methoxybenzyl)-6-methyl-1,3-dihydro-2H-benzo[d]imidazol-2-one

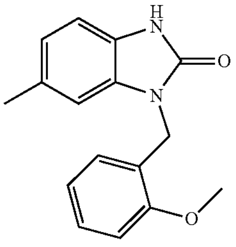 [SMILES: COc1ccccc1Cn1c(=O)[nH]c2ccc(C)cc21]

Step A: Preparation of tert-butyl 3-(2-methoxybenzyl)-5-methyl-2-oxo-2,3-dihydro-1H-benzo[d]imidazole-1-carboxylate

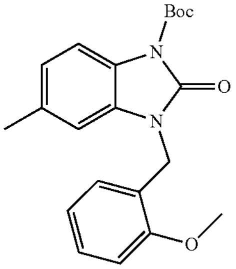 [SMILES: COc1ccccc1Cn1c(=O)n(C(=O)OC(C)(C)C)c2ccc(C)cc21]

Tert-butyl 5-methyl-2-oxo-2,3-dihydro-1H-benzo[d]imidazole-1-carboxylate (25 mg, 0.101 mmol), (2-methoxyphenyl)methanol (28 mg, 0.203 mmol) and triphenylphosphine, polymer-bound (27 mg, 0.103 mmol) in THF (0.5 mL) were added to a vial equipped with a stir bar. Di-tert-butyl azodicarboxylate (47 mg, 0.204 mmol) in THF (0.5 mL) was added at 0° C. The reaction mixture was heated to 80° C. for 16 hours. After 16 hours, the reaction mixture was filtered, and the filtrate was concentrated under reduced pressure, which was used to the next step without further purification. LCMS (ESI) m/z: 313 $[M+H]^+$ (observed as loss of (Bu).

Step B: 1-(2-methoxybenzyl)-6-methyl-1,3-dihydro-2H-benzo[d]imidazol-2-one

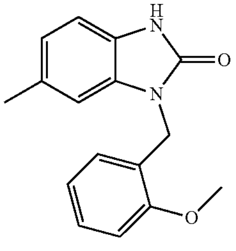 [SMILES: COc1ccccc1Cn1c(=O)[nH]c2ccc(C)cc21]

TFA (0.1 mL, 1.298 mmol) was added, at room temperature, to a stirred solution of tert-butyl 3-(2-methoxybenzyl)-5-methyl-2-oxo-2,3-dihydro-1H-benzo[d]imidazole-1-carboxylate (30 mg, 0.081 mmol) in DCM (2 mL). The reaction mixture was stirred for 30 minutes. After 30 minutes, the solvent was removed under reduced pressure, and the residue was purified by HPLC (eluting acetonitrile/water gradient with TFA modifier). $^1H$ NMR (500 MHZ, $CDCl_3$) δ 9.76 (br s, 1H), 7.20-7.26 (m, 1H), 7.06-7.10 (m, 1H), 6.94 (s, 1H), 6.90 (d, J=7.93 Hz, 1H), 6.86 (t, J=7.48 Hz, 1H), 6.81 (s, 2H), 5.11 (s, 2H), 3.85-3.94 (m, 3H), 2.35 (s, 3H). LCMS (ESI) m/z: 269 $[M+H]^+$.

Example 87

Preparation of 1-(1-phenylethyl)-1,3-dihydro-2H-benzo[d]imidazol-2-one

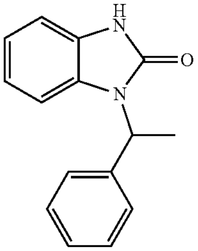 [SMILES: CC(c1ccccc1)n1c(=O)[nH]c2ccccc21]

Utilizing the procedure from Steps A-B in Example 86, tert-butyl 2-oxo-2,3-dihydro-1H-benzo[d]imidazole-1-carboxylate and 1-phenylethan-1-ol were elaborated to the final compound.

Step A: tert-butyl 2-oxo-3-(1-phenylethyl)-2,3-dihydro-1H-benzo[d]imidazole-1-carboxylate. LCMS (ESI) m/z: 283 $[M+H]^+$ (observed as loss of (Bu).

Step B: 1-(1-phenylethyl)-1,3-dihydro-2H-benzo[d]imidazol-2-one. $^1H$ NMR (500 MHz, MeOH-$d_4$) δ 7.42-7.34 (m, 4H), 7.31-7.26 (m, 1H), 7.11-7.07 (m, 1H), 7.02 (t, J=7.7 Hz, 1H), 6.90 (t, J=7.7 Hz, 1H), 6.77 (d, J=7.9 Hz, 1H), 5.81 (q, J=7.2 Hz, 1H), 1.92 (d, J=7.2 Hz, 3H). LCMS (ESI) m/z: 239 $[M+H]^+$.

Example 88

Preparation of 1-(1-cyclohexylethyl)-1,3-dihydro-2H-benzo[d]imidazol-2-one

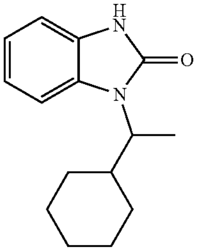 [SMILES: CC(C1CCCCC1)n1c(=O)[nH]c2ccccc21]

Utilizing the procedure from Steps A-B in Example 86, tert-butyl 2-oxo-2,3-dihydro-1H-benzo[d]imidazole-1-carboxylate and 1-cyclohexylethan-1-ol were elaborated to the final compound.

Step A: tert-butyl 3-(1-cyclohexylethyl)-2-oxo-2,3-dihydro-1H-benzo[d]imidazole-1-carboxylate. LCMS (ESI) m/z: 345 [M+H]$^+$.

Step B: 1-(1-cyclohexylethyl)-1,3-dihydro-2H-benzo[d]imidazol-2-one. $^1$H NMR (500 MHZ, MeOH-$d_4$) δ 7.25-7.23 (m, 1H), 7.09-7.06 (m, 3H), 4.19-4.13 (m, 1H), 2.08-2.05 (m, 2H), 1.86-1.84 (m, 1H), 1.68-1.62 (m, 2H), 1.53 (d, J=7.0 Hz, 3H), 1.35-1.32 (m, 2H), 1.13-1.08 (m, 3H), 0.93-0.92 (m, 1H). LCMS (ESI) m/z: 245 [M+H+].

Example 89

Preparation of 1-methyl-3-(3-(trifluoromethoxy)benzyl)-1,3-dihydro-2H-benzo[d]imidazol-2-one

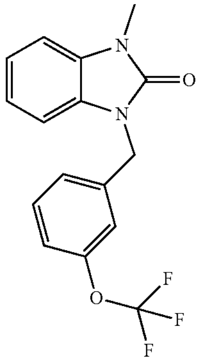 [SMILES: Cn1c(=O)n(Cc2cccc(OC(F)(F)F)c2)c2ccccc21]

Utilizing the procedure from Step A in Example 86, 1-methyl-1H-benzo[d]imidazol-2 (3H)-one and (3-(trifluoromethoxy)phenyl)methanol were elaborated to the final compound. $^1$H NMR (500 MHZ, MeOH-$d_4$) δ 7.47-7.42 (m, 1H), 7.32 (d, J=7.6 Hz, 1H), 7.26 (s, 1H), 7.23-7.19 (m, 2H), 7.18-7.15 (m, 1H), 7.12-7.05 (m, 2H), 5.18 (s, 2H), 3.50 (s, 3H). LCMS (ESI) m/z: 323

Example 90

Preparation of 5-chloro-1-(3-methoxybenzyl)-3-methyl-1,3-dihydro-2H-benzo[d]imidazol-2-one

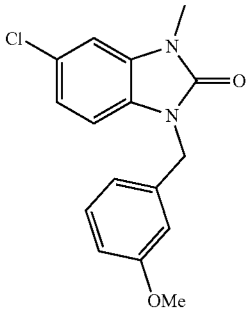 [SMILES: COc1cccc(Cn2c(=O)n(C)c3cc(Cl)ccc32)c1]

Utilizing the procedure from Steps A-B in Example 86, tert-butyl 6-chloro-2-oxo-2,3-dihydro-1H-benzo[d]imidazole-1-carboxylate and (3-methoxyphenyl)methanol were elaborated to 5-chloro-1-(3-methoxybenzyl)-1,3-dihydro-2H-benzo[d]imidazol-2-one.

Step A: tert-butyl 6-chloro-3-(3-methoxybenzyl)-2-oxo-2,3-dihydro-1H-benzo[d]imidazole-1-carboxylate. LCMS (ESI) m/z: 389 [M+H]$^+$.

Step B: 5-chloro-1-(3-methoxybenzyl)-1,3-dihydro-2H-benzo[d]imidazol-2-one. LCMS (ESI) m/z: 289 [M+H]$^+$.

Step C: 5-chloro-1-(3-methoxybenzyl)-3-methyl-1,3-dihydro-2H-benzo[d]imidazol-2-one

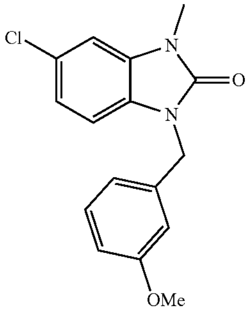 [SMILES: COc1cccc(Cn2c(=O)n(C)c3cc(Cl)ccc32)c1]

5-chloro-1-(3-methoxybenzyl)-1H-benzo[d]imidazol-2 (3H)-one (20 mg, 0.069 mmol) was dissolved in DMF (2 mL), and to this was added iodomethane (98 mg, 0.693 mmol) and cesium carbonate (68 mg, 0.209 mmol) at 0° C. After the addition was finished, the reaction was stirred at 50° C. for 15 hours. The mixture was filtered and purified by HPLC (eluting acetonitrile/water gradient with TFA modifier). $^1$H NMR (400 MHZ, $CDCl_3$) δ 7.24 (t, J=7.8 Hz, 1H), 7.00-6.96 (m, 2H), 6.87 (d, J=7.8 Hz, 1H), 6.84-6.79 (m, 2H), 6.77 (d, J=9.0 Hz, 1H), 5.03 (s, 2H), 3.77 (s, 3H), 3.45 (s, 3H). MS (ESI) m/z: 303 [M+H$^+$].

Example 91

Preparation of 1-(2-methoxybenzyl)-7-methyl-1,3-dihydro-2H-benzo[d]imidazol-2-one

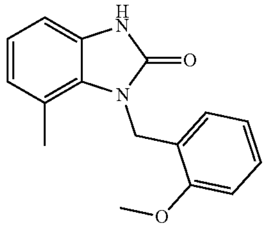 [SMILES: COc1ccccc1Cn1c(=O)[nH]c2cccc(C)c21]

Step A: N-(2-methoxybenzyl)-2-methyl-6-nitroaniline

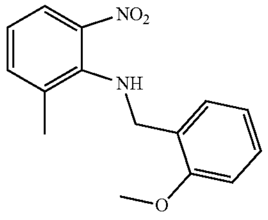 [SMILES: COc1ccccc1CNc1c(C)cccc1[N+](=O)[O-]]

2-fluoro-1-methyl-3-nitrobenzene (200 mg, 1.289 mmol) in THF (5 mL) was added to a vial equipped with a stir bar. (2-Methoxyphenyl)methanamine (177 mg, 1.289 mmol) and $K_2CO_3$ (356 mg, 2.58 mmol) were added at room temperature. After the addition was finished, the reaction was stirred at 80° C. for 15 hours. After 15 hours, the reaction was cooled to room temperature, and water (30 mL) was added. The mixture was washed with ethyl acetate (30 mL×2). The organic layers were collected, washed with brine, dried over $Na_2SO_4$, filtered and concentrated in vacuo. The residue was purified by silica gel chromatography with ethyl acetate and petroleum ether as eluent. LCMS (ESI) m/z: 273 $[M+H]^+$.

Step B: N1-(2-methoxybenzyl)-6-methylbenzene-1,2-diamine

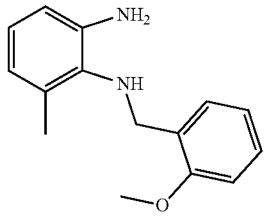 [SMILES: COc1ccccc1CNc1c(C)cccc1N]

N-(2-methoxybenzyl)-2-methyl-6-nitroaniline (100 mg, 0.367 mmol) was dissolved in MeOH (3 mL) under argon and then 10% Pd—C(39.1 mg, 0.037 mmol) was added at room temperature. The resulting mixture was stirred at room temperature under hydrogen (15 psi) atmosphere and stirred at room temperature for 15 minutes. The mixture was filtered and concentrated in vacuo. The residue was purified by prep-TLC with ethyl acetate and petroleum ether as the eluent. LCMS (ESI) m/z: 243 $[M+H]^+$.

Step C: 1-(2-methoxybenzyl)-7-methyl-1,3-dihydro-2H-benzo[d]imidazol-2-one

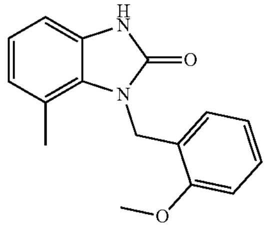 [SMILES: COc1ccccc1Cn1c(=O)[nH]c2cccc(C)c21]

CDI (40 mg, 0.247 mmol) was added to a mixture of N1-(2-methoxybenzyl)-6-methylbenzene-1,2-diamine (30 mg, 0.124 mmol) in THF (5 mL), and then triethylamine (0.06 mL, 0.430 mmol) was added. The reaction was stirred and heated at 80° C. for 15 hours. After 15 hours, the reaction mixture was cooled to room temperature. Water (30 mL) was added, and the mixture was washed with ethyl acetate (30 mL×2). The organic layers were collected, washed with brine (20 mL), dried over $Na_2SO_4$, filtered and concentrated in vacuo. The residue was purified by HPLC (eluting acetonitrile/water gradient with TFA modifier). $^1H$ NMR (500 MHz, $CDCl_3$) δ 9.68 (br s, 1 H), 7.25-7.24 (m, 1H), 6.99-6.90 (m, 3H), 6.83-6.80 (m, 1H), 6.77-6.76 (m, 2H), 5.32 (s, 2H), 3.92 (s, 3H), 2.26 (s, 3H). LCMS (ESI) m/z: 269 $[M+H]^+$.

Example 92

Preparation of 1-(2-methoxybenzyl)-4-methyl-1,3-dihydro-2H-benzo[d]imidazol-2-one

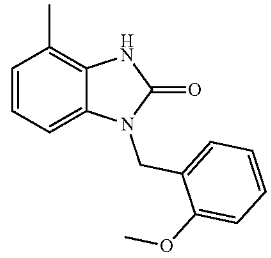 [SMILES: COc1ccccc1Cn1c(=O)[nH]c2c(C)cccc21]

The title compound was afforded utilizing the same procedure as noted above in Steps A-C for Example 91, except that 1-fluoro-3-methyl-2-nitrobenzene was used in Step A.

Step A: N-(2-methoxybenzyl)-2-methyl-6-nitroaniline. LCMS (ESI) m/z: 273 $[M+H]^+$.

Step B: N1-(2-methoxybenzyl)-6-methylbenzene-1,2-diamine. LCMS (ESI) m/z: 243 $[M+H]^+$.

Step C: 1-(2-methoxybenzyl)-4-methyl-1,3-dihydro-2H-benzo[d]imidazol-2-one. $^1H$ NMR (400 MHz, $CDCl_3$) δ 9.59 (br s, 1H), 7.25-7.23 (m, 1H), 7.14-7.12 (m, 1H), 6.93-6.79 (m, 5H), 5.12 (s, 2H), 3.91 (s, 3H), 2.40 (s, 3H). LCMS (ESI) m/z: 269 $[M+H]^+$.

Example 93

Preparation of 1-benzyl-4-(pyrrolidin-1-yl)-1,3-dihydro-2H-benzo[d]imidazol-2-one

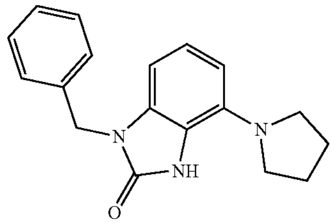 [SMILES: O=c1[nH]c2c(N3CCCC3)cccc2n1Cc1ccccc1]

Step A: 1-(3-fluoro-2-nitrophenyl)pyrrolidine

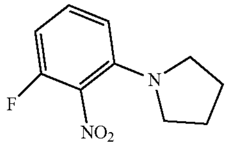 [SMILES: O=[N+]([O-])c1c(F)cccc1N1CCCC1]

1,3-Difluoro-2-nitrobenzene (500 mg, 3.14 mmol) was dissolved in DMSO (5 mL). Pyrrolidine (224 mg, 3.14 mmol) and $K_2CO_3$ (956 mg, 6.91 mmol) were added, and the reaction was stirred at room temperature for 1 hour. After 1 hour, the mixture was diluted with water (40 mL), and extracted by EtOAc (30 mL×3). The resulting organic layers were collected, washed with brine (10 mL), dried over $Na_2SO_4$, filtered and concentrated in vacuo. The residue was purified by silica gel chromatography with petroleum ether and ethyl acetate as eluent. LCMS (ESI) m/z: 211 [M+H$^+$].

Step B: N-benzyl-2-nitro-3-(pyrrolidin-1-yl) aniline

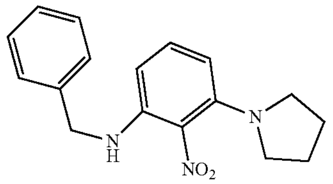 [SMILES: O=[N+]([O-])c1c(NCc2ccccc2)cccc1N1CCCC1]

1-(3-fluoro-2-nitrophenyl)pyrrolidine (200 mg, 0.951 mmol) was dissolved in DMSO (5 mL). Benzylamine (112 mg, 1.047) and $K_2CO_3$ (263 mg, 1.903 mmol) were added, and the reaction was heated to 110° C. for 16 hours. After 16 hours, the mixture was diluted with water (40 mL) and extracted with EtOAc (30 mL×3). The resulting organic layers were collected, washed with brine (10 mL), dried over $Na_2SO_4$, filtered and concentrated in vacuo. The residue was purified by silica gel chromatography with petroleum ether and ethyl acetate as eluent. LCMS (ESI) m/z: 298 [M+H$^+$].

Step C: N1-benzyl-3-(pyrrolidin-1-yl)benzene-1,2-diamine

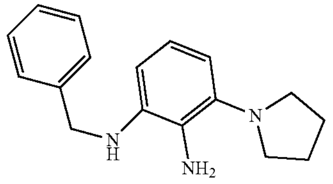 [SMILES: Nc1c(NCc2ccccc2)cccc1N1CCCC1]

N-benzyl-2-nitro-3-(pyrrolidin-1-yl)aniline (75 mg, 0.252 mmol) was dissolved in MeOH (5 mL). Pd—C(3 mg, 0.028 mmol) was added to the reaction, and the reaction was placed under an hydrogen atmosphere for 5 minutes. After 5 minutes the catalyst was removed by filtration. The filtrate was concentrated under reduced pressure afford the title compound as an oil. MS (ESI) m/z: 268 [M+H$^+$].

Step D: 1-benzyl-4-(pyrrolidin-1-yl)-1,3-dihydro-2H-benzo[d]imidazol-2-one

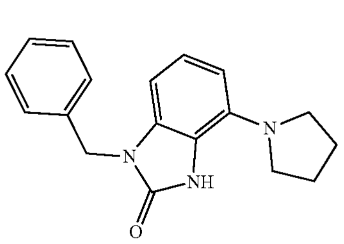 [SMILES: O=c1[nH]c2c(N3CCCC3)cccc2n1Cc1ccccc1]

N1-benzyl-3-(pyrrolidin-1-yl)benzene-1,2-diamine (20 mg, 0.075 mmol) was dissolved in THF (5 mL). CDI (36 mg, 0.222 mmol) and triethylamine (0.06 mL, 0.430 mmol) were added at 20° C. Upon completion of the addition, the reaction was stirred and heated at 80° C. for 15 hours. After 15 hours, the reaction was cooled to room temperature. Water (30 mL) was added, and the mixture was extracted with EtOAc (30 mL×2). The resulting organic layers were collected, washed with brine (20 mL), dried over $Na_2SO_4$, and filtered. The resulting filtrate was concentrated in vacuo, and the residue was purified by HPLC (eluting acetonitrile/water gradient with TFA modifier) to afford the title compound. $^1$HNMR (500 MHZ, MeOH-d4) δ 7.36-7.31 (m, 4H), 7.28 (br d, J=6.3 Hz, 1H), 6.91 (t, J=8.0 Hz, 1H), 6.50 (br d, J=7.8 Hz, 2H), 5.07 (s, 2H), 3.42-3.37 (m, 4H), 2.04 (td, J=3.3, 6.4 Hz, 4H). LCMS (ESI) m/z: 294 [M+H$^+$].

Example 94

Preparation of N-(4-((6-fluoro-2-oxo-2,3-dihydro-1H-benzo[d]imidazol-1-yl)methyl)benzyl)acetamide

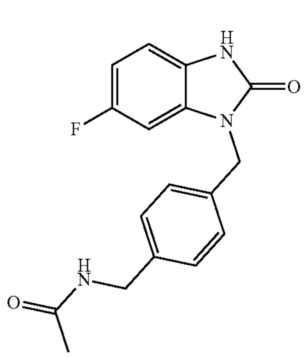 [SMILES: CC(=O)NCc1ccc(Cn2c(=O)[nH]c3ccc(F)cc32)cc1]

Step A: tert-butyl (4-(((5-fluoro-2-nitrophenyl) amino)methyl)benzyl)carbamate

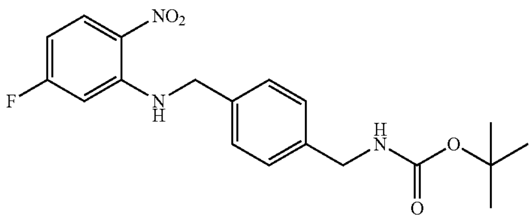 [SMILES: CC(C)(C)OC(=O)NCc1ccc(CNc2cc(F)ccc2[N+](=O)[O-])cc1]

2,4-difluoro-1-nitrobenzene (469 µl, 4.27 mmol), tert-butyl (4-(aminomethyl)benzyl)carbamate (1010 mg, 4.27 mmol), $K_2CO_3$ (886 mg, 6.41 mmol), and THF (1.07E+04 µl) were added to a vial equipped with a stir bar. The vial was sealed and heated to 80° C. for 18 hours. After 18 hours, the crude was washed with water and ethyl acetate. The combined organics were dried over magnesium sulfate, filtered, and concentrated under reduced pressure. The resulting material was dissolved in DCM, and loaded onto an 80 g silca gel column. The column was run from 100% hexanes to 100% ethyl acetate. The desired material eluted; fractions were collected and concentrated under reduced pressure. LC/MS (m/z): 398 (M+H)+ (observe+22)

Step B: tert-butyl (4-(((2-amino-5-fluorophenyl) amino)methyl)benzyl)carbamate

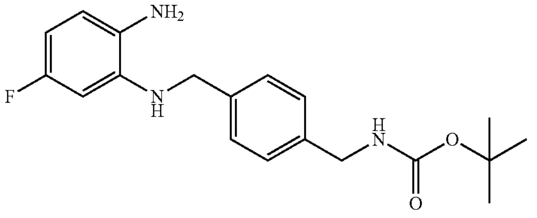

Zinc (355 mg, 5.44 mmol) and ethanol (1853 μl) were added to a vial equipped with a stir bar. The vial was cooled to 0° C. and the acetic acid (311 μl, 5.44 mmol) was added. The mixture was stirred for 5 minutes. After 5 minutes, tert-butyl (4-(((5-fluoro-2-nitrophenyl)amino)methyl)benzyl)carbamate (371 mg, 0.988 mmol) was added in ethanol (618 μl). The mixture was heated to 35° C. for 45 minutes. After 45 minutes, the mixture was filtered over CELITE, rinsing with ethyl acetate. The mixture was concentrated under reduced pressure. The resulting material was dissolved in DCM and loaded onto a 40 g silca gel column, eluting from 100% hexanes to 100% ethyl acetate. The desired product eluted; fractions were collected and concentrated under reduced pressure to afford the desired intermediate. LC/MS (m/z): 346 (M+H)+

Step C: tert-butyl (4-((6-fluoro-2-oxo-2,3-dihydro-1H-benzo[d]imidazol-1-yl)methyl)benzyl)carbamate

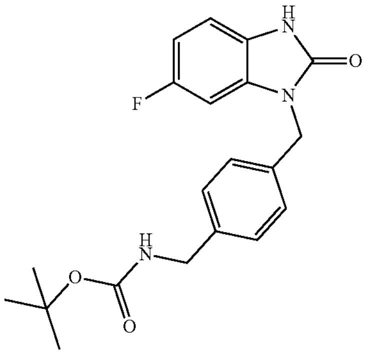 [SMILES: CC(C)(C)OC(=O)NCc1ccc(Cn2c(=O)[nH]c3ccc(F)cc32)cc1]

Tert-butyl (4-(((2-amino-5-fluorophenyl)amino)methyl) benzyl)carbamate (303 mg, 0.877 mmol), CDI (142 mg, 0.877 mmol), TEA (367 μl, 2.63 mmol), and DMF (2193 μl) were added to a vial equipped with a stir bar. The vial was sealed and heated to 80° C. for 4.5 hours. After 4.5 hours, the reaction mixture was cooled to room temperature. CDI (71.1 mg, 0.439 mmol) and TEA (122 μl, 0.877 mmol) were added to the reaction mixture, and heating at 80° C. resumed for 1 hour. After 1 hour, the reaction mixture was cooled to room temperature. The reaction mixture was washed with ethyl acetate and water. The combined organics were dried over magnesium sulfate, filtered, and concentrated under reduced pressure. The resulting material was carried on without purification. LC/MS (m/z): 316 (M+H)+ (observe loss of t-butyl).

Step D: 1-(4-(aminomethyl)benzyl)-6-fluoro-1,3-dihydro-2H-benzo[d]imidazol-2-one

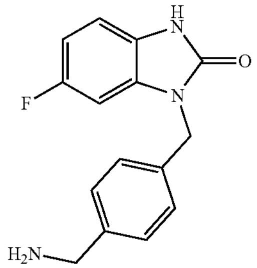 [SMILES: NCc1ccc(Cn2c(=O)[nH]c3ccc(F)cc32)cc1]

Tert-butyl (4-((6-fluoro-2-oxo-2,3-dihydro-1H-benzo[d]imidazol-1-yl)methyl)benzyl)carbamate (326 mg, 0.878 mmol), HCl (2194 μl, 8.78 mmol), and THF (2194 μl) were added to a vial equipped with a stir bar. The reaction mixture was stirred at room temperature for 18 hours. After 18 hours, the reaction mixture was concentrated under reduced pressure. The resulting material was dissolved in ACN/water. The material was frozen and dried on the lyopholizer for 16 hours to afford the desired intermediate. LC/MS (m/z): 272 (M+H)+.

Step E: N-(4-((6-fluoro-2-oxo-2,3-dihydro-1H-benzo[d]imidazol-1-yl)methyl)benzyl)acetamide

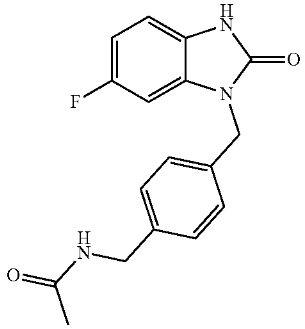 [SMILES: CC(=O)NCc1ccc(Cn2c(=O)[nH]c3ccc(F)cc32)cc1]

Acetic acid (21.10 μl, 0.369 mmol), HATU (210 mg, 0.553 mmol), and DMF (3686 μl) were added to a vial equipped with a stir bar. The reaction mixture was stirred for 5 minutes. After 5 minutes 1-(4-(aminomethyl)benzyl)-6-fluoro-1,3-dihydro-2H-benzo[d]imidazol-2-one (100 mg, 0.369 mmol) was added, followed by DIEA (193 μl, 1.106 mmol). The reaction mixture was stirred at room temperature for 24 hours. After 24 hours, the reaction mixture was filtered and submitted directly for HPLC purification (purified by HPLC, eluting acetonitrile/water gradient with basic modifier, linear gradient) to afford the title compound. LC/MS (m/z): 314 (M+H)+. $^1$H NMR (600 MHz, DMSO-d6) δ 10.98 (s, 1H), 8.34-8.15 (m, 1H), 7.24 (dd, J=50.0, 8.0 Hz, 4H), 6.99 (dd, J=9.1, 2.4 Hz, 1H), 6.97-6.90 (m, 1H), 6.83-6.73 (m, 1H), 4.95 (s, 2H), 4.18 (d, J=5.9 Hz, 2H), 1.83 (s, 3H).

Example 95

Preparation of N-(4-((6-fluoro-2-oxo-2,3-dihydro-1H-benzo[d]imidazol-1-yl)methyl)benzyl)propane-1-sulfonamide

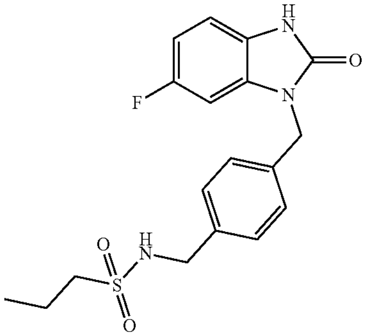 [SMILES: CCCS(=O)(=O)NCc1ccc(Cn2c(=O)[nH]c3ccc(F)cc32)cc1]

Step A: N-(4-((6-fluoro-2-oxo-2,3-dihydro-1H-benzo[d]imidazol-1-yl)methyl)benzyl)propane-1-sulfonamide

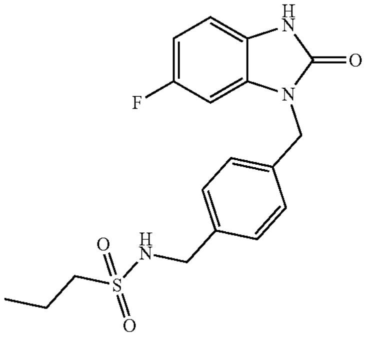 [SMILES: CCCS(=O)(=O)NCc1ccc(Cn2c(=O)[nH]c3ccc(F)cc32)cc1]

1-(4-(aminomethyl)benzyl)-6-fluoro-1,3-dihydro-2H-benzo[d]imidazol-2-one (30 mg, 0.111 mmol), TEA (46.2 μl, 0.332 mmol), and DMF (1106 μl) were added to a vial equipped with a stir bar. Propane-1-sulfonyl chloride (17.35 mg, 0.122 mmol) was added last, and the reaction mixture was stirred at room temperature for 1 hour. After 1 hour, the reaction mixture was filtered, and submitted directly for HPLC purification (purified by HPLC, eluting acetonitrile/water gradient with basic modifier, linear gradient) to afford the title compound. LC/MS (m/z): 378 (M+H)+. $^1$H NMR (600 MHz, DMSO-d6) δ 10.99 (s, 1H), 7.55 (t, J=6.3 Hz, 1H), 7.37-7.21 (m, 4H), 6.98 (dd, J=9.1, 2.4 Hz, 1H), 6.96-6.93 (m, 1H), 6.80-6.75 (m, 1H), 4.97 (s, 2H), 4.09 (d, J=6.3 Hz, 2H), 2.87-2.77 (m, 2H), 1.66-1.48 (m, 2H), 0.82 (t, J=7.4 Hz, 3H).

Example 96

Preparation of 1-methoxy-N-(4-((2-oxo-2,3-dihydro-1H-benzo[d]imidazol-1-yl)methyl)benzyl)cyclopropane-1-carboxamide

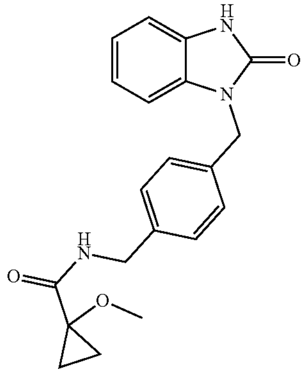 [SMILES: COC1(C(=O)NCc2ccc(Cn3c(=O)[nH]c4ccccc43)cc2)CC1]

Step A: tert-butyl (4-(((2-nitrophenyl)amino)methyl)benzyl)carbamate

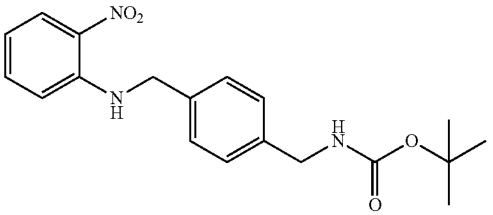 [SMILES: CC(C)(C)OC(=O)NCc1ccc(CNc2ccccc2[N+](=O)[O-])cc1]

1-fluoro-2-nitrobenzene (2.242 ml, 21.26 mmol), tert-butyl (4-(aminomethyl)benzyl)carbamate (5024 mg, 21.26 mmol), $K_2CO_3$ (4408 mg, 31.9 mmol), and THF (100 ml) were added to a vial equipped with a stir bar. The reaction mixture was sealed and heated to 80° C. for 16 hours. After 16 hours, the crude material was washed with water and ethyl acetate. The combined organics were dried over magnesium sulfate, filtered, and concentrated under reduced pressure to afford the title compound. LC/MS (m/z): 380 (M+H)+ (observe M+22).

Step B: tert-butyl (4-(((2-aminophenyl)amino)methyl)benzyl)carbamate

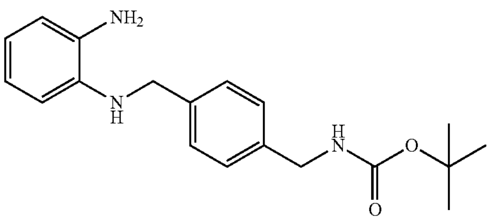

Zinc (7645 mg, 117 mmol) and ethanol (3.99E+04 μl) were added to a vial equipped with a stir bar. The vial was cooled to 0° C., and acetic acid (6694 μl, 117 mmol) was added. The mixture was stirred for 5 minutes. After 5 minutes, tert-butyl (4-(((2-nitrophenyl)amino)methyl)benzyl)carbamate (7599 mg, 21.26 mmol) was added in ethanol (1.33E+04 μl). The mixture was heated to 35° C. for 10 minutes. After 10 minutes, the mixture was cooled to room temperature and filtered over CELITE, rinsing with ethyl acetate. The resulting material was concentrated under reduced pressure. The resulting residue was dissolved in DCM and loaded onto a 120 g silica gel column. The desired product eluted; fractions were collected and concentrated under reduced pressure to afford the title compound. LC/MS (m/z): 328 (M+H)+.

Step C: tert-butyl (4-((2-oxo-2,3-dihydro-1H-benzo[d]imidazol-1-yl)methyl)benzyl)carbamate

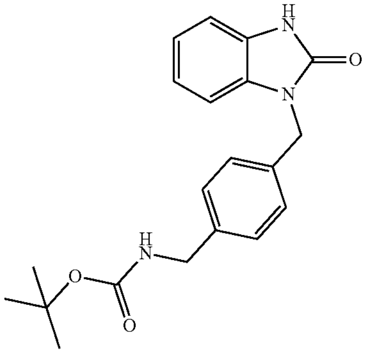 [SMILES: CC(C)(C)OC(=O)NCc1ccc(Cn2c(=O)[nH]c3ccccc32)cc1]

Tert-butyl (4-(((2-aminophenyl)amino)methyl)benzyl) carbamate (3.57 g, 10.90 mmol), CDI (1.768 g, 10.90 mmol), TEA (4.56 ml, 32.7 mmol), and DMF (27.3 ml) were added to a round bottom flask equipped with a stir bar. The reaction mixture was heated to 80° C. for 16 hours. After 16 hours, the reaction mixture was washed with ethyl acetate and water. The combined organics were dried over magnesium sulfate, filtered, and concentrated under reduced pressure to afford the title compound. LC/MS (m/z): 298 (M+H)+ (observe loss of tert-butyl)

Step D: 1-(4-(aminomethyl)benzyl)-1,3-dihydro-2H-benzo[d]imidazol-2-one

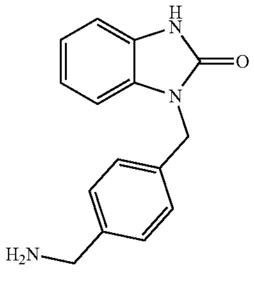 [SMILES: NCc1ccc(Cn2c(=O)[nH]c3ccccc32)cc1]

Tert-butyl (4-((2-oxo-2,3-dihydro-1H-benzo[d]imidazol-1-yl)methyl)benzyl)carbamate (3.85 g, 10.89 mmol), HCl (16.34 ml, 65.4 mmol), and THF (27.2 ml) were added to a round bottom flask equipped with a stir bar. The mixture was allowed to stir for 3 hours at room temperature. After 3 hours, the reaction mixture was heated to 40° C. for 19 hours. After 19 hours the reaction mixture was cooled to room temperature. The mixture was concentrated under reduced pressure. The material was triturated with ethyl acetate/hexanes/DCM. The material was filtered, and the title compound was obtained. LC/MS (m/z): 254 (M+H)+.

Step E: 1-methoxy-N-(4-((2-oxo-2,3-dihydro-1H-benzo[d]imidazol-1-yl)methyl)benzyl)cyclopropane-1-carboxamide

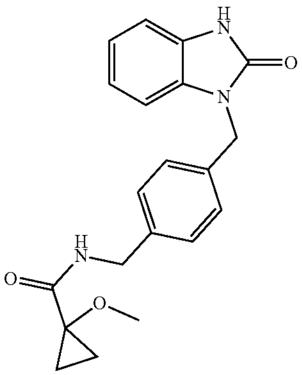 [SMILES: COC1(C(=O)NCc2ccc(Cn3c(=O)[nH]c4ccccc43)cc2)CC1]

1-(4-(aminomethyl)benzyl)-1,3-dihydro-2H-benzo[d]imidazol-2-one (30 mg, 0.118 mmol), HATU (67.5 mg, 0.178 mmol), and DMF (1500 μl) were stirred at room temperature for 5 minutes. After 5 minutes, 1-(4-(aminomethyl)benzyl)-1,3-dihydro-2H-benzo[d]imidazol-2-one (30 mg, 0.118 mmol) was added, followed by DIEA (62.1 μl, 0.355 mmol). The reaction mixture was allowed to stir at room temperature for 19 hours. After 19 hours, the reaction mixture was filtered and submitted directly for HPLC purification, eluting with an acetonitrile/water gradient with basic modifier, linear gradient to afford the title compound. LC/MS (m/z): 352 (M+H)+. $^1$H NMR (600 MHz, DMSO-d6) δ 10.93 (s, 1H), 8.60 (t, J=6.2 Hz, 1H), 7.31-7.17 (m, 4H), 7.02-6.90 (m, 4H), 4.96 (s, 2H), 4.28 (d, J=6.2 Hz, 2H), 3.24 (s, 3H), 1.10-0.92 (m, 4H).

Example 97

Preparation of 1-(3-(quinolin-8-yloxy)propyl)-1,3-dihydro-2H-benzo[d]imidazol-2-one

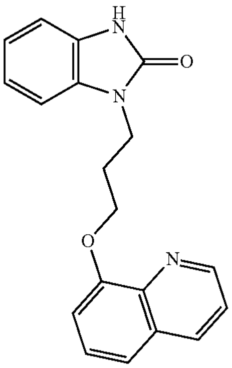 [SMILES: O=c1[nH]c2ccccc2n1CCCOc1cccc2cccnc12]

Step A: tert-butyl (3-(quinolin-8-yloxy)propyl)carbamate

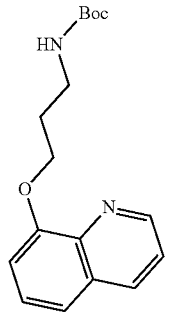 [SMILES: CC(C)(C)OC(=O)NCCCOc1cccc2cccnc12]

Quinolin-8-ol (0.5 g, 3.44 mmol) and THF (10 mL) were added to a vial equipped with a stir bar. Tert-butyl (3-hydroxypropyl)carbamate (0.604 g, 3.44 mmol), (E)-di-tert-butyl diazene-1,2-dicarboxylate (1.190 g, 5.17 mmol), diphenyl (p-tolyl) phosphine (1.428 g, 5.17 mmol) and tert-butyl (3-hydroxypropyl)carbamate (0.604 g, 3.44 mmol) were added to the reaction mixture, while stirring at 0° C. The reaction mixture was stirred at 80° C. for 16 hours. After 16 hours, the reaction mixture was cooled to room temperature, and concentrated under reduced pressure. Water (50 mL) was added to the residue and extracted with EtOAc (50 mL*2). The combined organic layers were collected, washed with brine (30 mL), dried over $Na_2SO_4$, and filtered. The resulting filtrate was concentrated in vacuo and was purified by flash silica gel chromatography with ethyl acetate and petroleum ether as eluent to afford the title compound. MS (ESI) m/z: 303 [M+H$^+$].

Step B: 3-(quinolin-8-yloxy)propan-1-amine

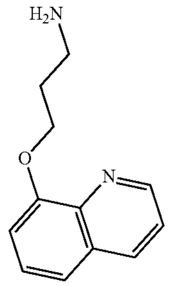 [SMILES: NCCCOc1cccc2cccnc12]

Tert-butyl (3-(quinolin-8-yloxy)propyl)carbamate (830 mg, 2.74 mmol) and DCM (10 ml) were added to a vial equipped with a stir bar. TFA (1.9 ml, 24.66 mmol) was added, and the reaction mixture was stirred at 30° C. for 16 hours. After 16 hours, the reaction mixture was concentrated in vacuo to afford the title compound. MS (ESI) m/z: 203 [M+H$^+$].

Step C: 2-nitro-N-(3-(quinolin-8-yloxy)propyl) aniline

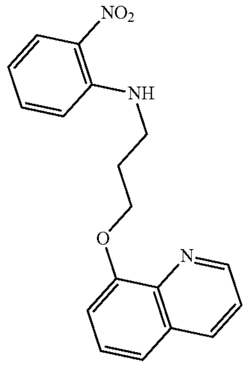

3-(quinolin-8-yloxy)propan-1-amine (555 mg, 2.74 mmol) and THF (15 mL) were added to a vial equipped with a stir bar. 1-fluoro-2-nitrobenzene (387 mg, 2.74 mmol) and $K_2CO_3$ (1138 mg, 8.23 mmol) were added, and the reaction mixture was heated to 80° C. for 16 hours. After 16 hours, the reaction mixture was cooled to room temperature. Water (80 mL) was added, and the mixture was washed with EtOAc (30 mL*3). The resulting organic layers were collected, washed with brine (20 mL), dried over $Na_2SO_4$, and filtered. The resulting filtrate was concentrated in vacuo. The resulting residue was purified by flash silica gel chromatography with ethyl acetate and petroleum ether as eluent to afford the title compound. MS (ESI) m/z: 324 [M+H$^+$].

Step D: N1-(3-(quinolin-8-yloxy)propyl)benzene-1,2-diamine

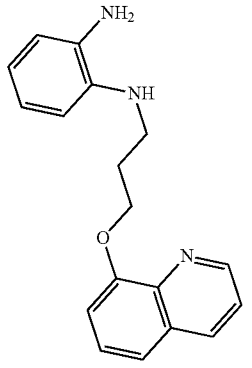 [SMILES: O=[N+]([O-])c1ccccc1NCCCOc1cccc2cccnc12]

2-nitro-N-(3-(quinolin-8-yloxy)propyl) aniline (150 mg, 0.464 mmol) and MeOH (5 mL) were added to a vial equipped with a stir bar. $NH_4Cl$ (aq) (5 mL) and zinc (607 mg, 9.28 mmol) were added, and the reaction was allowed to stir at 30° C. for 16 hours. After 16 hours, water (50 mL) was added, and the resulting material was washed with EtOAc (30 mL*2). The combined organic layers were collected, washed with brine (20 mL), dried over $Na_2SO_4$, and filtered. The resulting filtrate was concentrated in vacuo. The resulting residue was purified by flash silica gel chromatography with ethyl acetate and petroleum ether as eluent to afford the title compound. MS (ESI) m/z: 294 [M+H$^+$].

Step E: 1-(3-(quinolin-8-yloxy)propyl)-1H-benzo[d] imidazol-2 (3H)-one

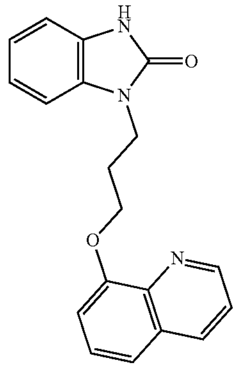 [SMILES: O=c1[nH]c2ccccc2n1CCCOc1cccc2cccnc12]

$N^1$-(3-(quinolin-8-yloxy)propyl)benzene-1,2-diamine (60 mg, 0.205 mmol) and THF (2.5 mL) were added to a vial equipped with a stir bar. Triethylamine (0.34 mL, 2.439 mmol) and CDI (199 mg, 1.227 mmol) were added, and the reaction mixture was stirred at 80° C. for 15 hours. After 15 hours, the resulting residue was purified by HPLC on a GILSON 281 instrument fitted with a Waters Boston Green ODS 150*30 5u using water (0.1% TFA)-MeCN, Mobile phase B acetonitrile, Detective wavelength: 220 nm to afford the title compound. MS (ESI) m/z: 320 [$M+H^+$]. $^1$H NMR (500 MHz, $CD_3OD$ δ 9.15-9.08 (m, 2H) 8.07 (dd, J=8.4, 5.2 Hz, 1H) 7.84-7.82 (m, 2H) 7.58-7.54 (m, 1H) 7.19-7.16 (m, 1H) 6.04-7.98 (m, 3H) 4.41 (t, J=5.7 Hz, 2H) 4.26 (t, J=6.7 Hz, 2H) 2.45 (q, J=6.3 Hz, 2H).

Example 98

Preparation of N-(((1r,4r)-4-((2-oxo-2,3-dihydro-1H-benzo[d]imidazol-1-yl)methyl)cyclohexyl) methyl)methanesulfonamide

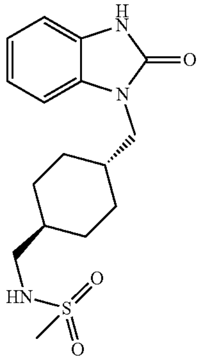

Step A: tert-butyl (((1r,4r)-4-(aminomethyl)cyclohexyl)methyl)carbamate

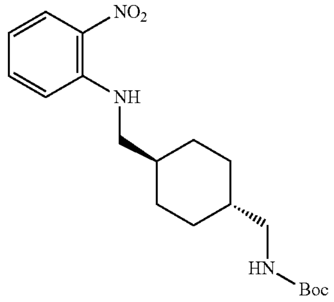 [SMILES: CC(C)(C)OC(=O)NC[C@H]1CC[C@H](CNc2ccccc2[N+](=O)[O-])CC1]

Tert-butyl (((1r,4r)-4-(aminomethyl)cyclohexyl)methyl) carbamate (500 mg, 2.063 mmol) and DMF (10 mL) were added to a vial equipped with a stir bar. 1-fluoro-2-nitrobenzene (349 mg, 2.476 mmol) and $K_2CO_3$ (570 mg, 4.13 mmol) were added, and the reaction mixture was stirred at 26° C. for 16 hours. After 16 hours, water (80 mL) was added and the mixture was washed with ethyl acetate (50 mL*3). The combined organic layers were collected, dried over $Na_2SO_4$, and filtered. The combined filtrate was concentrated in vacuo. The resulting residue was purified by flash silica gel chromatography with ethyl acetate and petroleum ether as eluent to afford the title compound. LCMS (ESI) m/z: 386 $[M+Na]^+$.

Step B: tert-butyl (((1r,4r)-4-(((2-aminophenyl) amino)methyl)cyclohexyl)methyl)carbamate

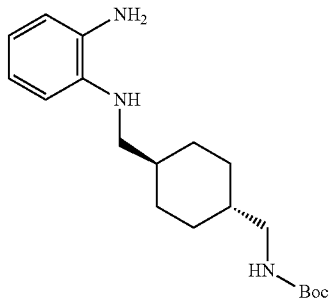 [SMILES: CC(C)(C)OC(=O)NC[C@H]1CC[C@H](CNc2ccccc2N)CC1]

Tert-butyl (((1r,4r)-4-(((2-nitrophenyl)amino)methyl)cyclohexyl)methyl)carbamate (700 mg, 1.926 mmol) and MeOH (20 mL) was added to a vial equipped with a stir bar. 10% Pd—C(70 mg) was added at 26° C., and the reaction was stirred at 26° C. under hydrogen (15 psi) for 2 hours. After 2 hours, the reaction was filtered and concentrated in vacuo to afford the title compound. LCMS (ESI) m/z: 278 $[M+H-56]^+$.

Step C: tert-butyl (((1r,4r)-4-((2-oxo-2,3-dihydro-1H-benzo[d]imidazol-1-yl)methyl) cyclohexyl)m-ethyl)carbamate

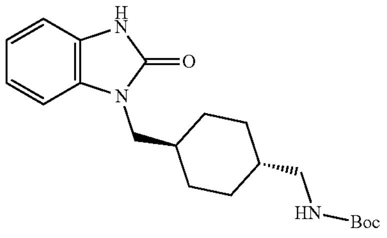 [SMILES: CC(C)(C)OC(=O)NC[C@H]1CC[C@H](Cn2c(=O)[nH]c3ccccc32)CC1]

Tert-butyl (((1r,4r)-4-(((2-aminophenyl)amino)methyl) cyclohexyl)methyl)carbamate (600 mg, 1.799 mmol) and THF (10 mL) were added to a vial equipped with a stir bar. CDI (875 mg, 5.40 mmol) and TEA (1.52 mL, 10.91 mmol) were added, and the reaction mixture was heated to 80° C. for 16 hours. After 16 hours, the reaction was cooled to room temperature. Water (40 mL) was added, and the mixture was washed with ethyl acetate (30 mL*3). The resulting organic layers were collected, dried over $Na_2SO_4$, and filtered. The resulting filtrate was concentrated in vacuo. The residue was purified by flash silica gel chromatography with ethyl acetate and petroleum ether as eluent to afford the title compound. LCMS (ESI) m/z: 304 $[M+H-56]^+$.

Step D: 1-(((1r,4r)-4-(aminomethyl)cyclohexyl) methyl)-1H-benzo[d]imidazol-2 (3H)-one

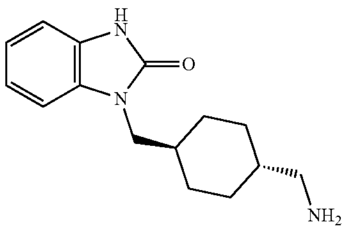 [SMILES: NC[C@H]1CC[C@H](Cn2c(=O)[nH]c3ccccc32)CC1]

Tert-butyl (((1r,4r)-4-((2-oxo-2,3-dihydro-1H-benzo[d] imidazol-1-yl)methyl)cyclohexyl)methyl)carbamate (240 mg, 0.668 mmol) and DCM (4 mL) were added to a vial equipped with a stir bar. TFA (2 mL, 26.0 mmol) was added, and the reaction mixture was stirred at 26° C. for 2 hours. After 2 hours, the solvent was concentrated in vacuo to afford the title compound. LCMS (ESI) m/z: 260 $[M+H]^+$.

Step E: N-(((1r,4r)-4-((2-oxo-2,3-dihydro-1H-benzo [d]imidazol-1-yl)methyl)cyclohexyl)methyl)meth-anesulfonamide

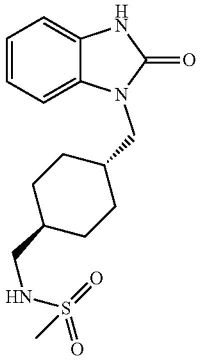

1-(((1r,4r)-4-(aminomethyl)cyclohexyl)methyl)-1H-benzo[d]imidazol-2 (3H)-one (50 mg, 0.193 mmol) and DMF (2 mL) were added to a vial equipped with a stir bar. TEA (0.08 mL, 0.574 mmol) and methane sulfonic anhydride (33 mg, 0.189 mmol) were added, and the reaction was stirred at 26° C. for 16 hours. After 16 hours, the solvent was concentrated in vacuo. The resulting residue was purified by reverse phase HPLC on a GILSON 281 instrument fitted with a Boston Green ODS 150×30 5u using water (0.1% TFA)-MeCN and acetonitrile as eluents followed by lyophilization to afford the title compound. MS (ESI) m/z: 338 $[M+H^+]$.

$^1$H NMR (400 MHZ, $CD_3OD$) δ 7.15-7.00 (m, 4H), 3.73 (d, J=7.4 Hz, 2H), 2.92-2.84 (m, 5H), 1.87-1.84 (m, 3H), 1.75-1.73 (m, 2H), 1.46 (br s, 1H), 1.19-1.05 (m, 2H), 1.01-0.89 (m, 2H).

Example 99

Preparation of N-((1r,4r)-4-((2-oxo-2,3-dihydro-1H-benzo[d]imidazol-1-yl)methyl)cyclohexyl)acetamide

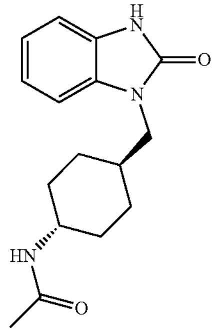

Step A: tert-butyl ((1s,4s)-4-(((2-nitrophenyl)amino)methyl)cyclohexyl)carbamate

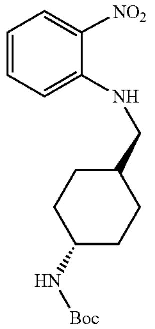

Tert-butyl ((1r,4r)-4-(aminomethyl)cyclohexyl)carbamate (1 g, 4.38 mmol) and DMF (15 mL) were added to a vial equipped with a stir bar. 1-fluoro-2-nitrobenzene (0.742 g, 5.26 mmol) and $K_2CO_3$ (1.211 g, 8.76 mmol) were added, and the reaction was heated to 80° C. for 16 hours. After 16 hours, water (100 mL) was added, and the mixture was washed with ethyl acetate (100 mL). The resulting organic layers were collected, dried over $Na_2SO_4$, and filtered. The resulting filtrate was concentrated in vacuo. The residue was purified by flash silica gel chromatography with ethyl acetate and petroleum ether as eluent to afford the title compound. MS (ESI) m/z: 294 [$M+H^+$] (observe loss of tert-butyl)

Step B: tert-butyl ((1s,4s)-4-(((2-aminophenyl)amino)methyl)cyclohexyl)carbamate

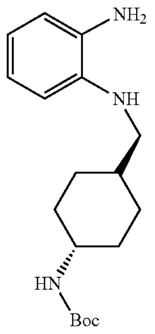

Tert-butyl ((1s,4s)-4-(((2-nitrophenyl)amino)methyl)cyclohexyl)carbamate (500 mg, 1.431 mmol) and MeOH (10 mL) were added to a vial equipped with a stir bar. Pd—C(50 mg, 0.047 mmol) was added, and the reaction was stirred at 26° C. under hydrogen (15 psi) for 4 hours. After 4 hours, the reaction mixture was filtered and the filtrate was concentrated in vacuo to afford the title compound. MS (ESI) m/z: 320 [M+H+].

Step C: tert-butyl ((1s,4s)-4-((2-oxo-2,3-dihydro-1H-benzo[d]imidazol-1-yl)methyl)cyclohexyl)carbamate

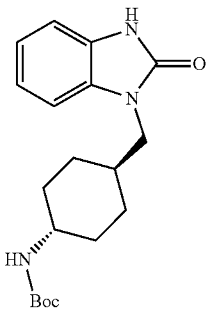

Tert-butyl ((1s,4s)-4-(((2-aminophenyl)amino)methyl)cyclohexyl)carbamate (450 mg, 1.409 mmol) and THF (10 mL) were added to a vial equipped with a stir bar. CDI (685 mg, 4.23 mmol) and TEA (1.2 mL, 8.61 mmol) were added, and the reaction was allowed to stir at 80° C. under nitrogen for 16 hours. After 16 hours, water (30 mL) was added, and the material was washed with ethyl acetate (30 mL*3). The resulting organic layers were collected, dried over $Na_2SO_4$, and filtered. The resulting filtrate was concentrated in vacuo. The resulting residue was purified by flash silica gel chromatography with ethyl acetate and petroleum ether as eluent to afford the title compound. MS (ESI) m/z: 290 [$M+H^+$] (observe loss of tert-butyl).

Step D: 1-(((1s,4s)-4-aminocyclohexyl)methyl)-1,3-dihydro-2H-benzo[d]imidazol-2-one

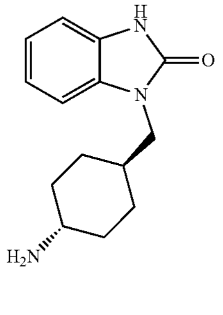

Tert-butyl ((1s,4s)-4-((2-oxo-2,3-dihydro-1H-benzo[d]imidazol-1-yl)methyl)cyclohexyl)carbamate (200 mg, 0.579 mmol) and DCM (15 mL) were added to a vial equipped with a stir bar. TFA (8 mL, 104 mmol) was added, and the reaction was allowed to stir at 26° C. for 16 hours. After 16 hours, the solvent was concentrated in vacuo to afford the title compound. MS (ESI) m/z: 246 [M+H+].

Step E: N-((1s,4s)-4-((2-oxo-2,3-dihydro-1H-benzo[d]imidazol-1-yl)methyl)cyclohexyl)acetamide

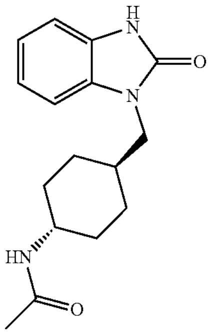

1-(((1s,4s)-4-aminocyclohexyl)methyl)-1H-benzo[d]imidazol-2 (3H)-one (70 mg, 0.285 mmol) in DMF (2 mL) were added to a vial equipped with a stir bar. TEA (0.14 mL, 1.004 mmol) and acetic anhydride (30 mg, 0.294 mmol) were added, and the reaction was stirred at 26° C. for 16 hours. After 16 hours, the solvent was concentrated in vacuo. The resulting residue was purified by reverse phase HPLC on a GILSON 281 instrument fitted with a Waters XSELECT C18 150*30 mm*5 um using water (0.1% TFA)-MeCN and acetonitrile as eluents followed by lyophilization to afford the title compound. MS (ESI) m/z: 288 $[M+H]^+$. $^1$H NMR (500 MHZ, $CDCl_3$) δ 8.59 (br s, 1H), 7.14-7.07 (m, 3H), 6.98 (d, J=7.0 Hz, 1H), 5.25 (br d, J=8.0 Hz, 1H), 3.72 (d, J=7.0 Hz, 2H), 3.80-3.66 (m, 1H), 2.06-1.98 (m, 2H), 1.95 (s, 3H), 1.82-1.78 (m, 3H), 1.27-1.21 (m, 2H), 1.09-1.06 (m, 2H).

Example 100

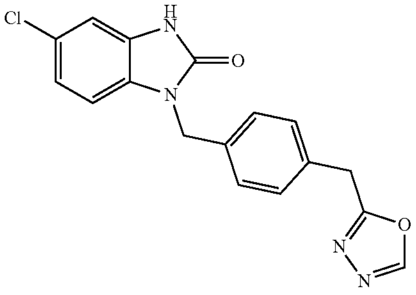

Step A: 2-(4-bromobenzyl)-1,3,4-oxadiazole

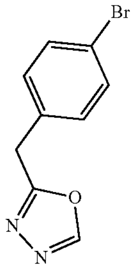 [SMILES: Brc1ccc(Cc2nnco2)cc1]

2-(4-bromophenyl)acetohydrazide (2.7 g, 11.79 mmol) and xylene (10 mL) were added to a vial equipped with a stir bar. AcOH (2 mL) and triethoxymethane (3.49 g, 23.57 mmol) were added at 26° C. (room temperature). The reaction was sealed and heated to 150° C. for 5 hours. After 5 hours, the reaction was cooled to room temperature. Water (30 mL) was added to the reaction mixture, and the material was washed with EtOAc (30 mL×2). The resulting organic layers were collected, washed with brine, dried over $Na_2SO_4$, and filtered. The resulting filtrate was concentrated in vacuo. The resulting residue was purified by flash silica gel chromatography with ethyl acetate and petroleum ether as eluent to afford the title compound. LCMS (ESI) m/z: 239 $[M+H]^+$.

Step B: tert-butyl (4-((1,3,4-oxadiazol-2-yl)methyl)benzyl)carbamate

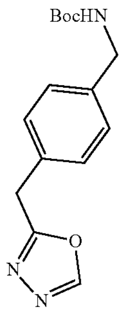 [SMILES: CC(C)(C)OC(=O)NCc1ccc(Cc2nnco2)cc1]

Potassium (((tert-butoxycarbonyl)amino)methyl)trifluoroborate (927 mg, 3.91 mmol), 2-(4-bromobenzyl)-1,3,4-oxadiazole (850 mg, 3.56 mmol), dioxane (20 mL), and water (2 mL) were added to a vial equipped with a stir bar. $K_2CO_3$ (1474 mg, 10.67 mmol), 2-dicyclohexylphosphino-2',4',6'-triisopropylbiphenyl (339 mg, 0.711 mmol) and Palladium(II) Acetate (80 mg, 0.356 mmol) were added, and the vial was sealed and heated to 110° C. under nitrogen. The reaction was allowed to stir for 16 hours. After 16 hours, the reaction mixture was cooled to room temperature, and water (20 mL) was added. The material was washed with EtOAc (20 mL×3), and the organic layers were collected, washed with brine (10 mL), dried over $Na_2SO_4$, and filtered. The resulting filtrate was concentrated in vacuo. The resulting residue was purified by flash silica gel chromatography with ethyl acetate and petroleum ether as eluent to afford the title compound. MS (ESI) m/z: 290 $[M+H]^+$.

Step C: (4-((1,3,4-oxadiazol-2-yl)methyl)phenyl)methanamine

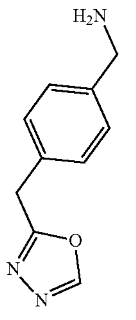 [SMILES: NCc1ccc(Cc2nnco2)cc1]

Tert-butyl 4-((1,3,4-oxadiazol-2-yl)methyl)benzylcarbamate (250 mg, 0.864 mmol) in DCM (10 mL) was added to a vial equipped with a stir bar. TFA (1 mL, 12.98 mmol) was added at 0° C., and the reaction was allowed to stir at 0° C. for 2 hours. After 2 hours, aq. $NaHCO_3$(~5 mL) was added to adjust the pH~9. The mixture was then diluted with water (~10 mL) and extracted with DCM (25 mL×6). The resulting organic layers were collected, dried over $Na_2SO_4$, and filtered. The resulting filtrate was concentrated in vacuo to afford the title compound. LCMS (ESI) m/z: 190 $[M+H]^+$.

Step D: N-(4-((1,3,4-oxadiazol-2-yl)methyl)benzyl)-4-chloro-2-nitroaniline

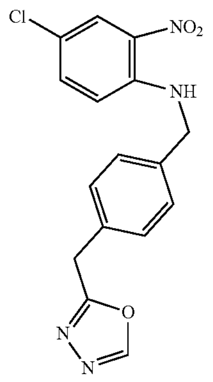

(4-((1,3,4-oxadiazol-2-yl)methyl)phenyl)methanamine (150 mg, 0.80 mmol) and DMF (5 mL) were added to a vial equipped with a stir bar. $K_2CO_3$ (220 mg, 1.6 mmol) and 4-chloro-1-fluoro-2-nitrobenzene (153 mg, 0.87 mmol) were added to the reaction mixture, and the reaction mixture was heated to 50° C. for 6 hours. After 6 hours, water (30 mL) was added, and the reaction mixture was extracted with ethyl acetate (10 mL×3). The resulting organic layers were collected, dried over $Na_2SO_4$, and filtered. The resulting filtrate was concentrated in vacuo. The resulting residue was purified by silica gel column chromatography with ethyl acetate and petroleum ether as eluent. LCMS (ESI) m/z: 367 $[M+Na]^+$.

Step E: N1-(4-((1,3,4-oxadiazol-2-yl)methyl)benzyl)-4-chlorobenzene-1,2-diamine

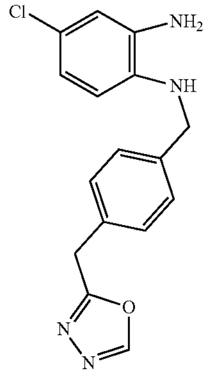 [SMILES: O=[N+]([O-])c1cc(Cl)ccc1NCc1ccc(Cc2nnco2)cc1]

N-(4-((1,3,4-oxadiazol-2-yl)methyl)benzyl)-4-chloro-2-nitroaniline (113 mg, 0.33 mmol) and MeOH (5 mL) was added to a vial equipped with a stir bar. Saturated $NH_4Cl$ in water (5 mL) and zinc (430 mg, 6.6 mmol) were added at room temperature, and the reaction was stirred for 5 hours. After 5 hours, water (10 mL) was added. The resulting mixture was extracted with ethyl acetate (10 mL×3). The resulting organic layers were collected, dried over $Na_2SO_4$, and filtered. The resulting filtrate was concentrated in vacuo to afford the title compound. LCMS (ESI) m/z: 315 $[M+H]^+$.

Step F:

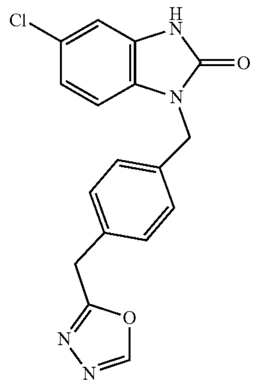 [SMILES: O=c1[nH]c2cc(Cl)ccc2n1Cc1ccc(Cc2nnco2)cc1]

N1-(4-((1,3,4-oxadiazol-2-yl)methyl)benzyl)-4-chlorobenzene-1,2-diamine (82 mg, 0.26 mmol) in THF (5 mL) was added to a vial equipped with a stir bar. TEA (160 mg, 1.6 mmol) and CDI (127 mg, 0.78 mmol) were added, and the reaction was heated to 80° C. and allowed to stir for 16 hours. After 16 hours, the solvent was concentrated in vacuo. The resulting residue was purified by reverse phase HPLC with water and acetonitrile as eluent and ammonium hydroxide as a basic modifier. Lyophilization afforded the title compound. LCMS (ESI) m/z: 341 $[M+H]^+$. $^1H$ NMR (500 MHZ, METHANOL-d4) δ 8.82 (s, 1H); 7.30 (s, 4H); 7.08 (d, J=1.98 Hz, 1H); 6.97-7.01 (m, 1H); 6.91-6.94 (m, 1H); 5.05 (s, 2H); 4.26 (s, 2H).

Example 101

Preparation of 3-((2-oxo-2,3-dihydro-1H-benzo[d]imidazol-1-yl)methyl)-N-(2,2,2-trifluoroethyl)benzamide

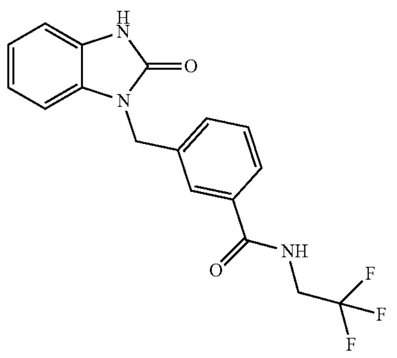 [SMILES: O=C(NCC(F)(F)F)c1cccc(Cn2c(=O)[nH]c3ccccc32)c1]

3-((2-oxo-2,3-dihydro-1H-benzo[d]imidazol-1-yl)methyl)benzoic acid (9.3 mgs, 0.037 mmol) (Intermediate 4)

was added to a vial with 2,2,2-trifluoroethan-1-amine hydrochloride (11.1 mgs, 0.082 mmol). DMA (0.40 mL) was added followed by propylphosphonic acid anhydride, cyclic trimer (23.5 mg, 0.074 mmol) and DIPEA (0.032 mL, 0.185 mmol). The mixture was then allowed to stir for 18 hours at room temperature. After 18 hours, the reaction mixture was filtered and the residue was was purified by HPLC (eluting acetonitrile/water gradient with TFA modifier). $^1$H NMR (500 MHZ, DMSO-$d_6$) δ 11.00 (s, 1H), 9.11 (t, J=6.2 Hz, 1H), 7.82 (s, 1H), 7.76 (d, J=7.1 Hz, 1H), 7.49-7.42 (m, 2H), 7.03-6.91 (m, 4H), 5.05 (s, 2H), 4.10-4.00 (m, 2H). LCMS (ESI) m/z: 350 [M+H$^+$]

Example 102

Preparation of 1-(3-(azetidine-1-carbonyl)benzyl)-1,3-dihydro-2H-benzo[d]imidazol-2-one

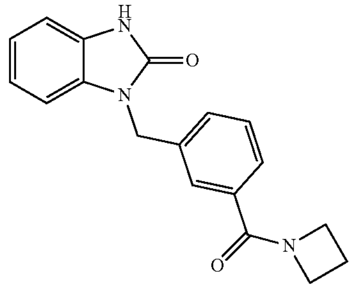 [SMILES: O=C(c1cccc(Cn2c(=O)[nH]c3ccccc32)c1)N1CCC1]

Utilizing the same procedure noted in Example 101, with the corresponding amine (azetidine), afforded the title compound. $^1$H NMR (500 MHZ, DMSO-$d_6$) δ 11.00 (s, 1H), 7.54-7.35 (m, 4H), 7.08-6.91 (m, 4H), 5.04 (s, 2H), 4.18 (t, J=7.6 Hz, 2H), 4.00 (t, J=7.7 Hz, 2H), 2.21 (p, J=7.7 Hz, 2H). LCMS (ESI) m/z: 308 [M+H$^+$].

Example 103

Preparation of 2-(3-((2-oxo-2,3-dihydro-1H-benzo[d]imidazol-1-yl)methyl)phenyl)-N-(pyridin-3-yl)acetamide

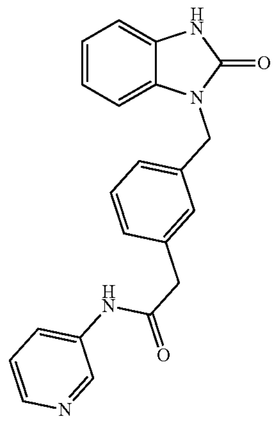 [SMILES: O=C(Cc1cccc(Cn2c(=O)[nH]c3ccccc32)c1)Nc1cccnc1]

Utilizing the same procedure noted in Example 101, 2-(3-((2-oxo-2,3-dihydro-1H-benzo[d]imidazol-1-yl)methyl)phenyl)acetic acid (Intermediate 5) and 3-aminopyridine were elaborated to the title compound. $^1$H NMR (500 MHZ, DMSO-$d_6$) δ 10.97 (s, 1H), 10.41 (s, 1H), 8.70 (d, J=2.4 Hz, 1H), 8.25 (dd, J=4.7, 1.3 Hz, 1H), 7.99 (d, J=8.5 Hz, 1H), 7.36-7.27 (m, 3H), 7.25-7.17 (m, 2H), 7.03-6.86 (m, 4H), 4.99 (s, 2H), 3.63 (s, 1H) (1 H is missing due to overlap with water peak). LCMS (ESI) m/z: 359 [M+H$^+$].

Example 104

Preparation of N-(3-cyanophenyl)-2-(3-((2-oxo-2,3-dihydro-1H-benzo[d]imidazol-1-yl)methyl)phenyl)acetamide

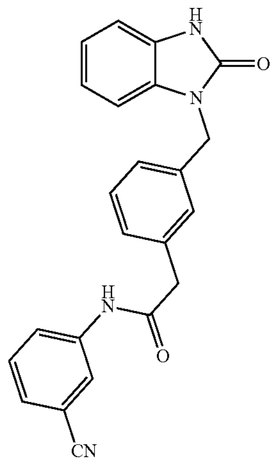 [SMILES: N#Cc1cccc(NC(=O)Cc2cccc(Cn3c(=O)[nH]c4ccccc43)c2)c1]

Utilizing the same procedure noted in Example 101, 2-(3-((2-oxo-2,3-dihydro-1H-benzo[d]imidazol-1-yl)methyl)phenyl)acetic acid (Intermediate 5) and 3-aminobenzonitrile, were elaborated to the title compound. $^1$H NMR (500 MHZ, DMSO-$d_6$) δ 10.97 (s, 1H), 10.52 (s, 1H), 8.03 (s, 1H), 7.76 (dt, J=7.1, 2.3 Hz, 1H), 7.54-7.49 (m, 2H), 7.31-7.27 (m, 2H), 7.25-7.17 (m, 2H), 7.01-6.94 (m, 3H), 6.92-6.88 (m, 1H), 4.98 (s, 2H), 3.63 (s, 1H) (1 H is missing due to overlap with water peak). LCMS (ESI) m/z: 383 [M+H$^+$].

Example 105

Preparation of N,N-dimethyl-2-(3-((2-oxo-2,3-dihydro-1H-benzo[d]imidazol-1-yl)methyl)phenyl)acetamide

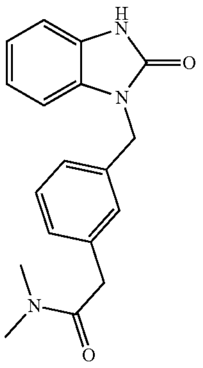 [SMILES: CN(C)C(=O)Cc1cccc(Cn2c(=O)[nH]c3ccccc32)c1]

Utilizing the same procedure noted in Example 101, 2-(3-((2-oxo-2,3-dihydro-1H-benzo[d] imidazol-1-yl) methyl)phenyl)acetic acid (Intermediate 5) and 3-aminobenzonitrile, were elaborated to the title compound. $^1$HNMR (500 MHZ, CDCl3) δ 8.71 (s, 1H), 7.24-7.15 (m, 3H), 7.09-6.99 (m, 3H), 6.88 (d, J=7.5 Hz, 1H), 5.06 (s, 2H), 3.69 (s, 2H), 2.95 (s, 6H). LCMS (ESI) m/z: 310 [M+H]+.

Example 106

Preparation of N-(3-fluorocyclopentyl)-2-(4-((2-oxo-2,3-dihydro-1H-benzo[d]imidazol-1-yl)methyl) phenyl)acetamide

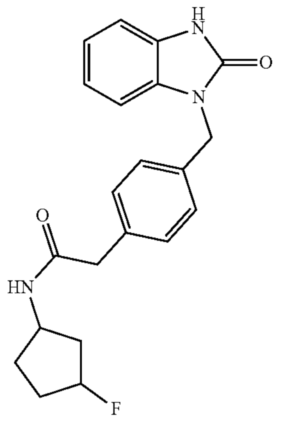 [SMILES: O=C(Cc1ccc(Cn2c(=O)[nH]c3ccccc32)cc1)NC1CCC(F)C1]

Utilizing the same procedure noted in Example 101, 2-(4-((2-oxo-2,3-dihydro-1H-benzo[d]imidazol-1-yl) methyl)phenyl)acetic acid (Intermediate 6) and (3-fluorocyclopentyl)-22-azane, were elaborated to the title compound. $^1$H NMR (500 MHZ, DMSO-$d_6$) δ 10.97 (s, 1H), 8.18 (d, J=7.0 Hz, 1H), 7.23-7.16 (m, 4H), 7.03-6.91 (m, 4H), 5.23-5.08 (m, 1H), 4.95 (s, 2H), 4.16-4.08 (m, 1H), 3.31 (s, 2H), 2.14-1.91 (m, 3H), 1.80-1.55 (m, 2H), 1.43-1.36 (m, 1H). LCMS (ESI) m/z: 368 [$M+H^+$].

Example 107

Preparation of N-methyl-2-(4-((2-oxo-2,3-dihydro-1H-benzo[d]imidazol-1-yl)methyl)phenyl)acetamide

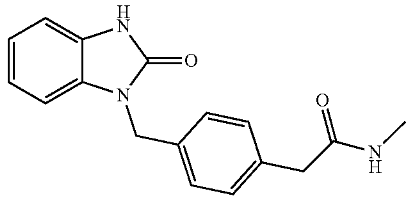 [SMILES: CNC(=O)Cc1ccc(Cn2c(=O)[nH]c3ccccc32)cc1]

Utilizing the same procedure noted in Example 101, 2-(3-((2-oxo-2,3-dihydro-1H-benzo[d] imidazol-1-yl) methyl)phenyl)acetic acid (Intermediate 5) and methanamine hydrochloride, were elaborated to the title compound. MS (ESI) m/z: 296 [$M+H^+$]. $^1$H NMR (500 MHZ, $CD_3OD$) δ 7.33-7.20 (m, 4H), 7.12-6.93 (m, 4H), 5.06 (s, 2H), 3.47 (s, 2H), 2.72-2.65 (m, 3H).

The Examples in Table 13 were synthesized according to the methods described in Example 107 employing the corresponding amine starting material.

TABLE 13

| Example No. | Structure | Name | Observed Mass [M + H]+ |
|---|---|---|---|
| Example 108 | 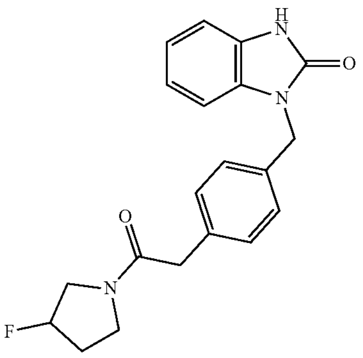 [SMILES: O=C(Cc1ccc(Cn2c(=O)[nH]c3ccccc32)cc1)N1CCC(F)C1] | 1-(4-(2-(3-fluoropyrrolidin-1-yl)-2-oxoethyl)benzyl)-1,3-dihydro-2H-benzo[d]imidazol-2-one | 354 [M + H]+ |

Example 109

Preparation of 1-benzyl-5-ethyl-1,3-dihydro-2H-benzo[d]imidazol-2-one

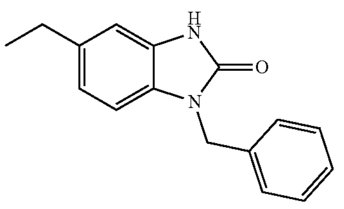 [SMILES: CCc1ccc2c(c1)[nH]c(=O)n2Cc1ccccc1]

Step A: 1-benzyl-5-ethyl-1,3-dihydro-2H-benzo[d]imidazol-2-one

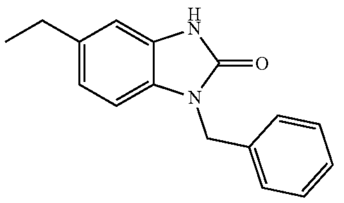 [SMILES: CCc1ccc2c(c1)[nH]c(=O)n2Cc1ccccc1]

Brettphos Pd G3 (30.2 mg, 0.033 mmol), Potassium Phosphate, tribasic (339 mg, 1.598 mmol), 2-bromo-1-chloro-4-ethylbenzene (219 mg, 0.999 mmol), and 1-benzylurea (100 mg, 0.666 mmol) were added to a vial equipped with a stir bar. The vial was purged with nitrogen and t-BuOH (6659 μl) was added to the reaction vial. The vial was sealed and heated to 110° C. for 19 hours. After 19 hours, the crude was washed with ethyl acetate and saturated $NaHCO_3$. The combined organics were dried over magnesium sulfate, filtered, and concentrated under reduced pressure. The residue was dissolved in DCM and loaded onto a 40 g column. The column was run from 100% hexanes to 100% ethyl acetate. The desired product was eluted; fractions were collected and concentrated under reduced pressure. The resulting material was dissolved in ACN/water; was frozen and dried on the lyopholizer for 16 hours to afford the title compound. LC/MS (m/z): 253 (M+H)+. $^1$H NMR (600 MHZ, DMSO-d6) δ 10.87 (s, 1H), 7.39-7.27 (m, 4H), 7.27-7.20 (m, 1H), 6.89 (d, J=7.9 Hz, 1H), 6.82 (s, 1H), 6.77 (d, J=7.8 Hz, 1H), 4.96 (s, 2H), 2.56 (q, J=7.4 Hz, 2H), 1.13 (t, J=7.5 Hz, 3H).

The Examples in Table 14 were synthesized according to the methods described in Example 109 employing the appropriate Br/Cl benzene starting materials.

TABLE 14

| Example No. | Structure | Name | Observed Mass [M + H]+ |
|---|---|---|---|
| Example 110 | 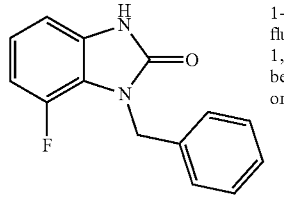 | 1-benzyl-7-fluoro-1,3-dihydro-2H-benzimidazol-2-one | 243 [M + H]+ |

Example 111

Preparation of 1-((2-(5-methylpyridin-2-yl)cyclopropyl)methyl)-1,3-dihydro-2H-benzo[d]imidazol-2-one

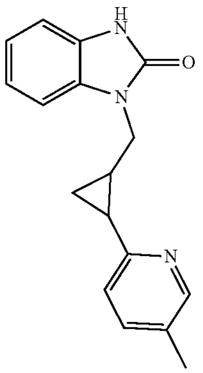 [SMILES: Cc1ccc(C2CC2Cn2c(=O)[nH]c3ccccc32)nc1]

Step A: (E)-tert-butyl 3-(3-(5-methylpyridin-2-yl)allyl)-2-oxo-2,3-dihydro-1H-benzo[d]imidazole-1-carboxylate

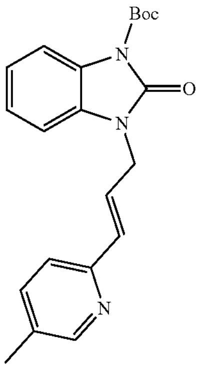 [SMILES: Cc1ccc(/C=C/Cn2c(=O)n(C(=O)OC(C)(C)C)c3ccccc32)nc1]

(E)-tert-butyl 2-oxo-3-(3-(4,4,5,5-tetramethyl-1,3,2-dioxaborolan-2-yl)allyl)-2,3-dihydro-1H-benzo[d]imidazole-1-carboxylate (755 mg, 1.886 mmol), $CH_3CN$ (2 mL) and water (0.2 mL) were added to a vial equipped with a stir bar. $K_3PO_4$ (801 mg, 3.77 mmol), 2-bromo-5-methylpyridine (397 mg, 2.263 mmol) and Pd(dtbpf)$Cl_2$ (49 mg, 0.075 mmol) were added to the vial. The vial was sealed and heated to 105° C. for 15 hours. After 15 hours, the reaction mixture was cooled to room temperature, and concentrated in vacuo. The resulting residue was purified by flash silica gel chromatography with ethyl acetate and petroleum ether as eluent to afford the title compound. LC/MS (ESI) m/z: 366 $[M+H]^+$.

Step B: tert-butyl 3-((2-(5-methylpyridin-2-yl)cyclopropyl)methyl)-2-oxo-2,3-dihydro-1H-benzo[d]imidazole-1-carboxylate

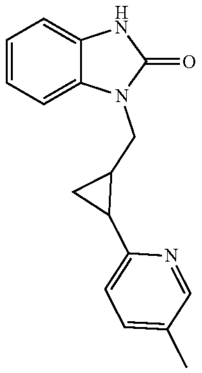 [SMILES: Cc1ccc(C2CC2Cn2c(=O)[nH]c3ccccc32)nc1]

1-methyl-1-nitrosourea (815 mg, 7.91 mmol) was added to an Erlenmeyer flask, containing a cooled (to 0° C. in an ice bath) mixture of $Et_2O$ (20 mL) and 40% aq KOH solution (4.2 mL). The resulting mixture was left to stand for 30 min, carefully shaking it several times. The resulting organic phase was decanted and dried (with KOH pellets) at 0° C. for 1 hour. After 1 hour, (E)-tert-butyl 3-(3-(5-methylpyridin-2-yl)allyl)-2-oxo-2,3-dihydro-1/-benzo[d]imidazole-1-carboxylate (289 mg, 0.791 mmol) and diacetoxypalladium (17.76 mg, 0.079 mmol) were dissolved in $Et_2O$ (10 mL), and was cooled to 0° C. The solution of diazomethane in $Et_2O$ was added dropwise. The reaction was stirred at 20° C. (room temperature) for 15 hours. After 15 hours, $CH_3COOH$ (5 mL) was added. The resulting crude afforded the title compound. LC/MS (ESI) m/z: 380 $[M+H]^+$.

Step C: 1-((2-(5-methylpyridin-2-yl)cyclopropyl)methyl)-1H-benzo[d]imidazol-2 (3H)-one

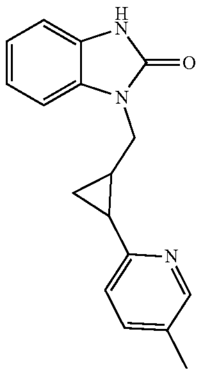 [SMILES: Cc1ccc(C2CC2Cn2c(=O)[nH]c3ccccc32)nc1]

Tert-butyl 3-((2-(5-methylpyridin-2-yl)cyclopropyl)methyl)-2-oxo-2,3-dihydro-1H-benzo[d]imidazole-1-carboxylate (150 mg, 0.395 mmol) and $CH_2Cl_2$ (10 mL) was added to a vial equipped with a stir bar. 2,2,2-Trifluoroacetic acid (135 mg, 1.186 mmol) was added, and the reaction mixture was allowed to stir at room temperature for 15 hours. After 15 hours, the reaction mixture was concentrated in vacuo. The resulting residue was filtered and purified by reverse phase HPLC on a GILSON 281 instrument fitted with a Phenomenex Synergi C18 (250*21.2 mm*4 μm) using water (0.1% TFA) and acetonitrile as eluents (Mobile phase A water (0.1% TFA), Mobile phase B acetonitrile, Detective wavelength: 220 nm) followed by lyophilization to afford the title compound. LC/MS (ESI) m/z: 280 $[M+H]^+$. $^1H$ NMR (500 MHZ, $CDCl_3$) δ 9.27 (br s, 1H), 8.61 (s, 1H), 7.88 (br d, J=7.9 Hz, 1H), 7.20 (d, J=8.2 Hz, 1H), 7.14-7.09 (m, 3H), 4.04-4.02 (m, 2H), 2.71-2.63 (m, 1H), 2.43 (s, 3H), 2.05-1.95 (m, 1H), 1.56-1.49 (m, 1H), 1.46-1.40 (m, 1H).

Step D: 1-((2-(5-methylpyridin-2-yl)cyclopropyl)methyl)-1H-benzo[d]imidazol-2 (3H)-one

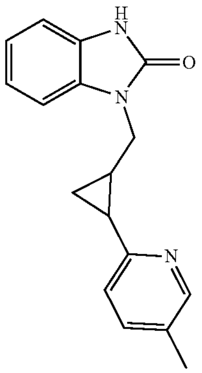 [SMILES: Cc1ccc(C2CC2Cn2c(=O)[nH]c3ccccc32)nc1]

Preparative resolution of 1-((2-(5-methylpyridin-2-yl)cyclopropyl)methyl)-1H-benzo[d]imidazol-2 (3H)-one was performed using supercritical fluid chromatography. A Chiralpak AS-H column (10 μm, 30 mm×250 mm, Chiral Technologies, West Chester, PA) was used as the chiral stationary phase. Injection and collection were carried out using the following gradient SFC conditions: A: $CO_2$, B: 0.1% $NH_3 \cdot H_2O$ MeOH, Gradient: from 5% to 40% of B, 220 nm UV wavelength, 100 bar outlet pressure, 38° C. column compartment temperature, 80 mL/min total flow rate. Retention times for peak collection were as follows: first eluting peak, 3.6 min; second eluting peak, 4.0 min. The title compound was afforded as Peak 2. LC/MS (ESI) m/z: 280 $[M+H]^+$. $^1H$ NMR (500 MHZ, $CDCl_3$) δ 9.43 (br s, 1H), 8.22 (s, 1H), 7.30 (br d, J=7.8 Hz, 1H), 7.11-7.08 (m, 3H), 7.08-7.04 (m, 1H), 7.02 (d, J=7.9 Hz, 1H), 4.03-3.92 (m, 2H), 2.24 (s, 3H), 2.19-2.15 (m, 1H), 1.92-1.81 (m, 1H), 1.30-1.25 (m, 1H), 1.16-1.11 (m, 1H).

Example 112

Preparation of 1-benzyl-1,3-dihydro-2H-thieno[2,3-d]imidazol-2-one

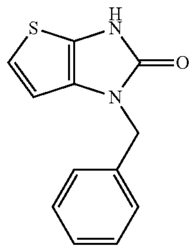 [SMILES: O=c1[nH]c2sccc2n1Cc1ccccc1]

Step A: 2H-thieno[3,2-d][1,3]oxazine-2,4 (1H)-dione

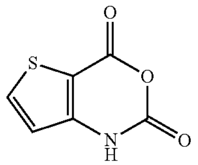 [SMILES: O=c1[nH]c2ccsc2c(=O)o1]

3-aminothiophene-2-carboxylic acid (736 mg, 2.57 mmol) and dioxane (15 ml) were added to a vial equipped with a stir bar, and heated to 70° C. while under Argon. Triphosgene (305 mg, 1.03 mmol) was added in small portions over 20 minutes. The resulting solution was stirred at 70° C. for 1 hour. After 1 hour, the reaction mixture was concentrated in vacuo. The residue was purified by flash silica gel chromatography with ethyl acetate and petroleum ether as eluent to afford the title compound. $^1$H NMR (400 MHZ, DMSO-$d_6$) δ 12.24 (br s, 1H), 8.24 (d, J=5.5 Hz, 1H), 6.94 (d, J=5.1 Hz, 1H).

Step B: 1-benzyl-2H-thieno[3,2-d][1,3]oxazine-2,4 (1H)-dione

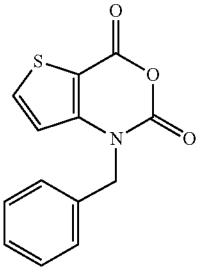 [SMILES: O=c1oc(=O)n(Cc2ccccc2)c2ccsc12]

1H-thieno[3,2-d][1,3]oxazine-2,4-dione (230 mg, 1.360 mmol) and DMF (4 mL) were added to a vial equipped with a stir bar. $K_2CO_3$ (225 mg, 1.632 mmol) and (bromomethyl) benzene (233 mg, 1.360 mmol) were added, and the reaction mixture was stirred at room temperature for 1 hour. After 1 hour, the reaction mixture was poured into water (20 mL) and extracted with DCM (30 mL×2). The resulting organic layers were collected, washed with brine (20 mL), dried over $Na_2SO_4$, filtered, and concentrated to afford the title compound. $^1$H NMR (400 MHZ, DMSO-$d_6$) δ 8.28 (d, J=5.5 Hz, 1H), 7.42-7.34 (m, 5H), 7.25 (d, J=5.1 Hz, 1H), 5.21 (s, 2H).

Step C: 3-(benzylamino) thiophene-2-carbonyl azide

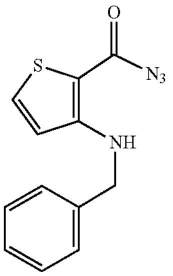 [SMILES: [N-]=[N+]=NC(=O)c1sccc1NCc1ccccc1]

1-benzyl-1H-thieno[3,2-d][1,3]oxazine-2,4-dione (50 mg, 0.193 mmol) in acetone (5 mL) was added to a vial equipped with a stir bar. Sodium azide (63 mg, 0.969 mmol) in water (0.5 mL) was added, and the reaction mixture was allowed to stir at 20° C. (room temperature) for 15 hours. After 15 hours, the reaction mixture was concentrated in vacuo. The resulting residue was treated with water (50 mL). The resulting material was filtered, washed with diethyl ether (30 mL), dried, and concentrated in vacuo. The resulting residue was purified by flash silica gel chromatography with ethyl acetate and petroleum ether as eluent to afford the title compound. LCMS (ESI) m/z: 259 $[M+H]^+$.

Step D: 1-benzyl-1H-thieno[2,3-d] imidazol-2 (3H)-one

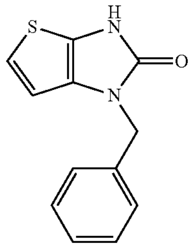 [SMILES: O=c1[nH]c2sccc2n1Cc1ccccc1]

3-(benzylamino) thiophene-2-carbonyl azide (72 mg, 0.279 mmol) in toluene (5 mL) was added to a vial equipped with a stir bar. The reaction mixture was heated to 110° C. for 15 hours. After 15 hours, the mixture was concentrated in vacuo. The resulting residue was filtered and purified by reverse phase HPLC on a GILSON 281 instrument fitted with a Phenomenex Synergi C18 (250*21.2 mm*4 μm) using water (0.1% TFA) and acetonitrile as eluents (Mobile phase A water (0.1% TFA), Mobile phase B acetonitrile, Detective wavelength: 220 nm) followed by lyophilization to afford the title compound. LCMS (ESI) m/z: 231 $[M+H]^+$. 1H NMR (400 MHZ, DMSO-$d_6$) δ 10.97 (s, 1H), 7.38-7.24 (m, 5H), 6.92 (d, J=5.4 Hz, 1H), 6.80 (d, J=5.1 Hz, 1H), 4.92 (s, 2H).

The Examples in Table 15 were synthesized according to the methods described in Example 112 employing the corresponding commerically available starting material in Step B.

TABLE 15

| Example # | Structure | Name | Observed Mass [M + H]+ |
|---|---|---|---|
| Example 113 | 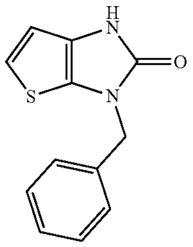 [SMILES: O=c1[nH]c2ccsc2n1Cc1ccccc1] | 3-benzyl-1,3-dihydro-2H-thieno[2,3-d]imidazol-2-one | 231 [M + H]+ |

Example 114

Preparation of 1-(4-(quinolin-8-yl)butyl)-1,3-dihydro-2H-benzo[d]imidazol-2-one

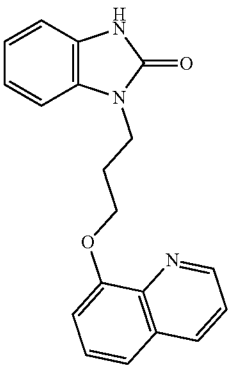 [SMILES: O=c1[nH]c2ccccc2n1CCCOc1cccc2cccnc12]

Step A: tert-butyl 3-(3-iodopropyl)-2-oxo-2,3-dihydro-1H-benzo[d]imidazole-1-carboxylate

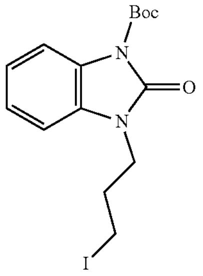 [SMILES: CC(C)(C)OC(=O)n1c(=O)n(CCCI)c2ccccc21]

1,3-diiodopropane (3.79 g, 12.81 mmol) and DMF (20 mL) was added to a vial equipped with a stir bar. Tert-butyl 2-oxo-2,3-dihydro-1H-benzo[d]imidazole-1-carboxylate (1.0 g, 4.27 mmol) and $K_2CO_3$ (0.885 g, 6.40 mmol) were added, and the reaction was stirred at 30° C. for 16 hours. After 16 hours, the mixture was concentrated and diluted with water (150 mL). The material was washed with ethyl acetate (80 mL×3), and the combined organic layers were washed with brine, dried over $Na_2SO_4$, and filtered. The resulting filtrate was concentrated in vacuo, and the residue was purified by flash silica gel chromatography with ethyl acetate and petroleum ether as eluent to afford the title compound. MS (ESI) m/z: 347 [$M+H^+$] (observe loss of tert-butyl).

Step B: (3-(3-(tert-butoxycarbonyl)-2-oxo-2,3-dihydro-1H-benzo[d]imidazol-1-yl)propyl)triphenylphosphonium iodide

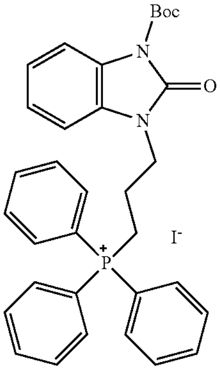 [SMILES: CC(C)(C)OC(=O)n1c(=O)n(CCC[P+](c2ccccc2)(c2ccccc2)c2ccccc2)c2ccccc21 ; [I-]]

Tert-butyl 3-(3-iodopropyl)-2-oxo-2,3-dihydro-1H-benzo[d]imidazole-1-carboxylate (200 mg, 0.497 mmol) and toluene (5 mL) were added to a vial equipped with a stir bar. Triphenylphosphine (143 mg, 0.547 mmol) was added, and the reaction was heated to 110° C. for 16 hours under nitrogen. After 16 hours, the mixture was filtered and washed with toluene (3 mL×3). The resulting material was concentrated in vacuo to afford the title compound. $^1$H NMR (500 MHz, $CDCl_3$) δ 7.83-7.60 (m, 15H), 7.55 (d, J=8.0 Hz, 1H), 7.17-7.15 (m, 1H), 7.12-7.09 (m, 1H), 7.04-6.99 (m, 1H), 4.34 (br t, J=7.0 Hz, 2H), 3.98-3.89 (m, 2H), 2.22-2.15 (m, 2H), 1.64 (s, 9H)

Step C: tert-butyl 2-oxo-3-(4-(quinolin-8-yl)but-3-en-1-yl)-2,3-dihydro-1H-benzo[d]imidazole-1-carboxylate

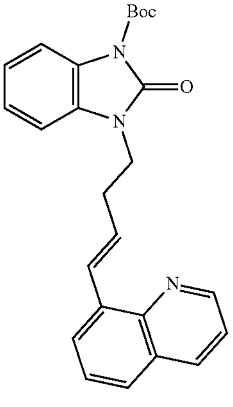 [SMILES: CC(C)(C)OC(=O)n1c(=O)n(CC/C=C/c2cccc3cccnc23)c2ccccc21]

(3-(3-(tert-butoxycarbonyl)-2-oxo-2,3-dihydro-1H-benzo[d]imidazol-1-yl)propyl)triphenylphosphonium iodide (660 mg, 0.993 mmol) and DMSO (8 mL) were added to a vial equipped with a stir bar. Potassium tert-butoxide (121 mg, 1.075 mmol) and quinoline-8-carbaldehyde (130 mg, 0.827 mmol) were added, and the reaction was stirred at 30° C. for 16 hours. After 16 hours, the mixture was concentrated and diluted with water (150 mL). The resulting material was extracted with ethyl acetate (80 mL×3), and the combined organic layers were collected, washed with brine, dried over $Na_2SO_4$, and filtered. The resulting filtrate was concentrated in vacuo to afford the title compound. MS (ESI) m/z: 416 [$M+H^+$].

Step D: (E)-1-(4-(quinolin-8-yl)but-3-en-1-yl)-1H-benzo[d]imidazol-2 (3H)-one

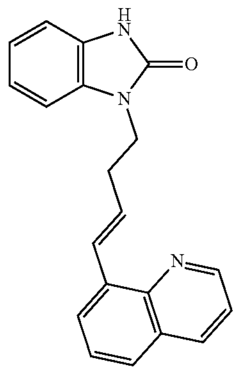 [SMILES: O=c1[nH]c2ccccc2n1CC/C=C/c1cccc2cccnc12]

Tert-butyl 2-oxo-3-(4-(quinolin-8-yl)but-3-en-1-yl)-2,3-dihydro-1H-benzo[d]imidazole-1-carboxylate (350 mg, 0.842 mmol) and DCM (5 mL) were added to a vial equipped with a stir bar. TFA (5 mL, 64.9 mmol) was added, and the reaction was stirred at 30° C. for 16 hours. After 16 hours, the mixture was concentrated under reduced pressure. Water (150 mL) was added, and the material was washed with ethyl acetate (80 mL×3). The resulting organic layers were collected, washed with brine, dried over $Na_2SO_4$, and filtered. The resulting filtrate was concentrated in vacuo. The resulting residue was purified by flash silica gel chromatography with ethyl acetate and petroleum ether as eluent to afford the title compound. MS (ESI) m/z: 316 [$M+H^+$]. $^1H$ NMR (500 MHz, $CDCl_3$) δ 9.18 (br d, J=4.5 Hz, 1H), 8.75 (br s, 1H), 8.38 (d, J=8.0 Hz, 1H), 7.86 (d, J=6.5 Hz, 1H), 7.80 (d, J=8.0 Hz, 1H), 7.63-7.54 (m, 3H), 7.16-7.01 (m, 4H), 6.40 (dd, J=7.0, 15.5 Hz, 1H), 4.15 (t, J=7.0 Hz, 2H), 2.84 (q, J=7.0 Hz, 2H).

Step E: 1-(4-(quinolin-8-yl)butyl)-1,3-dihydro-2H-benzo[d]imidazol-2-one

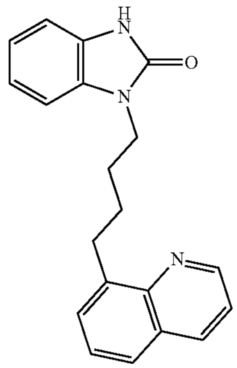

(E)-1-(4-(quinolin-8-yl)but-3-en-1-yl)-1H-benzo[d]imidazol-2 (3H)-one (35 mg, 0.111 mmol) and MeOH (2 mL) were added to a vial equipped with a stir bar. Pd/C (5 mg, 0.047 mmol) was added at 25° C., and the reaction was stirred at 25° C. under $H_2$ (15 psi) for 1 hour. After 1 hour, the reaction mixture was filtered and washed with MeOH. The resulting filtrate was purified by prep-HPLC (Method Column Boston Green ODS 150×30 5u Condition water (0.1% TFA)-ACN Begin B 22 End B 52 Gradient Time (min) 10 100% B Hold Time (min) 2 FlowRate (mL/min) 25 Injections 2) to afford the title compound. MS (ESI) m/z: 318 [$M+H^+$]. $^1$HNMR (500 MHZ, $CDCl_3$) δ 10.59 (br s, 1H), 9.62 (br d, J=4.5 Hz, 1H), 8.68 (d, J=7.5 Hz, 1H), 7.95-7.87 (m, 2H), 7.80 (d, J=6.5 Hz, 1H), 7.72-7.66 (m, 1H), 7.20-7.14 (m, 1H), 7.12-6.98 (m, 3H), 4.08 (br t, J=6.5 Hz, 2H), 3.50-3.37 (m, 2H), 2.02-1.91 (m, 2H), 1.76-1.62 (m, 2H).

Example 115

Preparation of 1-((1-(pyridin-2-yl) piperidin-4-yl) methyl)-1,3-dihydro-2H-benzo[d]imidazol-2-one

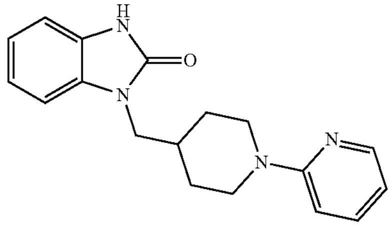 [SMILES: O=c1[nH]c2ccccc2n1CC1CCN(c2ccccn2)CC1]

Step A: tert-butyl 4-((2-oxo-2,3-dihydro-1H-benzo [d]imidazol-1-yl)methyl)piperidine-1-carboxylate

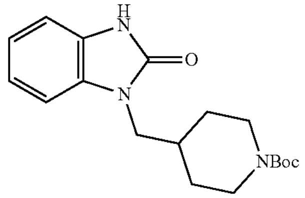 [SMILES: CC(C)(C)OC(=O)N1CCC(Cn2c(=O)[nH]c3ccccc32)CC1]

1H-benzo[d]imidazol-2 (3H)-one (500 mg, 3.73 mmol) and DMF (15 ml) were added to a vial equipped with a stir bar. NaH (142 mg, 3.54 mmol) was added, and the mixture was stirred for 30 minutes. After 30 minutes, tert-butyl 4-(bromomethyl) piperidine-1-carboxylate (1037 mg, 3.73 mmol) was added dropwise while stirring at 0° C. Upon completion of addition, the reaction was allowed to stir at 25° C. for 16 hours. After 16 hours, water (40 mL) was added, and the mixture was washed with EtOAC (50 mL*3). The combined organic layers were collected, washed with brine, dried over $Na_2SO_4$, and filtered. The resulting filtrate was concentrated in vaccuo. The resulting material was purified by flash silica gel chromatography with ethyl acetate and petroleum ether as eluent, and concentrated under reduce pressure to afford the title compound. LCMS (ESI) m/z: 276 $[M+H]^+$ (observe loss of tert-butyl).

Step B: 1-(piperidin-4-ylmethyl)-1,3-dihydro-2H-benzo[d]imidazol-2-one

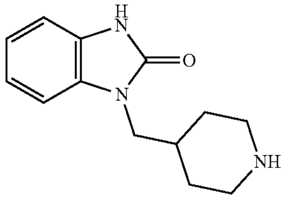 [SMILES: O=c1[nH]c2ccccc2n1CC1CCNCC1]

Tert-butyl 4-((2-oxo-2,3-dihydro-1H-benzo[d]imidazol-1-yl)methyl)piperidine-1-carboxylate (230 mg, 0.694 mmol) and DCM (20 ml) were added to a vial equipped with a stir bar. TFA (2 ml, 26.0 mmol) was added, and the mixture was stirred at 25° C. for 16 hours. After 16 hours, water (100 mL) was added, and the material was washed with ethyl acetate (50 mL×3). The resulting organics layers were collected, washed with brine, dried over $Na_2SO_4$, and filtered. The resulting filtrate was concentrated in vacuo. The resulting residue was used in the following step without further purification. LCMS (ESI) m/z: 232 $[M+H]^+$.

Step C: 1-((1-(pyridin-2-yl)piperidin-4-yl)methyl)-1,3-dihydro-2H-benzo[d]imidazol-2-one

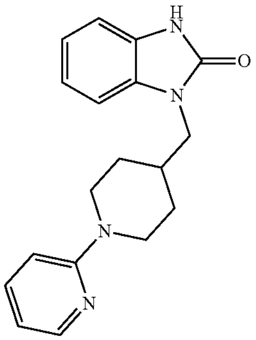 [SMILES: O=c1[nH]c2ccccc2n1CC1CCN(c2ccccn2)CC1]

2-fluoropyridine (12.59 mg, 0.130 mmol) and DMF (2 mL) were added to a vial equipped with a stir bar. 1-(piperidin-4-ylmethyl)-1H-benzo[d]imidazol-2 (3H)-one (30 mg, 0.130 mmol) and $K_2CO_3$ (17.93 mg, 0.130 mmol) was added at 20° C. under nitrogen. The reaction was stirred at 120° C. for 16 hours. After 16 hours, the reaction was cooled to room temperature. The mixture was filtered and concentrated in vacuo. The resulting residue was purified by prep-HPLC (Column Boston Green ODS 150*30 mm*5 μm, Condition water (0.1% TFA)-MeCN Begin B 47, End B 67 Gradient Time (min) 10, 100% B Hold Time (min) 2 Flow Rate (mL/min) 25) to afford the title compound. LCMS (ESI) m/z: 309 $[M+H]^+$. $^1H$ NMR (400 MHZ, METHANOL-$d_4$) δ 8.00-7.90 (m, 1H), 7.89-7.87 (m, 1H), 7.39 (d, J=9.4 Hz, 1H), 7.22-7.15 (m, 1H), 7.14-7.06 (m, 3H), 6.95 (t, J=6.7 Hz, 1H), 4.18 (br d, J=13.7 Hz, 2H), 3.86-3.84 (m, 2H), 3.29-3.21 (m, 2H), 2.36-2.32 (m, 1H), 1.91-1.87 (m, 2H), 1.56-1.45 (m, 2H).

Assay

IL4I1 Enzymatic Assay

Interleukin 4 inducible protein 1 (IL4I1) is an L-amino oxidase that catalyzes the oxidation of aromatic residues (Phe, Trp and Tyr): L-amino acid+$H_2O$+$O_2$→2-oxo acid+$NH_3$+$H_2O_2$. Equal molar of $H_2O_2$ and the corresponding alpha-ketoacid are produced when IL4I1 and substrate are added. In this assay, the hydrogen peroxide generated by IL4I1 is then detected through a coupled reaction with Amplex Red (10-acetyl-3,7-dihydroxyphenoxazine) and Horse Peroxidase (HRP) to produce Resorufin product that could be detected in the form of fluorescence signals. The assessment of the inhibitory effect of small molecules ($EC_{50}$) on IL4I1 is measured by the effectiveness of the compounds to inhibit the production of $H_2O_2$.

Using this assay, the potency ($EC_{50}$) of each compound was determined from a ten-point (1:3 serial dilution) titration curve using the following outlined procedure. To each well of a black flat-bottom Greiner (Cat #781076) 384 well-plate, 25 nL of compound (0.1% DMSO in final assay volume of 25 μL) was dispensed, followed by the addition of 12.5 μL of 1x assay buffer (50 mM Hepes 7.0 and 0.005% Tween20 (Sigma, Cat #P8341; low peroxide grade)) containing 2 nM of recombinant IL4I1 (R&D Systems, Cat #5684-AO-020). Plates were placed in an ambient temperature humidified chamber for a four-hour pre-incubation with compound. Subsequently, each reaction was initiated by the addition of 12.5 μL 1x assay buffer containing 2 mM of each aromatic amino acids (Phe/Tyr/Trp), 0.1 mM Amplex Red and 2 U/mL of HRP. The final reaction in each well of 25 μL consists of 1 nM of IL411, 1 mM of each residues (Phe, Tyr and Trp), 0.05 mM Amplex Red and 1 U/mL of HRP. It should be noted that the concentrations of Amplex Red and HRP used here are in excess such that the conversion of $H_2O_2$ to Resorufin product occurs instantaneously and non-rate limiting. Reactions were allowed to proceed for 120 minutes followed by fluorescence readout on a Spectramax with the following set parameters: 544 nm excitation/590 nm emission, 570 nm cutoff (EnVision is an alternative reader). Dose-response curves were generated by plotting percent effect (% product conversion; Y-axis) vs. $Log_{10}$ compound concentrations (X-axis). $EC_{50}$ values were calculated using a non-linear regression, four-parameters sigmoidal dose-response model and are shown in Table 16.

TABLE 16

| Potency | |
|---|---|
| Potency Example | EC50 (nM) (240 min) |
| 1 | 13 |
| 22 | 13 |
| 3 | 53 |
| 4 | 6 |
| 5 | 15 |
| 6 | 6 |
| 7 | 8 |
| 8 | 11 |
| 9 | 16 |
| 10 | 22 |
| 11 | 6 |
| 12 | 8 |
| 13 | 6 |
| 14 | 2 |
| 15 | 19 |
| 16 | 24 |
| 17 | 12 |
| 18 | 8 |
| 19 | 14 |
| 20 | 7 |
| 21 | 8 |
| 22 | 8 |
| 23 | 18 |
| 24 | 24 |

TABLE 16-continued

| Potency Example | Potency EC50 (nM) (240 min) |
|---|---|
| 25 | 47 |
| 26 | 6 |
| 27 | 7 |
| 28 | 33 |
| 29 | 5 |
| 30 | 9 |
| 31 | 15 |
| 32 | 11 |
| 33 | 15 |
| 34 | 153 |
| 35 | 2 |
| 36 | 9 |
| 37 | 1600 |
| 38 | 6 |
| 39 | 5 |
| 40 | 7 |
| 41 | 127 |
| 42 | 2 |
| 43 | 10 |
| 44 | 13 |
| 45 | 21 |
| 46 | 9 |
| 47 | 3 |
| 48 | 16 |
| 49 | 10 |
| 50 | 9 |
| 51 | 54 |
| 52 | 18 |
| 53 | 12 |
| 54 | 7 |
| 55 | 0.8 |
| 56 | 2477 |
| 57 | 3038 |
| 58 | 936 |
| 59 | 2931 |
| 60 | 8665 |
| 61 | 8 |
| 62 | 1235 |
| 63 | 4527 |
| 64 | 56 |
| 65 | 24 |
| 66 | 16 |
| 67 | 9 |
| 68 | 1391 |
| 69 | 2267 |
| 70 | 14 |
| 71 | 45 |
| 72 | 6 |
| 73 | 24 |
| 74 | 7 |
| 75 | 16 |
| 76 | 9 |
| 77 | 6 |
| 78 | 443 |
| 79 | 113 |
| 80 | 27 |
| 81 | 10 |
| 82 | 48 |
| 83 | 13 |
| 84 | 10 |
| 85 | 389 |
| 86 | 74 |
| 87 | 8903 |
| 88 | 10,000 |
| 89 | 29 |
| 90 | 227 |
| 91 | 1344 |
| 92 | 396 |
| 93 | 1340 |
| 94 | 9 |
| 95 | 6 |
| 96 | 21 |
| 97 | 45 |
| 98 | 1574 |
| 99 | 2693 |
| 100 | 784 |
| 101 | 90 |
| 102 | 8 |
| 103 | 4 |
| 104 | 5 |
| 105 | 10 |
| 106 | 38 |
| 107 | 5 |
| 108 | 8 |
| 109 | 4943 |
| 110 | 9157 |
| 111 | 4 |
| 112 | 1318 |
| 113 | 2847 |
| 114 | 107 |
| 115 | 1298 |

What is claimed is:

1. A compound, or a pharmaceutically acceptable salt thereof, having the Formula Ia Ia

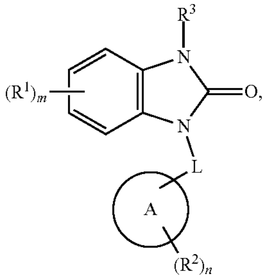

wherein,

A is aryl;

L is a straight or branched ($C_1$-$C_5$) alkylenyl, wherein one or more —$CH_2$— groups in L are optionally and independently replaced with a moiety selected from the group consisting of O, and NH;

each occurrence of $R^1$ is independently halogen, $C_1$-$C_6$alkyl, or cycloheteroalkyl;

each occurrence of $R^2$ is independently

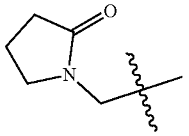,
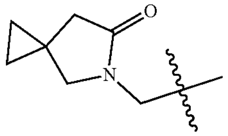,
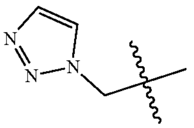,
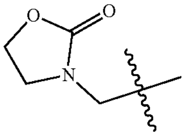,
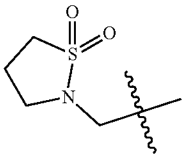,
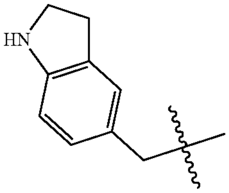,

-continued

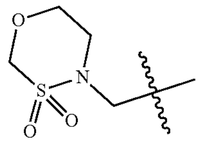,
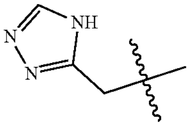,
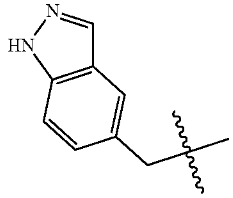,
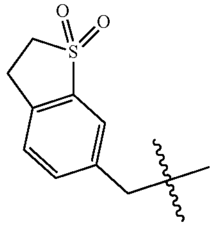, or
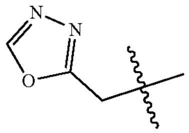.

$R^3$ is hydrogen, $C_1$-$C_6$alkyl or halo$C_1$-$C_6$alkyl;

m is 0, 1 or 2; and n is 1, 2 or 3.

2. The compound of claim 1, or pharmaceutically acceptable salt thereof, wherein L is $—CH_2—$, $—CH_2CH_2—$, $—CH_2CH_2CH_2CH_2—$, $—CH_2CH_2CH_2O—$, or $—CHCH_3—$.

3. The compound of claim 1, or a pharmaceutically acceptable salt thereof, wherein A is phenyl.

4. The compound of claim 1, or a pharmaceutically acceptable salt thereof, wherein m is 0.

5. The compound of claim 1, or a pharmaceutically acceptable salt thereof, wherein m is 1 or 2 and $R^1$ is fluorine, chlorine, pyrrolidine, methyl or ethyl.

6. The compound of claim 1, or a pharmaceutically acceptable salt thereof, wherein $R^3$ is hydrogen, methyl or difluoromethyl.

7. A method of treating cancer comprising administering to a patient in need thereof a compound of claim 1 or a pharmaceutically acceptable salt thereof.

8. A pharmaceutical composition comprising a compound of claim 1, or a pharmaceutically acceptable salt thereof and a pharmaceutically acceptable carrier.

9. A pharmaceutical composition comprising a compound of claim 1 and a pharmaceutically acceptable carrier.

10. A compound having the following structure

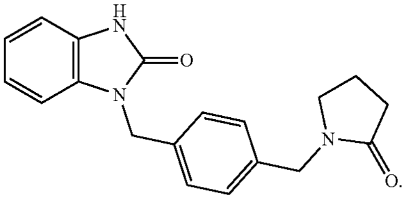 [SMILES: O=C1CCCN1Cc1ccc(Cn2c(=O)[nH]c3ccccc32)cc1].

11. A compound having the following structure

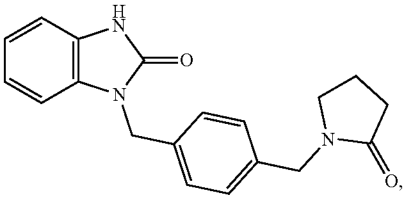 [SMILES: O=C1CCCN1Cc1ccc(Cn2c(=O)[nH]c3ccccc32)cc1], or a pharmaceutically acceptable salt thereof.

12. A method of treating cancer comprising administering to a patient in need thereof a compound of claim 11, or pharmaceutically acceptable salt thereof.

13. A pharmaceutical composition comprising a compound of claim 11, or a pharmaceutically acceptable salt thereof, and a pharmaceutically acceptable carrier.

14. A pharmaceutical composition comprising a compound of claim 10 and a pharmaceutically acceptable carrier.

15. A compound having the following structure

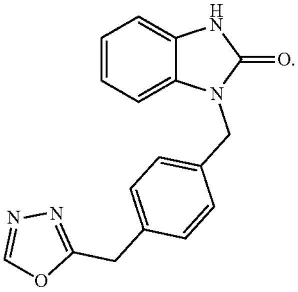 [SMILES: O=c1[nH]c2ccccc2n1Cc1ccc(Cc2nnco2)cc1].

16. A compound having the following structure

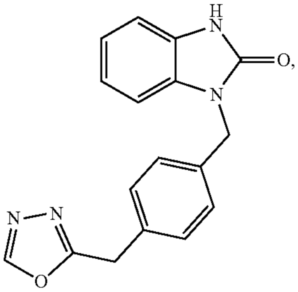 [SMILES: O=c1[nH]c2ccccc2n1Cc1ccc(Cc2nnco2)cc1], or a pharmaceutically acceptable salt thereof.

17. A method of treating cancer comprising administering to a patient in need thereof a compound of claim 16, or pharmaceutically acceptable salt thereof.

18. A pharmaceutical composition comprising a compound of claim 16, or a pharmaceutically acceptable salt thereof, and a pharmaceutically acceptable carrier.

19. A pharmaceutical composition comprising a compound of claim 15 and a pharmaceutically acceptable carrier.

20. A compound having the following structure

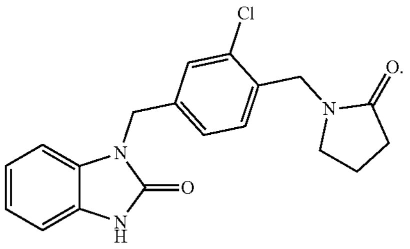 [SMILES: O=C1CCCN1Cc1ccc(Cn2c(=O)[nH]c3ccccc32)cc1Cl]

21. A compound having the following structure

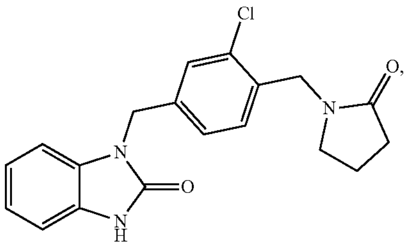

or a pharmaceutically acceptable salt thereof.

22. A method of treating cancer comprising administering to a patient in need thereof a compound of claim 21, or pharmaceutically acceptable salt thereof.

23. A pharmaceutical composition comprising a compound of claim 21, or a pharmaceutically acceptable salt thereof, and a pharmaceutically acceptable carrier.

24. A pharmaceutical composition comprising a compound of claim 20 and a pharmaceutically acceptable carrier.

25. A compound selected from:

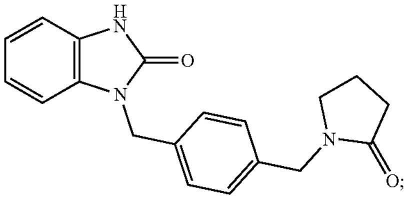

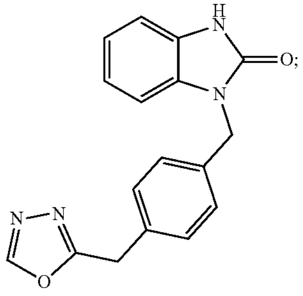

-continued

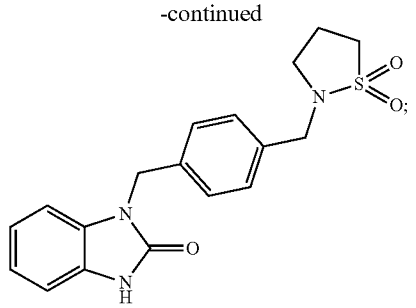

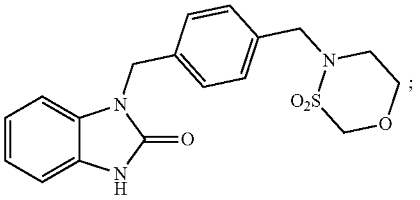

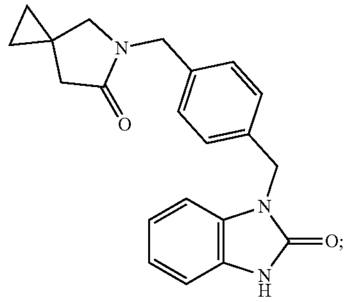

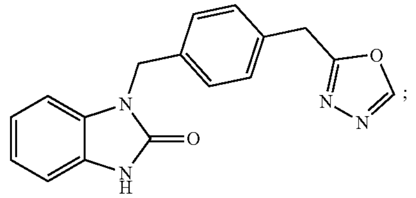

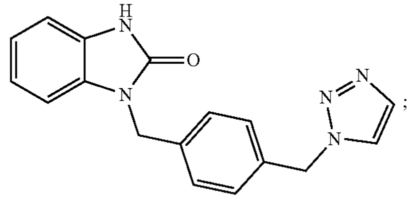

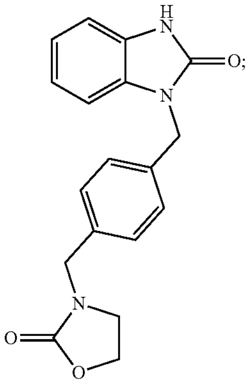

-continued
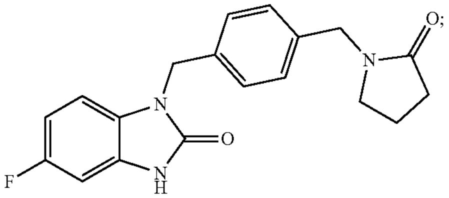
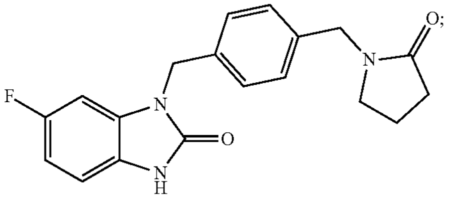
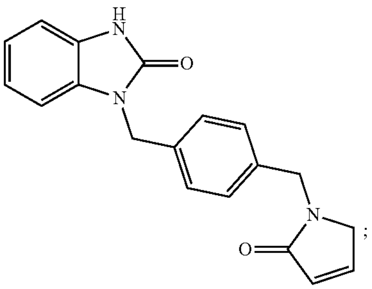
-continued
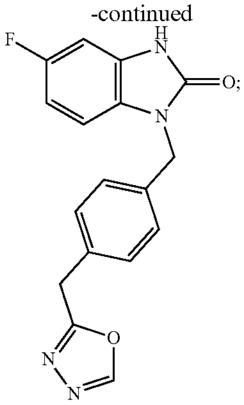
or
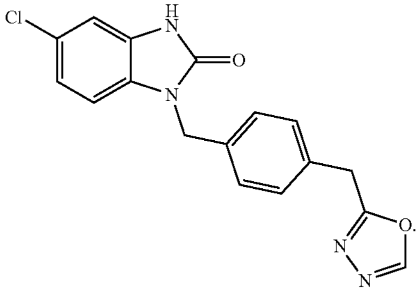
* * * * *